United States Patent
Zhang et al.

(10) Patent No.: US 10,202,650 B2
(45) Date of Patent: Feb. 12, 2019

(54) **METHODS FOR MONITORING *ELOVL2*, *KLF14* AND *PENK* GENE EXPRESSION FOLLOWING TREATMENT WITH VITAMIN C**

(71) Applicants: The Regents of the University of California, Oakland, CA (US); YouHealth Biotech, Limited, Grand Cayman (KY)

(72) Inventors: Kang Zhang, San Diego, CA (US); Rui Hou, Shenyang (CN); Lianghong Zheng, Shenyang (CN)

(73) Assignees: YOUHEALTH BIOTECH, LIMITED, Grand Cayman (KY); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/610,407

(22) Filed: May 31, 2017

(65) Prior Publication Data
US 2017/0342496 A1  Nov. 30, 2017

Related U.S. Application Data

(60) Provisional application No. 62/343,752, filed on May 31, 2016.

(51) Int. Cl.
*C12Q 1/6876* (2018.01)
*C12Q 1/6883* (2018.01)
*G01N 33/574* (2006.01)

(52) U.S. Cl.
CPC ..... *C12Q 1/6883* (2013.01); *G01N 33/57407* (2013.01); *G01N 33/57434* (2013.01); *C12Q 2600/106* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,525,462 A | 6/1996 | Takarada et al. | |
| 5,786,146 A | 7/1998 | Herman et al. | |
| 5,972,602 A | 10/1999 | Hyland et al. | |
| 6,017,704 A | 1/2000 | Herman et al. | |
| 6,033,854 A | 3/2000 | Kurnit et al. | |
| 6,114,117 A | 9/2000 | Hepp et al. | |
| 6,127,120 A | 10/2000 | Graham et al. | |
| 6,180,349 B1 | 1/2001 | Ginzinger et al. | |
| 6,200,756 B1 | 3/2001 | Herman et al. | |
| 6,265,171 B1 | 7/2001 | Herman et al. | |
| 6,306,597 B1 | 10/2001 | Macevicz | |
| 6,331,393 B1 | 12/2001 | Laird et al. | |
| 6,344,317 B2 | 2/2002 | Urnovitz | |
| 6,448,001 B2 | 9/2002 | Oku et al. | |
| 6,528,632 B1 | 3/2003 | Catanzariti et al. | |
| 6,797,470 B2 | 9/2004 | Barany et al. | |
| 7,011,944 B2 | 3/2006 | Prudent et al. | |
| 7,037,687 B2 | 5/2006 | Williams et al. | |
| 7,083,917 B2 | 8/2006 | Barany et al. | |
| 7,166,434 B2 | 1/2007 | Barany et al. | |
| 7,169,560 B2 | 1/2007 | Lapidus et al. | |
| 7,186,512 B2 | 3/2007 | Martienssen et al. | |
| 7,232,656 B2 | 6/2007 | Balasubramanian et al. | |
| 7,320,865 B2 | 1/2008 | Barany et al. | |
| 7,332,285 B2 | 2/2008 | Barany et al. | |
| 7,364,858 B2 | 4/2008 | Barany et al. | |
| 7,429,453 B2 | 9/2008 | Barany et al. | |
| 7,459,274 B2 | 12/2008 | Lakey et al. | |
| 7,553,627 B2 | 6/2009 | Laird et al. | |
| 7,598,035 B2 | 10/2009 | Macevicz | |
| 7,611,869 B2 | 11/2009 | Fan | |
| 7,645,596 B2 | 1/2010 | Williams et al. | |
| 7,700,324 B1 | 4/2010 | Issa et al. | |
| 7,769,400 B2 | 8/2010 | Backholm et al. | |
| 7,901,880 B2 | 3/2011 | Jeddeloh et al. | |
| 7,910,296 B2 | 3/2011 | Jeddeloh et al. | |
| 8,323,890 B2 | 12/2012 | Laird et al. | |
| 2005/0069879 A1 | 3/2005 | Berlin | |
| 2009/0155791 A1 | 6/2009 | Wojdacz et al. | |

(Continued)

FOREIGN PATENT DOCUMENTS

WO   WO-03064701 A2   8/2003
WO   WO-2005012578 A1   2/2005

(Continued)

OTHER PUBLICATIONS

Canali et al. Genes & Nutrition. May 2014. 9(3): 390.*
Blaschke et al. Nature. 2013. 500(7461): 222-226.*
Blaschke et al. Vitamin C induces Tet-dependent DNA demethylation in ESCs to promote a blastocyst-like state. Nature 500(7461)222-226 (2013).
Chung et al. Vitamin C promotes widespread yet specific DNA demethylation of the epigenome in human embryonic stem cells. Stem Cells 28(10):1848-1855 (2010).
Gustafson et al. Epigenetic reprogramming of melanoma cells by vitamin C treatment. Clinical Epigenetics 7(51):1-11 (2015).
PCT/US2017/035283 International Search Report and Written Opinion dated Aug. 29, 2017.

(Continued)

*Primary Examiner* — Carla J Myers
(74) *Attorney, Agent, or Firm* — Wilson Sonsini Goodrich & Rosati

(57) ABSTRACT

Disclosed herein are methods of increasing the expression rate of epigenetic markers such as ELOVL2, KLF14, and PENK with administration of a therapeutic agent (e.g., vitamin C or its derivatives, analogs, metabolites, prodrugs, or pharmaceutically acceptable salts thereof). Also described herein are methods of modulating the methylation pattern of epigenetic markers such as ELOVL2, KLF14, and PENK with administration of a therapeutic agent (e.g., vitamin C or its derivatives, analogs, metabolites, prodrugs, or pharmaceutically acceptable salts thereof).

21 Claims, 60 Drawing Sheets
Specification includes a Sequence Listing.

(56) References Cited

U.S. PATENT DOCUMENTS

| | | |
|---|---|---|
| 2010/0144836 A1 | 6/2010 | Van et al. |
| 2015/0259742 A1 | 9/2015 | Zhang et al. |

FOREIGN PATENT DOCUMENTS

| | | | |
|---|---|---|---|
| WO | WO-2005111209 A1 | | 11/2005 |
| WO | WO-2006056480 A2 | | 6/2006 |
| WO | WO-2009021141 A1 | | 2/2009 |
| WO | WO-2009049916 A2 | | 4/2009 |
| WO | WO 2014-75083 | * | 5/2014 |
| WO | WO-2015048121 A1 | | 4/2015 |

OTHER PUBLICATIONS

Steegenga et al. Genome-wide age-related changes in DNA methylation and Gene expression in human PBMCs. Age 36:1523-1540 (2014).
Acevedo et al. Analysis of the mechanisms mediating tumor-specific changes in gene expression in human liver tumors. Cancer Res. 68:2641-2651 (2008).
Balic et al. High quality assessment of DNA methylation in archival tissues from colorectal cancer patients using quantitative high-resolution melting analysis. J. Mol. Diagn. 11:102-108 (2009).
Ball et al. Targeted and genome-scale strategies reveal gene-body methylation signatures in human cells. Nat. Biotechnol 27:361-368 (2009).
Bibkova et al. High-throughput DNA methylation profiling using universal bead arrays. Genome Res. 16:383-393 (2006).
Bo et al. New feature subset selection procedures for classification of expression profiles. Genome Biology 3(4):research0017.1-0017.11 (2002).
Breiman. Random Forests. Machine Learning 45:5-32 (2001).
Candiloro et al. Assessing combined methylation-sensitive high resolution melting and pyrosequencing for the analysis of heterogeneous DNA methylation. Epigenetics 6(4):500-507 (2011).
Costello et al. Restriction landmark genome scanning. Meth. Mol Biol 200:53-70 (2002).
Cottrell et al. A real-time PCR assay for DNA-methylation using methylation-specific blockers. Nucleic Acids Res. 32:e10 (2004).
Cottrell et al. Discovery and validation of 3 novel DNA methylation markers of prostate cancer prognosis. J. Urology 177:1753-1758 (2007).
Degraves et al. High-Sensitivity Quantitative PCR Platform. Biotechniques 34(1):106-115 (2003).
Deiman et al. Characteristics and applications of nucleic acid sequence-based amplification (NASBA). Mol. Biotechnol. 20(2):163-179 (2002).
Deng et al. Targeted bisulfite sequencing reveals changes in DNA methylation associated with nuclear reprogramming. Nat. Biotechnol 27:353-360 (2009).
Dudoit et al. Comparison of Discrimination Methods for the Classification of Tumors Using Gene Expression Data. Journal of the American Statistical Association 97:77-87 (2002).
Eads et al. MethyLight: a high-throughput assay to measure DNA methylation. Nucleic Acid Res. 28:e32 (2000).
Fackler et al. Quantitative multiplex methylation-specific PCR analysis doubles detection of tumor cells in breast ductal fluid. Clin. Cancer Res. 12(11 Pt 1):3306-3310 (2006).
Fackler et al. Quantitative multiplex methylation-specific PCR assay for the detection of promoter hypermethylation in multiple genes in breast cancer. Cancer Res. 64(13):4442-4452 (2004).
Friedman. Regularized Discriminant Analysis. Journal of The American Statistical Association 84:165-175 (1989).
Frommer et al. A genomic sequencing protocol that yields a positive display of 5- methylcytosine residues in individual DNA strands. PNAS USA 89:1827-1831 (1992).
Garagnani et al. Methylation of ELOVL2 gene as a new apigenetic marker of age. Aging Cell 11:1132-1134 (2012).
Gebhard et al. Genome-wide profiling of CpG methylation identifies novel targets of aberrant hypermethylation in myeloid leukemia. Cancer Res. 66:6118-6128 (2006).
Gebhard et al. Rapid and sensitive detection of CpG-methylation using methyl-binding (MB)-PCR. Nucleic Acids Res. 34:e82 (2006).
Gibson et al. A novel method for real time quantitative RT-PCR. Genome Research 6:995-1001 (1996).
Gonzalgo et al. Rapid quantitation of methylation differences at specific sites using methylation-sensitive single nucleotide primer extension (Ms-SNuPE). Nucleic Acids Res. 25:2529-2531 (1997).
Harris et al. Single-molecule DNA sequencing of a viral genome. Science 320:106-109 (2008).
Herman et al. Methylation-specific PCR: a novel PCR assay for methylation status of CpG islands. PNAS USA 93:9821-9826 (1996).
Horak et al. ChIP-chip: a genomic approach for identifying transcription factor binding sites. Methods Enzymol 350:469-483 (2002).
Itzkowitz et al. Improved fecal DNA test for colorectal cancer screening. Clin Gastroenterol. Hepatol. 5(1):111-117 (2007).
Koga et al. Genome-wide screen of promoter methylation identifies novel markers in melanoma. Genome Res. 19:1462-1470 (2009).
Lieb. Genome-wide mapping of protein-DNA interactions by chromatin immunoprecipitation and DNA microarray hybridization. Methods Mol Biol 224:99-109 (2003).
Margulies et al. Genome sequencing in microfabricated high-density picolitre reactors. Nature 437:376-380 (2005).
McClelland et al. Effect of site-specific modification on restriction endonucleases and DNA modification methyltransferases. Nucleic Acids Res. 22(17):3640-3659 (1994).
Nakano et al. Single-molecule PCR using water-in-oil emulsion. J. Biotech. 102:117-124 (2003).
Nogrady. Medicinal Chemistry A Biochemical Approach, Oxford University Press, New York, pp. 388-392 (1985).
Nolte. Branched DNA signal amplification for direct quantitation of nucleic acid sequences in clinical specimens. Adv. Clin. Chem. 33:201-235 (1998).
O'Geen et al. Comparison of sample preparation methods for ChIP-chip assays. BioTechniques 41(5):577-580 (2006).
Olek et al. The pre-implantation ontogeny of the H19 methylation imprint Nat. Genet. 17(3):275-276 (1997).
Pelizzola et al. MEDME: an experimental and analytical methodology for the estimation of DNA methylation levels based on microarray derived MeDIP-enrichment. Genome Res. 18:1652-1659 (2008).
Radmacher et al. A paradigm for class prediction using gene expression profiles. Journal of Computational Biology 9:505-511 (2002).
Ramaswamy et al. Multiclass cancer diagnosis using tumor gene expression signatures. PNAS USA 98:15149-15154 (2001).
Rauch et al. High-resolution mapping of DNA hypermethylation and hypomethylation in lung cancer. PNAS USA 105:252-257 (2008).
Rein et al. Identifying 5-methylcytosine and related modifications in DNA genomes. Nucleic Acids Res. 26(10):2255-2264 (1998).
Ruczinski et al. Logic Regression. Journal of Computational and Graphical Statistics 12:475-5111 (2003).
Saulnier et al. An Efficient Method for the Synthesis of Guanidino Prodrugs. Bioorganic and Medicinal Chemistry Letters 4(16):1985-1990 (1994).
Shiraishi et al. Isolation of DNA fragments associated with methylated CpG islands in human adenocarcinomas of the lung using a methylated DNA binding column and denaturing gradient gel electrophoresis. PNAS USA 96(6):2913-2918 (1999).
Silverman et al. Chapter 8: Prodrugs and drug delivery systems. In: The Organic Chemistry of Drug Design and Drug Action. San Diego: Academic Press, Inc. p. 352-401 (1992).
Simon et al. Pitfalls in the use of DNA microarray data for diagnostic and prognostic classification. Journal of the National Cancer Institute 95:14-18 (2003).
Soni et al. Progress toward ultrafast DNA sequencing using solid-state nanopores. Clin. Chem. 53:1996-2001 (2007).
Tost et al. DNA methylation analysis by pyrosequencing. Nature Protocols 2:2265-2275 (2007).

(56) References Cited

OTHER PUBLICATIONS

Toyota et al. Identification of differentially methylated sequences in colorectal cancer by methylated CpG island amplification. Cancer Res. 59:2307-2312 (1999).
Ushijima et al. Methylation-Sensitive Representational Difference Analysis (MS-RDA). Methods Mol Biol507:117-130 (2009).
Weber et al. Chromosome-wide and promoter-specific analyses identify sites of differential DNA methylation in normal and transformed human cells. Nat. Genet. 37:853-862 (2005).
Wojdacz et al. Methylation-sensitive high resolution melting (MS-HRM): a new approach for sensitive and high-throughput assessment of methylation. Nucleic Acids Res. 35(6):e41 (2007).
Wojdacz et al. Methylation-sensitive high-resolution melting. Nature Protocols 3(12):1903-1908 (2008).
Wright et al. A random variance model for detection of differential gene expression in small microarray experiments. Bioinformatics 19(18):2448-2455 (2003).
Xiong et al COBRA: a sensitive and quantitative DNA methylation assay. Nucleic Acids Res. 25:2532-2534 (1997).
Zou et al. Association of Clinical Chemistry (AACC) poster presentation on Jul. 28, 2010. Sensitive Quantification of Methylated Markers with a Novel Methylation Specific Technology. Available at www.exactsciences.com (10 pgs).

* cited by examiner

| Population n=1674 | | |
|---|---|---|
| Characteristic | P Value | Coefficient |
| weight BMI>20 | | |
| weight BMI<20 | 0.0020 | -0.0522 |
| Without Diabetes | | |
| Diabetes Type I | <2e-16 | 0.1231 |
| Diabetes Type II | 3.30E-06 | 0.0515 |
| Female | | |
| Male | 0.0003 | 0.0157 |

Faster Aging

Bioage Difference (years)

Slower Aging $Fit^{BMI}$

Underweight          Overweight

| Padlock ID | Sample | Predicted bioage | Chronological Age |
|---|---|---|---|
| S85-rosa55-aging-cap53 | AG15693 CK | 61.9 | 48 |
| S87-rosa57-aging-cap53 | AG15694 CK | 49.92 | 25 |
| S89-rosa59-aging-cap53 | AG15695 CK | 52 | 20 |

Fig. 9

| | UCSC_RefGene_Name | |
|---|---|---|
| 1 | ELOVL2 | cg16867657, cg24724428, cg21572722 |
| 2 | | cg10501210 |
| 3 | FHL2 | cg22454769, cg06639320, cg24079702 |
| 4 | TRIM59 | cg07553761 |
| 7 | OTUD7A | cg04875128, cg01763090 |
| 8 | KLF14 | cg08097417, cg14361627, cg22285878, cg07955995, cg00094518 |
| 10 | CCDC102B | cg19283806 |
| 13 | RASSF5 | cg08128734 |
| 14 | MKLN1 | cg03473532 |
| 15 | EPHX3;EPHX3 | cg14556683 |
| 16 | | cg23500537 |
| 17 | | cg03032497 |
| 18 | SLC6A4 | cg14692377 |
| 19 | ZYG11A | cg06784991, cg06335143, cg24466241 |
| 20 | | cg23744638 |
| 21 | | cg02650266, cg05991454 |
| 22 | PENK | cg16419235 |
| 23 | NHLRC1 | cg22736354 |
| 24 | SST | cg00481951, cg25478614 |
| 25 | ZNF423 | cg04208403 |

Fig. 14A

|  |  |  | Methylation Age |
|---|---|---|---|
| IMR90 | Young | PD 32.56 | -7.89 |
|  | Middle | PD 37.48 | -2.8 |
|  | Old | PD 41.08 | 2.49 |
| WI38 | Young | PD 33.77 | -5.3 |
|  | Middle | PD 47.64 | 5.4 |
|  | old | PD 63.7 | 13.2 |

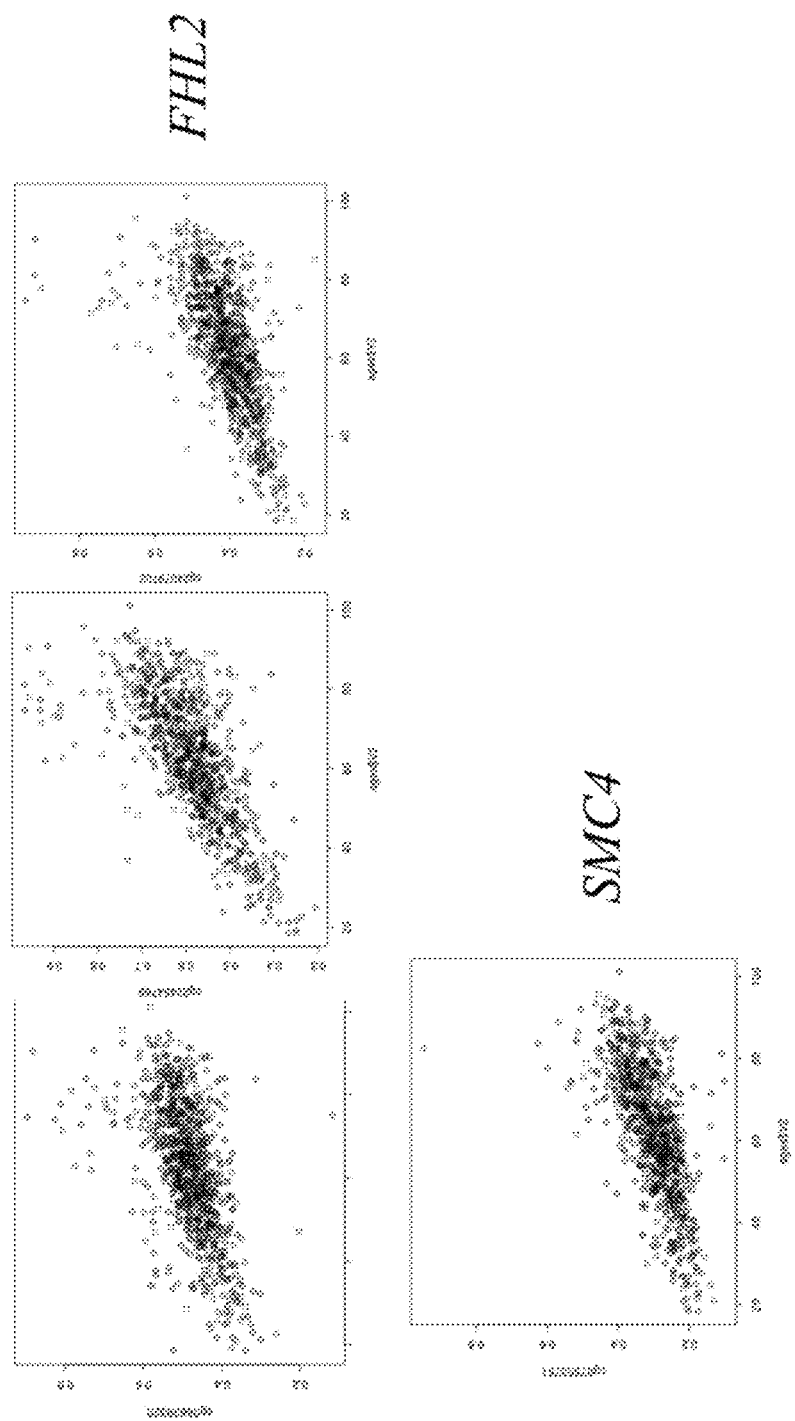

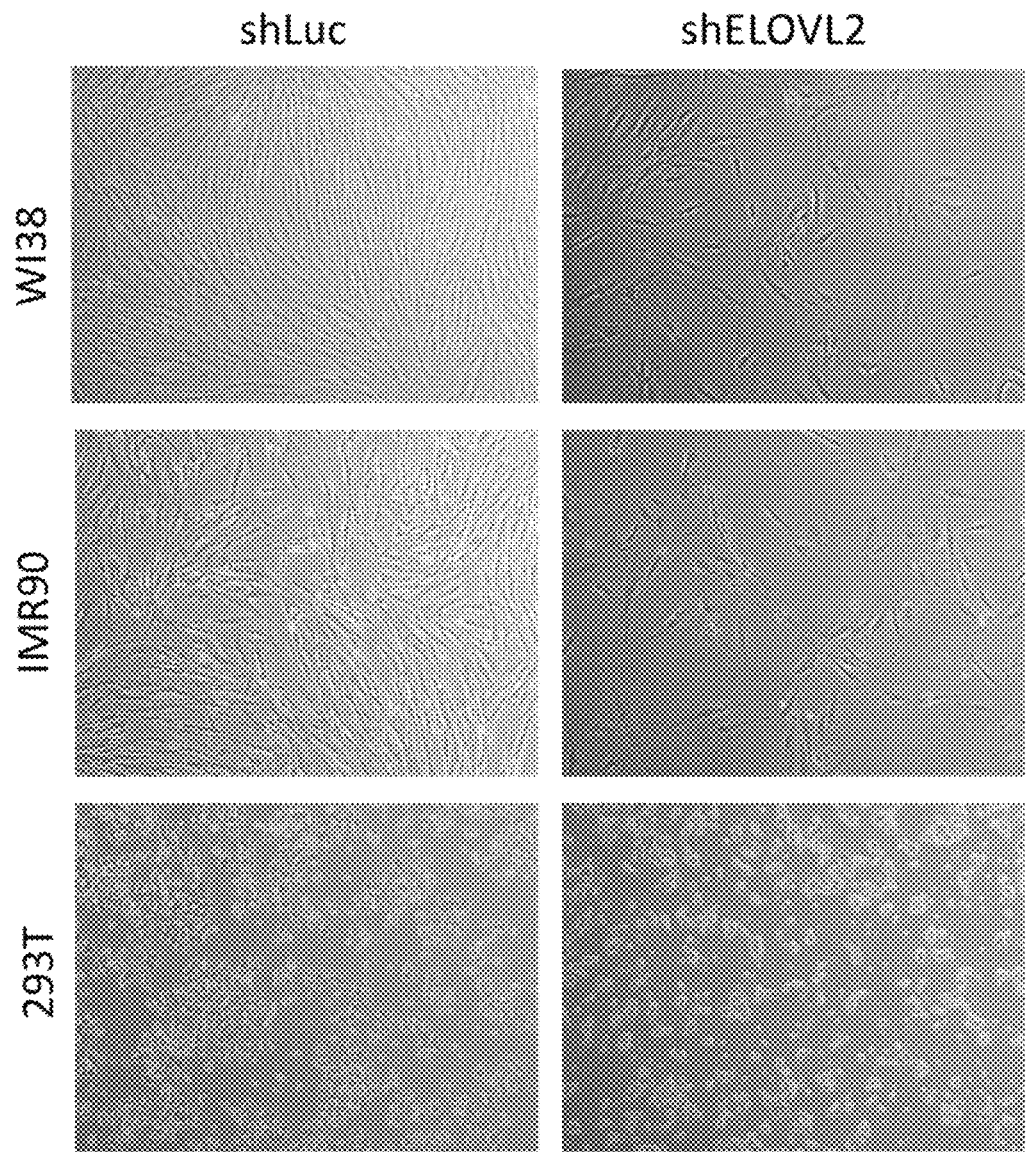

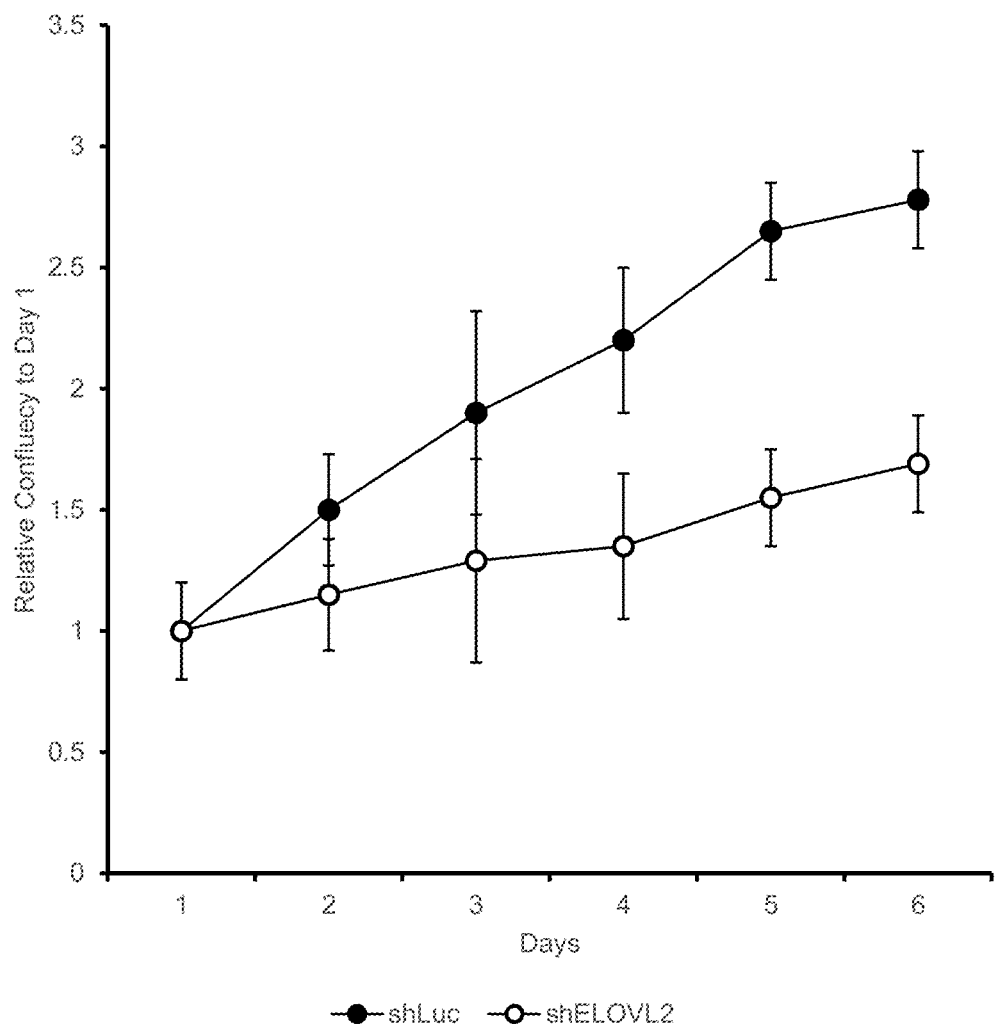

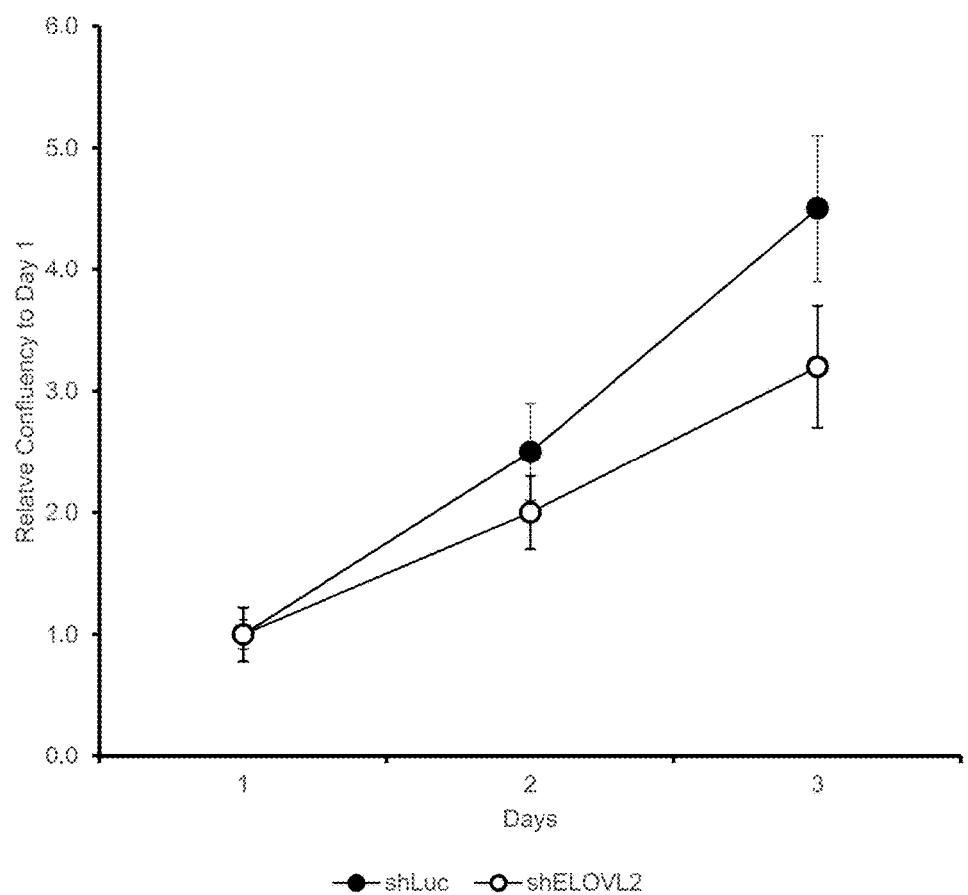

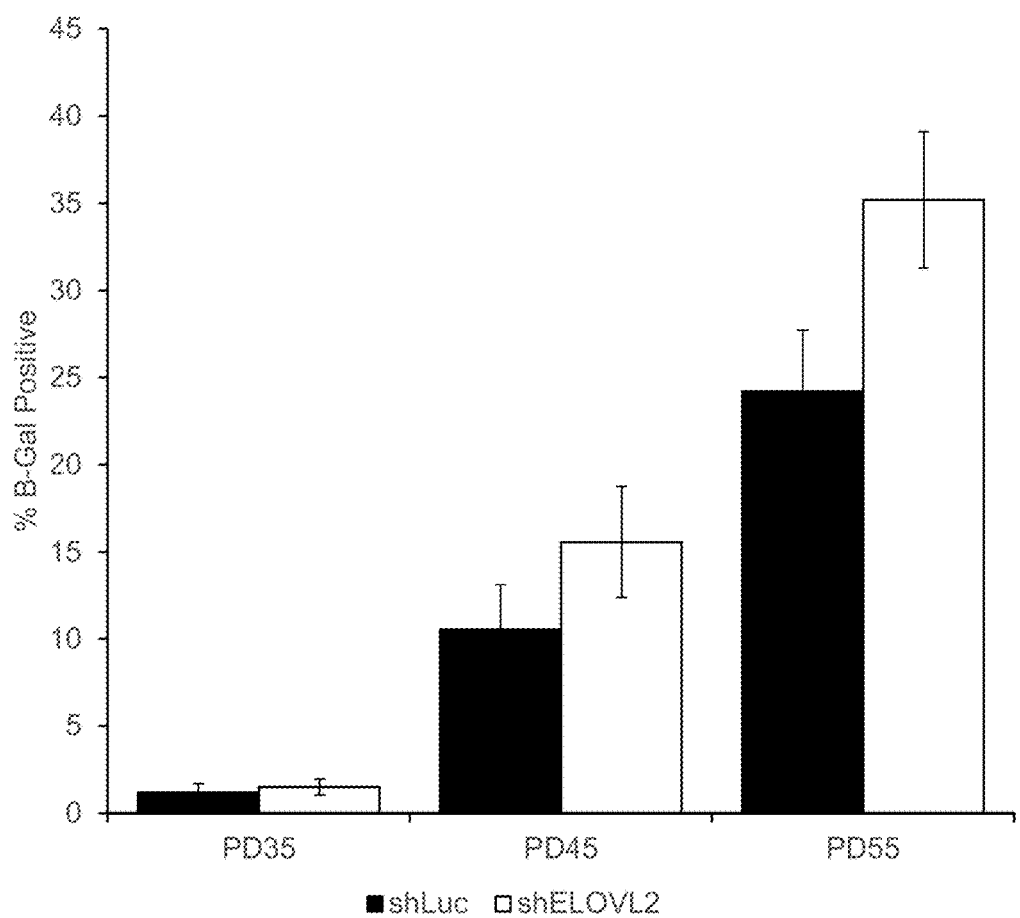

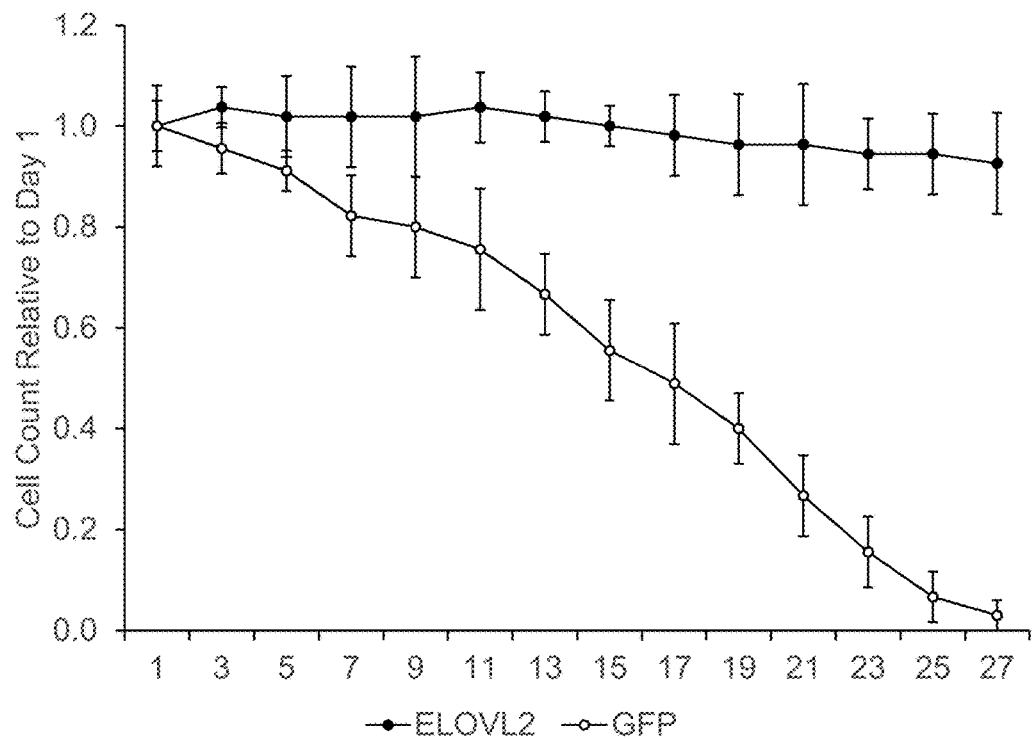

*Effect of KLF14 knockdown on other genes*

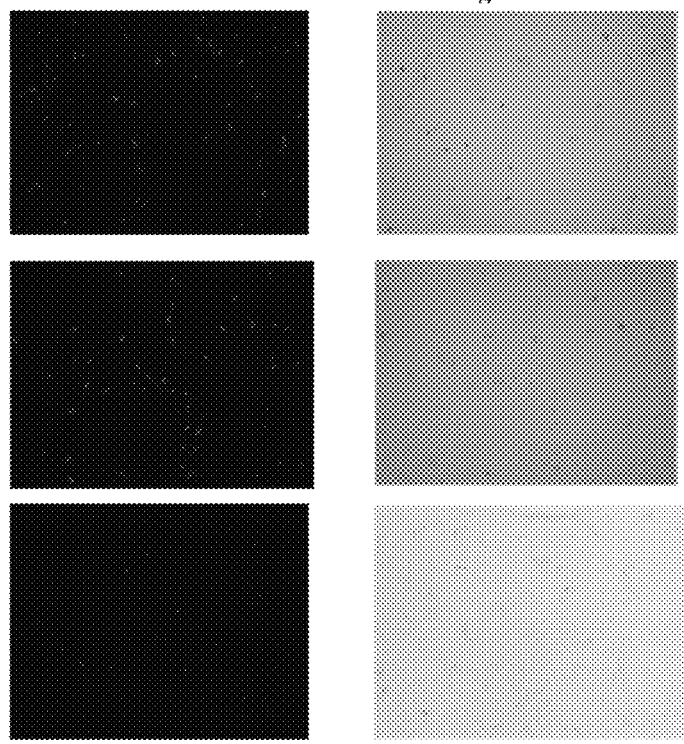

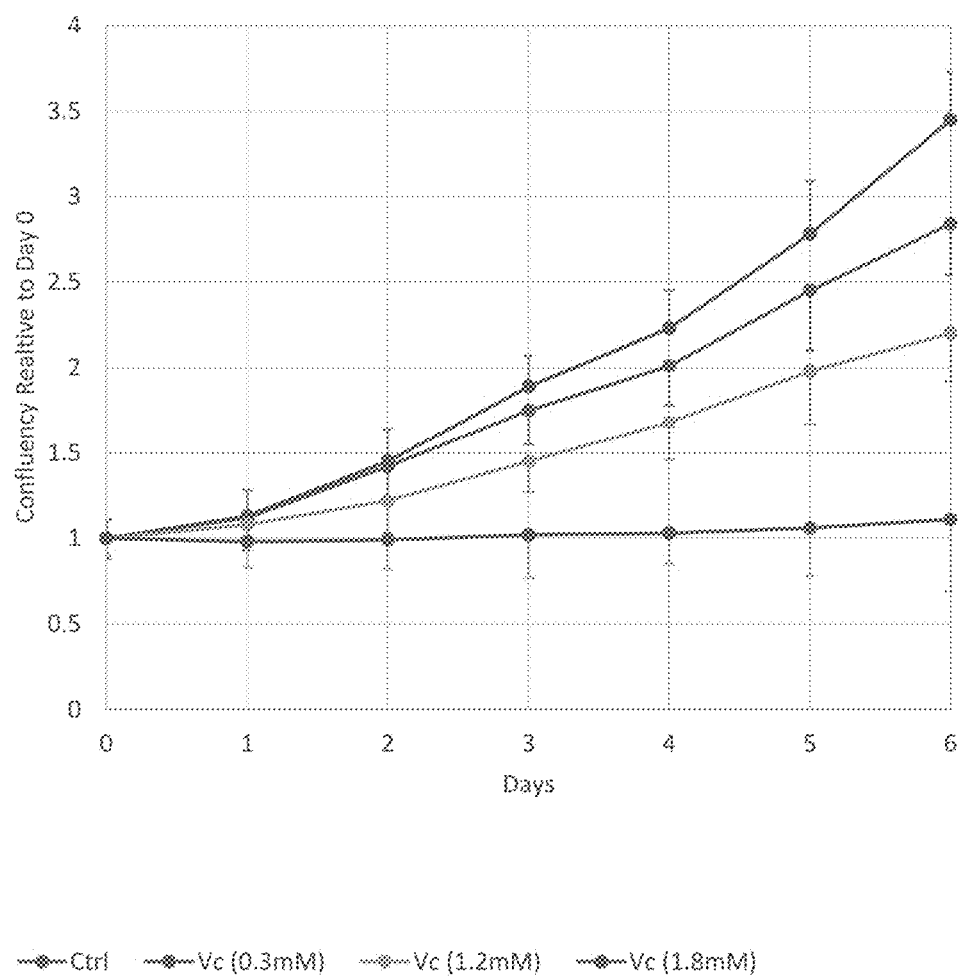

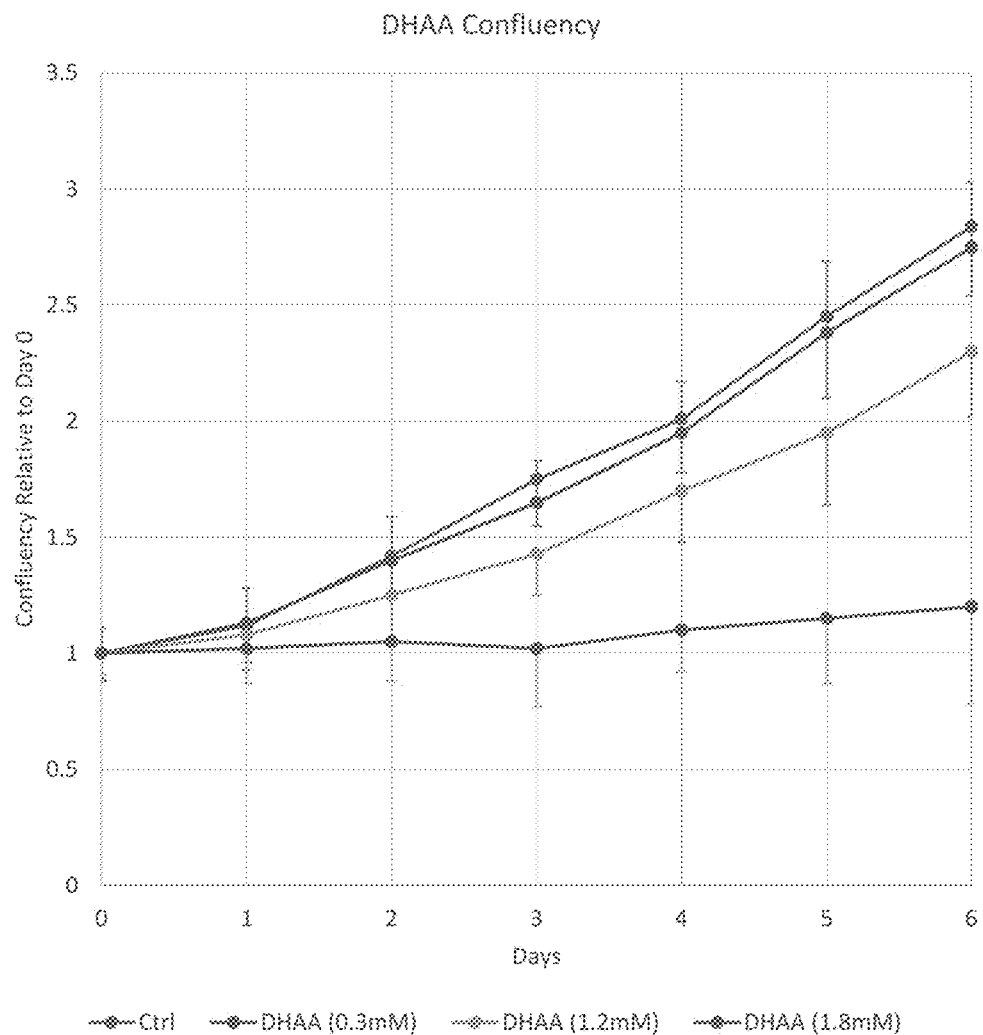

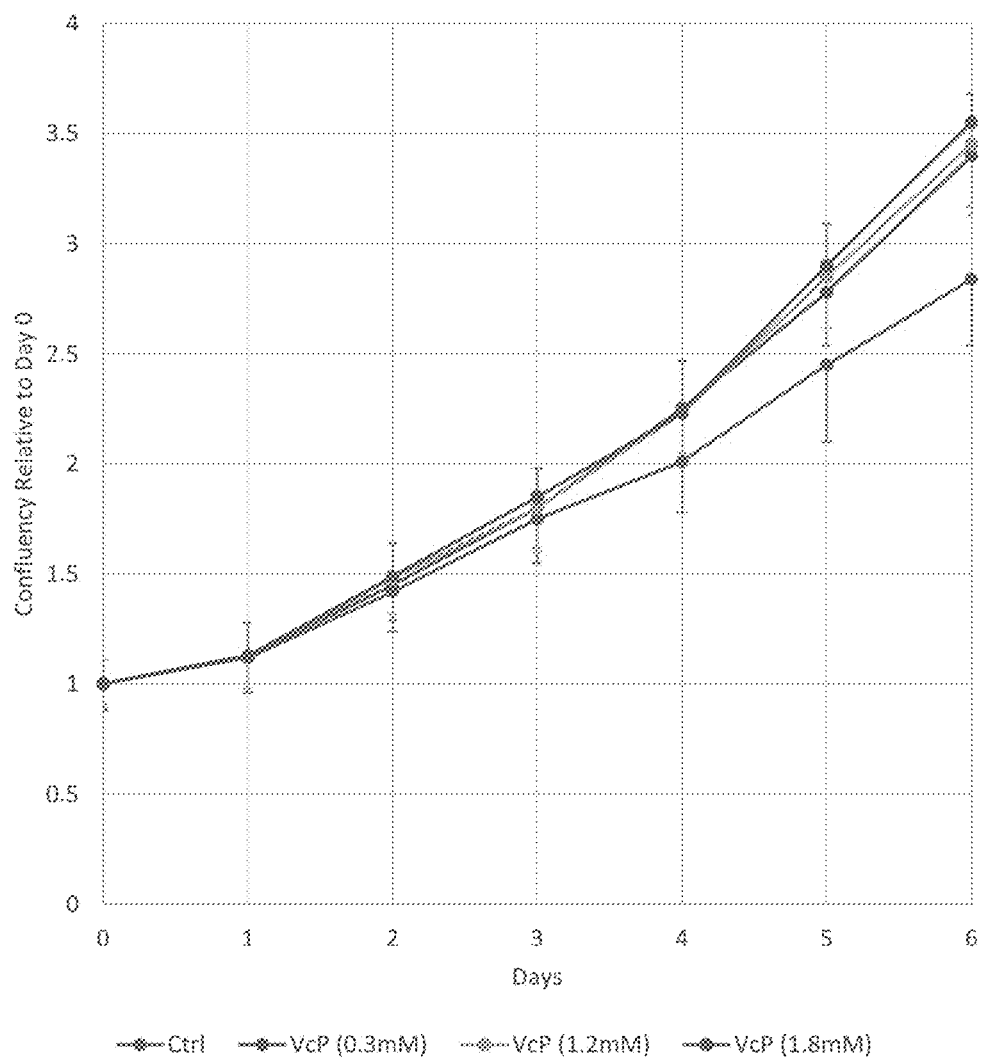

Fig. 28

|  | chromlogical Age | Methy-Age |
|---|---|---|
| Fetal lens | 0 | 13.7 |
| 78Y human conjuctiva epichanial P2 | 78 | 72.1 |
| 5535 c14p12C iPSC | 15 | -2.3 |
| 5535 fibroblast p2 | 15 | 13.3 |
| WT83 c9p28 iPSC | 38 | -1.34 |
| WT83 fibroblast p3 | 38 | 31.88 |
| WT126 c5p27 iPSC | 34 | -2.4 |
| WT126 fibroblast p6 | 34 | 27.4 |

Y- 12 days old
O- 2.3 years old

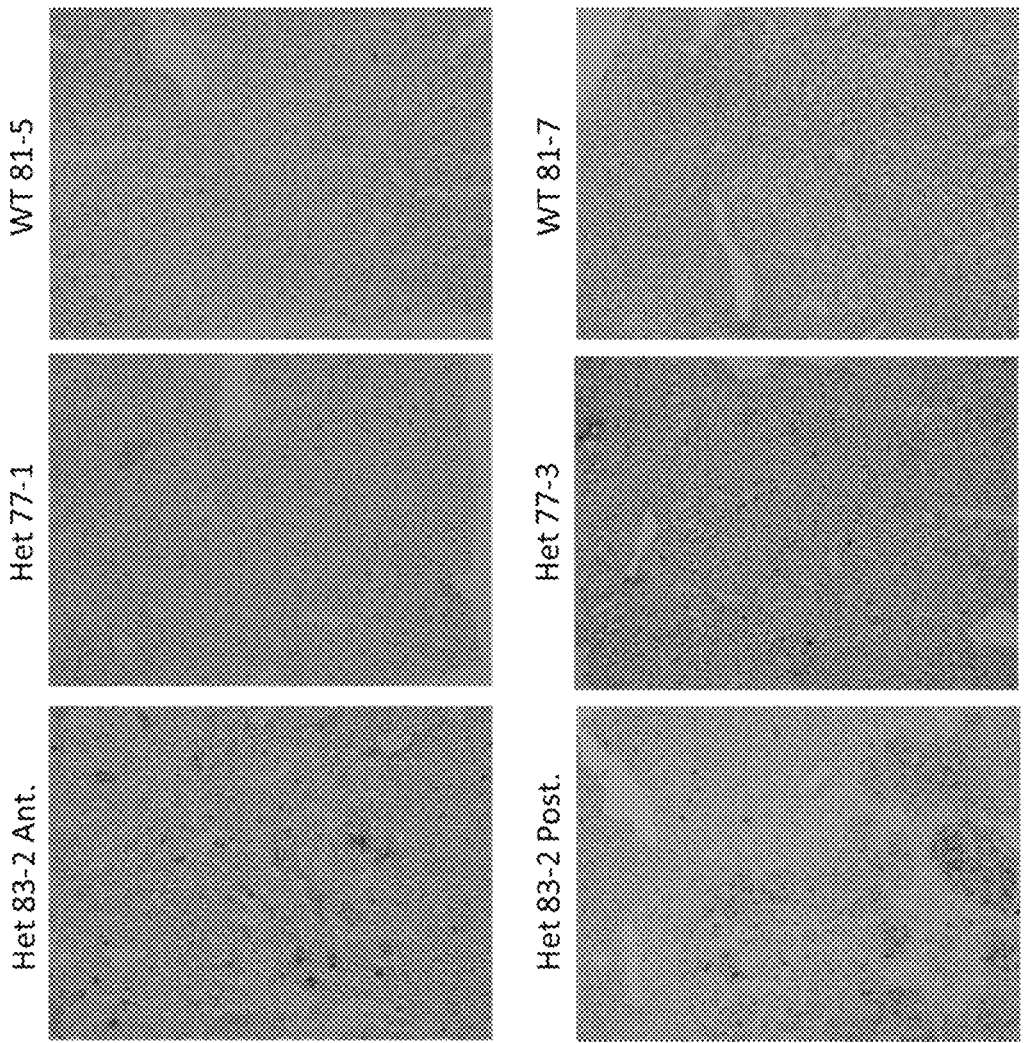

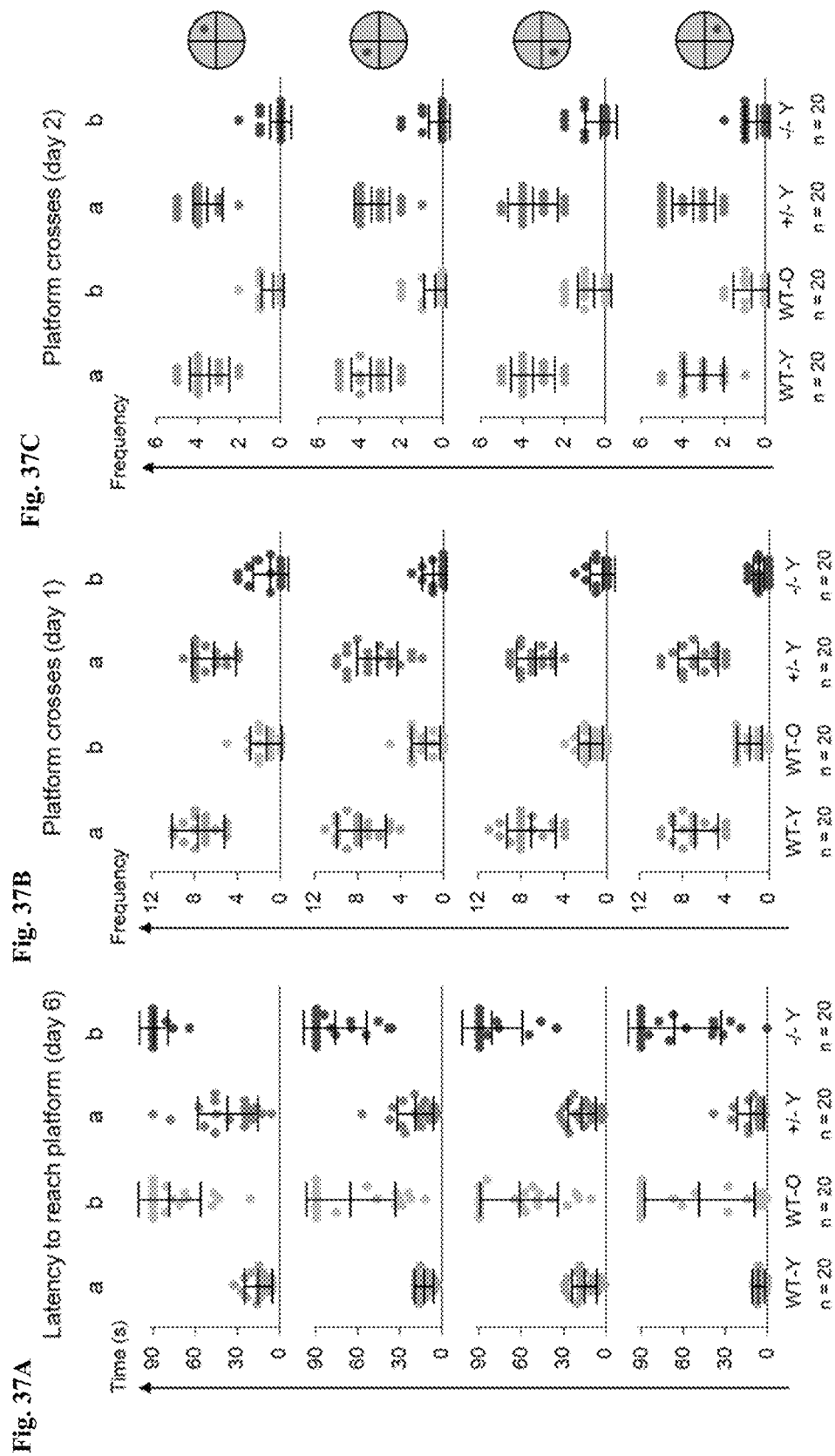

METHODS FOR MONITORING *ELOVL2*, *KLF14* AND *PENK* GENE EXPRESSION FOLLOWING TREATMENT WITH VITAMIN C

CROSS-REFERENCE

This application claims the benefit of U.S. Provisional Application No. 62/343,752, filed on May 31, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 26, 2017, is named 49697-706_601_SL.txt and is 28,975 bytes in size.

BACKGROUND OF THE DISCLOSURE

The rate and progression of aging varies from person to person and are further influenced by environmental factors, lifestyle choices, and/or physical fitness. In some instances, studies have shown that the state of the epigenome (e.g., mutation within the genome and/or methylation) correlate with age. As such, DNA methylation are utilized, for example, for determining age or changes in the rate of aging based on environmental factors, lifestyle choices, and/or physical fitness.

SUMMARY OF THE DISCLOSURE

Provided herein are therapeutic agents capable of increasing the gene expression of an epigenetic marker described herein. Also provided herein are therapeutic agents capable of decreasing the methylation level/status of an epigenetic marker described herein.

In some embodiments, disclosed herein is a method of increasing the expression rate of genes: ELOVL2, KLF14, PENK, or a combination thereof in a first subject, comprising: (a) administering to the first subject a therapeutically effective dose of a therapeutic agent for a first time period; (b) obtaining a sample from the first subject; and (c) determining whether the expression level of ELOVL2, KLF14, PENK, or a combination thereof has increased in the first subject relative to a control by contacting the sample with a probe that recognizes ELOVL2, KLF14, or PENK and detecting binding between ELOVL2, KLF14, or PENK and the probe.

In some embodiments, the therapeutic agent comprises vitamin C or its derivatives, analogs, metabolites, prodrugs, or pharmaceutically acceptable salts thereof. In some embodiments, the therapeutic agent comprises vitamin C or its derivatives or pharmaceutically acceptable salts thereof. In some embodiments, the therapeutic agent is vitamin C. In some embodiments, the therapeutic agent is L-ascorbic acid 2-phosphate.

In some embodiments, the expression level of ELOVL2 gene is determined by contacting the sample with a probe that recognizes ELOVL2 and detecting binding between the probe and ELOVL2. In some embodiments, the expression level of KLF14 gene is determined by contacting the sample with a probe that recognizes KLF14 and detecting binding between the probe and KLF14. In some embodiments, the expression levels of ELOVL2 and KLF14 are determined by contacting the sample with a probe that recognizes ELOVL2 and a probe that recognizes KLF14 and detecting each respective binding between the probes and ELOVL2 and KLF14. In some embodiments, the expression levels of ELOVL2, KLF14, and PENK are determined.

In some embodiments, an increase in the expression rate of genes: ELOVL2, KLF14, PENK, or a combination thereof further correlates to a decrease in cell senescence.

In some embodiments, an increase in the expression rate of genes: ELOVL2, KLF14, PENK, or a combination thereof further correlates to an increase in cell proliferation.

In some embodiments, an increase in the expression rate of genes: ELOVL2, KLF14, PENK, or a combination thereof further correlates to an increase in cell survival.

In some embodiments, an increase in the expression rate of genes: ELOVL2, KLF14, PENK, or a combination thereof further correlates to a decrease in DNA methylation.

In some embodiments, an increase in the expression rate of genes: ELOVL2, KLF14, PENK, or a combination thereof leads to a methylation pattern that mimics the methylation pattern of a sample obtained from a second subject. In some embodiments, the second subject is younger in chronological age relative to the first subject. In some embodiments, the second subject is younger in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

In some embodiments, the control comprises the expression level of genes: ELOVL2, KLF14, PENK, or a combination thereof obtained from a sample from the subject prior to administration of the therapeutic agent. In some embodiments, the control comprises a normalized expression level of ELOVL2, KLF14, PENK, or a combination thereof obtained from a set of samples without exposure to the therapeutic agent. In some embodiments, the set of samples are a set of cell samples.

In some embodiments, the method further comprises increasing the dose of the therapeutic agent if the expression level of genes: ELOVL2, KLF14, PENK, or a combination thereof has not increased relative to the control. In some embodiments, the method further comprises increasing the dose of the therapeutic agent if the expression level of ELOVL2, KLF14, PENK, or a combination thereof has increased relative to the control and at a rate that is below a target range.

In some embodiments, the method further comprises decreasing or maintaining the dose of the therapeutic agent if the expression level of genes: ELOVL2, KLF14, PENK, or a combination thereof has increased relative to the control. In some embodiments, the method further comprises maintaining the dose of the therapeutic agent if the expression level of ELOVL2, KLF14, PENK, or a combination thereof has increased relative to the control and at a rate that is within a target range. In some embodiments, the method further comprises decreasing the dose of the therapeutic agent if the expression level of ELOVL2, KLF14, PENK, or a combination thereof has increased relative to the control and at a rate that is above a target range.

In some embodiments, the dose of the therapeutic agent is increased, decreased, or maintained for a second period of time prior to redetermining the expression level of genes: ELOVL2, KLF14, PENK, or a combination thereof.

In some embodiments, the first period of time comprises at least one day, two days, three days, four days, five days, one week, two weeks, three weeks, four weeks, one month, two months, three months, four months, five months, six months, 1 year, two years, three years, or more.

In some embodiments, the second period of time comprises at least one day, two days, three days, four days, five days, one week, two weeks, three weeks, four weeks, one month, two months, three months, four months, five months, six months, 1 year, two years, three years, or more.

In some embodiments, the method further comprises determining the expression level of FHL2, SMC4, SLC12A5, TEZM151A, TTF2, TRIM45, TRIM59, ACSS3, ARID5A, BLMH, BRD4, CD28, EPHX3, RIN1, SLX1, BDNF, NDF, GDNF, cortisol, or a combination thereof. In some embodiments, the method further comprises determining the expression level of FHL2, SMC4, SLC12A5, TEZM151A, TTF2, TRIM45, TRIM59, ACSS3, ARID5A, BLMH, BRD4, CD28, EPHX3, SLX1, or a combination thereof. In some embodiments, the method further comprises determining the expression level of an epigenetic marker selected from Table 1.

In some embodiments, provided herein is a method of modulating the methylation pattern of ELOVL2, KLF14, PENK, or a combination thereof in a first subject, comprising: (a) administering to the first subject a therapeutically effective dose of a therapeutic agent for a first time period; (b) obtaining a sample from the first subject; and (c) determining whether the methylation pattern of ELOVL2, KLF14, PENK, or a combination thereof has changed in the first subject relative to a control by contacting the sample with a set of probes and detecting a set of hybridization products to determine the methylation pattern of ELOVL2, KLF14, PENK, or a combination thereof.

In some embodiments, the therapeutic agent comprises vitamin C or its derivatives, analogs, metabolites, prodrugs, or pharmaceutically acceptable salts thereof. In some embodiments, the therapeutic agent comprises vitamin C or its derivatives or pharmaceutically acceptable salts thereof. In some embodiments, the therapeutic agent is vitamin C. In some embodiments, the therapeutic agent is L-ascorbic acid 2-phosphate.

In some embodiments, the sample is further treated with a deaminating agent prior to determining the methylation pattern.

In some embodiments, the methylation pattern of ELOVL2 is determined. In some embodiments, the methylation pattern of KLF14 is determined. In some embodiments, the methylation pattern of PENK is determined. In some embodiments, the methylation patterns of ELOVL2 and KLF14 are determined. In some embodiments, the methylation patterns of ELOVL2, KLF14, and PENK are determined.

In some embodiments, a change in the methylation pattern of ELOVL2, KLF14, PENK, or a combination thereof is a decrease in methylation status of ELOVL2, KLF14, PENK, or a combination thereof.

In some embodiments, a decrease in the methylation status of ELOVL2, KLF14, PENK, or a combination thereof further correlates to a decrease in cell senescence.

In some embodiments, a decrease in the methylation status of ELOVL2, KLF14, PENK, or a combination thereof further correlates to an increase in cell proliferation.

In some embodiments, a decrease in the methylation status of ELOVL2, KLF14, PENK, or a combination thereof further correlates to an increase in cell survival.

In some embodiments, a decrease in the methylation status of ELOVL2, KLF14, PENK, or a combination thereof leads to a methylation pattern that mimics the methylation pattern of a sample obtained from a second subject. In some embodiments, the second subject is younger in chronological age relative to the first subject. In some embodiments, the second subject is younger in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

In some embodiments, the control comprises the methylation pattern of ELOVL2, KLF14, PENK, or a combination thereof obtained from a sample from the subject prior to administration of the therapeutic agent.

In some embodiments, the control comprises a normalized methylation pattern of ELOVL2, KLF14, PENK, or a combination thereof obtained from a set of samples without exposure to the therapeutic agent. In some embodiments, the set of samples are a set of cell samples.

In some embodiments, the method further comprises increasing the dose of the therapeutic agent if the methylation pattern of ELOVL2, KLF14, PENK, or a combination thereof has not changed relative to the control. In some embodiments, the method further comprises increasing the dose of the therapeutic agent if the methylation pattern of ELOVL2, KLF14, PENK, or a combination thereof has changed relative to the control and to a degree lower than a target range.

In some embodiments, the method further comprises decreasing or maintaining the dose of the therapeutic agent if the methylation pattern of ELOVL2, KLF14, PENK, or a combination thereof has changed relative to the control. In some embodiments, the method further comprises maintaining the dose of the therapeutic agent if the methylation pattern of ELOVL2, KLF14, PENK, or a combination thereof has changed relative to the control and to a degree within a target range. In some embodiments, the method further comprises decreasing the dose of the therapeutic agent if the methylation pattern of ELOVL2, KLF14, PENK, or a combination thereof has changed relative to the control and to a degree above a target range.

In some embodiments, the dose of the therapeutic agent is increased, decreased, or maintained for a second period of time prior to redetermining the methylation pattern of ELOVL2, KLF14, PENK, or a combination thereof.

In some embodiments, the first period of time comprises at least one day, two days, three days, four days, five days, one week, two weeks, three weeks, four weeks, one month, two months, three months, four months, five months, six months, 1 year, two years, three years, or more.

In some embodiments, the second period of time comprises at least one day, two days, three days, four days, five days, one week, two weeks, three weeks, four weeks, one month, two months, three months, four months, five months, six months, 1 year, two years, three years, or more.

In some embodiments, the method further comprises determining the expression level of FHL2, SMC4, SLC12A5, TEZM151A, TTF2, TRIM45, TRIM59, ACSS3, ARID5A, BLMH, BRD4, CD28, EPHX3, RIN1, SLX1, BDNF, NDF, GDNF, cortisol, or a combination thereof. In some embodiments, the method further comprises determining the methylation pattern of FHL2, SMC4, SLC12A5, TEZM151A, TTF2, TRIM45, TRIM59, ACSS3, ARID5A, BLMH, BRD4, CD28, EPHX3, SLX1, or a combination thereof. In some embodiments, the method further comprises determining the methylation pattern of an epigenetic marker selected from Table 1.

In some embodiments, the therapeutically effective dose of vitamin C or its derivatives, analogs, metabolites, prodrugs, or pharmaceutically acceptable salts thereof comprises from about 0.1 µg/mL to about 200 µg/mL. In some embodiments, the therapeutically effective dose of vitamin C or its derivatives, analogs, metabolites, prodrugs, or pharmaceutically acceptable salts thereof comprises from about 1 µg/mL to about 150 µg/mL. In some embodiments, the therapeutically effective dose of vitamin C or its derivatives, analogs, metabolites, prodrugs, or pharmaceutically acceptable salts thereof comprises from about 5 µg/mL to about 100 µg/mL. In some embodiments, the therapeutically effective dose of vitamin C or its derivatives, analogs, metabolites, prodrugs, or pharmaceutically acceptable salts thereof comprises from about 10 µg/mL to about 100 µg/mL. In some embodiments, the therapeutically effective dose of vitamin C or its derivatives, analogs, metabolites, prodrugs, or pharmaceutically acceptable salts thereof comprises from about 20 µg/mL to about 100 µg/mL. In some embodiments, the therapeutically effective dose of vitamin C or its derivatives, analogs, metabolites, prodrugs, or pharmaceutically acceptable salts thereof comprises from about 30 µg/mL to about 100 µg/mL. In some embodiments, the therapeutically effective dose of vitamin C or its derivatives, analogs, metabolites, prodrugs, or pharmaceutically acceptable salts thereof comprises from about 50 µg/mL to about 100 µg/mL. In some embodiments, the therapeutically effective dose of vitamin C or its derivatives, analogs, metabolites, prodrugs, or pharmaceutically acceptable salts thereof comprises from about 1 µg/mL to about 50 µg/mL. In some embodiments, the therapeutically effective dose of vitamin C or its derivatives, analogs, metabolites, prodrugs, or pharmaceutically acceptable salts thereof comprises from about 5 µg/mL to about 50 µg/mL. In some embodiments, the therapeutically effective dose of vitamin C or its derivatives, analogs, metabolites, prodrugs, or pharmaceutically acceptable salts thereof comprises from about 10 µg/mL to about 50 µg/mL. In some embodiments, the therapeutically effective dose of vitamin C or its derivatives, analogs, metabolites, prodrugs, or pharmaceutically acceptable salts thereof comprises from about 50 µg/mL to about 200 µg/mL.

In some embodiments, a dose of vitamin C or its derivatives, analogs, metabolites, prodrugs, or pharmaceutically acceptable salts thereof greater than 200 µg/mL increases reactive oxidative species. In some embodiments, a dose of vitamin C or its derivatives, analogs, metabolites, prodrugs, or pharmaceutically acceptable salts thereof greater than 200 µg/mL leads to a methylation pattern that mimics the methylation pattern of a sample obtained from a third subject who is older in chronological age relative to the first subject.

In some embodiments, the third subject is older in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

In some embodiments, the method further comprises administering to the first subject an additional therapeutic agent.

In some embodiments, the sample is a cell sample. In some embodiments, the sample is a blood sample. In some embodiments, the sample is a tissue sample.

In some embodiments, the sample is obtained from a subject having a metabolic disease or condition. In some embodiments, the metabolic disease or condition comprises diabetes or pre-diabetes. In some embodiments, diabetes is type I diabetes. In some embodiments, diabetes is type II diabetes. In some embodiments, diabetes is type IV diabetes.

In some embodiments, the sample is obtained from a subject having a ELOVL2-associated disease or indication. In some embodiments, the sample is obtained from a subject having a KLF14-associated disease or indication. In some embodiments, the sample is obtained from a subject having a PENK-associated disease or indication.

In some embodiments, the sample is obtained from a subject having Werner syndrome.

In some embodiments, the sample is obtained from a subject having progeria.

In some embodiments, the sample is obtained from a subject having post-traumatic stress disorder.

In some embodiments, the sample is obtained from a subject having an elevated body mass index (BMI). In some embodiments, the elevated BMI is a BMI of 25 kg/m$^2$, 26 kg/m$^2$, 27 kg/m$^2$, 28 kg/m$^2$, 29 kg/m$^2$, 30 kg/m$^2$, 35 kg/m$^2$, 40 kg/m$^2$ or more.

BRIEF DESCRIPTION OF THE DRAWINGS

Various aspects of the disclosure are set forth with particularity in the appended claims. The patent application file contains at least one drawing executed in color. Copies of this patent application with color drawing(s) will be provided by the Office upon request and payment of the necessary fee.

A better understanding of the features and advantages of the present disclosure will be obtained by reference to the following detailed description that sets forth illustrative embodiments, in which the principles of the disclosure are utilized, and the accompanying drawings of which:

FIG. 1A shows cell images of 12-well plate treated with low concentration vitamin C at Day 0, 4 and 5 for PD46. FIG. 1B shows confluency plot calculated through ImageJ of PD46, n=2. FIG. 1C and FIG. 1D illustrate expression graphs for ARM and SLC2A1 for PD46, n=3. FIG. 1E shows cell images of 12-well treated with high concentration vitamin C at Day 0, 4 and 5 for PD48. FIG. 1F shows confluency plot calculated through ImageJ of PD48, n=2. FIG. 1G and FIG. 1H show expression graphs for ARM and SLC2A1 for PD48, n=3.

FIG. 2A shows cell images of 12-well at Day 0, 1 and 2 of treatment for PD42. FIG. 2B shows confluency plot calculated through ImageJ of PD42, n=2. FIG. 2C and FIG. 2D show expression graphs for ARM and SLC2A1 for PD42, n=3. FIG. 2E shows cell images of 12-well at Day 0, 5 and 7 of treatment for PD58. FIG. 2F shows confluency plot calculated through ImageJ of PD58, n=2. FIG. 2G and FIG. 2H illustrate expression graphs for ARM and SLC2A1 for PD53, n=3. FIG. 2I shows cell images of senescence and DAPI staining of PD45.5 fibroblasts. FIG. 2J shows graph of percentage senescence for younger PD32 fibroblast and older PD45.5 fibroblast. n=3.

FIG. 3A shows cell images of 12-well at Day 0 and Day 8 of treatment for PD55. FIG. 3B shows confluency plot calculated through ImageJ for PD55, n=2. FIG. 3C and FIG. 3D illustrate expression graph for ARM and SLC2A1 for PD55, n=3.

FIG. 4A shows diagram of postulated pathway for interconversion of DHAA to vitamin C and their effect on fibroblast cells. FIG. 4B shows cell images of 12-well at Day 10 of treatment for PD54. FIG. 4C shows confluency plot calculated through ImageJ of PD54, n=2. FIG. 4D and FIG. 4E illustrate expression graphs for ARM and SLC2A1 for PD54 or PD55, respectively, n=3. FIG. 4F shows graph of percentage senescence of PD45 fibroblast. n=3. FIG. 4G shows fluorescent ROS assay showing fluorescent ROS relative to total fibroblasts in PD48 fibroblasts.

FIG. 6A illustrates the correlation of BMI with biological age. FIG. 6B illustrates the correlation of biological aging between male and female.

FIG. 9 illustrates an exemplary list of genes and CpG sites that are utilized for biological age prediction.

FIG. 14A-FIG. 14C shows the biological age (or methylation age) increases with age. FIG. 14A shows the biological age increases with cell line population doubling. FIG. 14B shows the increase in methylation level of ELOVL2, PENK, and KLF14. FIG. 14C shows the increase in methylation level of FHL2 and SMC4.

FIG. 18A-FIG. 18D show that ELOVL2 knockdown reduces cell proliferation. FIG. 18A shows a decrease of cells in ELOVL2 knockdown relative to the control (shLuc) in all three cell lines, WI38, IMR90, and 293T. FIG. 18B-FIG. 18D show the PD45 confluency of ELOVL2 knockdown relative to the control (shLuc) in the respective cell lines; WI38 (FIG. 18B), IMR90 (FIG. 18C), and 293T (FIG. 18D).

FIG. 19A-FIG. 19C show ELOVL2 knockdown increases senescence in cell lines: WI38 (FIG. 19A), IMR90 (FIG. 19B) and 293T (FIG. 19C).

FIG. 20 shows ELOVL2 overexpression increases survival in old cells (PD56).

FIG. 24 shows a senescence assay of the knockdown cells.

FIG. 25A-FIG. 25C show WI38 PD55 confluency in the presence of different concentrations of vitamin C (FIG. 25A), L-dehydro ascorbic acid (DHAA or DHA) (FIG. 25B), or L-ascorbic acid 2-phosphate (VcP) (FIG. 25C).

FIG. 28 shows reversal of biological age by reprogramming of aged fibroblast into iPSCs.

FIG. 33A-FIG. 33B illustrate liver cell senescence in a 2-year old ELOVL2 heterozygous knockout mouse. FIG. 33A illustrates β-galactosidase staining of mouse liver cells Het 83-2, Het 77-1, and WT 81-5. Of the three types of cells tested, Het 83-2 exhibits the highest β-galactosidase activity (FIG. 33B).

FIG. 37A-FIG. 37C show senescence and Elovl2 deletion affecting the spatial memory of mice in a Morris water maze. FIG. 37A shows the spatial memory performance of old wild type, young wild type, young Elovl2$^{+/-}$, and young Elovl2$^{-/-}$ mice. FIG. 37B and FIG. 37C show the frequency of platform crossing.

FIG. 38A shows the relative level in the hippocampus of the mice. FIG. 38B shows the relative level in the cortex of the mice.

DETAILED DESCRIPTION OF THE DISCLOSURE

Figure 1A:
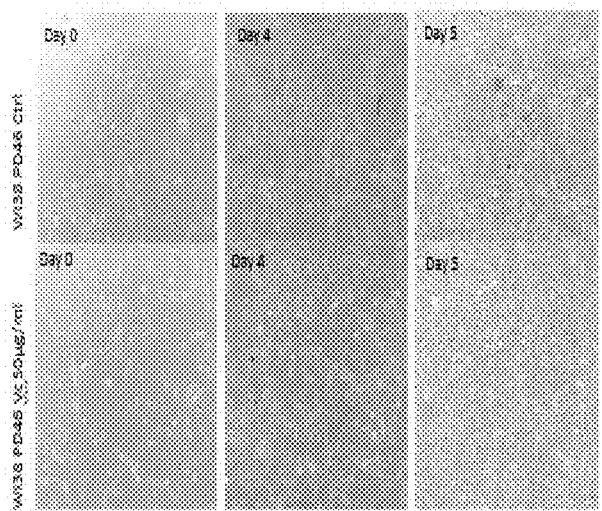
FIG. 1A-FIG. 1H illustrate phenotypic and genotypic effects of concentration dependent vitamin C treatment were analyzed on WI38 PD46 and 48 fibroblast cells.
Figure 1B:
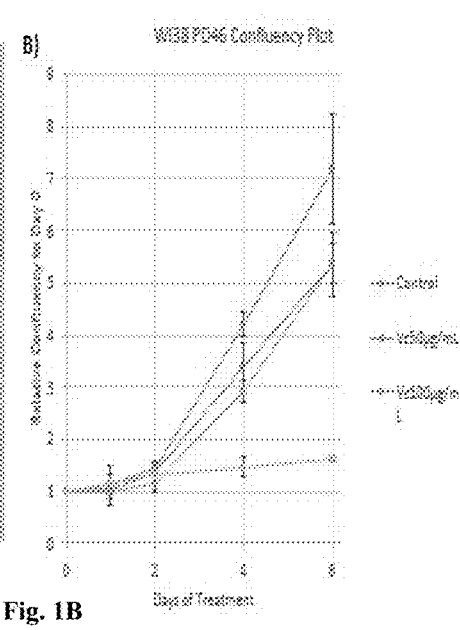
Figure 1C:
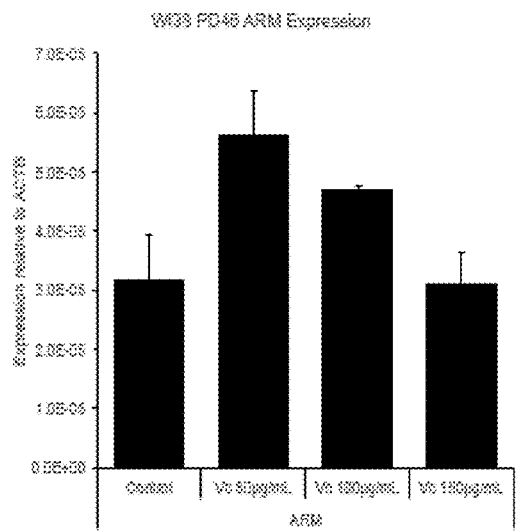
Figure 1D:
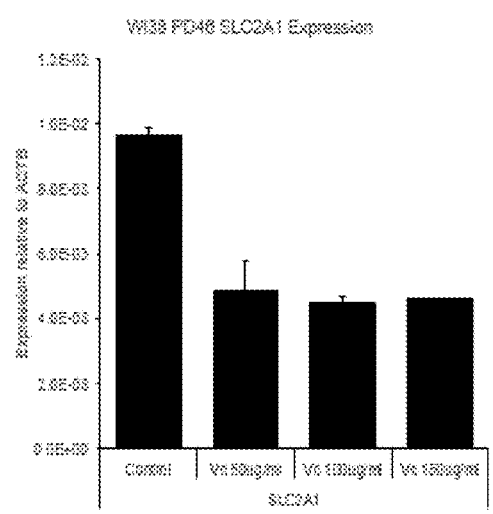
Figure 1E:
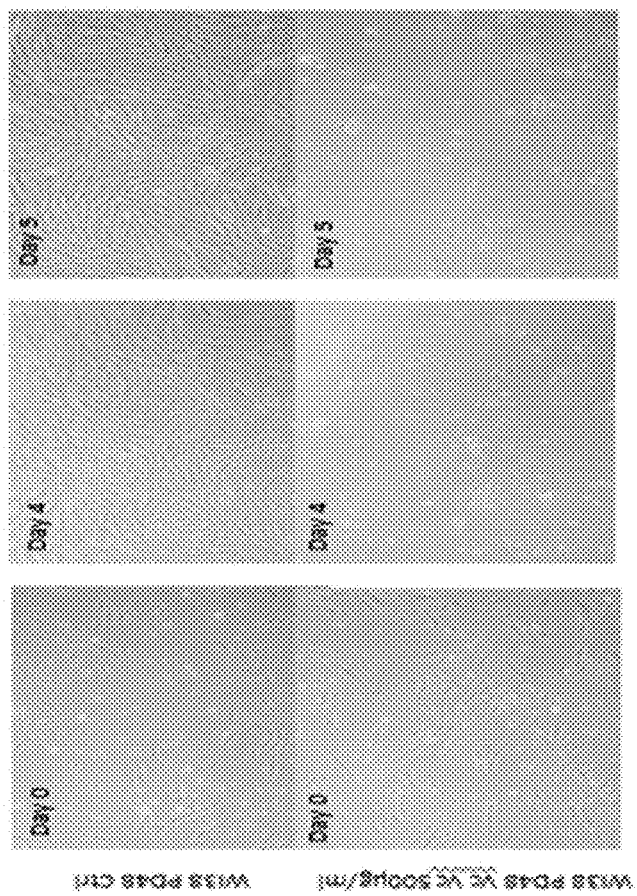
Figure 1F:
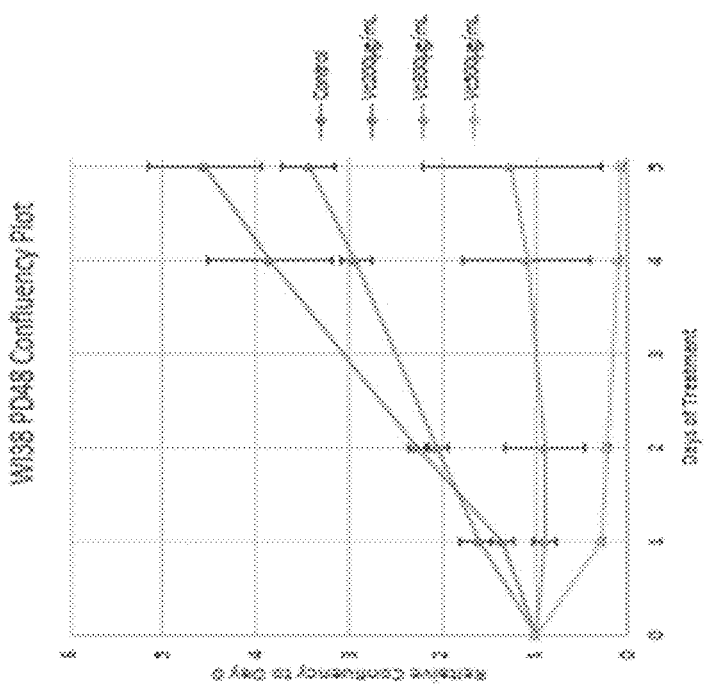
Figure 1G:
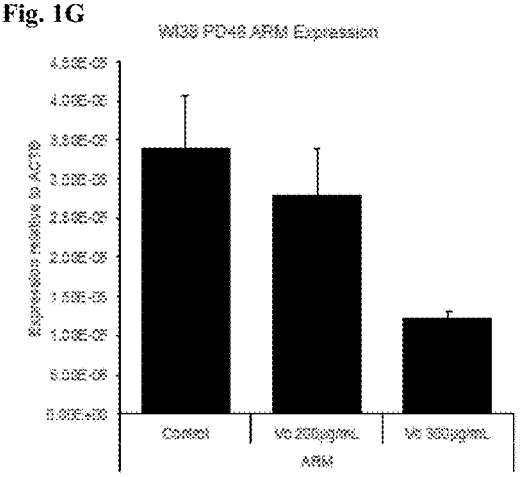
Figure 1H:
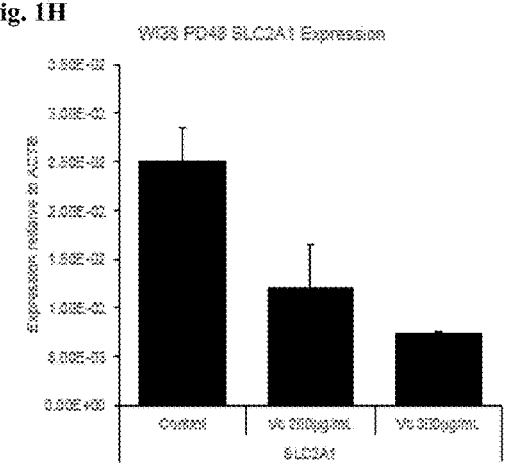
Figure 2A:
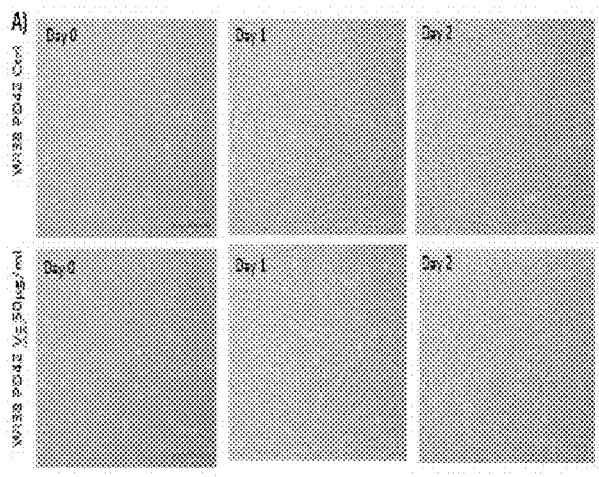
FIG. 2A-FIG. 2J illustrate phenotypic and genotypic effects of vitamin C treatment were analyzed on younger WI38 PD42 and older WI38 PD58 fibroblasts.
Figure 2B:
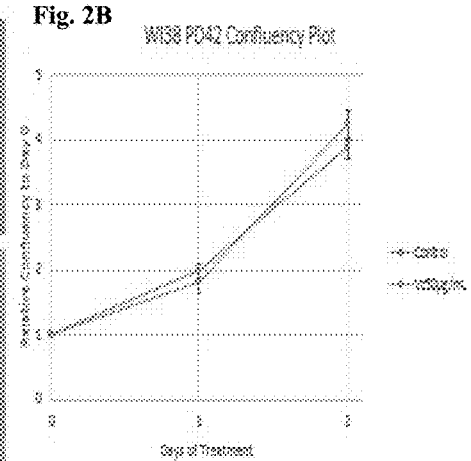
Figure 2C:
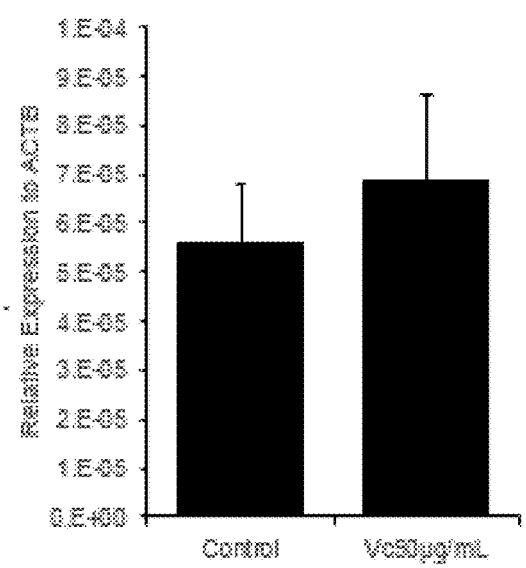
Figure 2D:
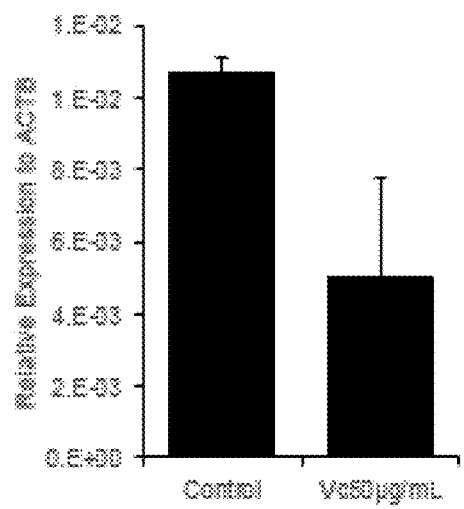
Figure 2E:
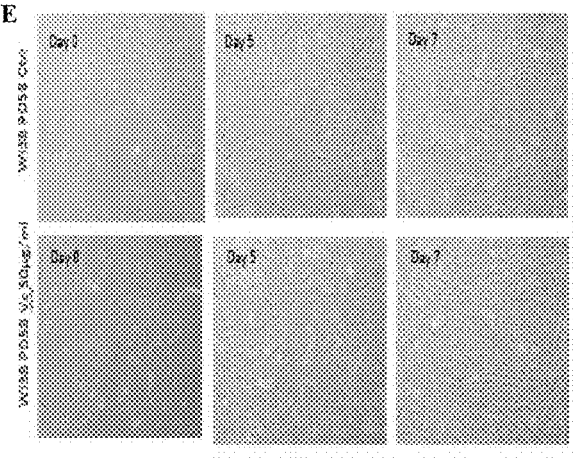
Figure 2F:
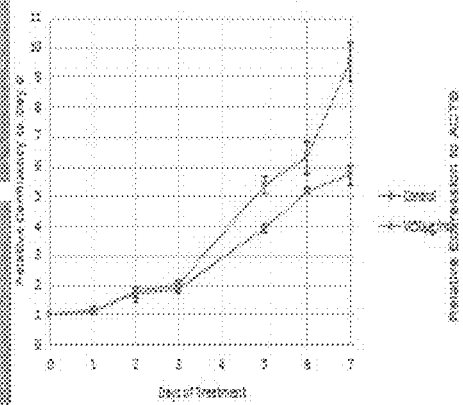
Figure 2G:
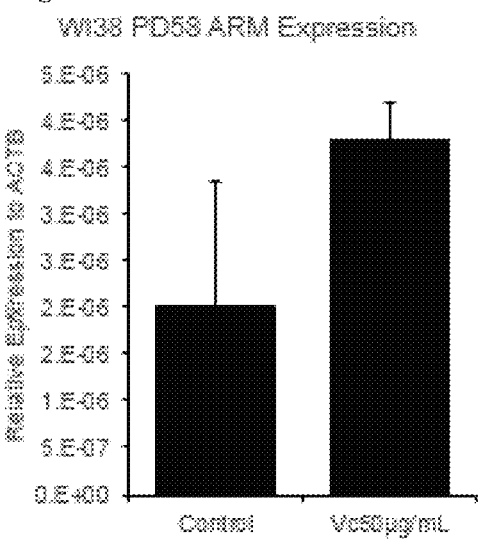
Figure 2H:
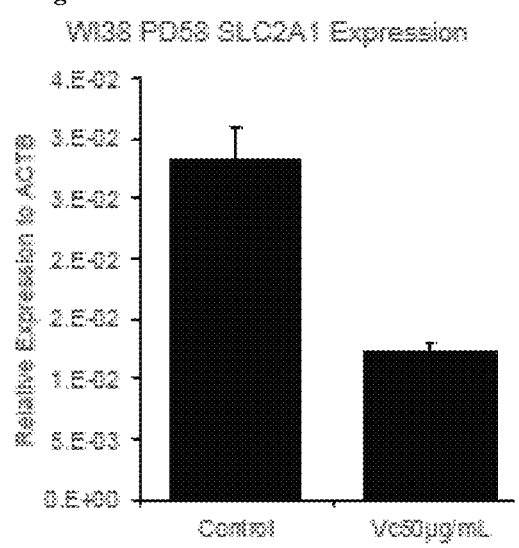
Figure 2I:
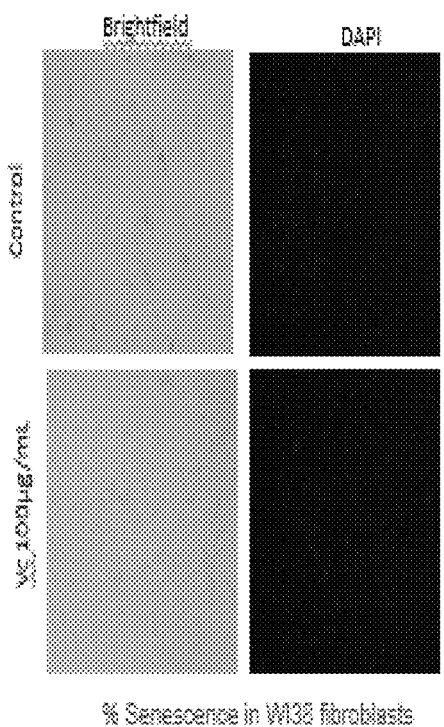
Figure 2J:
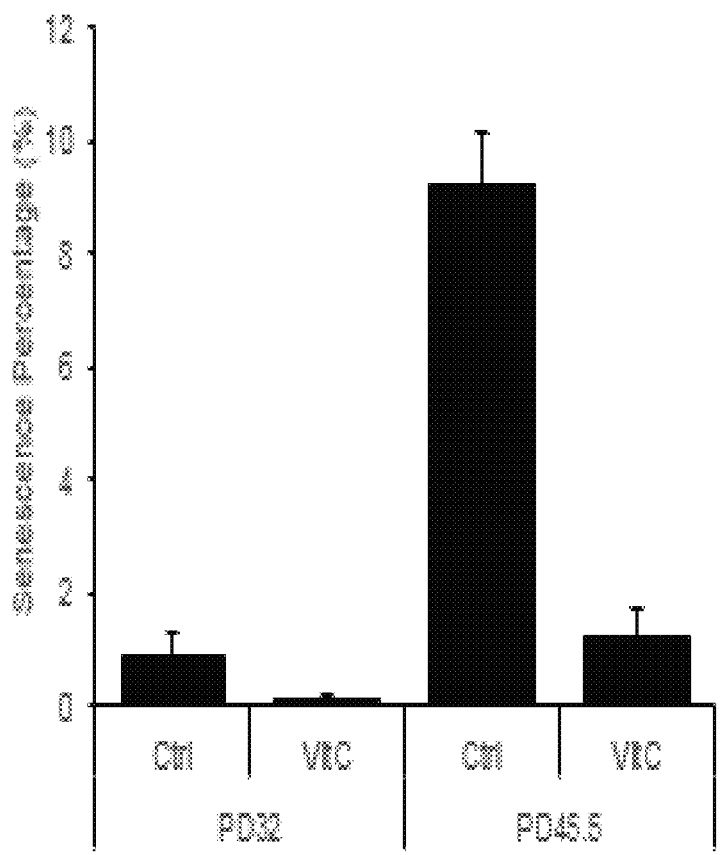
Figure 3A:
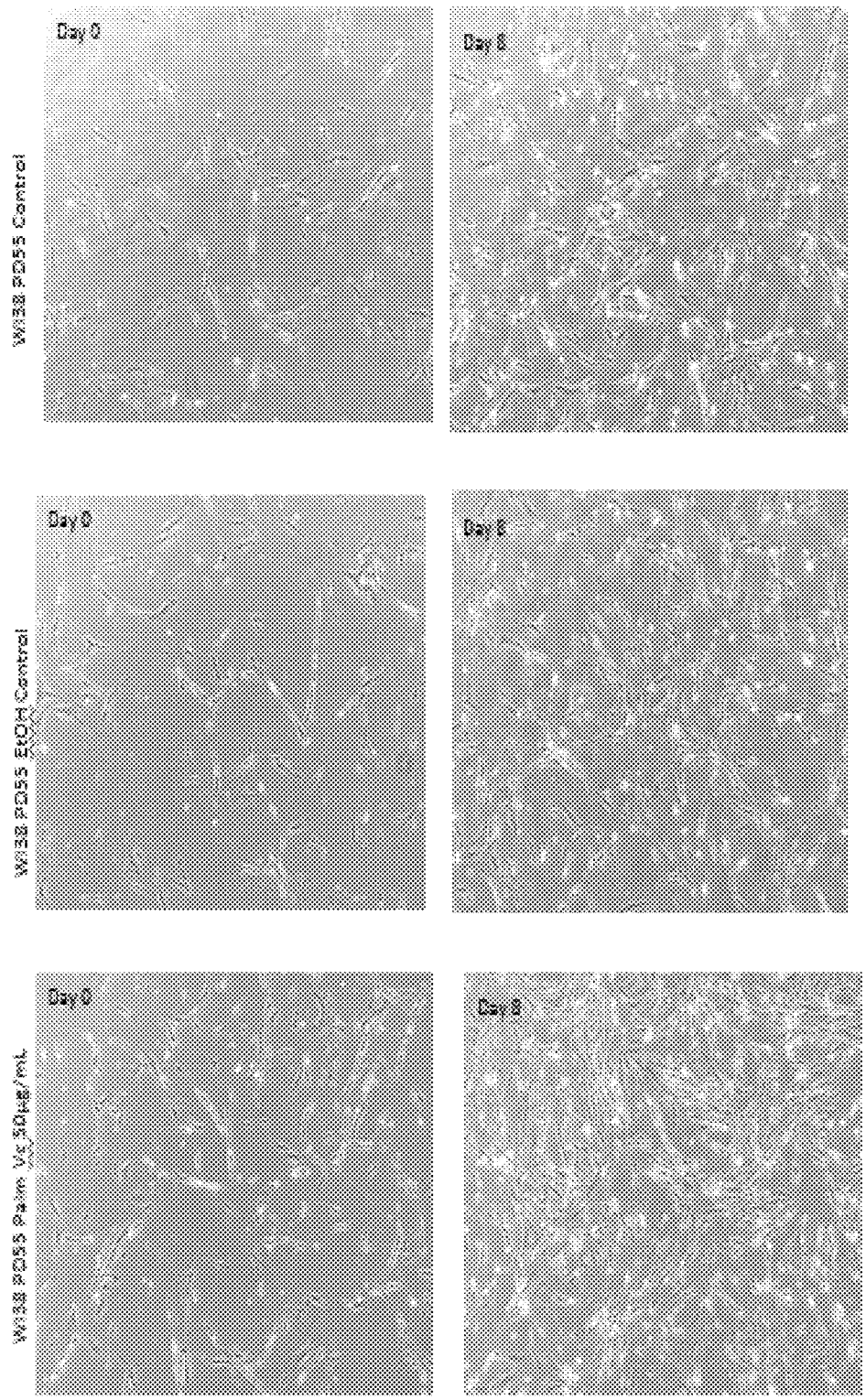
FIG. 3A-FIG. 3D show phenotypic and genotypic effects of 6-O-Palmitoyl L-ascorbic acid treatment were analyzed on younger WI38 PD55 fibroblasts.
Figure 3B:
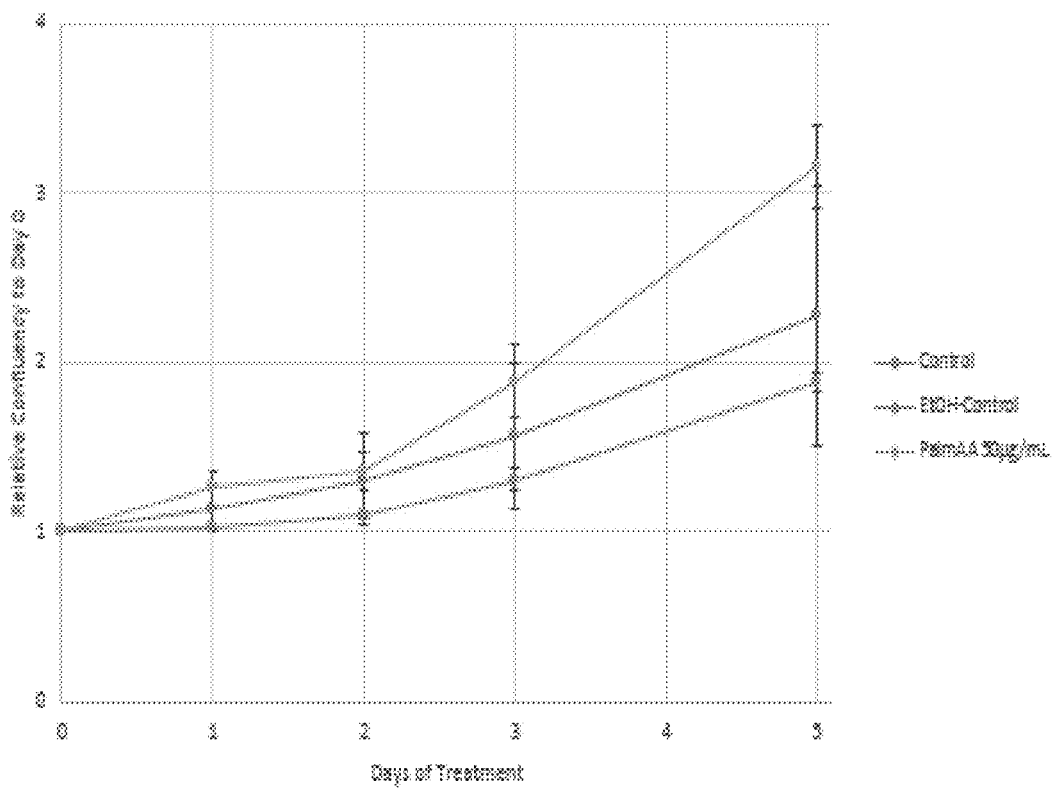
Figure 3C:
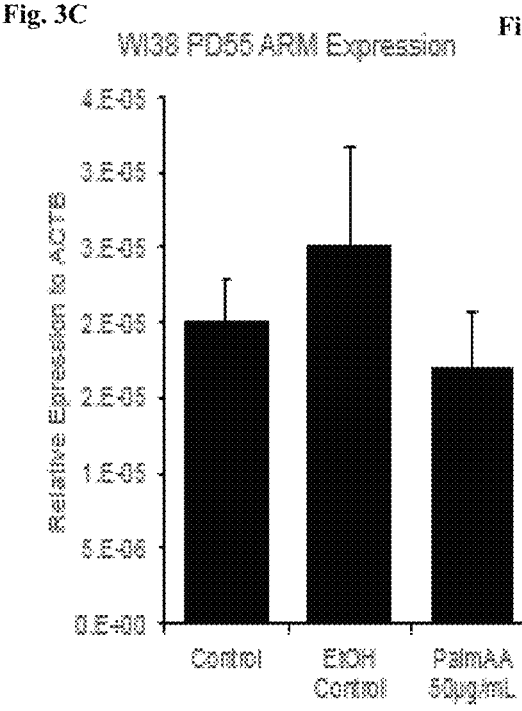
Figure 3D:
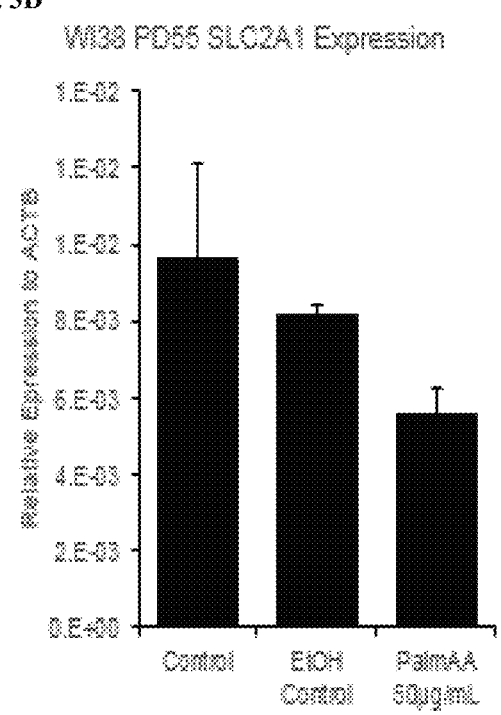
Figure 4A:
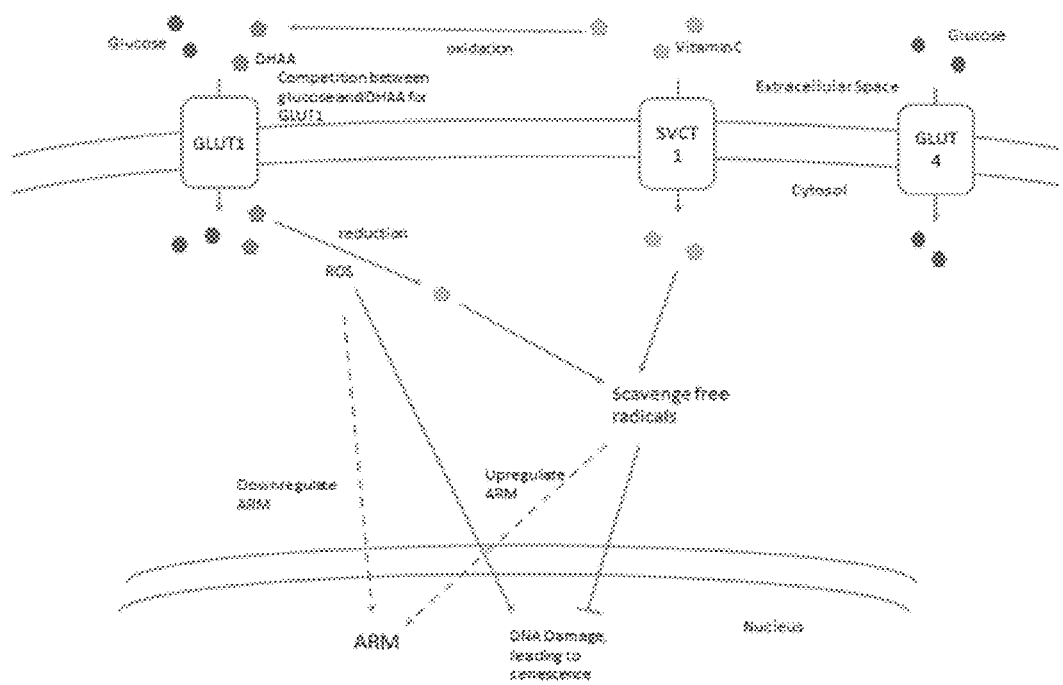
FIG. 4A-FIG. 4G show phenotypic and genotypic effects of dehydroascorbic acid and vitamin C treatment complemented with the addition of insulin were analyzed on WI38 PD54 fibroblast cells.
Figure 4B:
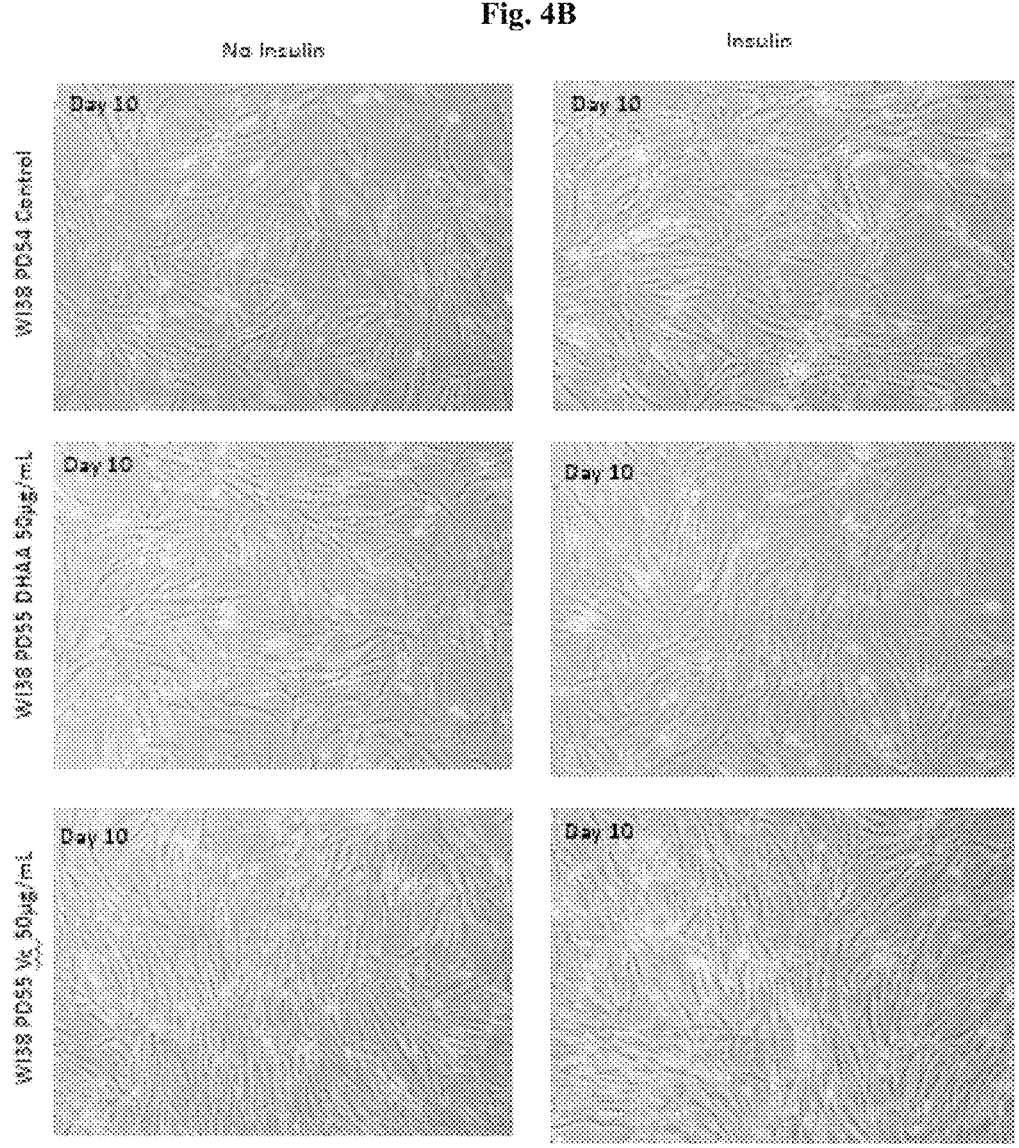
Figure 4C:
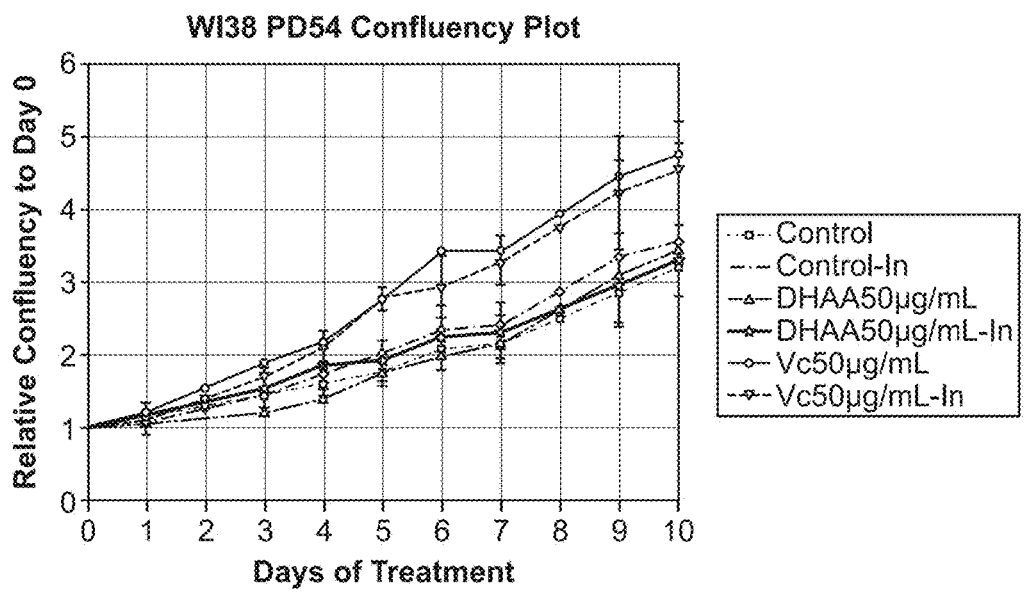
Figure 4D:
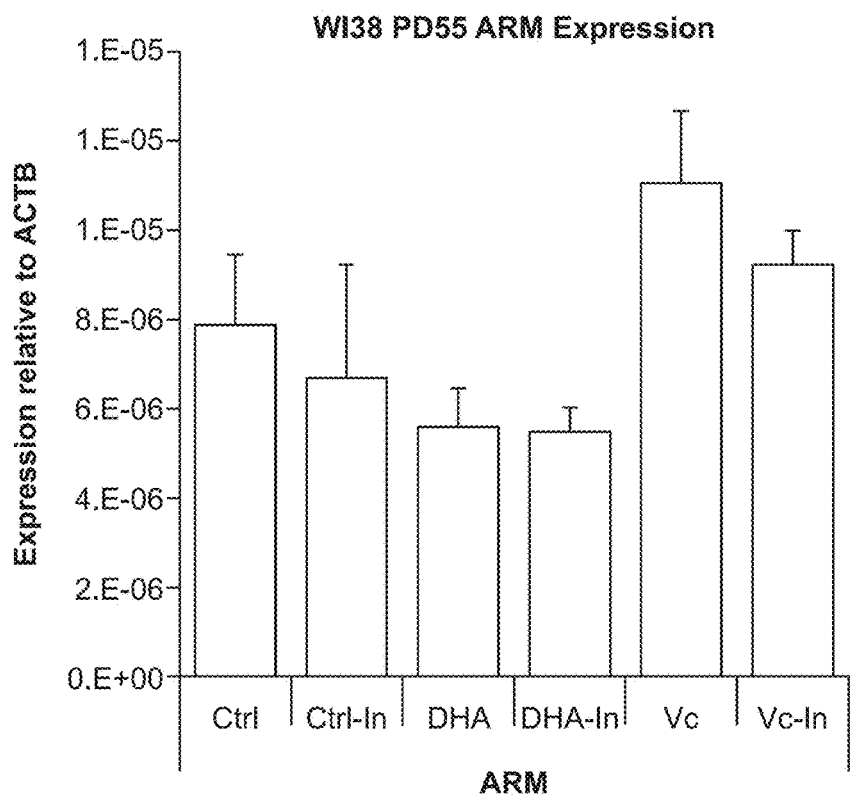
Figure 4E:
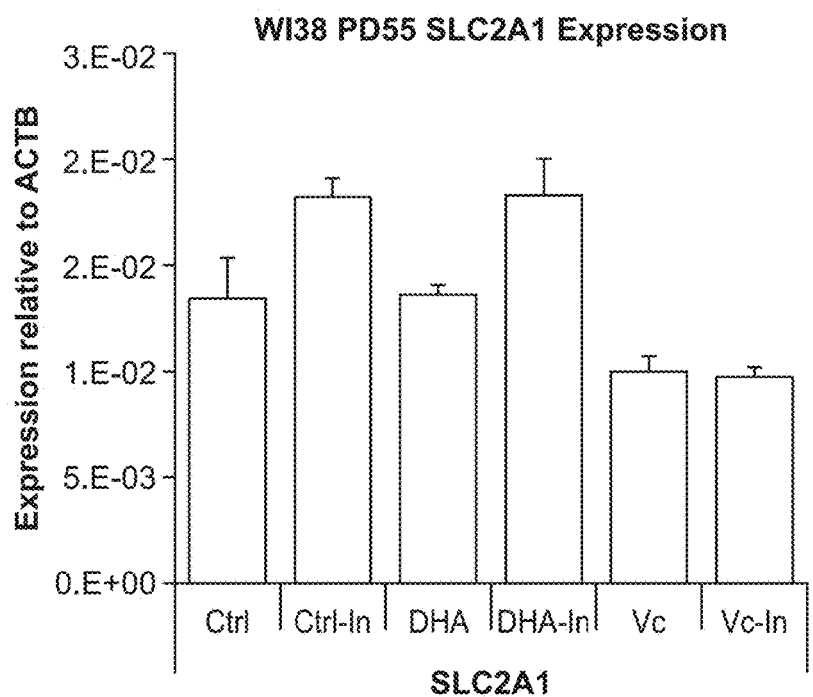
Figure 4F:
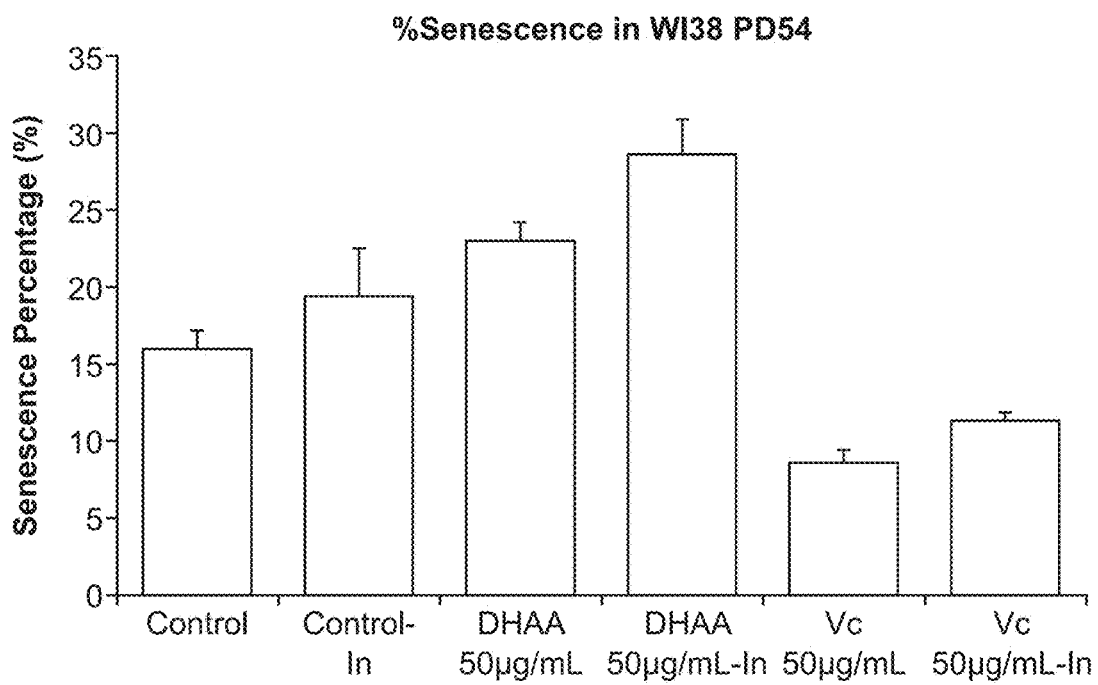
Figure 4G:
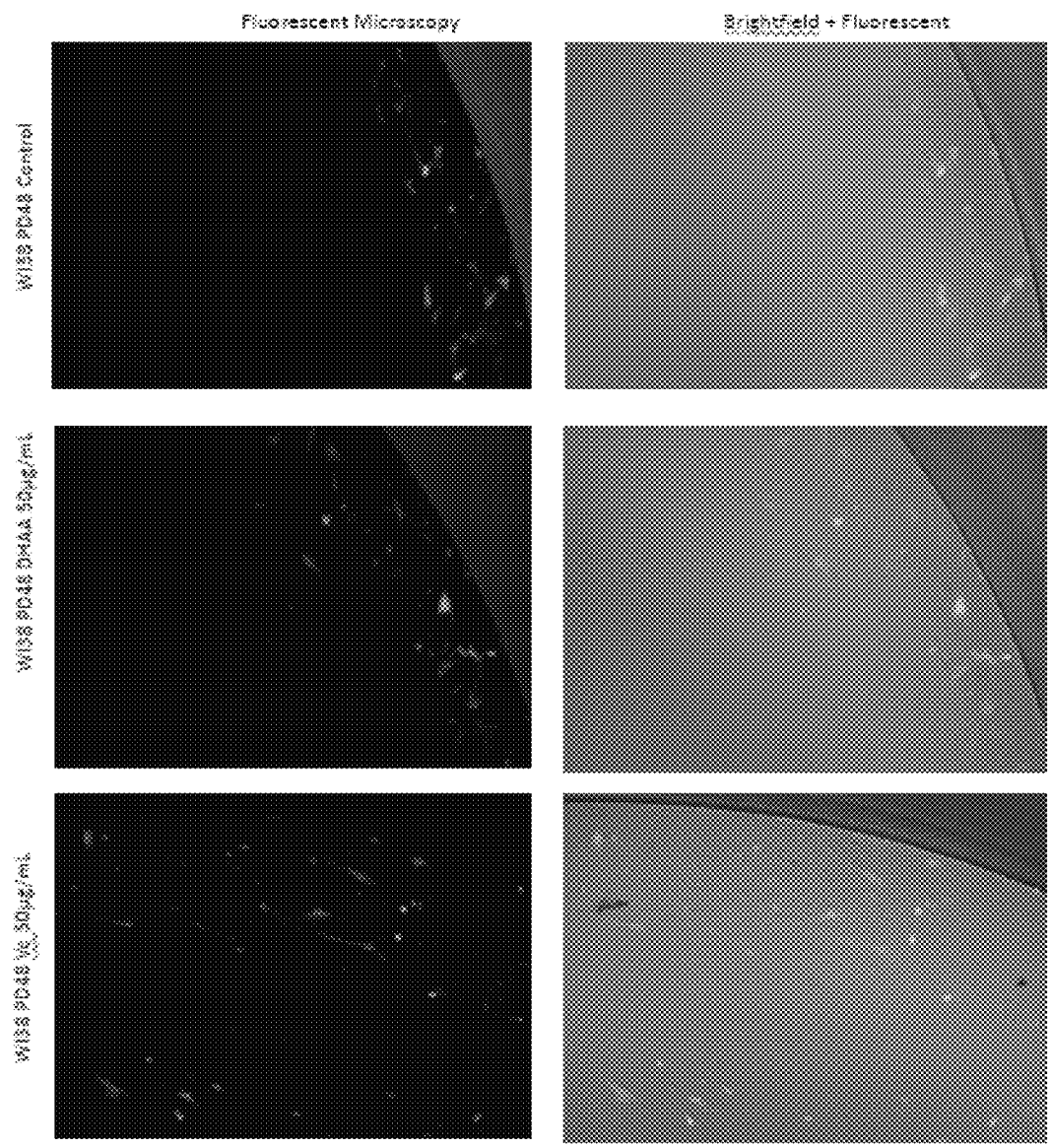

Aging is a complex process that is characterized with a global decline in physiological functions and an increased risk for aging-related diseases or conditions. In some instances, the rate of aging correlates with the methylation status and/or expression levels of different epigenetic markers. As such in some cases, methylation status and/or expression levels of an epigenetic marker is utilized, for example, for determining or predicting the rate of aging of a subject;

the progression, relapse, or refractory event of an aging-related disease or condition; or for monitoring the efficacy of a particular treatment option.

In some embodiments, disclosed herein is a method of retarding and/or reversing the biological age of a subject. In some instances, also described herein is a method of mimicking the biological age of a first subject to the biological age (e.g., an age based on the expression level or methylation profile of an epigenetic marker) of a second subject, in which the second subject is younger in chronological age (or actual age) than the first subject. In some cases, the method of retarding and/or reversing the biological age of a subject comprises administration to the subject a therapeutically effective dose of a therapeutic agent. In additional cases, the method of mimicking the biological age of a first subject to the biological age of a second subject comprises administration to the subject a therapeutically effective dose of a therapeutic agent.

In some instances, also described herein is a method of retarding and/or reversing the biological age of a subject suffering from a disease or condition. In some cases, the disease or condition is an aging-related disease or condition. In some cases, the method comprises administration to the subject suffering from a disease or condition a therapeutically effective dose of a therapeutic agent.

In some instances, additional described herein is a method of screening therapeutic agents to determine a therapeutic agent that is capable of retarding and/or reversing the biological age of a subject.

In some instances, also described herein include a method of reprogramming a cell to be transformed into an induced pluripotent stem cell (iPSC).

In additional instances, described herein include kits for use with one or more of the methods described herein.

Methods of Use

In some embodiments, disclosed herein is a method of retarding and/or reversing the biological age of a subject. In some instances, the method comprises increasing the expression rate or expression level of one or more epigenetic markers. In some instances, the one or more epigenetic markers are one or more genes. In some instances, the one or more epigenetic markers comprise ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, or an epigenetic marker selected from Table 1. In some instances, the one or more epigenetic markers comprise ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, or a combination thereof. In some cases, the one or more epigenetic markers comprise ELOVL2, KLF14, PENK, or a combination thereof.

In some embodiments, disclosed herein is a method of increasing the expression rate of ELOVL2, KLF14, PENK or a combination thereof in a first subject, comprising (a) administering to the first subject a therapeutically effective dose of a therapeutic agent for a first time period; (b) obtaining a sample from the first subject; and (c) determining whether the expression level of ELOVL2, KLF14, PENK or a combination thereof has increased in the first subject relative to a control by contacting the sample with a probe that recognizes ELOVL2, KLF14, or PENK and detecting binding between ELOVL2, KLF14, or PENK and the probe.

In some embodiments, the expression level of ELOVL2 is determined by contacting the sample with a probe that recognizes ELOVL2 and detecting binding between the probe and ELOVL2. In some cases, the expression level of KLF14 is determined by contacting the sample with a probe that recognizes KLF14 and detecting binding between the probe and KLF14. In some instances, the expression levels of ELOVL2 and KLF14 are determined by contacting the sample with a probe that recognizes ELOVL2 and a probe that recognizes KLF14 and detecting each respective binding between the probes and ELOVL2 and KLF14. In additional instances, the expression levels of ELOVL2, KLF14, and PENK are determined.

ELOVL fatty acid elongase 2 (ELOVL2) encodes a transmembrane protein involved in catalyzing the rate-limiting step of the long-chain fatty acids elongation cycle. In some instances, the methylation level or methylation status of ELOVL2 correlates to chronological age or the actual age of a subject (e.g., a human). For example, the methylation state or level of ELOVL2 increases as a subject ages. In some instances, biological age of a subject refers to the methylation level or methylation status of ELOVL2. In some cases, a CpG site within ELOVL2 comprises cg23606718, cg16867657, cg24724428, or cg21572722. In some cases, the biological age of a subject is based on the methylation level or status of cg23606718, cg16867657, cg24724428, and/or cg21572722. In some cases, the biological age of a subject is based on the methylation level or status of cg23606718 and/or cg16867657.

Furthermore, in some cases, the expression level of ELOVL2 decreases as a subject ages. In some cases, the biological age of a subject refers to the expression level of ELOVL2.

Kruppel-like factor 14 (KLF14), also known as basic transcription element-binding protein 5 (BTEBS), encodes a member of the Kruppel-like family of transcription factors. In some instances, KLF14 protein regulates the transcription of TGFβRII and is a master regulator of gene expression in adipose tissue. In some instances, the methylation level or methylation status of KLF14 correlates to chronological age or the actual age of a subject (e.g., a human). For example, the methylation state or level of KLF14 increases as a subject ages. In some instances, biological age of a subject refers to the methylation level or methylation status of KLF14. In some cases, a CpG site within KLF14 comprises cg14361627, cg08097417, cg07955995, cg20426994, cg04528819, cg09499629, and/or cg22285878. In some cases, the biological age of a subject is based on the methylation level or status of cg14361627, cg08097417, cg07955995, cg20426994, cg04528819, cg09499629, and/or cg22285878.

In some cases, the expression level of KLF14 decreases as a subject ages. In some cases, the biological age of a subject refers to the expression level of KLF14.

Proenkephalin (PENK) encodes a preproprotein that is proteolytically processed to generate multiple protein products. In some instances, the products of PENK comprise pentapeptide opioids Met-enkephalin and Leu-enkephalin. In some instances, the methylation level or methylation status of PENK correlates to chronological age or the actual age of a subject (e.g., a human). For example, the methylation state or level of PENK increases as a subject ages. In some instances, biological age of a subject refers to the methylation level or methylation status of PENK. In some cases, a CpG site within PENK comprises cg16419235. In some cases, the biological age of a subject is based on the methylation level or status of cg16419235.

In some cases, the expression level of PENK decreases as a subject ages. In some cases, the biological age of a subject refers to the expression level of PENK.

In some instances, the method further comprises determining the expression level of FHL2, SMC4, SLC12A5, TEZM151A, TTF2, TRIM45, TRIM59, ACSS3, ARID5A, BLMH, BRD4, CD28, EPHX3, RIN1, SLX1, or a combination thereof.

In some cases, the method additionally comprises determining the expression level of an epigenetic marker selected from Table 1.

In some embodiments, a neurotrophin is correlated with the biological age of a subject. In some instances, the expression level of a neurotrophin is correlated with the biological age of a subject. In some cases, the expression level is an elevated expression level. In some instances, the neurotrophin is brain-derived neurotrophic factor (BDNF), nerve growth factor (NGF), or glial cell-derived neurotrophic factor (GDNF). BDNF is involved in supporting the survival of existing neurons and participate in the growth and differentiation of new neurons and synapses. NGF, similar to BDNF, is involved in the development and phenotypic maintenance of neurons in the peripheral nervous system (PNS) and the functional integrity of cholinergic neurons in the central nervous system (CNS). GDNF is involved in promoting the survival and differentiation of dopaminergic neurons.

In some instances, disclosed herein is a method of increasing the expression rate or level of a neurotrophin in a subject, comprising administering to the subject a therapeutically effective dose of a therapeutic agent for a first time period, obtaining a sample from the subject, and determining whether the expression level or rate of the neurotrophin has increased in the subject relative to a control by contacting the sample with a probe that recognizes the neurotrophin and detecting binding between the neurotrophin and the probe. In some cases, the neurotrophin is BDNF, NGF, or GDNF. In some cases, a method described herein comprises increasing the expression rate or level of BDNF gene in a subject, comprising administering to the subject a therapeutically effective dose of a therapeutic agent for a first time period, obtaining a sample from the subject, and determining whether the expression level or rate of BDNF gene has increased in the subject relative to a control by contacting the sample with a probe that recognizes BDNF and detecting binding between BDNF and the probe. In some cases, a method described herein comprises increasing the expression rate or level of NGF gene in a subject, comprising administering to the subject a therapeutically effective dose of a therapeutic agent for a first time period, obtaining a sample from the subject, and determining whether the expression level or rate of NGF gene has increased in the subject relative to a control by contacting the sample with a probe that recognizes NGF and detecting binding between NGF and the probe. In some cases, a method described herein comprises increasing the expression rate or level of GDNF gene in a subject, comprising administering to the subject a therapeutically effective dose of a therapeutic agent for a first time period, obtaining a sample from the subject, and determining whether the expression level or rate of GDNF gene has increased in the subject relative to a control by contacting the sample with a probe that recognizes GDNF and detecting binding between GDNF and the probe. In some cases, an elevated expression level of BDNF is correlated with a biological age that is younger than the chronological age (or actual age) of the subject. In some cases, an elevated expression level of NGF is correlated with a biological age that is younger than the chronological age (or actual age) of the subject. In some cases, an elevated expression level of GDNF is correlated with a biological age that is younger than the chronological age (or actual age) of the subject.

In some embodiments, a cortisol level is correlated with the biological age of a subject. Cortisol is a steroid hormone, under the glucocorticoid class of hormones. It is produced by the zona fasciculata of the adrenal cortex within the adrenal gland. In some instances, cortisol, which activates glucocorticoid receptors that act as transcription factors, modulate DNA methylation levels. In such cases, the DNA methylation is genome-wide DNA methylation.

In some instances, an elevated cortisol level is observed with administration of a therapeutically effective dose of a therapeutic agent to a subject. In some cases, the elevated cortisol level modulates the DNA methylation level, in which the methylation level subsequently correlates with a biological age of the subject that is younger than the chronological age (or actual age) of the subject.

In some instances, the therapeutic agent comprises vitamin C or its derivatives, analogs, metabolites, prodrugs, or pharmaceutically acceptable salts thereof. In some cases, the therapeutic agent comprises vitamin C or its derivatives or pharmaceutically acceptable salts thereof. In some instances, the therapeutic agent is vitamin C. In some cases, vitamin C is L-ascorbic acid. In some cases, vitamin C is ascorbate.

In some instances, the therapeutic agent is a vitamin C derivative. In some instances, a derivative improves its solubility, absorption, biological half-life, and the like, or decreases the toxicity of the molecule, eliminate or attenuate any undesirable side effect of vitamin C. In some instances, a vitamin C derivative includes an isotopically labeled compound (e.g., with a radioisotope). In some instances, isotopes that are suitable for incorporation into vitamin C derivatives include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, and $^{36}Cl$. In some instances, isotopically-labeled compounds, for example those into which radioactive isotopes such as $^{3}H$ and $^{14}C$ are incorporated, are useful in drug and/or substrate tissue distribution assays.

In some embodiments, a derivative of vitamin C is a deuterated version of the compound. In some instances, a deuterated version of the compound comprises at least one, two, three, four, five, six, seven, eight, nine, ten, or more deuterium substitutions. In some cases, substitution with isotopes such as deuterium affords certain therapeutic advantages resulting from greater metabolic stability, such as, for example, increased in vivo half-life or reduced dosage requirements.

In some cases, vitamin C derivatives comprise 6-O-palmitoyl L-ascorbic acid, ascorbyl palmitate, magnesium ascorbyl phosphate (MAP), ascorbyl tetra-isopalmitoyl (tetrahexyldecyl ascorbate), sodium ascorbyl phosphate (SAP), ascorbyl glucoside (ascorbic acid 2-glucoside), ethyl ascorbic acid, or L-ascorbyl stearate. In some cases, the vitamin C derivative is L-ascorbic acid 2-phosphate. In some instances, a vitamin C derivative further comprises a vitamin C derivative salt.

As used herein, a pharmaceutically acceptable salt or a derivative salt comprises a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

In some instances, the therapeutic agent is a vitamin C analog. In some instances, a vitamin C analog refers to compounds that are structurally and functionally similar to, or mimics the effects of, vitamin C. In some instances, an analog mimics the biological effect of vitamin C. In other instances, an analog mimics the physical effect of vitamin C. In some cases, the vitamin C analog comprises 2-O-(beta-D-glucopyranosyl) ascorbic acid (AA-2βG).

In some instances, the therapeutic agent is a vitamin C metabolite. In some instances, a metabolite refers to the intermediates and products of vitamin C that is formed when vitamin C is metabolized. In additional embodiments, vitamin C is metabolized upon administration to an organism in need to produce a metabolite that is then used to produce a desired effect, including a desired therapeutic effect. In some instances, a metabolite of vitamin C is an active metabolite. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, in some instances, enzymes produce specific structural alterations to a compound. In some instances, a metabolite of vitamin C further enhances vitamin C uptake. In some instances, a vitamin C metabolite comprises L-threonic acid.

In some instances, the therapeutic agent is a vitamin C prodrug. In some instances, a prodrug has improved solubility in pharmaceutical compositions over the parent drug. In some embodiments, upon in vivo administration, a prodrug is chemically converted to the biologically, pharmaceutically or therapeutically active form of vitamin C. In some embodiments, a prodrug is enzymatically metabolized by one or more steps or processes to the biologically, pharmaceutically or therapeutically active form of vitamin C. In some instances, to produce a prodrug, a pharmaceutically active compound is modified such that the active compound will be regenerated upon in vivo administration. In some instances, the prodrug is designed to alter the metabolic stability or the transport characteristics of a drug, to mask side effects or toxicity, to improve the flavor of a drug or to alter other characteristics or properties of a drug. In some instances, prodrugs are designed as reversible drug derivatives, for use as modifiers to enhance drug transport to site-specific tissues. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985). In some instances, prodrugs of vitamin C comprise, for example, those described in PCT Publication No. WO2015048121.

In some instances, the therapeutic agent does not include an oxidized form of vitamin C. In some cases, the therapeutic agent does not include dehydroascorbic acid (DHA).

In some embodiments, administration of a therapeutic agent (e.g., vitamin C or its derivatives, analogs, metabolites, prodrugs, or pharmaceutically acceptable salts thereof), induces an increase in the expression level of one or more epigenetic markers: ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, a marker selected from Table 1, or a combination thereof. In some instances, administration of a therapeutic agent (e.g., vitamin C or its derivatives, analogs, metabolites, prodrugs, or pharmaceutically acceptable salts thereof), induces an increase in the expression level of one or more epigenetic markers: ELOVL2, KLF14, PENK, FHL2, SMC4, SLC12A5, TEZM151A, TTF2, TRIM45, TRIM59, ACSS3, ARID5A, BRD4, CD28, EPHX3, RIN1, SLX1, or a combination thereof. In some cases, administration of a therapeutic agent (e.g., vitamin C or its derivatives, analogs, metabolites, prodrugs, or pharmaceutically acceptable salts thereof), induces an increase in the expression level of one or more epigenetic markers: ELOVL2, KLF14, PENK, or a combination thereof.

In some embodiments, an increase in the expression rate or level of ELOVL2, KLF14, PENK or a combination thereof further correlates to a decrease in cell senescence.

In some cases, an increase in the expression rate or level of ELOVL2, KLF14, PENK or a combination thereof further correlates to an increase in cell proliferation.

In some cases, an increase in the expression rate or level of ELOVL2, KLF14, PENK or a combination thereof further correlates to an increase in cell survival.

In additional cases, an increase in the expression rate or level of ELOVL2, KLF14, PENK, or a combination thereof further correlates to a decrease in DNA methylation. In some instances, an increase in the expression rate of ELOVL2, KLF14, PENK, or a combination thereof leads to a methylation pattern that mimics the methylation pattern of a sample obtained from a second subject. In some cases, the second subject is younger in chronological age relative to the first subject. In some cases, the second subject is younger in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

In some cases, the first period of time comprises at least one day, two days, three days, four days, five days, one week, two weeks, three weeks, four weeks, one month, two months, three months, four months, five months, six months, 1 year, two years, three years, or more.

In some embodiments, the method further comprises increasing the dose of the therapeutic agent (e.g., vitamin C or its derivatives, analogs, metabolites, prodrugs, or pharmaceutically acceptable salts thereof) if the expression level of ELOVL2, KLF14, PENK, or a combination thereof has not increased relative to the control. In some cases, the method comprises increasing the dose of the therapeutic agent if the expression level of ELOVL2, KLF14, PENK, or a combination thereof has increased relative to the control and at a rate that is below a target range.

In other embodiments, the method further comprises decreasing or maintaining the dose of the therapeutic agent (e.g., vitamin C or its derivatives, analogs, metabolites, prodrugs, or pharmaceutically acceptable salts thereof) if the expression level of ELOVL2, KLF14, PENK, or a combination thereof has increased relative to the control. In some cases, the method comprises decreasing the dose of the therapeutic agent if the expression level of ELOVL2, KLF14, PENK, or a combination thereof has increased relative to the control and at a rate that is above a target range. In other cases, the method comprises maintaining the dose of the therapeutic agent if the expression level of ELOVL2, KLF14, PENK, or a combination thereof has increased relative to the control and at a rate that is within a target range.

In some instances, the dose of the therapeutic agent is increased, decreased, or maintained for a second period of time prior to redetermining the expression level of ELOVL2, KLF14, PENK, or a combination thereof. In some cases, the second period of time comprises at least one day, two days, three days, four days, five days, one week, two weeks, three weeks, four weeks, one month, two months, three months, four months, five months, six months, 1 year, two years, three years, or more.

In some instances, the method further comprises administering to the first subject an additional therapeutic agent.

In some instances, the method further comprises administering a therapeutic agent to induce reprogramming of a cell into an induced pluripotent stem cell (iPSC). In some instances, the therapeutic agent is vitamin C or its derivatives, analogs, metabolites, prodrugs, or pharmaceutically acceptable salts thereof. In some cases, the therapeutic agent comprises vitamin C or its derivatives or pharmaceutically acceptable salts thereof. In some instances, the therapeutic agent is vitamin C. In some cases, the therapeutic agent is L-ascorbic acid 2-phosphate.

In some embodiments, administration of a therapeutic agent (e.g., vitamin C or its derivatives, analogs, metabolites, prodrugs, or pharmaceutically acceptable salts thereof), induces an increase in the expression level of a neurotrophin (e.g., BDNF, NGF, or GDNF). In some cases, administration of a therapeutic agent (e.g., vitamin C or its derivatives, analogs, metabolites, prodrugs, or pharmaceutically acceptable salts thereof), induces an increase in the expression level of BDNF. In some cases, administration of a therapeutic agent (e.g., vitamin C or its derivatives, analogs, metabolites, prodrugs, or pharmaceutically acceptable salts thereof), induces an increase in the expression level of NGF. In some cases, administration of a therapeutic agent (e.g., vitamin C or its derivatives, analogs, metabolites, prodrugs, or pharmaceutically acceptable salts thereof), induces an increase in the expression level of GDNF. In some cases, the therapeutic agent comprises vitamin C or its derivatives or pharmaceutically acceptable salts thereof. In some instances, the therapeutic agent is vitamin C. In some cases, the therapeutic agent is L-ascorbic acid 2-phosphate.

In some instances, an increase in the expression rate or level of a neurotrophin (e.g., BDNF, NGF, or GDNF) further correlates to a decrease in cell senescence. In some cases, an increase in the expression rate or level of BDNF further correlates to a decrease in cell senescence.

In some instances, an increase in the expression rate or level of a neurotrophin (e.g., BDNF, NGF, or GDNF) further correlates to an increase in cell proliferation. In some cases, an increase in the expression rate or level of BDNF further correlates to an increase in cell proliferation.

In some instances, an increase in the expression rate or level of a neurotrophin (e.g., BDNF, NGF, or GDNF) further correlates to an increase in cell survival. In some cases, an increase in the expression rate or level of BDNF further correlates to an increase in cell survival.

In some embodiments, the dose of a therapeutic agent is increased during the course of a treatment regimen if the expression rate or level of a neurotrophin (e.g., BDNF, NGF, or GDNF) is not increased relative to a control. In some cases, the dose of a therapeutic agent is increased during the course of a treatment regimen if the expression rate or level of a neurotrophin (e.g., BDNF, NGF, or GDNF) is increased relative to a control but is at a rate that is below a target range.

In other embodiments, the dose of a therapeutic agent is decreased or maintained during the course of a treatment regimen if the expression rate or level of a neurotrophin (e.g., BDNF, NGF or GDNF) has increased relative to a control. In such embodiments, the dose of a therapeutic agent is decreased or maintained during the course of a treatment regimen if the expression rate or level of a neurotrophin (e.g., BDNF, NGF, or GDNF) has increased relative to a control, but is at a rate that is above a target range.

In additional embodiments, the dose of a therapeutic agent is maintained during the course of a treatment regimen if the expression rate or level of a neurotrophin (e.g., BDNF, NGF, or GDNF) has increased relative to a control. In such embodiments, the dose of a therapeutic agent is maintained during the course of a treatment regimen if the expression rate or level of a neurotrophin (e.g., BDNF, NGF, or GDNF) has increased relative to a control, but is at a rate that is within a target range.

In some embodiments, administration of a therapeutic agent (e.g., vitamin C or its derivatives, analogs, metabolites, prodrugs, or pharmaceutically acceptable salts thereof), induces an increase in the expression level of cortisol. In some cases, the therapeutic agent comprises vitamin C or its derivatives or pharmaceutically acceptable salts thereof. In some instances, the therapeutic agent is vitamin C. In some cases, the therapeutic agent is L-ascorbic acid 2-phosphate.

Methods in Reducing Methylation Level or Methylation Status

In some embodiments, disclosed herein is a method of retarding and/or reversing the biological age of a subject and the method comprises modulating the methylation pattern or level of one or more markers. In some instances, the one or more markers comprise ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, a neurotrophin (e.g., BDNF, NGF or GDNF), cortisol, or an epigenetic marker selected from Table 1. In some instances, the one or more markers comprise ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, a neurotrophin (e.g., BDNF, NGF or GDNF), cortisol, or a combination thereof. In some instances, the one or more markers comprise ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, or a combination thereof. In some cases, the one or more markers comprise ELOVL2, KLF14, PENK, or a combination thereof.

In some embodiments, disclosed herein is a method of modulating the methylation pattern of ELOVL2, KLF14, PENK, or a combination thereof in a first subject, comprising (a) administering to the first subject a therapeutically effective dose of a therapeutic agent for a first time period; (b) obtaining a sample from the first subject; and (c) determining whether the methylation pattern of ELOVL2, KLF14, PENK, or a combination thereof has changed in the first subject relative to a control by contacting the sample with a set of probes and detecting a set of hybridization products to determine the methylation pattern of ELOVL2, KLF14, PENK, or a combination thereof. In some instances, the methylation pattern of ELOVL2 is determined. In some instances, the methylation pattern of KLF14 is determined. In some instances, the methylation pattern of PENK is determined. In some cases, the methylation patterns of ELOVL2 and KLF14 are determined. In some cases, the methylation patterns of ELOVL2, KLF14, and PENK are determined.

In some instances, the therapeutic agent comprises vitamin C or its derivatives, analogs, metabolites, prodrugs, or pharmaceutically acceptable salts thereof. In some cases, the therapeutic agent comprises vitamin C or its derivatives or pharmaceutically acceptable salts thereof. In some instances, the therapeutic agent is vitamin C. In some cases, vitamin C is L-ascorbic acid. In some cases, vitamin C is ascorbate.

In some instances, the therapeutic agent is a vitamin C derivative. In some cases, vitamin C derivatives comprise 6-O-palmitoyl L-ascorbic acid, ascorbyl palmitate, magnesium ascorbyl phosphate (MAP), ascorbyl tetra-isopalmitoyl (tetrahexyldecyl ascorbate), sodium ascorbyl phosphate (SAP), ascorbyl glucoside (ascorbic acid 2-glucoside), ethyl ascorbic acid, or L-ascorbyl stearate. In some cases, the vitamin C derivative is L-ascorbic acid 2-phosphate. In some instances, a vitamin C derivative further comprises a vitamin C derivative salt.

In some instances, the therapeutic agent is a vitamin C analog. In some cases, the vitamin C analog comprises 2-O-(beta-D-glucopyranosyl) ascorbic acid (AA-2βG).

In some instances, the therapeutic agent is a vitamin C metabolite. In some instances, a vitamin C metabolite comprises L-threonic acid.

In some instances, the therapeutic agent is a vitamin C prodrug. In some instances, prodrugs of vitamin C comprise, for example, those described in PCT Publication No. WO2015048121.

In some instances, the therapeutic agent does not include an oxidized form of vitamin C. In some cases, the therapeutic agent does not include dehydroascorbic acid (DHA).

In some embodiments, administration of a therapeutic agent (e.g., vitamin C or its derivatives, analogs, metabolites, prodrugs, or pharmaceutically acceptable salts thereof), induces a decrease in the methylation status of one or more epigenetic markers: ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, a marker selected from Table 1, or a combination thereof. In some instances, administration of a therapeutic agent (e.g., vitamin C or its derivatives, analogs, metabolites, prodrugs, or pharmaceutically acceptable salts thereof), induces a decrease in the methylation status of one or more epigenetic markers: ELOVL2, KLF14, PENK, FHL2, SMC4, SLC12A5, TEZM151A, TTF2, TRIM45, TRIM59, ACSS3, ARID5A, BRD4, CD28, EPHX3, SLX1, or a combination thereof. In some cases, administration of a therapeutic agent (e.g., vitamin C or its derivatives, analogs, metabolites, prodrugs, or pharmaceutically acceptable salts thereof), induces a decrease in the methylation status of one or more epigenetic markers: ELOVL2, KLF14, PENK, or a combination thereof.

In some embodiments, a decrease in the methylation status of ELOVL2, KLF14, PENK, or a combination thereof further correlates to a decrease in cell senescence.

In some embodiments, a decrease in the methylation status of ELOVL2, KLF14, PENK, or a combination thereof further correlates to an increase in cell proliferation.

In some embodiments, a decrease in the methylation status of ELOVL2, KLF14, PENK, or a combination thereof further correlates to an increase in cell survival.

In some embodiments, a decrease in the methylation status of ELOVL2, KLF14, PENK, or a combination thereof leads to a methylation pattern that mimics the methylation pattern of a sample obtained from a second subject. In some cases, the second subject is younger in chronological age relative to the first subject. In some cases, the second subject is younger in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

In some cases, the first period of time comprises at least one day, two days, three days, four days, five days, one week, two weeks, three weeks, four weeks, one month, two months, three months, four months, five months, six months, 1 year, two years, three years, or more.

In some embodiments, the method further comprises increasing the dose of the therapeutic agent if the methylation pattern of ELOVL2, KLF14, PENK, or a combination thereof has not changed relative to the control. In some cases, the method comprises increasing the dose of the therapeutic agent if the methylation pattern of ELOVL2, KLF14, PENK, or a combination thereof has changed relative to the control and to a degree lower than a target range.

In other embodiments, the method further comprises decreasing or maintaining the dose of the therapeutic agent if the methylation pattern of ELOVL2, KLF14, PENK, or a combination thereof has changed relative to the control. In some cases, the method comprises decreasing the dose of the therapeutic agent if the methylation pattern of ELOVL2, KLF14, PENK, or a combination thereof has changed relative to the control and to a degree above a target range. In additional cases, the method comprises maintaining the dose of the therapeutic agent if the methylation pattern of ELOVL2, KLF14, PENK, or a combination thereof has changed relative to the control and to a degree within a target range.

In some instances, the dose of the therapeutic agent is increased, decreased, or maintained for a second period of time prior to redetermining the methylation pattern of ELOVL2, KLF14, PENK, or a combination thereof.

In some cases, the second period of time comprises at least one day, two days, three days, four days, five days, one week, two weeks, three weeks, four weeks, one month, two months, three months, four months, five months, six months, 1 year, two years, three years, or more.

In some instances, the method further comprises administering to the first subject an additional therapeutic agent.

Control

Various methodologies described herein include a step that involves comparing a value, level, feature, characteristic, property, etc. to a suitable control, referred to interchangeably herein as an appropriate control, a control sample, or as a control. In some embodiments, a control is a value, level, feature, characteristic, property, etc., determined in a cell, a tissue, an organ, or a sample obtained from a patient. In some instances, the cell, tissue, organ, or sample is a young cell, tissue, organ, or sample. In some cases, the cell tissue, organ, or sample is an aged cell, tissue, organ, or sample. In some instances, the cell, tissue, organ, or sample is obtained from an individual with a chronological age of less than 1, 2, 3, 4, 5, 10, 12, 14, 15, 18, 20, 25, 30, 35, 40, 45, or 50 years. In some instances, the cell, tissue, organ, or sample is obtained from an individual with a chronological age of more than 1, 2, 3, 4, 5, 10, 12, 14, 15, 18, 20, 25, 30, 35, 40, 45, or 50 years.

In some cases, the control comprises the expression level of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, RIN1, SLX1, a neurotrophin (e.g., BDNF, NGF or GDNF), cortisol, an epigenetic marker selected from Table 1, or a combination thereof obtained from a sample from the subject prior to administration of the therapeutic agent. In some cases, the control comprises the expression level of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, a neurotrophin (e.g., BDNF, NGF or GDNF), cortisol, or a combination thereof obtained from a sample from the subject prior to administration of the therapeutic agent. In some cases, the control comprises the expression level of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, or a combination thereof obtained from a sample from the subject prior to administration of the therapeutic agent. In some cases, the control comprises the expression level of ELOVL2, KLF14, PENK, or a combination thereof obtained from a sample from the subject prior to administration of the therapeutic agent.

In some cases, the control comprises a normalized expression level of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SIX1, a neurotrophin (e.g., BDNF, NGF or GDNF), cortisol, an epigenetic marker selected from Table 1, or a combination thereof obtained from a set of samples without exposure to the therapeutic agent. In some cases, the control comprises a normalized expression level of ELOVL2, KLF14, PENK, FHL2, SMC4, SLC12A5, TEZM151A, TTF2, TRIM45, TRIM59, ACSS3, ARID5A, BRD4, CD28, EPHX3, SIX1, a neurotrophin (e.g., BDNF, NGF or GDNF), cortisol, or a combination thereof obtained from a set of samples without exposure to the therapeutic agent. In some cases, the control comprises a normalized expression level of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SLX1, or a combination thereof obtained from a set of samples without exposure to the therapeutic agent. In some cases, the control comprises a normalized expression level of ELOVL2, KLF14, PENK, or a combination thereof obtained from a set of samples without exposure to the therapeutic agent. In some cases, the set of samples are a set of cell samples.

In some cases, the control comprises the methylation pattern of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SIX1, an epigenetic marker selected from Table 1, or a combination thereof obtained from a sample from the subject prior to administration of the therapeutic agent. In some cases, the control comprises the methylation pattern of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SIX1, or a combination thereof obtained from a sample from the subject prior to administration of the therapeutic agent. In some cases, the control comprises the methylation pattern of ELOVL2, KLF14, PENK or a combination thereof obtained from a sample from the subject prior to administration of the therapeutic agent.

In some cases, the control comprises a normalized methylation pattern of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SIX1, an epigenetic marker selected from Table 1, or a combination thereof obtained from a set of samples without exposure to the therapeutic agent. In some cases, the control comprises a normalized methylation pattern of ELOVL2, KLF14, PENK, FHL2, SMC4, SLC12A5, TEZM151A, TTF2, TRIM45, TRIM59, ACSS3, ARID5A, BLMH, BRD4, CD28, EPHX3, SIX1, or a combination thereof obtained from a set of samples without exposure to the therapeutic agent. In some cases, the control comprises a normalized methylation pattern of ELOVL2, KLF14, PENK or a combination thereof obtained from a set of samples without exposure to the therapeutic agent. In some cases, the set of samples are a set of cell samples.

In some instances, a control is a positive control, e.g., a methylation profile obtained from a sample of an aged individual, or is a negative control, e.g., a methylation profile obtained from a sample of a young individual. In some instances, a control is also referred to as a training set or training dataset.

Diseases or Indications

In some embodiments, one or more samples are obtained from a subject having a disease or indication. In some instances, the disease or condition is an aging-related disease or condition. In some instances, the disease or indication is a metabolic disease or condition. In some instances, the disease or indication is an ELOVL2-associated disease or indication, a KLF14-associated disease or indication, or a PENK-associated disease or indication. In some cases, the disease or indication is Werner syndrome, progeria, or post-traumatic stress disorder.

In some embodiments, also disclosed herein is a method of increasing the expression level of an epigenetic marker (e.g., ELOVL2, KLF14, PENK, or a combination thereof) in a subject having a disease or indication by administering to the subject a therapeutically effective dose of a therapeutic agent and determining whether the expression level of the epigenetic marker (e.g., ELOVL2, KLF14, PENK, or a combination thereof) has been elevated. In some embodiments, further described herein is a method of modulating the methylation pattern of an epigenetic marker (e.g., ELOVL2, KLF14, PENK, or a combination thereof) in a subject having a disease or indication by administering to the subject a therapeutically effective dose of a therapeutic agent and determining whether the methylation pattern of the epigenetic marker (e.g., ELOVL2, KLF14, PENK, or a combination thereof) has been changed. In some instances, the disease or indication is a metabolic disease or condition. In some instances, the disease or indication is an ELOVL2-associated disease or indication, a KLF14-associated disease or indication, or a PENK-associated disease or indication. In some cases, the disease or indication is Werner syndrome, progeria, or post-traumatic stress disorder.

Diabetes

In some embodiments, a metabolic disease or condition is diabetes (diabetes mellitus, DM). In some instances, diabetes is type 1 diabetes, type 2 diabetes, type 3 diabetes, type 4 diabetes, double diabetes, latent autoimmune diabetes (LAD), gestational diabetes, neonatal diabetes mellitus (NDM), maturity onset diabetes of the young (MODY), Wolfram syndrome, Alström syndrome, prediabetes, or diabetes insipidus. Type 2 diabetes, also called non-insulin dependent diabetes, is the most common type of diabetes accounting for 95% of all diabetes cases. In some instances, type 2 diabetes is caused by a combination of factors, including insulin resistance due to pancreatic beta cell dysfunction, which in turn leads to high blood glucose levels. In some cases, increased glucagon levels stimulate the liver to produce an abnormal amount of unneeded glucose, which contributes to high blood glucose levels.

Type 1 diabetes, also called insulin-dependent diabetes, comprises about 5% to 10% of all diabetes cases. Type 1 diabetes is an autoimmune disease where T cells attack and destroy insulin-producing beta cells in the pancreas. In some embodiments, Type 1 diabetes is caused by genetic and environmental factors.

In some embodiments, the term double diabetes is used to describe patients diagnosed with both type 1 and 2 diabetes.

Type 4 diabetes is a recently discovered type of diabetes affecting about 20% of diabetic patients age 65 and over. In some embodiments, type 4 diabetes is characterized by age-associated insulin resistance.

In some embodiments, type 3 diabetes is used as a term for Alzheimer's disease resulting in insulin resistance in the brain.

LAD, also known as slow onset type 1 diabetes, is a slow developing form of type 1 diabetes where diagnosis frequently occurs after age 30. In some embodiments, LAD is further classified into latent autoimmune diabetes in adults (LADA) or latent autoimmune diabetes in the young (LADY) or latent autoimmune diabetes in children (LADC).

Prediabetes, also known as borderline diabetes, is a precursor stage to diabetes mellitus. In some cases, prediabetes is characterized by abnormal OGTT, fasting plasma glucose test, and hemoglobin A1C test results. In some embodiments, prediabetes is further classified into impaired fasting glycaemia or impaired fasting glucose (IFG) and impaired glucose tolerance (IGT). IFG is a condition in which blood glucose levels are higher than normal levels, but not elevated enough to be diagnosed as diabetes mellitus. IGT is a pre-diabetic state of abnormal blood glucose levels associated with insulin resistance and increased risk of cardiovascular pathology.

In some embodiments, the sample is obtained from a subject having diabetes. In some instances, the sample is obtained from a subject having type 1 diabetes, type 2 diabetes, type 3 diabetes, type 4 diabetes, double diabetes, latent autoimmune diabetes (LAD), gestational diabetes, neonatal diabetes mellitus (NDM), maturity onset diabetes of the young (MODY), Wolfram syndrome, Alström syndrome, prediabetes, or diabetes insipidus. In some cases, the sample is obtained from a subject having type 1 diabetes. In other cases, the sample is obtained from a subject having type 2 diabetes. In additional cases, the sample is obtained from a subject having prediabetes.

In some embodiments, also disclosed herein is a method of increasing the expression level of an epigenetic marker (e.g., ELOVL2, KLF14, PENK, or a combination thereof) in a subject having diabetes by administering to the subject a therapeutically effective dose of a therapeutic agent and determining whether the expression level of the epigenetic marker (e.g., ELOVL2, KLF14, PENK, or a combination thereof) has been elevated. In some embodiments, further described herein is a method of modulating the methylation pattern of an epigenetic marker (e.g., ELOVL2, KLF14, PENK, or a combination thereof) in a subject having diabetes by administering to the subject a therapeutically effective dose of a therapeutic agent and determining whether the methylation pattern of the epigenetic marker (e.g., ELOVL2, KLF14, PENK, or a combination thereof) has been changed.

In some embodiments, the sample is obtained from a subject having an elevated body mass index (BMI). In some instances, the elevated BMI is from about 25 kg/m² to about 40 kg/m². In some instances, the elevated BMI is from about 25 kg/m² to about 29.9 kg/m², from about 30 kg/m² to about 34.9 kg/m², or from about 35 kg/m² to about 39 kg/m². In some cases, the elevated BMI is a BMI of 25 kg/m², 26 kg/m², 27 kg/m², 28 kg/m², 29 kg/m², 30 kg/m², 35 kg/m², 40 kg/m² or more.

In some embodiments, also disclosed herein is a method of increasing the expression level of an epigenetic marker (e.g., ELOVL2, KLF14, PENK, or a combination thereof) in a subject having an elevated BMI by administering to the subject a therapeutically effective dose of a therapeutic agent and determining whether the expression level of the epigenetic marker (e.g., ELOVL2, KLF14, PENK, or a combination thereof) has been elevated. In some embodiments, further described herein is a method of modulating the methylation pattern of an epigenetic marker (e.g., ELOVL2, KLF14, PENK, or a combination thereof) in a subject having an elevated BMI by administering to the subject a therapeutically effective dose of a therapeutic agent and determining whether the methylation pattern of the epigenetic marker (e.g., ELOVL2, KLF14, PENK, or a combination thereof) has been changed.

Werner Syndrome

In some embodiments, the sample is obtained from a subject having Werner syndrome. Werner syndrome (also known as adult progeria or WS) is an autosomal recessive progeroid syndrome with phenotype of premature aging. In some instances, patient with Werner syndrome is characterized with growth retardation, short stature, premature graying of hair, alopecia (hair loss), wrinkling, prematurely aged faces with beaked noses, skin atrophy (wasting away) with scleroderma-like lesions, lipodystrophy (loss of fat tissues), abnormal fat deposition leading to thin legs and arms, and/or severe ulcerations around the Achilles tendon and malleoli (around ankles).

In some instances, Werner syndrome is caused by mutations in the WRN (Werner Syndrome, RecQ helicase-like) gene which encodes a 1432 amino acid protein, WRNp protein, which is involved in DNA repair and replication. In some instances, a patient with Werner syndrome losses the activity of WRNp protein, and further exhibits accelerated telomere shortening and telomere dysfunction.

In some embodiments, also disclosed herein is a method of increasing the expression level of an epigenetic marker (e.g., ELOVL2, KLF14, PENK, or a combination thereof) in a subject having Werner syndrome by administering to the subject a therapeutically effective dose of a therapeutic agent and determining whether the expression level of the epigenetic marker (e.g., ELOVL2, KLF14, PENK, or a combination thereof) has been elevated. In some embodiments, further described herein is a method of modulating the methylation pattern of an epigenetic marker (e.g., ELOVL2, KLF14, PENK, or a combination thereof) in a subject having Werner syndrome by administering to the subject a therapeutically effective dose of a therapeutic agent and determining whether the methylation pattern of the epigenetic marker (e.g., ELOVL2, KLF14, PENK, or a combination thereof) has been changed.

Progeria

In some embodiments, the sample is obtained from a subject having progeria. Progeria (or Hutchinson-Gilford progeria syndrome, HGPS, or progeria syndrome) is a rare genetic disorder in which the symptoms resemble premature aging. In some instances, progeria is manifested at a young age. In some instances, the first sign of symptoms occurs during the first few months of infancy and include a failure to thrive and a localized scleroderma-like skin condition. In some instances, secondary conditions occur around 18-24 months and include alopecia and a distinctive physical appearance (e.g., a small face with a shallow recessed jaw and/or a pinched nose). In some cases, additional symptoms include wrinkled skin, atherosclerosis, kidney failure, loss of eyesight, and/or cardiovascular disorders.

In some instances, progeria is caused by a cytosine to thymine mutation at position 1824 of the LMNA gene. In some cases, the mutation induces a 5' cryptic splice site which then leads to the production of a prelamin A protein variant. The preliamin A protein variant subsequently induces an abnormally shaped nucleus and impedes cell division, leading to progeria.

In some embodiments, also disclosed herein is a method of increasing the expression level of an epigenetic marker (e.g., ELOVL2, KLF14, PENK, or a combination thereof) in a subject having progeria by administering to the subject a therapeutically effective dose of a therapeutic agent and determining whether the expression level of the epigenetic marker (e.g., ELOVL2, KLF14, PENK, or a combination thereof) has been elevated. In some embodiments, further described herein is a method of modulating the methylation pattern of an epigenetic marker (e.g., ELOVL2, KLF14, PENK, or a combination thereof) in a subject having progeria by administering to the subject a therapeutically effective dose of a therapeutic agent and determining whether the methylation pattern of the epigenetic marker (e.g., ELOVL2, KLF14, PENK, or a combination thereof) has been changed.

Post-Traumatic Stress Disorder

In some embodiments, the sample is obtained from a subject having post-traumatic stress disorder (PTSD). Post-traumatic stress disorder (PTSD) is a metal disorder developed after experiencing a traumatic event. In some embodiments, also disclosed herein is a method of increasing the expression level of an epigenetic marker (e.g., ELOVL2, KLF14, PENK, or a combination thereof) in a subject having PTSD by administering to the subject a therapeutically effective dose of a therapeutic agent and determining whether the expression level of the epigenetic marker (e.g., ELOVL2, KLF14, PENK, or a combination thereof) has been elevated. In some embodiments, further described herein is a method of modulating the methylation pattern of an epigenetic marker (e.g., ELOVL2, KLF14, PENK, or a combination thereof) in a subject having PTSD by administering to the subject a therapeutically effective dose of a therapeutic agent and determining whether the methylation pattern of the epigenetic marker (e.g., ELOVL2, KLF14, PENK, or a combination thereof) has been changed.

Pharmaceutical Compositions and Formulations

In some embodiments, the pharmaceutical composition and formulations comprising a therapeutic agent (e.g., vitamin C or its derivatives, analogs, metabolites, prodrugs, or pharmaceutically acceptable salts thereof) are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition comprising a therapeutic agent (e.g., vitamin C or its derivatives, analogs, metabolites, prodrugs, or pharmaceutically acceptable salts thereof) is formulated for oral administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pa. 1975, Liberman, H. A. and Lachman, L., Eds., *Pharmaceutical Dosage Forms*, Marcel Decker, New York, N.Y., 1980, and *Pharmaceutical Dosage Forms and Drug Delivery Systems*, Seventh Ed. (Lippincott Williams & Wilkins1999).

In some instances, the pharmaceutical formulations further include pH adjusting agents or buffering agents which include acids such as acetic, boric, citric, lactic, phosphoric, and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases, and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions. Suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, and glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil)(Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, a therapeutic agent described herein is administered for one or more times a day. In some embodiments, a therapeutic agent described herein is administered once per day, twice per day, three times per day or more. In some cases, a therapeutic agent described herein is administered daily, every day, every alternate day, five days a week, once a week, every other week, two weeks per month, three weeks per month, once a month, twice a month, three times per month, or more. In some cases, a therapeutic agent described herein is administered for at least 1 month, 2 months, 3 months, 4 months, 5 months, 6 months, 7 months, 8 months, 9 months, 10 months, 11 months, 12 months, 18 months, 2 years, 3 years, or more.

In some instances, a therapeutic agent described herein is administered at a dose range of from about 0.1 μg/mL to about 200 μg/mL. In some instances, the therapeutic agent described herein is administered at a dose range of from about 1 μg/mL to about 150 μg/mL, from about 5 μg/mL to about 100 μg/mL, from about 10 μg/mL to about 100 μg/mL, from about 20 μg/mL to about 100 μg/mL, from about 30 μg/mL to about 100 μg/mL, from about 50 μg/mL to about 100 μg/mL, from about 1 μg/mL to about 50 μg/mL, from about 5 μg/mL to about 50 μg/mL, from about 10 μg/mL to about 50 μg/mL, from about 20 μg/mL to about 50 μg/mL, from about 30 μg/mL to about 50 μg/mL, from about 50 μg/mL to about 200 μg/mL, from about 80 μg/mL to about 200 μg/mL, from about 100 μg/mL to about 200 μg/mL, or from about 150 μg/mL to about 200 μg/mL.

In some instances, the therapeutic agent described herein is administered at a dose of about 0.1 μg/mL, 1 μg/mL, 5 μg/mL, 10 μg/mL, 15 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, 110 μg/mL, 120 μg/mL, 130 μg/mL, 140 μg/mL, 150 μg/mL, 160 μg/mL, 170 μg/mL, 180 μg/mL, 190 μg/mL, or about 200 μg/mL.

In some instances, the therapeutic agent is vitamin C or its derivatives, analogs, metabolites, prodrugs, or pharmaceutically acceptable salts thereof. In some instances, vitamin C or its derivatives, analogs, metabolites, prodrugs, or pharmaceutically acceptable salts thereof is administered at a dose range of from about 0.1 μg/mL to about 200 μg/mL. In some instances, vitamin C or its derivatives, analogs, metabolites, prodrugs, or pharmaceutically acceptable salts thereof is administered at a dose range of from about 1 μg/mL to about 150 μg/mL, from about 5 μg/mL to about 100 μg/mL, from about 10 μg/mL to about 100 μg/mL, from about 20 μg/mL to about 100 μg/mL, from about 30 μg/mL to about 100 μg/mL, from about 50 μg/mL to about 100 μg/mL, from about 1 μg/mL to about 50 μg/mL, from about 5 μg/mL to about 50 μg/mL, from about 10 μg/mL to about 50 μg/mL, from about 20 μg/mL to about 50 μg/mL, from about 30 μg/mL to about 50 μg/mL, from about 50 μg/mL to about 200 μg/mL, from about 80 μg/mL to about 200 μg/mL, from about 100 μg/mL to about 200 μg/mL, or from about 150 μg/mL to about 200 μg/mL.

In some instances, vitamin C or its derivatives, analogs, metabolites, prodrugs, or pharmaceutically acceptable salts thereof is administered at a dose of about 0.1 μg/mL, 1 μg/mL, 5 μg/mL, 10 μg/mL, 15 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, 110 μg/mL, 120 μg/mL, 130 μg/mL, 140 μg/mL, 150 μg/mL, 160 μg/mL, 170 μg/mL, 180 μg/mL, 190 μg/mL, or about 200 μg/mL.

In some embodiments, a dose of vitamin C or its derivatives, analogs, metabolites, prodrugs, or pharmaceutically acceptable salts thereof greater than 200 μg/mL increases reactive oxidative species. In some cases, a dose of vitamin C or its derivatives, analogs, metabolites, prodrugs, or pharmaceutically acceptable salts thereof greater than 200 μg/mL leads to a methylation pattern that mimics the methylation pattern of a sample obtained from a third subject who is older in chronological age relative to the first subject. In some instances, the third subject is older in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Detection Methods

In some embodiments, a number of methods are utilized to measure, detect, determine, identify, and characterize the expression level and the methylation status/level of a gene or a epigenetic marker (i.e., a region/fragment of DNA or a region/fragment of genome DNA (e.g., CpG island-containing region/fragment)) in determining the biological age of a subject and the progression or regression of the biological age of the subject in the presence of a therapeutic agent.

In some instances, the expression level and/or the methylation profile is generated from a biological sample isolated from an individual. In some embodiments, the biological sample is a biopsy. In some instances, the biological sample is a tissue sample. In other instances, the biological sample is a cell-free biological sample. In other instances, the biological sample is a circulating tumor DNA sample. In one embodiment, the biological sample is a cell free biological sample containing circulating tumor DNA.

In some embodiments, an epigenetic marker (also referred herein as a marker) is obtained from a tissue sample. In some instances, a tissue corresponds to any cell(s). Different types of tissue correspond to different types of cells (e.g., liver, lung, blood, connective tissue, and the like), but also healthy cells vs. tumor cells or to tumor cells at various stages of neoplasia, or to displaced malignant tumor cells. In some embodiments, a tissue sample further encompasses a clinical sample, and also includes cells in culture, cell supernatants, organs, and the like. Samples also comprise fresh-frozen and/or formalin-fixed, paraffin-embedded tissue blocks, such as blocks prepared from clinical or pathological biopsies, prepared for pathological analysis or study by immunohistochemistry.

In some embodiments, an epigenetic marker is obtained from a liquid sample. In some embodiments, the liquid sample comprises blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In some embodiments, the biological fluid is blood, a blood derivative or a blood fraction, e.g., serum or plasma. In a specific embodiment, a sample comprises a blood sample. In another embodiment, a serum sample is used. In another embodiment, a sample comprises urine. In some embodiments, the liquid sample also encompasses a sample that has been manipulated in any way after their procurement, such as by centrifugation, filtration, precipitation, dialysis, chromatography, treatment with reagents, washed, or enriched for certain cell populations.

In some embodiments, an epigenetic marker is methylated or unmethylated in a normal sample (e.g., normal or control tissue without disease, or normal or control body fluid, stool, blood, serum, amniotic fluid), most importantly in healthy stool, blood, serum, amniotic fluid or other body fluid. In other embodiments, an epigenetic marker is hypomethylated or hypermethylated in a sample from a patient having or at risk of a disease (e.g., one or more indications described herein); for example, at a decreased or increased (respectively) methylation frequency of at least about 50%, at least about 60%, at least about 70%, at least about 75%, at least about 80%, at least about 85%, at least about 90%, at least about 95%, or about 100% in comparison to a normal sample. In one embodiment, a sample is also hypomethylated or hypermethylated in comparison to a previously obtained sample analysis of the same patient having or at risk of a disease (e.g., one or more indications described herein), particularly to compare progression of a disease.

In some embodiments, a methylome comprises a set of epigenetic markers, such as an epigenetic marker described above. In some instances, a methylome that corresponds to the methylome of a tumor of an organism (e.g., a human) is classified as a tumor methylome. In some cases, a tumor methylome is determined using tumor tissue or cell-free (or protein-free) tumor DNA in a biological sample. Other examples of methylomes of interest include the methylomes of organs that contribute DNA into a bodily fluid (e.g. methylomes of tissue such as brain, breast, lung, the prostrate and the kidneys, plasma, etc.).

In some embodiments, a plasma methylome is the methylome determined from the plasma or serum of an animal (e.g., a human). In some instances, the plasma methylome is an example of a cell-free or protein-free methylome since plasma and serum include cell-free DNA. The plasma methylome is also an example of a mixed methylome since it is a mixture of tumor and other methylomes of interest. In some instances, the urine methylome is determined from the urine sample of a subject. In some cases, a cellular methylome corresponds to the methylome determined from cells (e.g., tissue cells from an organ such as brain, lung, breast and the like) of the patient. The methylome of the blood cells is called the blood cell methylome (or blood methylome).

In some embodiments, DNA (e.g., genomic DNA such as extracted genomic DNA or treated genomic DNA) is isolated by any means standard in the art, including the use of commercially available kits. Briefly, wherein the DNA of interest is encapsulated in by a cellular membrane the biological sample is disrupted and lysed by enzymatic, chemical or mechanical means. In some cases, the DNA solution is then cleared of proteins and other contaminants e.g. by digestion with proteinase K. The DNA is then recovered from the solution. In such cases, this is carried out by means of a variety of methods including salting out, organic extraction or binding of the DNA to a solid phase support. In some instances, the choice of method is affected by several factors including time, expense and required quantity of DNA.

Wherein the sample DNA is not enclosed in a membrane (e.g. circulating DNA from a cell free sample such as blood or urine) methods standard in the art for the isolation and/or purification of DNA are optionally employed (See, for example, Bettegowda et al. Detection of Circulating Tumor DNA in Early- and Late-Stage Human Malignancies. Sci. Transl. Med, 6(224): ra24. 2014). Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. In some cases, the person skilled in the art also make use of devices such as filter devices e.g. ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

In some instances, once the nucleic acids have been extracted, methylation analysis is carried out by any means known in the art. A variety of methylation analysis procedures are known in the art and may be used to practice the methods disclosed herein. These assays allow for determination of the methylation state of one or a plurality of CpG sites within a tissue sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes. The second major step involves (i) amplification and detection, or (ii) direct detection, by a variety of methods such as (a) PCR (sequence-specific amplification) such as Taqman®, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, Nucl. Acids Res. 24:5058-5059), or COBRA (Combined Bisulfite Restriction Analysis) (Xiong and Laird, 1997, Nucleic Acids Res. 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Frommer et al, 1992, Proc. Nat. Acad. Sci. USA, 89, 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfo nation buffer; DNA recovery reagents or kits (e.g., precipitation, ultrafiltration, affinity column); desulfonation buffer; and DNA recovery components.

In an embodiment, the methylation profile of selected CpG sites is determined using methylation-Specific PCR (MSP). MSP allows for assessing the methylation status of virtually any group of CpG sites within a CpG island, independent of the use of methylation-sensitive restriction enzymes (Herman et al, 1996, Proc. Nat. Acad. Sci. USA, 93, 9821-9826; U.S. Pat. Nos. 5,786,146, 6,017,704, 6,200,756, 6,265,171 (Herman and Baylin); U.S. Pat. Pub. No. 2010/0144836 (Van Engeland et al)). Briefly, DNA is modified by a deaminating agent such as sodium bisulfite to convert unmethylated, but not methylated cytosines to uracil, and subsequently amplified with primers specific for methylated versus unmethylated DNA. In some instances, typical reagents (e.g., as might be found in a typical MSP-based kit) for MSP analysis include, but are not limited to: methylated and unmethylated PCR primers for specific gene (or methylation-altered DNA sequence or CpG island), optimized PCR buffers and deoxynucleotides, and specific probes. The ColoSure™ test is a commercially available test for colon cancer based on the MSP technology and measurement of methylation of the vimentin gene (Itzkowitz et al, 2007, Clin Gastroenterol. Hepatol. 5(1), 111-117). Alternatively, one may use quantitative multiplexed methylation specific PCR (QM-PCR), as described by Fackler et al. Fackler et al, 2004, Cancer Res. 64(13) 4442-4452; or Fackler et al, 2006, Clin. Cancer Res. 12(11 Pt 1) 3306-3310.

In an embodiment, the methylation profile of selected CpG sites is determined using MethyLight and/or Heavy Methyl Methods. The MethyLight and Heavy Methyl assays are a high-throughput quantitative methylation assay that utilizes fluorescence-based real-time PCR (Taq Man®) technology that requires no further manipulations after the PCR step (Eads, C. A. et al, 2000, Nucleic Acid Res. 28, e 32; Cottrell et al, 2007, J. Urology 177, 1753, U.S. Pat. No. 6,331,393 (Laird et al)). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. In some cases, sequence discrimination occurs either at the level of the amplification process or at the level of the fluorescence detection process, or both. In some cases, the MethyLight assay is used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites. Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase. The MethyLight technology is used for the commercially available tests for lung cancer (epi proLung BL Reflex Assay); colon cancer (epi proColon assay and mSEPT9 assay) (Epigenomics, Berlin, Germany) PCT Pub. No. WO 2003/064701 (Schweikhardt and Sledziewski).

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, Nuc. Acids Res. 32:e10).

The Ms-SNuPE technique is a quantitative method for assessing methylation differences at specific CpG sites based on bisulfite treatment of DNA, followed by single-nucleotide primer extension (Gonzalgo and Jones, 1997, Nucleic Acids Res. 25, 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. In some cases, small amounts of DNA are analyzed (e.g., microdissected pathology sections), and the method avoids utilization of restriction enzymes for determining the methylation status at CpG sites. Typical reagents (e.g., as is found in a typical Ms-SNuPE-based kit) for Ms-SNuPE analysis include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfate conversion reagents may include: DNA denaturation buffer; sulfonation buffer; DNA recovery regents or kit (e.g., precipitation, ultrafiltration, affinity column); desulfonation buffer; and DNA recovery components.

In another embodiment, the methylation status of selected CpG sites is determined using differential Binding-based Methylation Detection Methods. For identification of differentially methylated regions, one approach is to capture methylated DNA. This approach uses a protein, in which the methyl binding domain of MBD2 is fused to the Fc fragment of an antibody (MBD-FC) (Gebhard et al, 2006, Cancer Res. 66:6118-6128; and PCT Pub. No. WO 2006/056480 A2 (Relhi)). This fusion protein has several advantages over conventional methylation specific antibodies. The MBD FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC, on the other hand, binds DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard et al, 2006, Nucleic Acids Res. 34: e82). Consequently this method, called Methyl-CpG immunoprecipitation (MCIP), not only enriches, but also fractionates genomic DNA according to methylation level, which is particularly helpful when the unmethylated DNA fraction should be investigated as well.

In an alternative embodiment, a 5-methyl cytidine antibody to bind and precipitate methylated DNA. Antibodies are available from Abeam (Cambridge, Mass.), Diagenode (Sparta, N.J.) or Eurogentec (c/o AnaSpec, Fremont, Calif.). Once the methylated fragments have been separated they may be sequenced using microarray based techniques such as methylated CpG-island recovery assay (MIRA) or methylated DNA immunoprecipitation (MeDIP) (Pelizzola et al, 2008, Genome Res. 18, 1652-1659; O'Geen et al, 2006, BioTechniques 41(5), 577-580, Weber et al, 2005, Nat. Genet. 37, 853-862; Horak and Snyder, 2002, Methods Enzymol, 350, 469-83; Lieb, 2003, Methods Mol Biol, 224, 99-109). Another technique is methyl-CpG binding domain column/segregation of partly melted molecules (MBD/SPM, Shiraishi et al, 1999, Proc. Natl. Acad. Sci. USA 96(6):2913-2918).

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. No. 7,910,296; U.S. Pat. No. 7,901,880; and U.S. Pat. No. 7,459,274. In some embodiments, amplification can be performed using primers that are gene specific.

For example, there are methyl-sensitive enzymes that preferentially or substantially cleave or digest at their DNA recognition sequence if it is non-methylated. Thus, an unmethylated DNA sample is cut into smaller fragments than a methylated DNA sample. Similarly, a hypermethylated DNA sample is not cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, HpaII, HhaI, MaeII, BstUI and AciI. In some instances, an enzyme that is used is HpaII that cuts only the unmethylated sequence CCGG. In other instances, another enzyme that is used is HhaI that cuts only the unmethylated sequence GCGC. Both enzymes are available from New England BioLabs®, Inc. Combinations of two or more methyl-sensitive enzymes that digest only unmethylated DNA are also used. Suitable enzymes that digest only methylated DNA include, but are not limited to, DpnI, which only cuts at fully methylated 5'-GATC sequences, and McrBC, an endonuclease, which cuts DNA containing modified cytosines (5-methylcytosine or 5-hydroxymethylcytosine or N4-methylcytosine) and cuts at recognition site 5' . . . PumC(N4o-3ooo) PumC . . . 3' (New England BioLabs, Inc., Beverly, Mass.). Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al. Molecular Biology: A Laboratory Approach, Cold Spring Harbor, N.Y. 1989) provide a general description of methods for using restriction enzymes and other enzymes.

In some instances, a methylation-dependent restriction enzyme is a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use with one or more methods described herein.

In some cases, a methylation-sensitive restriction enzyme is a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al, 22(17) NUCLEIC ACIDS RES. 3640-59 (1994). Suitable methylation-sensitive restriction enzymes that do not cleave DNA at or near their recognition sequence when a cytosine within the recognition sequence is methylated at position C5 include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinPl I, HinC II, Hpa II, Hpy99 I, HpyCH4 IV, Kas I, Mbo I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position N6 include, e.g., Mbo I. One of skill in the art will appreciate that any methylation-sensitive restriction enzyme, including homologs and orthologs of the restriction enzymes described herein, is also suitable for use with one or more of the methods described herein. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

In alternative embodiments, adaptors are optionally added to the ends of the randomly fragmented DNA, the DNA is then digested with a methylation-dependent or methylation-sensitive restriction enzyme, and intact DNA is subsequently amplified using primers that hybridize to the adaptor sequences. In this case, a second step is performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

In some instances, the quantity of methylation of a locus of DNA is determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

The methylated CpG island amplification (MCA) technique is a method that can be used to screen for altered methylation patterns in genomic DNA, and to isolate specific sequences associated with these changes (Toyota et al, 1999, Cancer Res. 59, 2307-2312, U.S. Pat. No. 7,700,324 (Issa et al)). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Additional methylation detection methods include those methods described in, e.g., U.S. Pat. No. 7,553,627; U.S. Pat. No. 6,331,393; U.S. patent Ser. No. 12/476,981; U.S. Patent Publication No. 2005/0069879; Rein, et al, 26(10) NUCLEIC ACIDS RES. 2255-64 (1998); and Olek et al, 17(3) NAT. GENET. 275-6 (1997).

In another embodiment, the methylation status of selected CpG sites is determined using Methylation-Sensitive High Resolution Melting (HRM). Recently, Wojdacz et al. reported methylation-sensitive high resolution melting as a technique to assess methylation. (Wojdacz and Dobrovic, 2007, Nuc. Acids Res. 35(6) e41; Wojdacz et al. 2008, Nat.

Prot. 3(12) 1903-1908; Balic et al, 2009 J. Mol. Diagn. 11 102-108; and US Pat. Pub. No. 2009/0155791 (Wojdacz et al)). A variety of commercially available real time PCR machines have HRM systems including the Roche Light-Cycler480, Corbett Research RotorGene6000, and the Applied Biosystems 7500. HRM may also be combined with other amplification techniques such as pyrosequencing as described by Candiloro et al. (Candiloro et al, 2011, Epigenetics 6(4) 500-507).

In another embodiment, the methylation status of selected CpG locus is determined using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al). For methylation analysis, the assay can be adopted to detect bisulfate introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Other methods for DNA methylation analysis include restriction landmark genomic scanning (RLGS, Costello et al, 2002, Meth. Mol Biol, 200, 53-70), methylation-sensitive-representational difference analysis (MS-RDA, Ushijima and Yamashita, 2009, Methods Mol Biol 507, 1 17-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al, 2009, Genome Res., 19, 1462-1470; Acevedo et al, 2008, Cancer Res., 68, 2641-2651; Rauch et al, 2008, Proc. Nat. Acad. Sci. USA, 105, 252-257). Others have reported bisulfate conversion, padlock probe hybridization, circularization, amplification and next generation or multiplexed sequencing for high throughput detection of methylation (Deng et al, 2009, Nat. Biotechnol 27, 353-360; Ball et al, 2009, Nat. Biotechnol 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyro sequencing (WO 2009/049916 (Bayeyt et al).

In some instances, quantitative amplification methods (e.g., quantitative PCR or quantitative linear amplification) are used to quantify the amount of intact DNA within a locus flanked by amplification primers following restriction digestion. Methods of quantitative amplification are disclosed in, e.g., U.S. Pat. No. 6,180,349; U.S. Pat. No. 6,033,854; and U.S. Pat. No. 5,972,602, as well as in, e.g., DeGraves, et al, 34(1) BIOTECHNIQUES 106-15 (2003); Deiman B, et al., 20(2) MOL. BIOTECHNOL. 163-79 (2002); and Gibson et al, 6 GENOME RESEARCH 995-1001 (1996).

Following reaction or separation of nucleic acid in a methylation specific manner, the nucleic acid in some cases are subjected to sequence-based analysis. For example, once it is determined that one particular genomic sequence from an aged sample is hypermethylated or hypomethylated compared to its counterpart, the amount of this genomic sequence can be determined. Subsequently, this amount can be compared to a standard control value and used to determine the biological age of the sample. In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits may use any nucleic acid amplification or detection methods known to one skilled in the art, such as those described in U.S. Pat. No. 5,525,462 (Takarada et al); U.S. Pat. No. 6,114,117 (Hepp et al); U.S. Pat. No. 6,127,120 (Graham et al); U.S. Pat. No. 6,344,317 (Urnovitz); U.S. Pat. No. 6,448,001 (Oku); U.S. Pat. No. 6,528,632 (Catanzariti et al); and PCT Pub. No. WO 2005/111209 (Nakajima et al).

In some embodiments, the nucleic acids are amplified by PCR amplification using methodologies known to one skilled in the art. One skilled in the art will recognize, however, that amplification can be accomplished by any known method, such as ligase chain reaction (LCR), Q-replicas amplification, rolling circle amplification, transcription amplification, self-sustained sequence replication, nucleic acid sequence-based amplification (NASBA), each of which provides sufficient amplification. Branched-DNA technology is also optionally used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, Adv. Clin. Chem. 33:201-235).

The PCR process is well known in the art and include, for example, reverse transcription PCR, ligation mediated PCR, digital PCR (dPCR), or droplet digital PCR (ddPCR). For a review of PCR methods and protocols, see, e.g., Innis et al, eds., PCR Protocols, A Guide to Methods and Application, Academic Press, Inc., San Diego, Calif. 1990; U.S. Pat. No. 4,683,202 (Mullis). PCR reagents and protocols are also available from commercial vendors, such as Roche Molecular Systems. In some instances, PCR is carried out as an automated process with a thermostable enzyme. In this process, the temperature of the reaction mixture is cycled through a denaturing region, a primer annealing region, and an extension reaction region automatically. Machines specifically adapted for this purpose are commercially available.

In some embodiments, amplified sequences are also measured using invasive cleavage reactions such as the Invader® technology (Zou et al, 2010, Association of Clinical Chemistry (AACC) poster presentation on Jul. 28, 2010, "Sensitive Quantification of Methylated Markers with a Novel Methylation Specific Technology; and U.S. Pat. No. 7,011,944 (Prudent et al)).

Suitable next generation sequencing technologies are widely available. Examples include the 454 Life Sciences platform (Roche, Branford, Conn.) (Margulies et al. 2005 Nature, 437, 376-380); lllumina's Genome Analyzer, GoldenGate Methylation Assay, or Infinium Methylation Assays, i.e., Infinium HumanMethylation 27K BeadArray or Vera-Code GoldenGate methylation array (Illumina, San Diego, Calif.; Bibkova et al, 2006, Genome Res. 16, 383-393; U.S. Pat. Nos. 6,306,597 and 7,598,035 (Macevicz); U.S. Pat. No. 7,232,656 (Balasubramanian et al.)); QX200™ Droplet Digital™ PCR System from Bio-Rad; or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453 (Barany et al); the Helicos True Single Molecule DNA sequencing technology (Harris et al, 2008 Science, 320, 106-109; U.S. Pat. Nos. 7,037,687 and 7,645,596 (Williams et al); 7,169,560 (Lapidus et al); U.S. Pat. No. 7,769,400 (Harris)), the single molecule, real-time (SMRT™) technology of Pacific Biosciences, and sequencing (Soni and Meller, 2007, Clin. Chem. 53, 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). These systems allow the sequencing of many nucleic acid molecules isolated from a specimen at high orders of multiplexing in a parallel fashion. Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, Nat. Prot. 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al, 2003, J. Biotech. 102, 117-124). Such a system can be used to exponentially amplify amplification products generated by a process described herein, e.g., by ligating a heterologous nucleic acid to the first amplification product generated by a process described herein.

CpG Methylation Data Analysis Methods

In certain embodiments, the methylation values measured for markers of an epigenetic marker panel are mathematically combined and the combined value is correlated to the underlying diagnostic question. In some instances, methylated marker values are combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate an epigenetic marker or marker combination described herein. In one embodiment, the method used in a correlating methylation status of an epigenetic marker or marker combination, e.g. to diagnose a cancer or an aging-related disease or disorder, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. O., Pattern Classification, Wiley Interscience, 2nd Edition (2001).

In one embodiment, the correlated results for each methylation panel are rated by their correlation to the disease or tumor type positive state, such as for example, by p-value test or t-value test or F-test. Rated (best first, i.e. low p- or t-value) markers are then subsequently selected and added to the methylation panel until a certain diagnostic value is reached. Such methods include identification of methylation panels, or more broadly, genes that were differentially methylated among several classes using, for example, a random-variance t-test (Wright G. W. and Simon R, Bioinformatics 19:2448-2455, 2003). Other methods include the step of specifying a significance level to be used for determining the epigenetic markers that will be included in the marker panel. Epigenetic markers that are differentially methylated between the classes at a univariate parametric significance level less than the specified threshold are included in the panel. It doesn't matter whether the specified significance level is small enough to exclude enough false discoveries. In some problems better prediction is achieved by being more liberal about the marker panels used as features. In some cases, the panels are biologically interpretable and clinically applicable, however, if fewer markers are included. Similar to cross-validation, marker selection is repeated for each training set created in the cross-validation process. That is for the purpose of providing an unbiased estimate of prediction error. The methylation panel for use with new patient sample data is the one resulting from application of the methylation selection and classifier of the "known" methylation information, or control methylation panel.

In some embodiments, models for utilizing methylation profile to predict the class of future samples are also used. In some cases, these models are based on the Compound Covariate Predictor (Radmacher et al. Journal of Computational Biology 9:505-511, 2002), Diagonal Linear Discriminant Analysis (Dudoit et al. Journal of the American Statistical Association 97:77-87, 2002), Nearest Neighbor Classification (also Dudoit et al.), and Support Vector Machines with linear kernel (Ramaswamy et al. PNAS USA 98:15149-54, 2001). The models incorporated markers that were differentially methylated at a given significance level (e.g. 0.01, 0.05 or 0.1) as assessed by the random variance t-test (Wright G. W. and Simon R. Bioinformatics 19:2448-2455, 2003). The prediction error of each model using cross validation, preferably leave-one-out cross-validation (Simon et al. Journal of the National Cancer Institute 95:14-18, 2003 is optionally estimated. For each leave-one-out cross-validation training set, the entire model building process is repeated, including the epigenetic marker selection process. It may also be evaluated whether the cross-validated error rate estimate for a model is significantly less than expected from random prediction. The class labels can be randomly permuted and the entire leave-one-out cross-validation process is then repeated. The significance level is the proportion of the random permutations that gives a cross-validated error rate no greater than the cross-validated error rate obtained with the real methylation data.

Another classification method is the greedy-pairs method described by Bo and Jonassen (Genome Biology 3(4): research0017.1-0017.11, 2002). The greedy-pairs approach starts with ranking all markers based on their individual t-scores on the training set. This method attempts to select pairs of markers that work well together to discriminate the classes.

Furthermore, a binary tree classifier for utilizing methylation profile can be used to predict the class of future samples. The first node of the tree incorporated a binary classifier that distinguished two subsets of the total set of classes. The individual binary classifiers are based on the "Support Vector Machines" incorporating markers that were differentially expressed among markers at the significance level (e.g. 0.01, 0.05 or 0.1) as assessed by the random variance t-test (Wright G. W. and Simon R. Bioinformatics 19:2448-2455, 2003). Classifiers for all possible binary partitions are evaluated and the partition selected is that for which the cross-validated prediction error is minimum. The process is then repeated successively for the two subsets of classes determined by the previous binary split. The prediction error of the binary tree classifier can be estimated by cross-validating the entire tree building process. This overall cross-validation includes re-selection of the optimal partitions at each node and re-selection of the markers used for each cross-validated training set as described by Simon et al. (Simon et al. Journal of the National Cancer Institute 95:14-18, 2003). Several-fold cross validation in which a fraction of the samples is withheld, a binary tree developed on the remaining samples, and then class membership is predicted for the samples withheld. This is repeated several times, each time withholding a different percentage of the samples. The samples are randomly partitioned into fractional test sets (Simon R and Lam A. BRB-ArrayTools User Guide, version 3.2. Biometric Research Branch, National Cancer Institute).

Thus, in one embodiment, the correlated results for each marker b) are rated by their correct correlation to the disease, preferably by p-value test. It is also possible to include a step in that the markers are selected d) in order of their rating.

In additional embodiments, factors such as the value, level, feature, characteristic, property, etc. of a transcription rate, mRNA level, translation rate, protein level, biological activity, cellular characteristic or property, genotype, phenotype, etc. can be utilized in addition prior to, during, or after administering a therapy to a patient to enable further analysis of the patient's cancer status.

In some embodiments, a diagnostic test to correctly predict status is measured as the sensitivity of the assay, the specificity of the assay or the area under a receiver operated characteristic ("ROC") curve. In some instances, sensitivity is the percentage of true positives that are predicted by a test to be positive, while specificity is the percentage of true negatives that are predicted by a test to be negative. In some cases, an ROC curve provides the sensitivity of a test as a function of 1-specificity. The greater the area under the ROC curve, for example, the more powerful the predictive value of the test. Other useful measures of the utility of a test include positive predictive value and negative predictive value. Positive predictive value is the percentage of people who test positive that are actually positive. Negative predictive value is the percentage of people who test negative that are actually negative.

In some embodiments, one or more of the epigenetic biomarkers disclosed herein show a statistical difference in different samples of at least $p<0.05$, $p<10^{-2}$, $p<10^{-3}$, $p<10^{4}$, or $p<10^{-5}$. Diagnostic tests that use these biomarkers may show an ROC of at least 0.6, at least about 0.7, at least about 0.8, or at least about 0.9. The biomarkers are differentially methylated in different subjects with different ages, and the biomarkers for each age range are differentially methylated, and, therefore, are useful in aiding in the determination of a subject's biological age (or bioage) and its correlation to chronological age. In certain embodiments, the biomarkers are measured in a patient sample using the methods described herein and compared, for example, to predefined biomarker levels and correlated to the patient's chronological age. In other embodiments, the correlation of a combination of biomarkers in a patient sample is compared, for example, to a predefined set of biomarkers. In some embodiments, the measurement(s) is then compared with a relevant diagnostic amount(s), cut-off(s), or multivariate model scores that distinguish between different biological ages. As is well understood in the art, by adjusting the particular diagnostic cut-off(s) used in an assay, one can increase sensitivity or specificity of the diagnostic assay depending on the preference of the diagnostician. In some embodiments, the particular diagnostic cut-off is determined, for example, by measuring the amount of biomarker hypermethylation or hypomethylation in a statistically significant number of samples from patients with different ages, and drawing the cut-off to suit the desired levels of specificity and sensitivity.

Kits/Article of Manufacture

In some embodiments, provided herein include kits for detecting and/or characterizing the expression level and/or methylation profile of an epigenetic marker described herein. In some instances, the kit comprises a plurality of primers or probes to detect or measure the methylation status/levels of one or more samples. Such kits comprise, in some instances, at least one polynucleotide that hybridizes to at least one of the methylation marker sequences described herein and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further comprise detectable labels, optionally linked to a polynucleotide, e.g., a probe, in the kit.

In some embodiments, the kits comprise one or more (e.g., 1, 2, 3, 4, or more) different polynucleotides (e.g., primers and/or probes) capable of specifically amplifying at least a portion of a DNA region of an epigenetic marker described herein. Optionally, one or more detectably-labeled polypeptides capable of hybridizing to the amplified portion are also included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfate.

In some embodiments, the kits comprise sodium bisulfate, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of an epigenetic marker described herein.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of an epigenetic marker described herein.

In some embodiments, the kits comprise a methylation binding moiety and one or more polynucleotides to quantify the number of copies of at least a portion of a DNA region of a marker described herein. A methylation binding moiety refers to a molecule (e.g., a polypeptide) that specifically binds to methyl-cytosine.

Examples include restriction enzymes or fragments thereof that lack DNA cutting activity but retain the ability to bind methylated DNA, antibodies that specifically bind to methylated DNA, etc.).

In some embodiments, the kit includes a packaging material. As used herein, the term "packaging material" can refer to a physical structure housing the components of the kit. In some instances, the packaging material maintains sterility of the kit components, and is made of material commonly used for such purposes (e.g., paper, corrugated fiber, glass, plastic, foil, ampules, etc.). Other materials useful in the performance of the assays are included in the kits, including test tubes, transfer pipettes, and the like. In some cases, the kits also include written instructions for the use of one or more of these reagents in any of the assays described herein.

In some embodiments, kits also include a buffering agent, a preservative, or a protein/nucleic acid stabilizing agent. In some cases, kits also include other components of a reaction mixture as described herein. For example, kits include one or more aliquots of thermostable DNA polymerase as described herein, and/or one or more aliquots of dNTPs. In some cases, kits also include control samples of known amounts of template DNA molecules harboring the individual alleles of a locus. In some embodiments, the kit includes a negative control sample, e.g., a sample that does not contain DNA molecules harboring the individual alleles of a locus. In some embodiments, the kit includes a positive control sample, e.g., a sample containing known amounts of one or more of the individual alleles of a locus.

Certain Terminology

Unless defined otherwise, all technical and scientific terms used herein have the same meaning as is commonly understood by one of skill in the art to which the claimed subject matter belongs. It is to be understood that the general description and the detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

A "site" corresponds to a single site, which in some cases is a single base position or a group of correlated base positions, e.g., a CpG site. A "locus" corresponds to a region that includes multiple sites. In some instances, a locus includes one site.

As used herein, the terms "biological age (bioage)," "chemical age," "methylomic age," and "molecular age" are equivalent or synonymous. The biological age is determined using a set of age-associated markers (e.g., epigenetic markers) of a subject or an organism. In the current disclosure, the biological age is determined from an analysis of the modification status of specific CpG dinucleotide and, in particular, e.g., the methylation status at the C-5 position of cytosine.

Chronological age is the actual age of a subject or organism. In some instances, for animals and humans, chronological age is based on the age calculated from the moment of conception or based on the age calculated from the time and date of birth. The chronological age of the cell, tissue or organ may be determined from the chronological age of the subject or organism from which the cell, tissue or organ is obtained, plus the duration of the cell, tissue or organ is placed in culture. Alternatively, in the case of cell or tissue culture, the chronological age may be related to the total or accumulative time in culture or passage number.

EXAMPLES

These examples are provided for illustrative purposes only and not to limit the scope of the claims provided herein.

Example 1. Effect of Vitamin C on Senescence and Proliferation in Human Fibroblasts The proliferation effects of vitamin C on WI38 fibroblasts were tested. This cell line is useful as an aging model since it is a mortal human cell line that follows the Hayflick limit, in that it undergoes a certain number of cell divisions before stopping. The senescence level in WI38 increased as the cell line divided. Vitamin C and its derivative were tested to determine whether they would increase the proliferation rate of fibroblast cells and upregulate an established age-related marker (ARM), e.g., ELOVL2, which was found to decrease with age in WI38 fibroblasts. A membrane-soluble derivative of vitamin C, 6-O-Palmitoyl-L-ascorbic acid (PalmAA), which has an additional fatty acid that allows it to pass through the cell membrane, was also tested. The oxidized derivative of vitamin C, dehydroascorbic acid (DHAA), as Vitamin C is actively converted to DHAA in cell culture media, was tested as well. Insulin was also added to this experiment to upregulate Glut-1 transporter, through which DHAA enters the cell.

Vitamin C induced a dose-dependent response on WI38 fibroblasts. Low concentrations of vitamin C (50 μg/mL to 100 μg/mL) induced fibroblast proliferation while higher concentrations of vitamin C (200 μg/mL to 500 μg/mL) slowed or inhibited fibroblast cell growth while causing cell death. Furthermore, the proliferative effect of 50 μg/mL vitamin C was more pronounced on older fibroblast cells compared to younger fibroblast cells. 6-O-Palmitoyl L-ascorbic acid, a derivative of vitamin C that is permeable to the cell membrane, induced minimal proliferation and caused no gene expression change in the age related marker. On the other hand, dehydroascorbic acid (DHAA), the oxidized form of vitamin C, induced lower cell proliferation compared to an equal concentration of vitamin C.

FIG. 1 shows phenotypic and genotypic effects of concentration dependent vitamin C treatment were analyzed on WI38 PD46 and 48 fibroblast cells. A) Cell images of 12-well plate treated with low concentration vitamin C at Day 0, 4 and 5 for PD46. B) Confluency plot calculated through ImageJ of PD46, n=2. C) and D) Expression graphs for ARM (e.g., ELOVL2) and SLC2A1 for PD46, n=3. E) Cell images of 12-well treated with high concentration vitamin C at Day 0, 4 and 5 for PD48. F) Confluency plot calculated through ImageJ of PD48, n=2. G) and I) Expression graphs for ARM and SLC2A1 for PD48, n=3.

FIG. 2 illustrates phenotypic and genotypic effects of vitamin C treatment were analyzed on younger WI38 PD42 and older WI38 PD58 fibroblasts. A) Cell images of 12-well at Day 0, 1 and 2 of treatment for PD42. B) Confluency plot calculated through ImageJ of PD42, n=2. C) and D) Expression graphs for ARM (e.g., ELOVL2) and SLC2A1 for PD42, n=3. E) Cell images of 12-well at Day 0, 5 and 7 of treatment for PD58. F) Confluency plot calculated through ImageJ of PD58, n=2. G) and H) Expression graphs for ARM (e.g., ELOVL2) and SLC2A1 for PD53, n=3. I) Cell images of senescence and DAPI staining of PD45.5 fibroblasts. J) Graph of percentage senescence for younger PD32 fibroblast and older PD45.5 fibroblast. n=3.

FIG. 3 shows phenotypic and genotypic effects of 6-O-Palmitoyl L-ascorbic acid treatment were analyzed on younger WI38 PD55 fibroblasts. A) Cell images of 12-well at Day 0 and Day 8 of treatment for PD55. B) Confluency plot calculated through ImageJ for PD55, n=2. C) and D) Expression graph for ARM (e.g., ELOVL2) and SLC2A1 for PD55, n=3.

FIG. 4 shows phenotypic and genotypic effects of dehydroascorbic acid and vitamin C treatment complemented with the addition of insulin were analyzed on WI38 PD54 fibroblast cells. A) Diagram of postulated pathway for interconversion of DHAA to vitamin C and their effect on fibroblast cells. B) Cell images of 12-well at Day 10 of treatment for PD54. C) Confluency plot calculated through ImageJ of PD54, n=2. D and E) Expression graphs for ARM (e.g., ELOVL2) and SLC2A1 for PD54, n=3. F) Graph of percentage senescence for younger PD32 fibroblast and older PD45.5 fibroblast. n=3. G) Fluorescent ROS assay showing fluorescent ROS relative to total fibroblasts in PD48 fibroblasts.

Example 2. Diabetes and Progeria Affect Biological Aging Rate

In some embodiments, it was shown that patients with diabetes or progeria have an accelerated biological aging rate.

Figures 5, 6A:
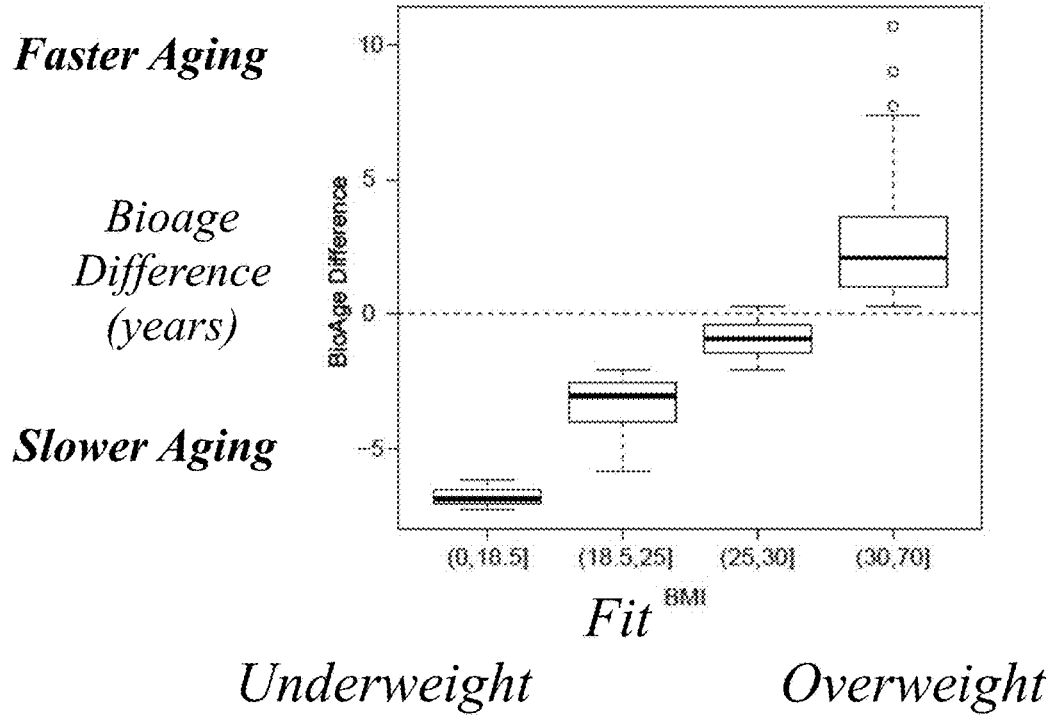
FIG. 5 illustrates that patients with diabetes have an older biological age than patients who do not have diabetes.
FIG. 6A-FIG. 6B show correlation of biological age with BMI and gender.

FIG. 5 illustrates that patients with diabetes have an older biological age than patients who do not have diabetes. In some instances, patients with type I diabetes (T1DM) are about 12% older in biological age than normal patients. In some cases, patients with type II diabetes (T2DM) are about 5% older in biological age than normal patients.

FIG. 6A illustrates the correlation of BMI with biological age. In some cases, as the BMI increases, the rate of increase in biological aging also increases.

Figure 6B:
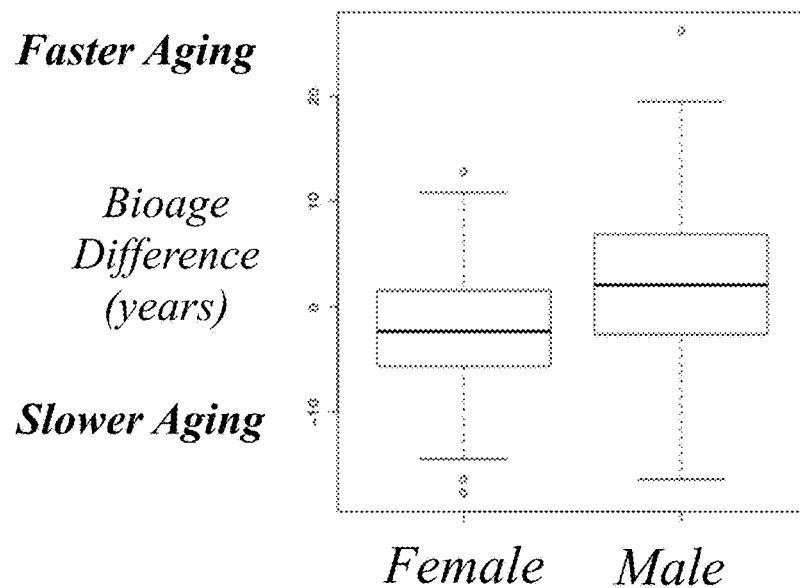

FIG. 6B illustrates the correlation of biological aging between male and female. In some cases, male is about 1% older in biological age than female.

Figures 7, 8:
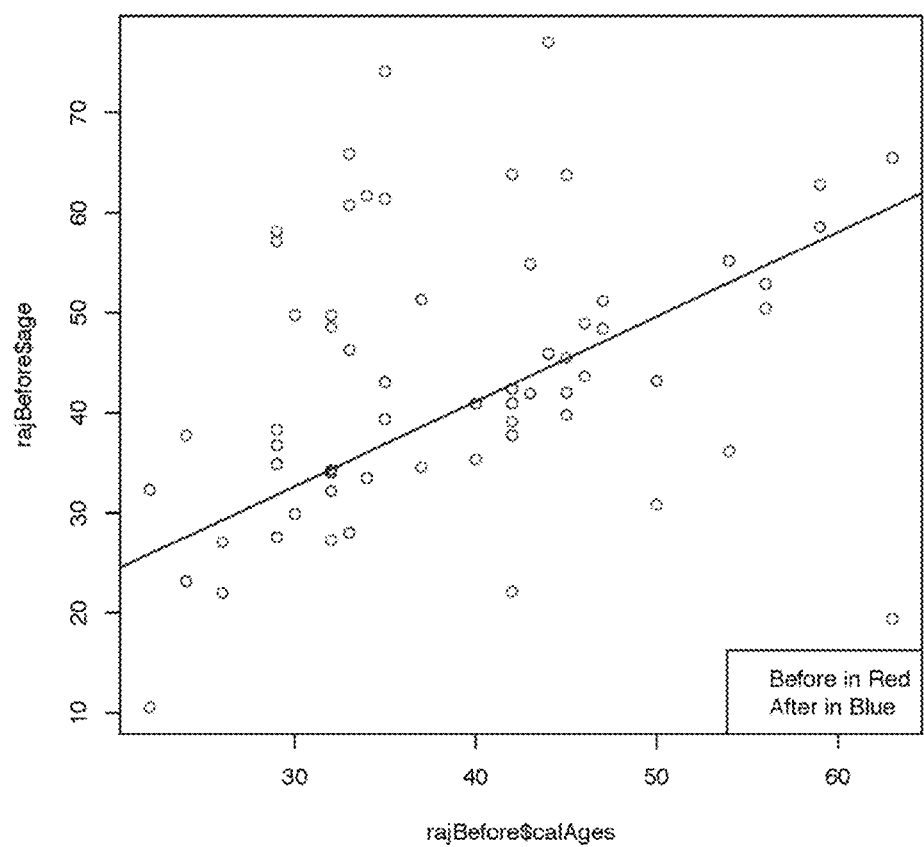
FIG. 7 shows biological age prediction using an exemplary 71 methylation markers in three progeria cell lines. Each biological age (bioage) is higher than chronological age.
FIG. 8 shows that external influences, such as diet and exercise, reverse biological age in a 6 month trial.

FIG. 7 shows biological age prediction using an exemplary 71 methylation markers in three progeria cell lines. Each biological age (bioage) is higher than chronological age.

Example 3. Environmental Factors Affect Biological Aging Rate

In some embodiments, it was shown that external influences such as environmental factors further modulates the biological aging rate.

FIG. 8 shows that external influences, such as diet and exercise, in some cases, reverses biological age in a 6 month trial. Additional external influences such as stress and/or pharmacologics further influences biological aging.

FIG. 9 shows an exemplary list of genes and CpG sites that are utilized for biological age prediction.

Figure 10:
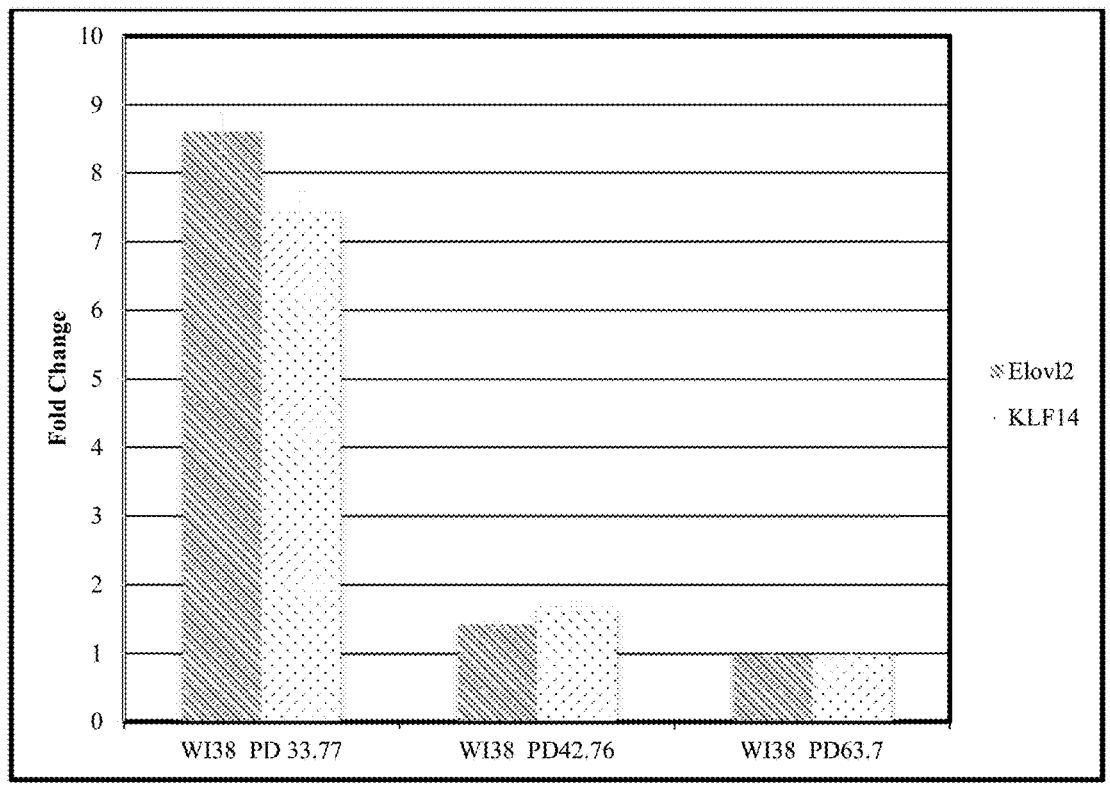
FIG. 10 shows a decrease in expression of ELOVL2 and KLF14 in older fibroblasts.

Example 4. Methylation Level and Expression Level of Epigenetic Markers ELOVL2 and KLF14 changes with age FIG. 10 shows a decrease in expression of ELOVL2 and KLF14 in older fibroblasts.

Figure 11A:
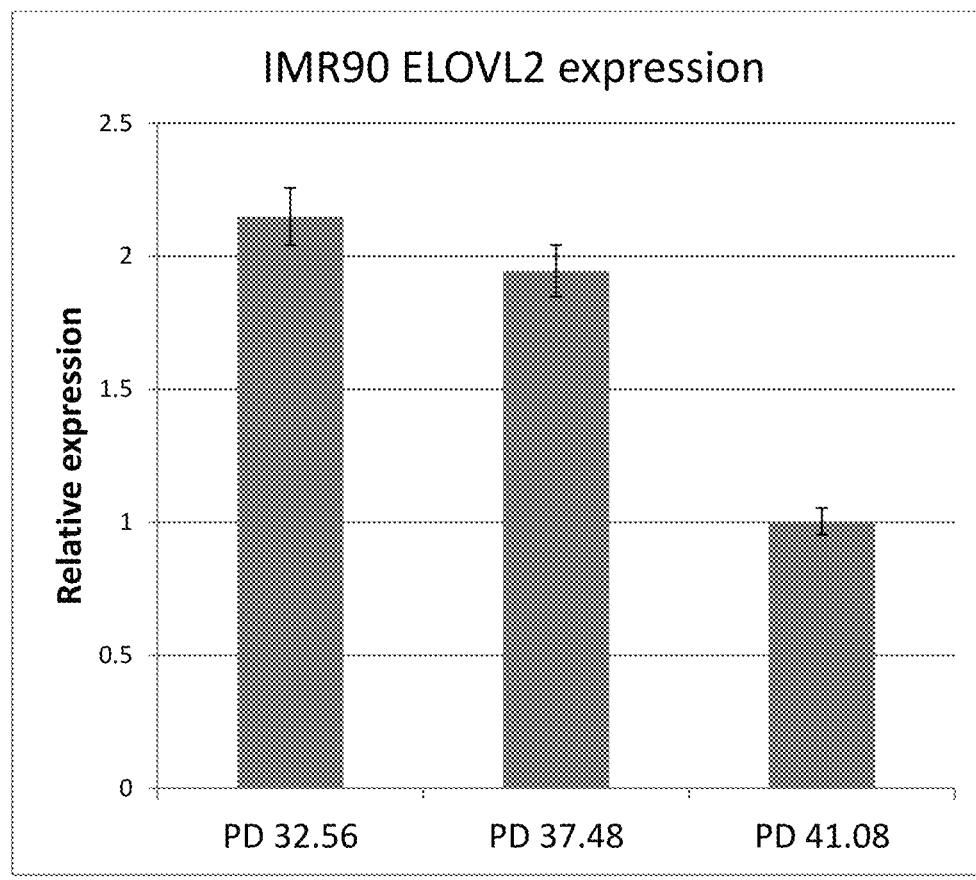
FIG. 11A-FIG. 11B show decrease in expression of ELOVL2 in cell line IMR90 (FIG. 11A) and cell line WI38 (FIG. 11B).
Figure 11B:
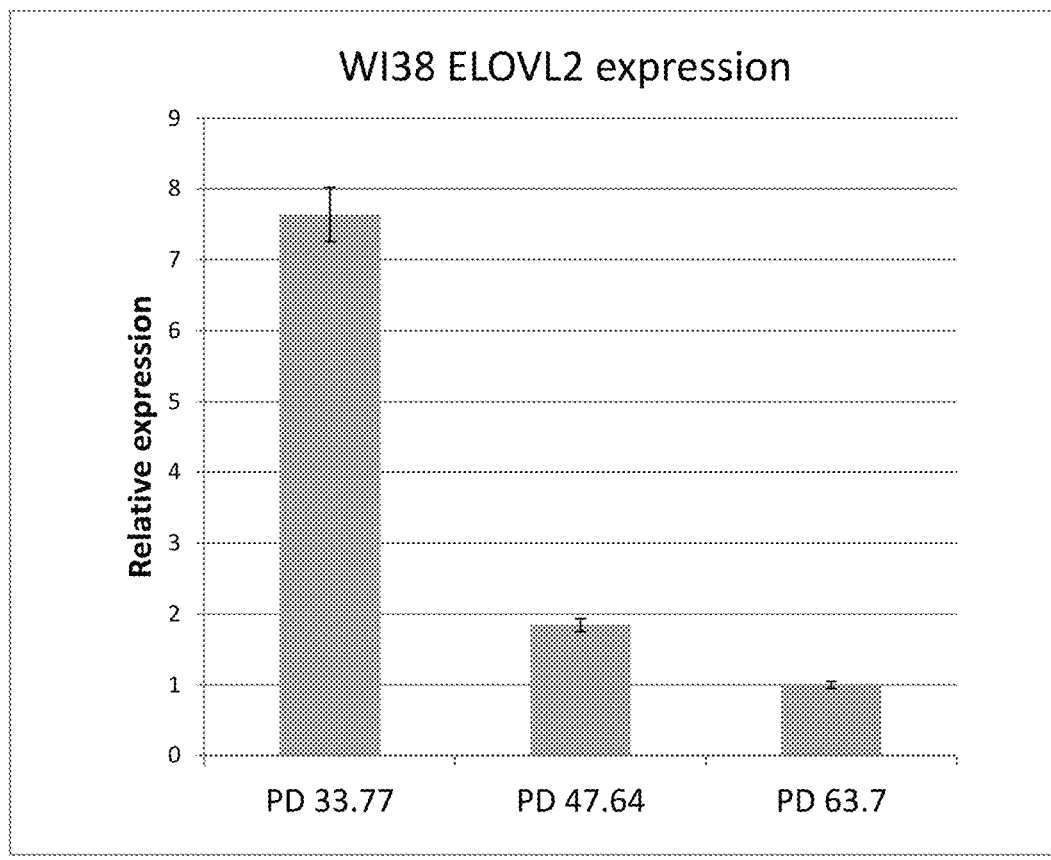

FIG. 11 shows a decrease in expression of ELOVL2 in cell line IMR90 (A) and cell line WI38 (B).

Figure 12A:
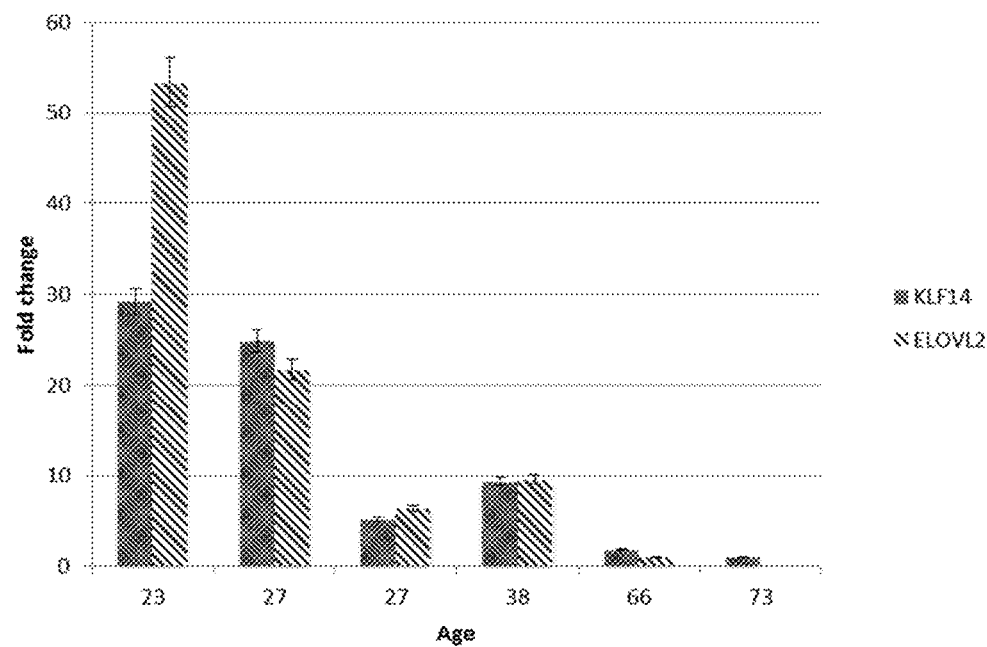
FIG. 12A-FIG. 12C show the expression level of ELOVL2 and KLF14 in human blood (FIG. 12A), a human fibroblast cell line WI38 (FIG. 12B), and human lens tissue (FIG. 12C).
Figure 12B:
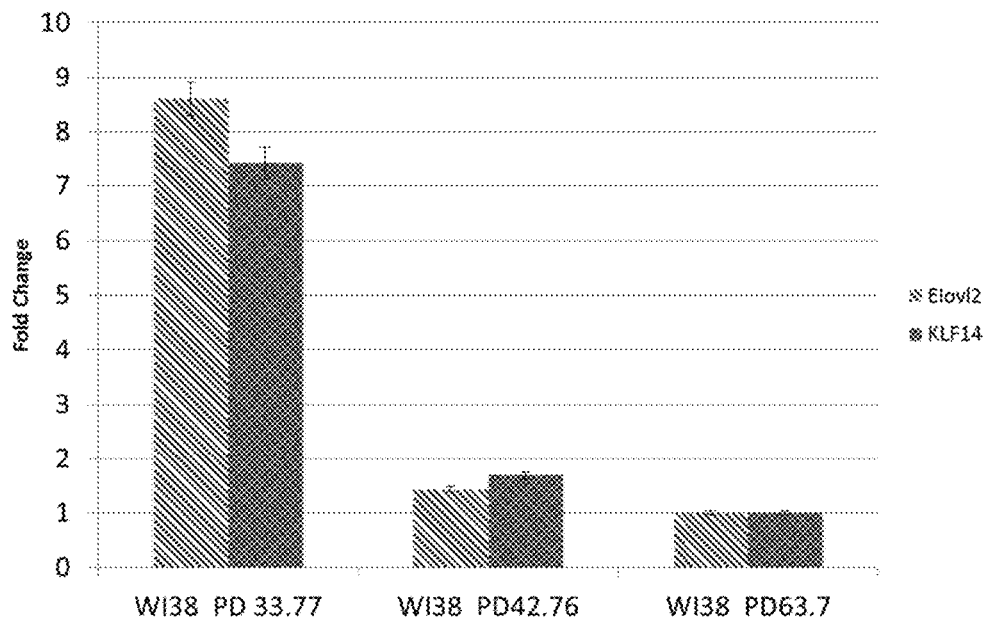
Figure 12C:
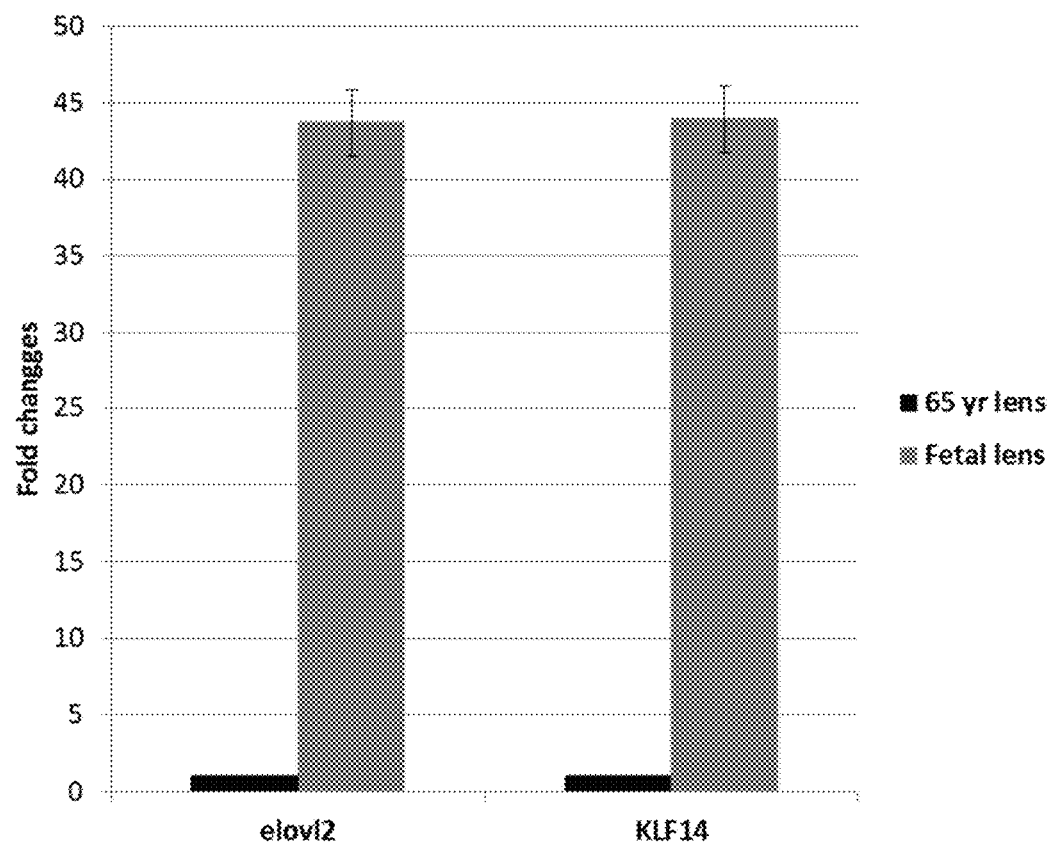

FIG. 12 shows the expression level of ELOVL2 and KLF14 in human blood (A), a human fibroblast cell line WI38 (B) and human lens tissue (C).

Figure 13:
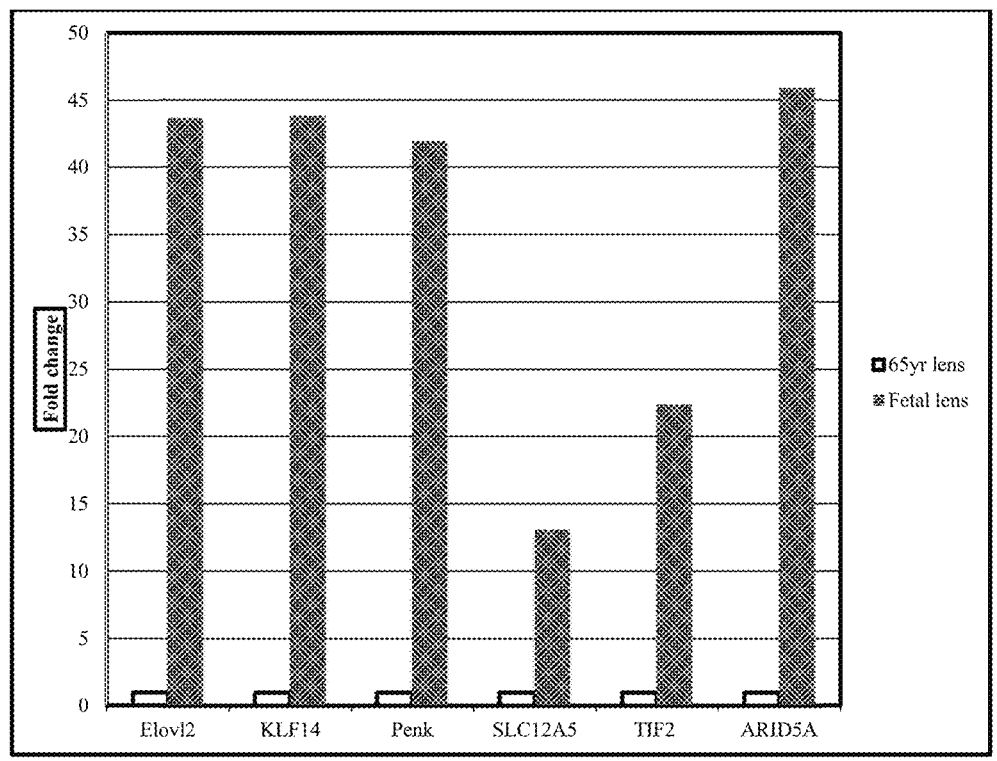
FIG. 13 shows the expression level of an exemplary list of genes.

FIG. 13 shows the expression level of an exemplary list of genes.

Figure 14B:
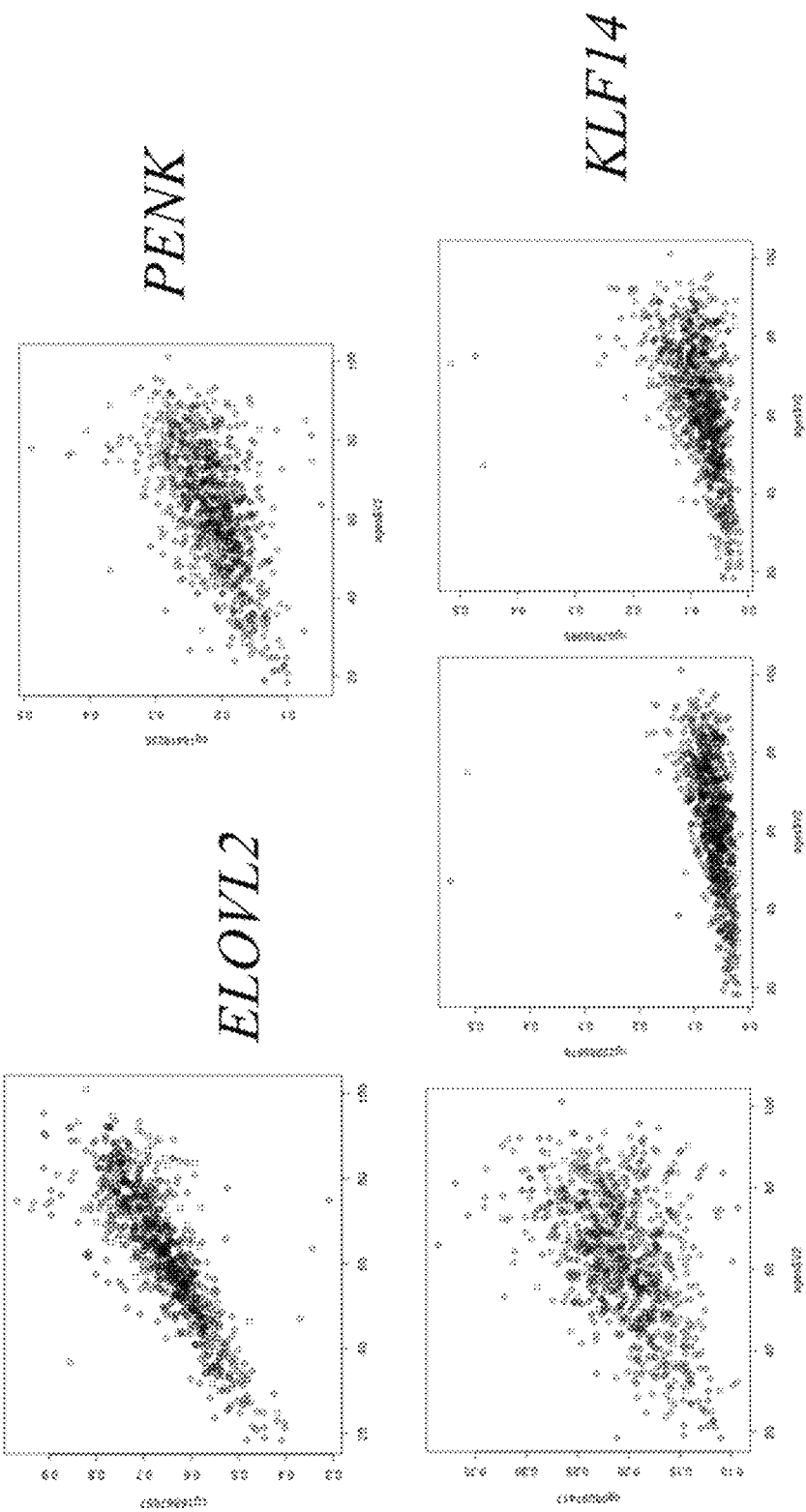

FIG. 14A-FIG. 14C shows the biological age (or methylation age) increases with age. FIG. 14A shows the biological age increases with cell line population doubling. FIG. 14B shows the increase in methylation level of ELOVL2, PENK, and KLF14. FIG. 14C shows the increase in methylation level of FHL2 and SMC4.

Figure 15:
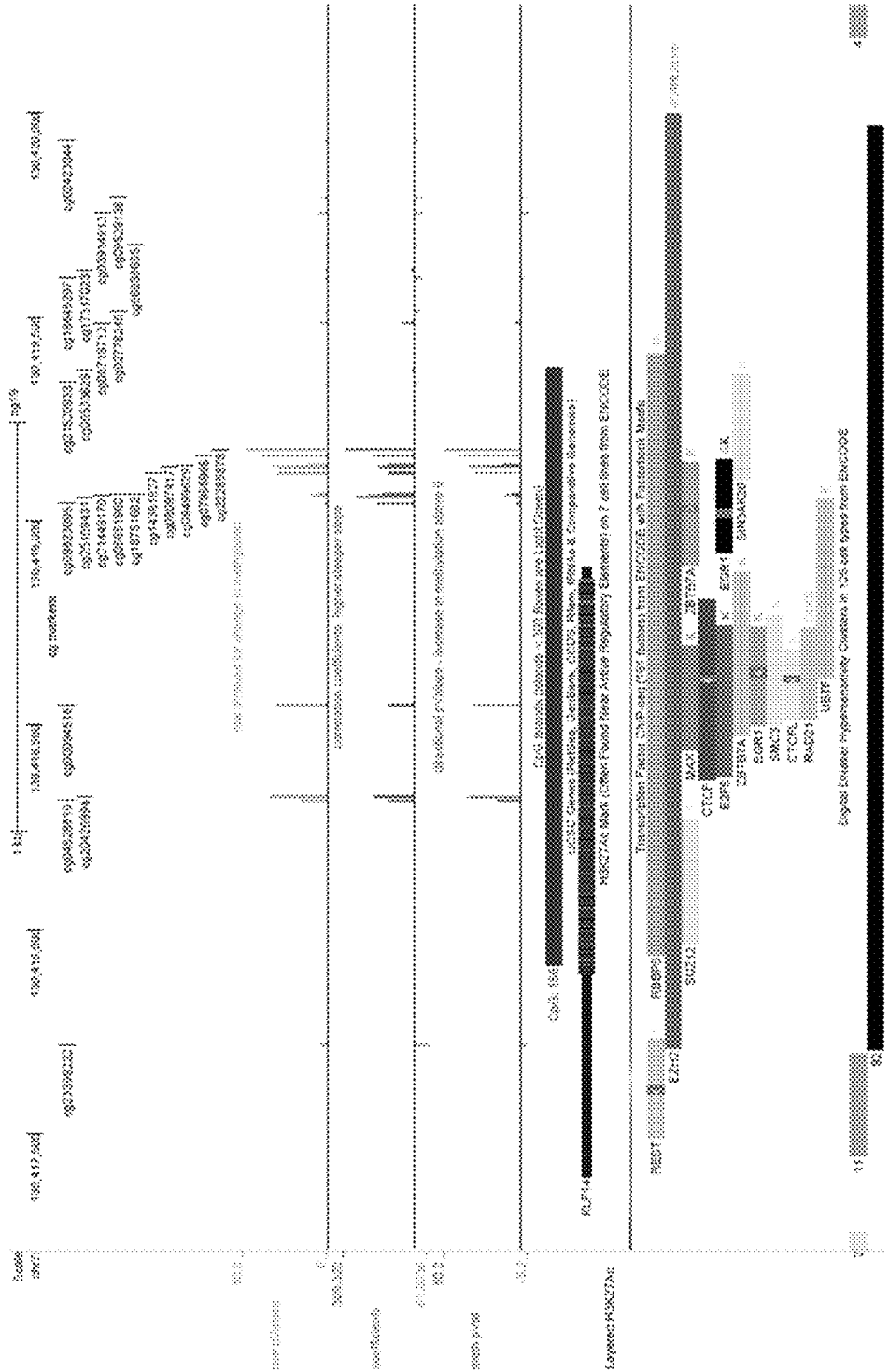
FIG. 15 shows human KLF14 locus showing methylation CpG islands.

FIG. 15 shows human KLF14 locus showing methylation CpG islands.

Figure 16:
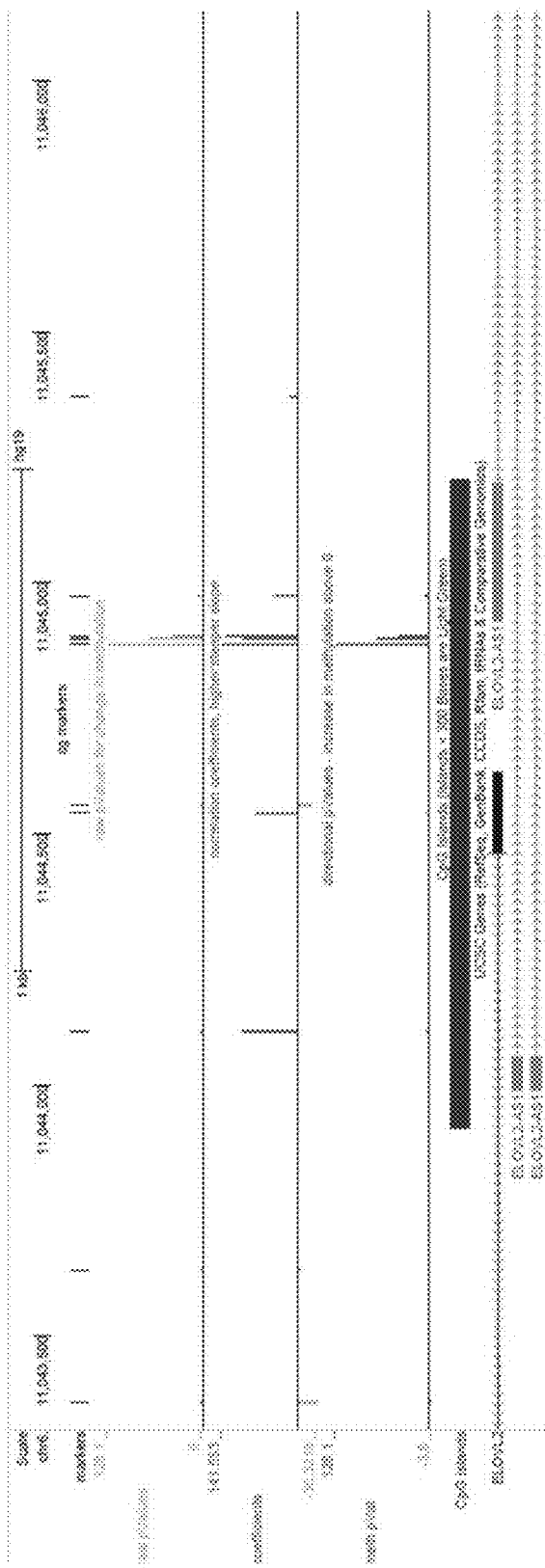
FIG. 16 shows human ELOVL2 locus showing methylation CpG islands.

FIG. 16 shows human ELOVL2 locus showing methylation CpG islands.

Figure 17A:
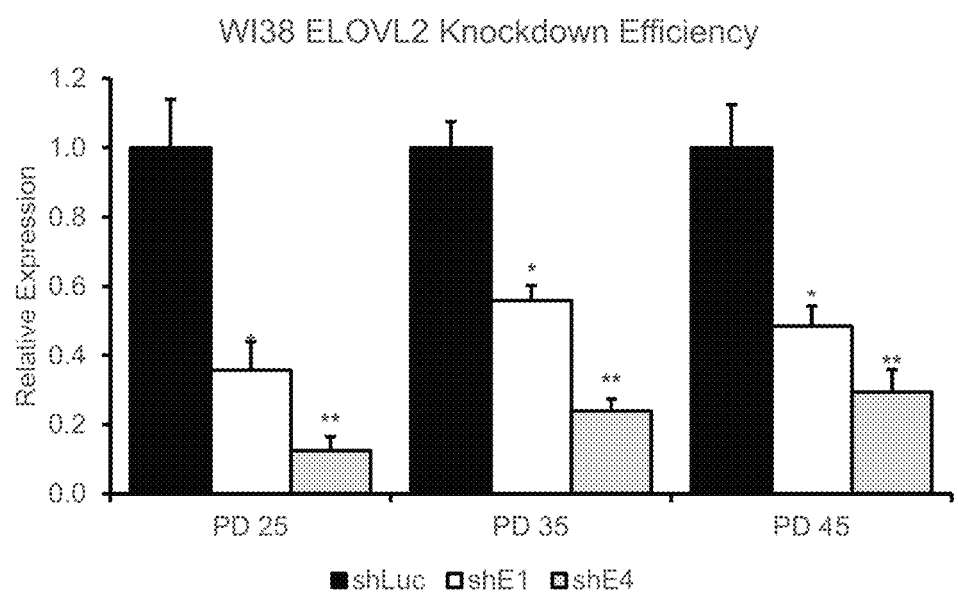
FIG. 17A-FIG. 17C show ELOVL2 knockdown efficiency in three cell lines: WI38 (FIG. 17A), IMR90 (FIG. 17B), and 293T (FIG. 17C).
Figure 17B:
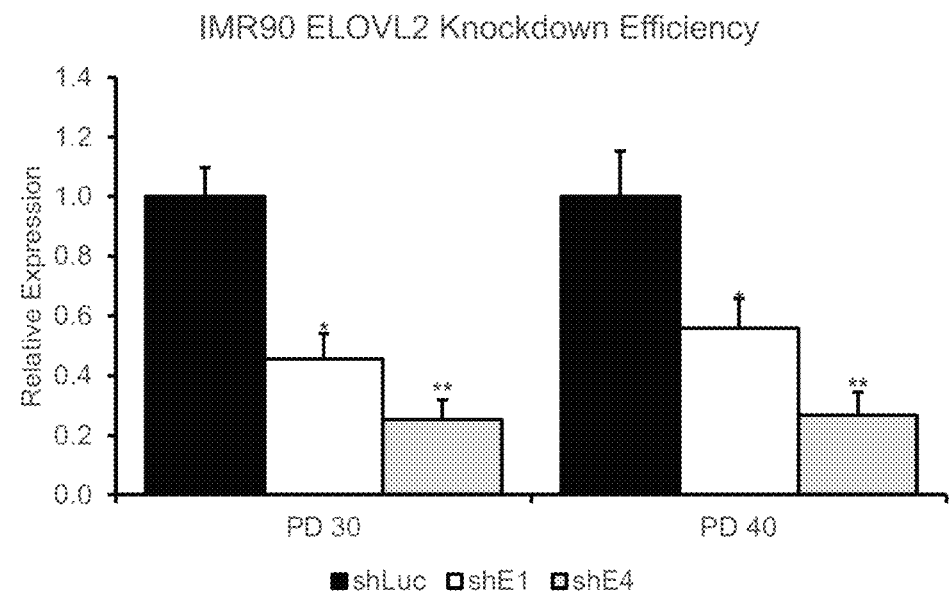
Figure 17C:
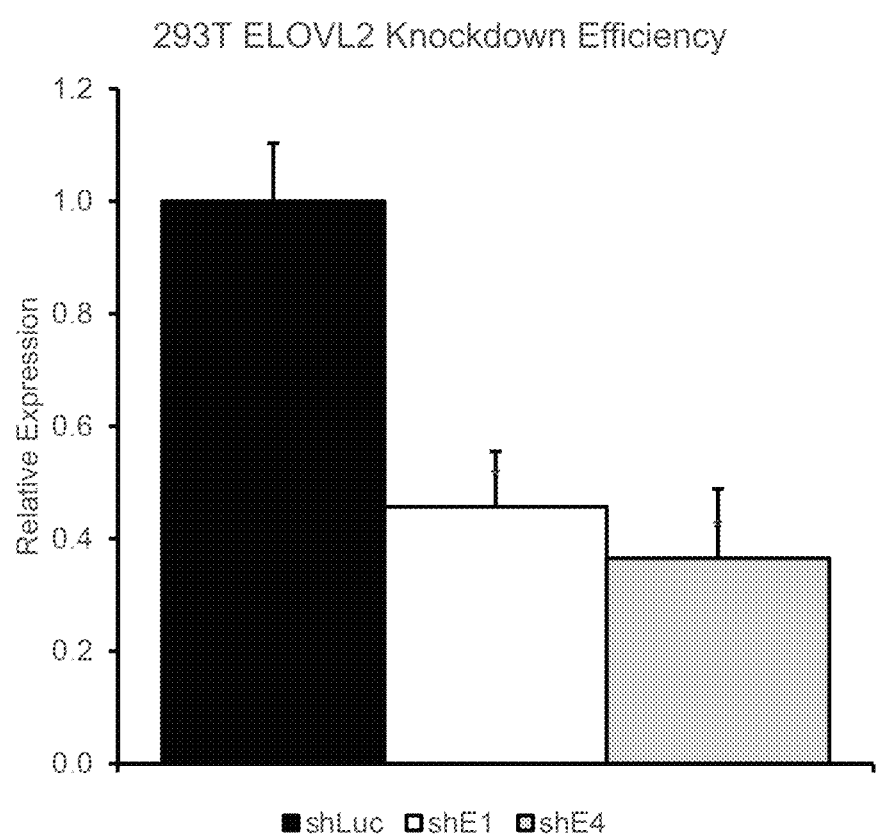

Example 5. Knockdown of KLF14 and ELOVL2 Increases Cellular Aging and Senescence and Reduces Cell Proliferation FIG. 17 shows ELOVL2 knockdown efficiency in three cell lines: WI38 (A), IMR90 (B), and 293T (C).

Figure 18B:
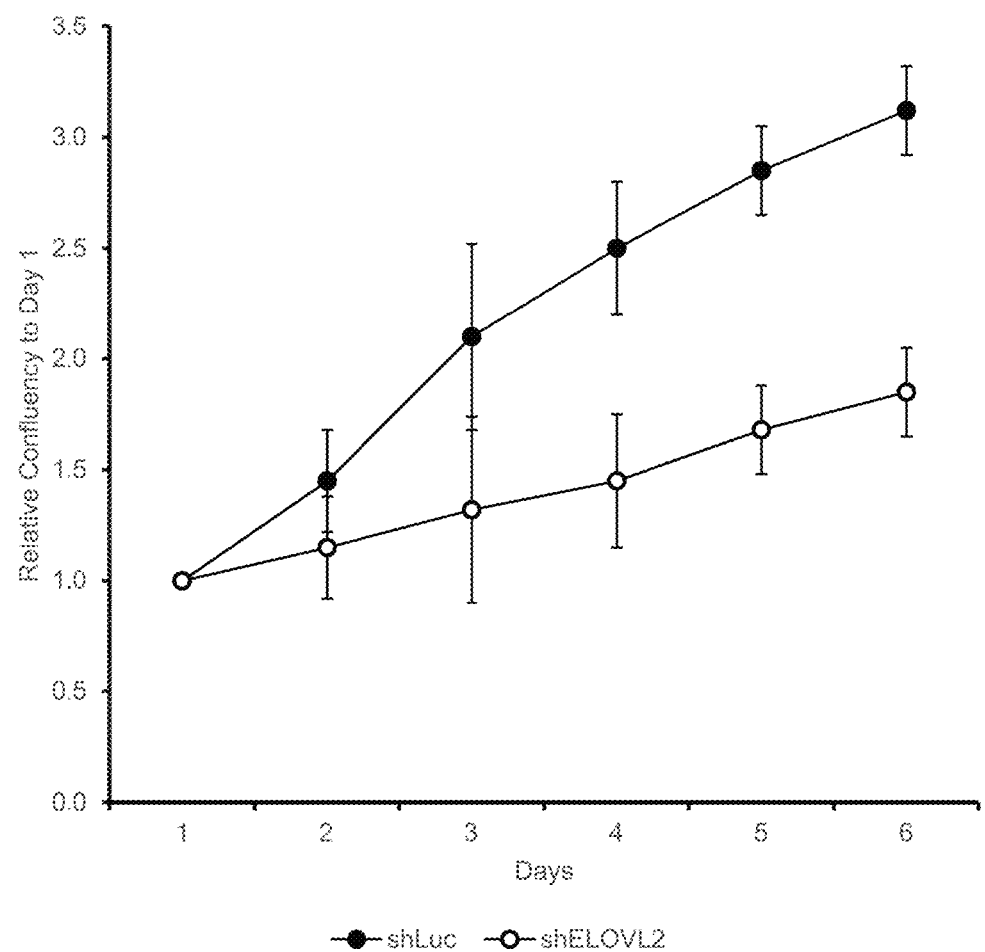

FIG. 18A-FIG. 18D show that ELOVL2 knockdown reduces cell proliferation. FIG. 18A shows a decrease of cells in ELOVL2 knockdown relative to the control (shLuc) in all three cell lines, WI38, IMR90, and 293T. FIG. 18B-FIG. 18D show the PD45 confluency of ELOVL2 knockdown relative to the control (shLuc) in the respective cell lines; WI38 (FIG. 18B), IMR90 (FIG. 18C), and 293T (FIG. 18D).

Figure 19A:
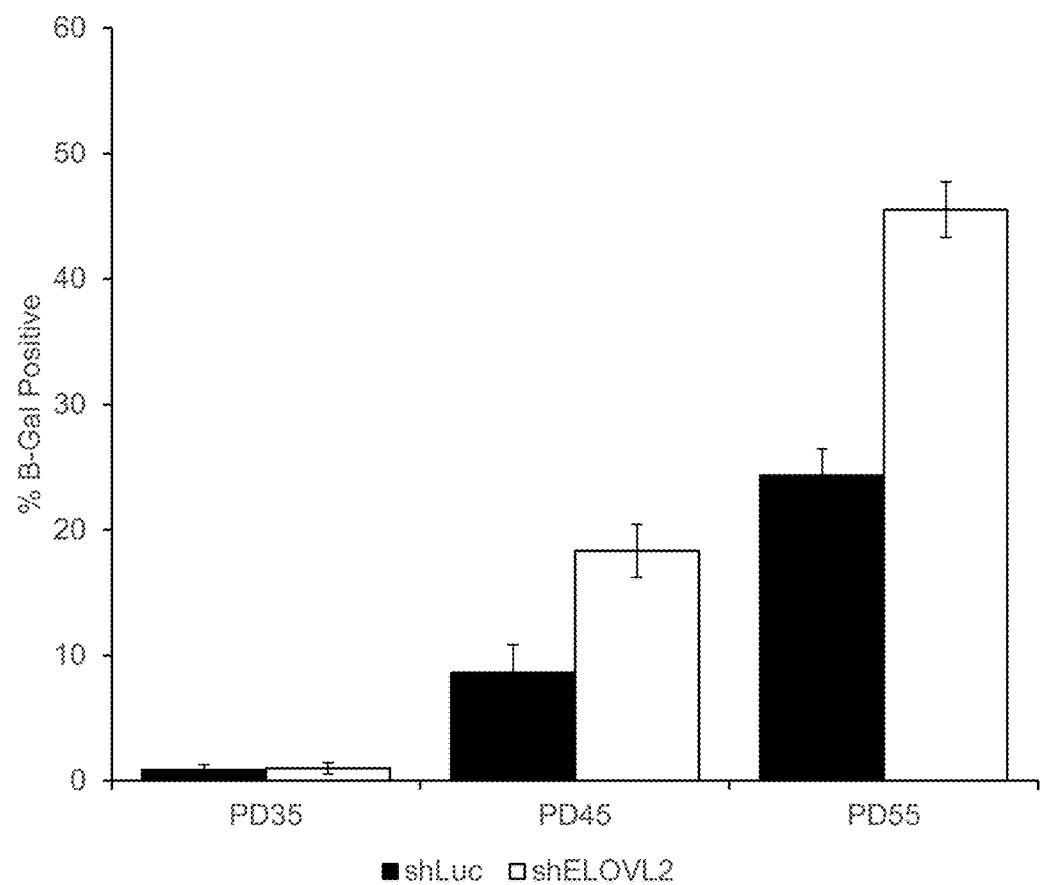
Figure 19C:
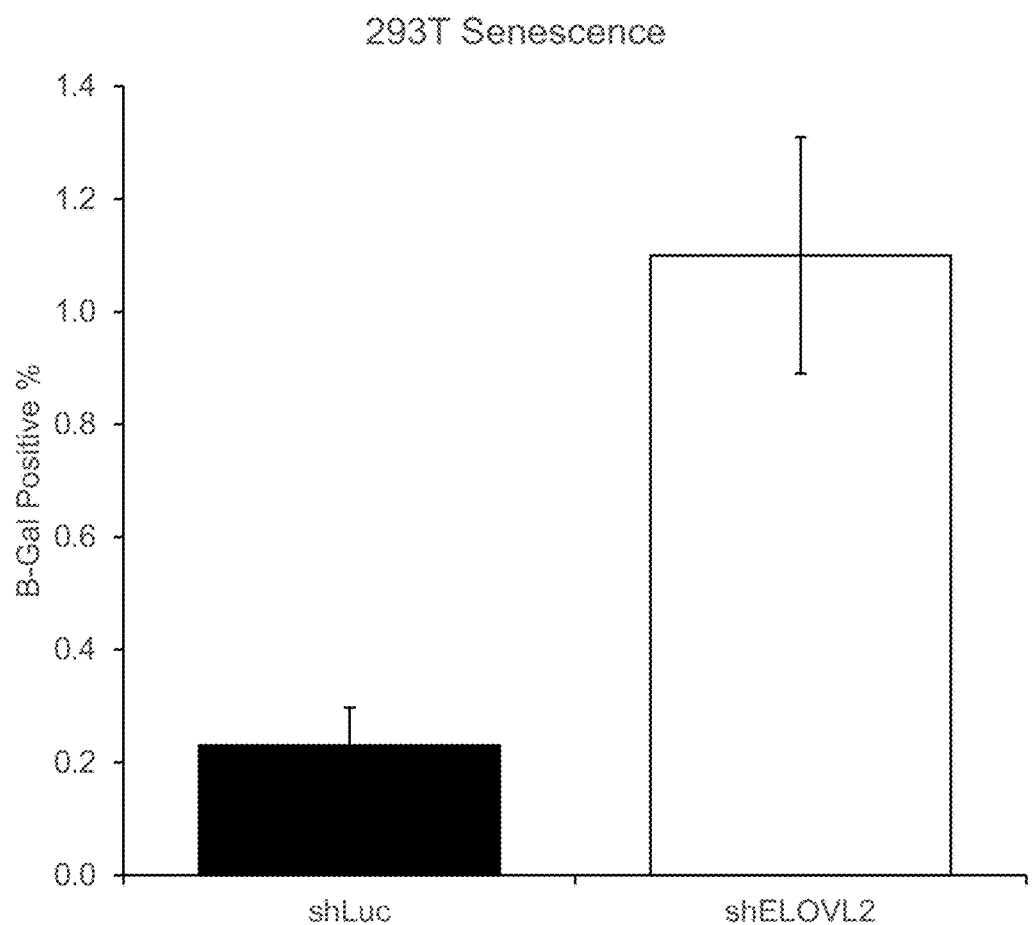

FIG. 19A-FIG. 19C show ELOVL2 knockdown increases senescence.

FIG. 20 shows ELOVL2 overexpression increases survival in old cells (PD56).

Figure 21:
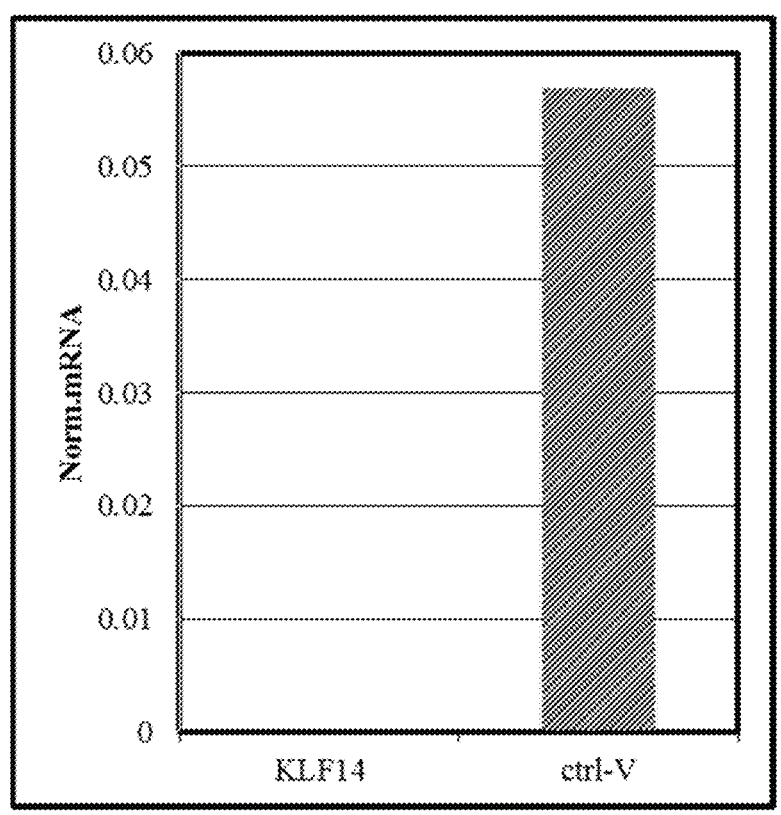
FIG. 21 shows knockdown of KLF14 in WI38 cells.

FIG. 21 shows knockdown of KLF14 in WI38 cells.

Figure 22:
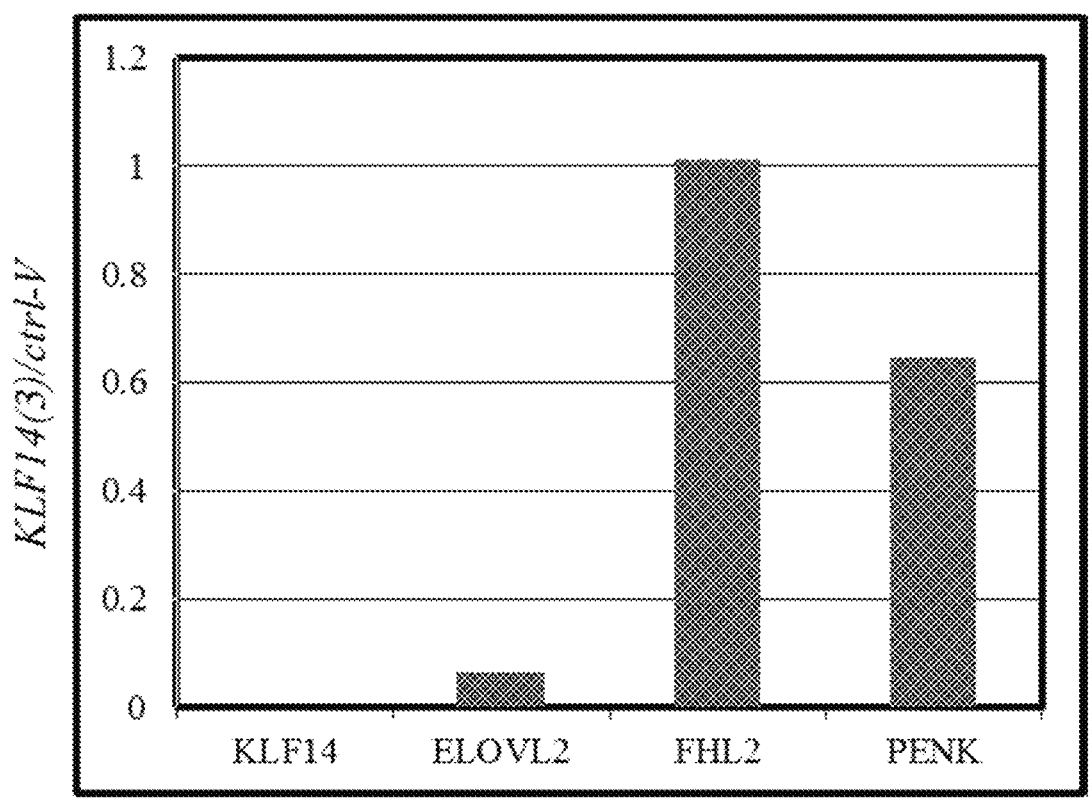
FIG. 22 shows the effect of KLF14 knockdown on other genes. The KLF14 knockdown is about 99.5%.

FIG. 22 shows the effect of KLF14 knockdown on other genes. The KLF14 knockdown is about 99.5%.

Figure 23:
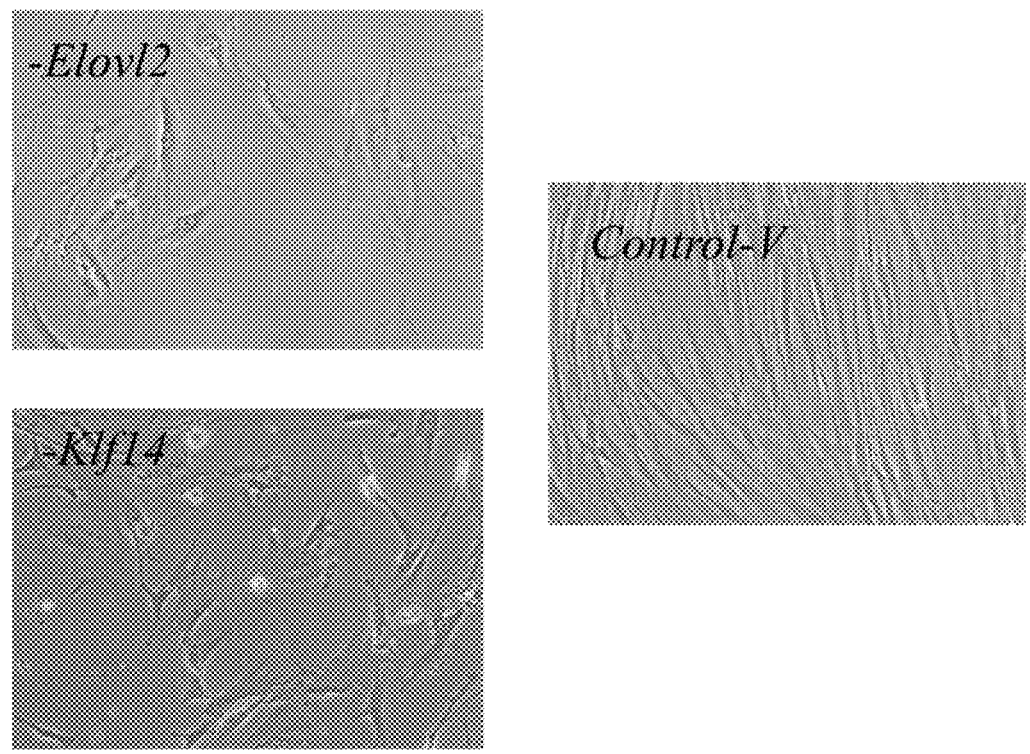
FIG. 23 illustrates the morphology of knockdown of ELOVL2 and KLF14 in cells.

FIG. 23 illustrates the morphology of knockdown of ELOVL2 and KLF14 in cells.

FIG. 24 shows a senescence assay of the knockdown cells. As shown by a beta-gal assay, an increase in blue cells indicates that knockdown of ELOVL2 or KLF14 increases cell senescence.

Example 6. Incubation with Vitamin C Reduces Biological Age of Fibroblast and Reprograms Fibroblast into iPSC WI38 cells at PD55 ($55^{th}$ population doubling) were incubated with different concentrations of vitamin C (Vc), L-dehydro ascorbic acid (DHAA or DHA), or L-ascorbic acid 2-phosphate (VcP). DHAA (or DHA) is an oxidized form of vitamin C. L-ascorbic acid 2-phosphate (VcP) is a vitamin C derivative. Three concentrations were used for each tested compound and the concentrations included 0.3 mM (equivalent to 50 mG), 1.2 mM, or 1.8 mM.

A low concentration of vitamin C (at 0.3 mM) is observed to increase cell proliferation while a higher concentration of vitamin C (at 1.2 mM or 1.8 mM) is observed to have a slower cell proliferation rate relative to the concentration at 0.3 mM (FIG. 25A). An increased cell proliferation is not observed for DHAA (FIG. 25B). At all three concentrations of L-ascorbic acid 2-phosphate (VcP), cell proliferation is observed (FIG. 25C).

Figure 26:
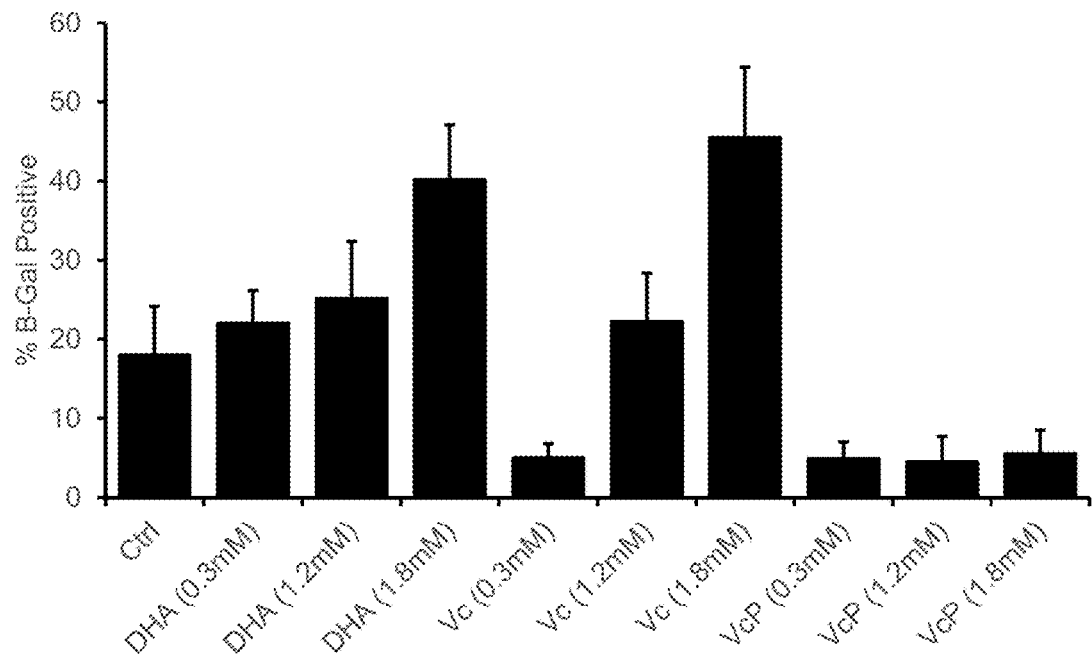
FIG. 26 illustrates cell senescence of WI38 PD55 in the presence of different concentrations of vitamin C, L-dehydro ascorbic acid (DHAA or DHA), or L-ascorbic acid 2-phosphate (VcP).

Similarly, a low concentration of vitamin C and all concentrations of L-ascorbic acid 2-phosphate (VcP) are observed as protective against cell senescence (FIG. 26) as measured by a betal gal staining assay. DHAA did not exert a protective effect against cell senescence.

Figure 27:
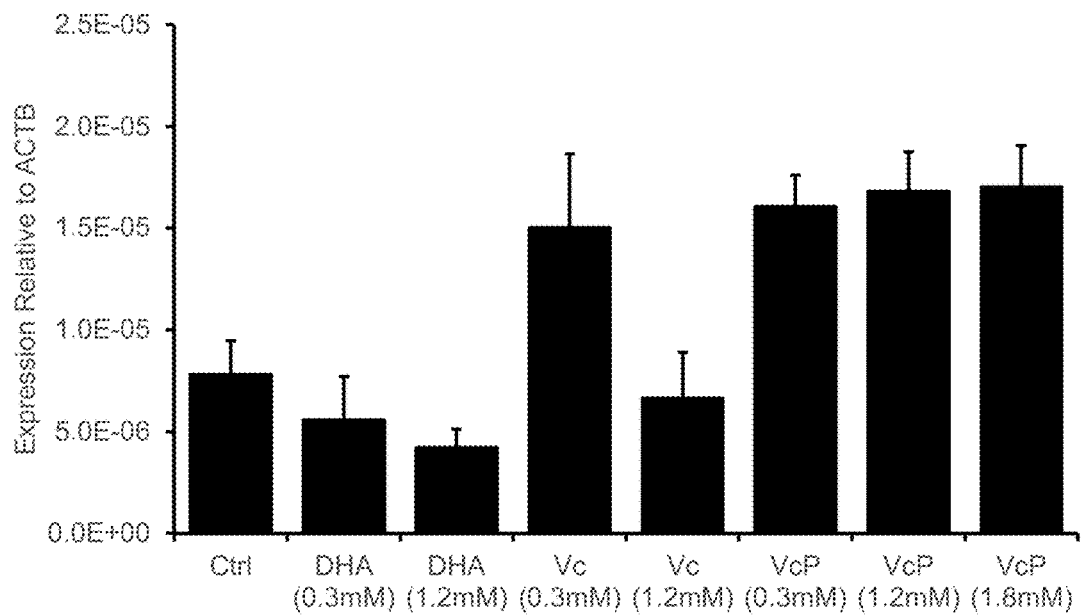
FIG. 27 illustrates ELOVL2 expression in aging WI38 cells (PD55).

The expression of ELOVL2 is also observed to be increased with a low concentration of vitamin C and all concentrations of L-ascorbic acid 2-phosphate (VcP) but not with DHAA (FIG. 27).

The biological age is also observed to be reversed in the presence of a low concentration of vitamin C and is reverted into iPSCs from aged fibroblast (FIG. 28).

Example 7. ELOVL2 and KLF14 Expression and Methylation Levels in a Mouse Model

Figure 29:
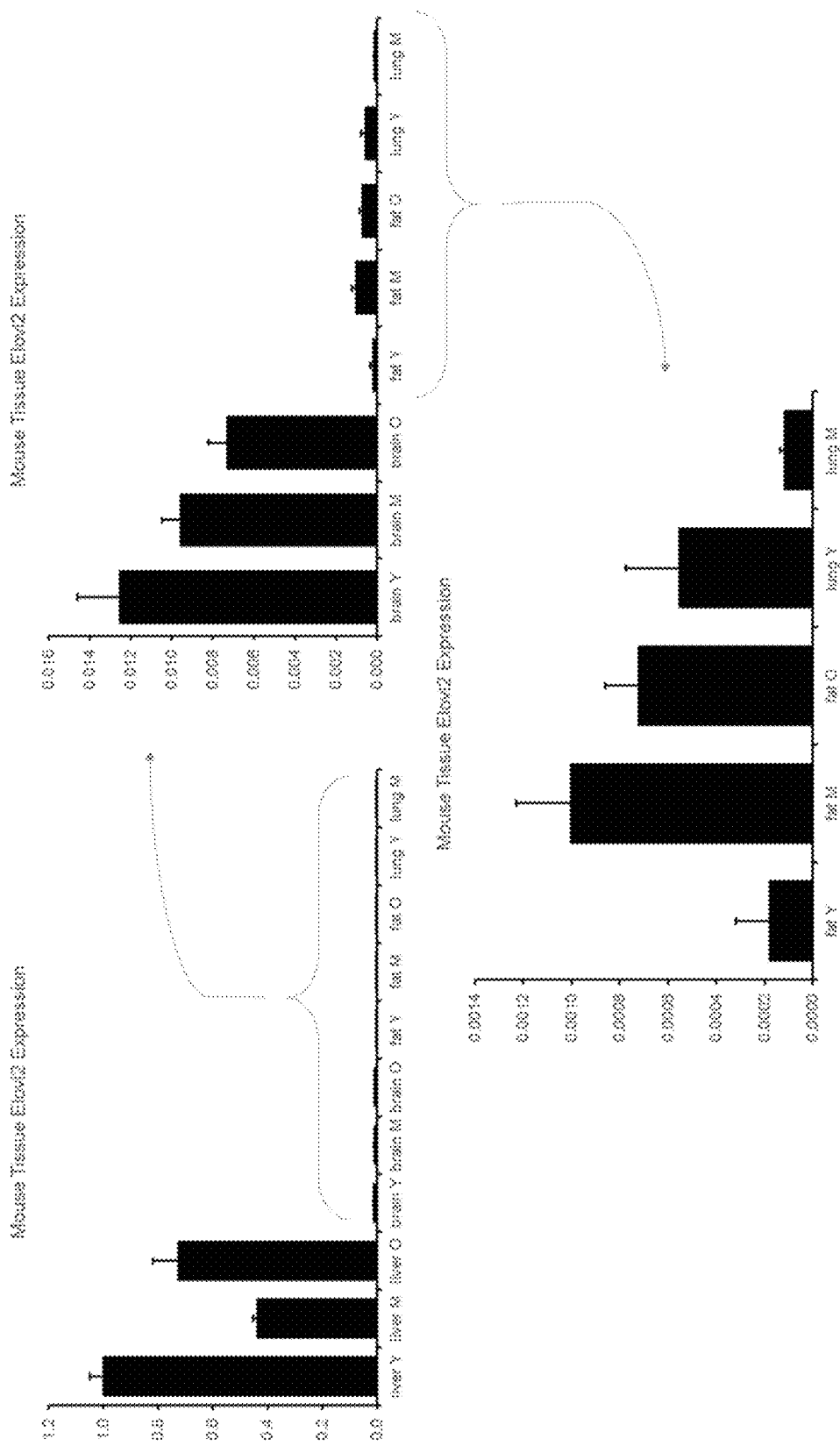
FIG. 29 shows the expressions of ELOVL2 in different mouse tissues.
Figure 30:
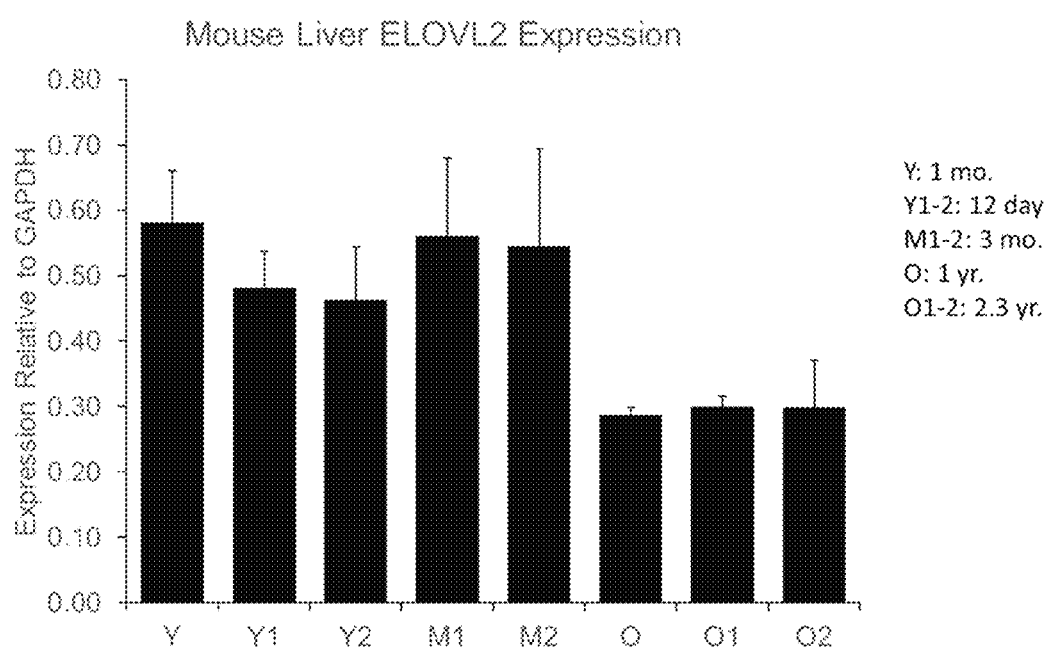
FIG. 30 illustrates ELOVL2 expression in a mouse liver sample.

ELOVL2 expression level was measured in different aged mouse tissue samples: liver, brain, lung and fatty tissue. ELOVL2 is observed to decrease with age (FIG. 29). Similarly in different aged mouse liver samples, ELOVL2 expression is observed as highest in young mice (age 12 days to 1 month) and lowest in old mice (age 1-2.3 years) (FIG. 30).

Figure 31:
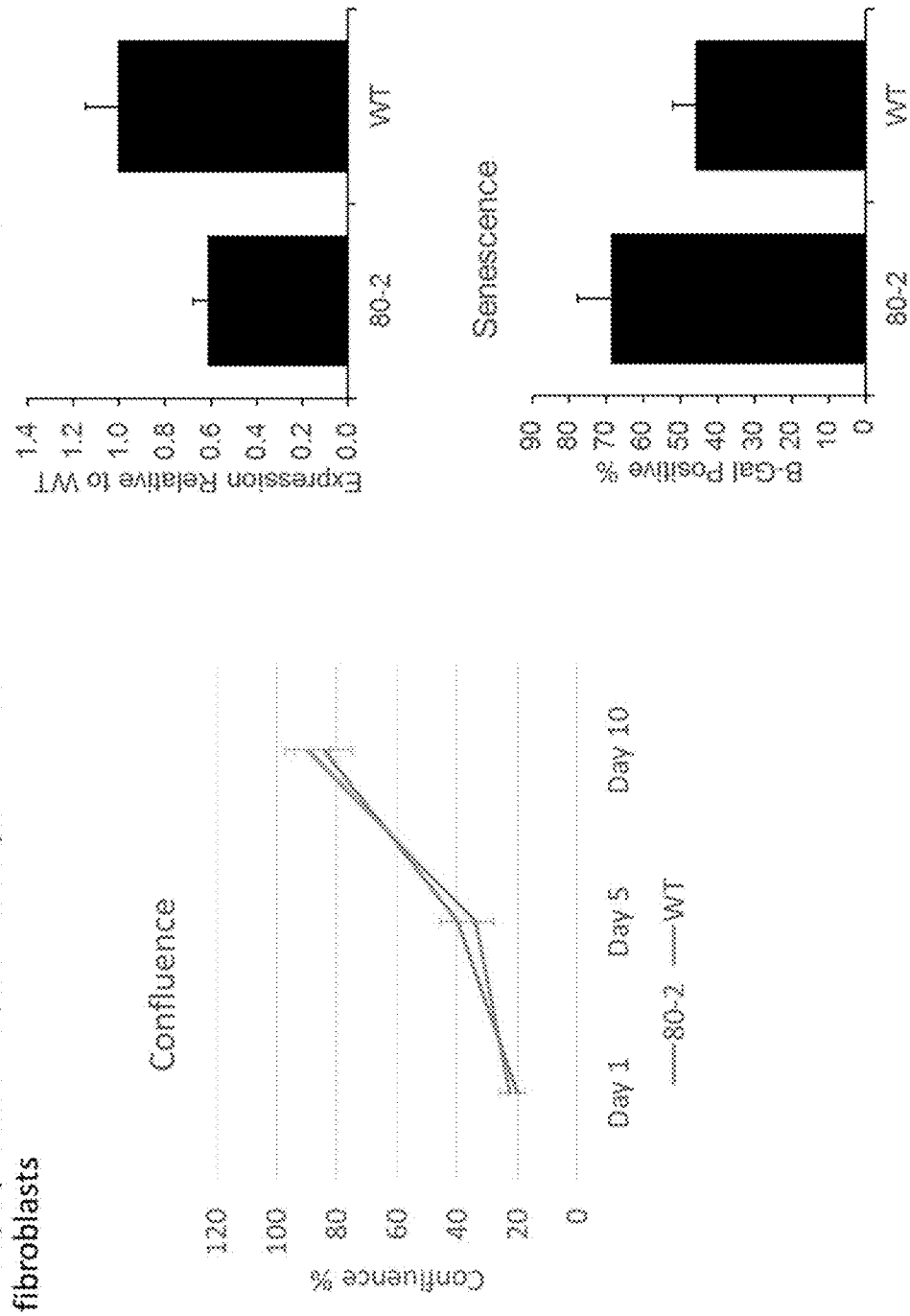
FIG. 31 illustrates ELOVL2 expression and senescence in a heterozygous knockout mouse model.

Expression of ELOVL2 in fibroblast cells of heterozygous knockout mice (8 bp frameshift, truncation) is decreased by about 50% and cell senescence (e.g., B-Gal positive) is increased by about 50% (FIG. 31).

Figure 32:
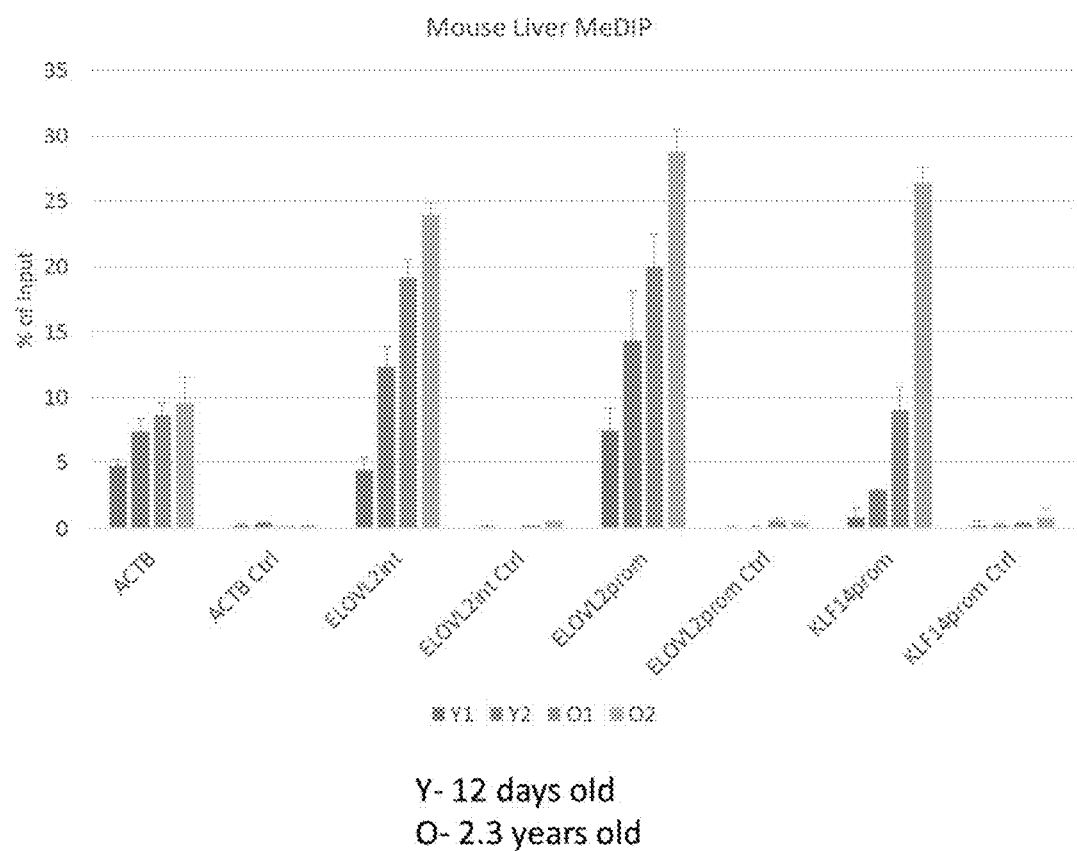
FIG. 32 illustrates a comparison of ELOVL2 and KLF14 methylation levels in the liver samples of young vs. aged mice.

In addition, the methylation level of ELOVL2 and KLF14 are measured in both young (12 days old) mice and old (2.3 years old) mice. The methylation level is observed to increase over age (FIG. 32).

Figure 33B:
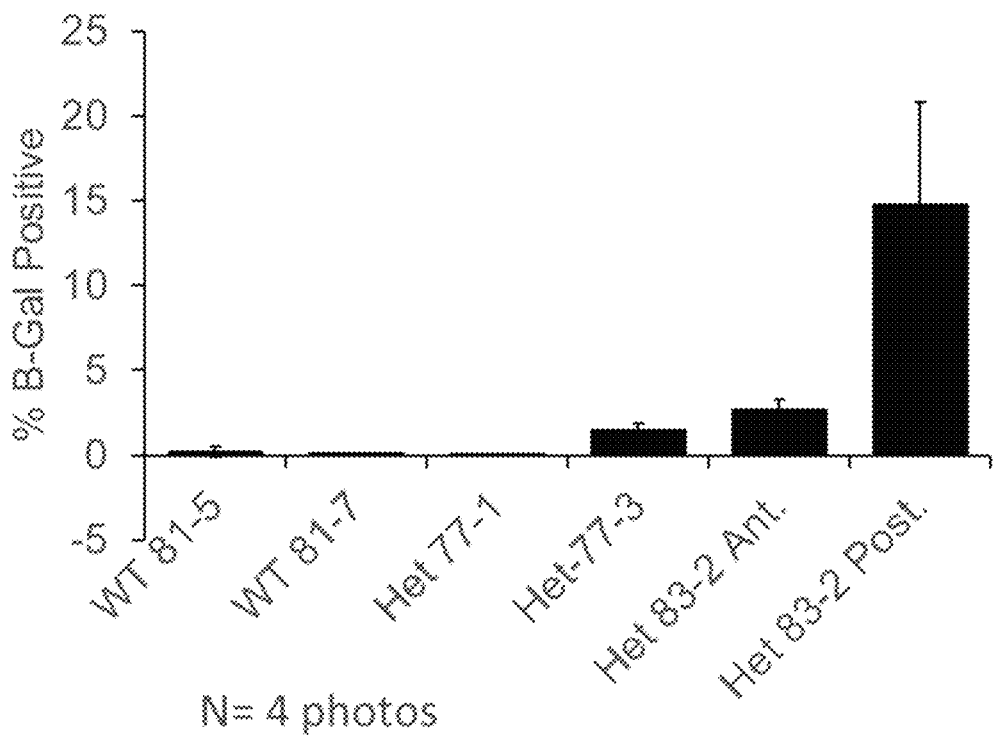

Liver cell senescence in 2-yr. old Elovl2 heterozygous knockout mice (Het 83-2, Het-77-1, and Het 83-2) have much increased cell senescence compared to same age control mice (WT81-5, WT81-7) (FIG. 33A and FIG. 33B).

Figure 34:
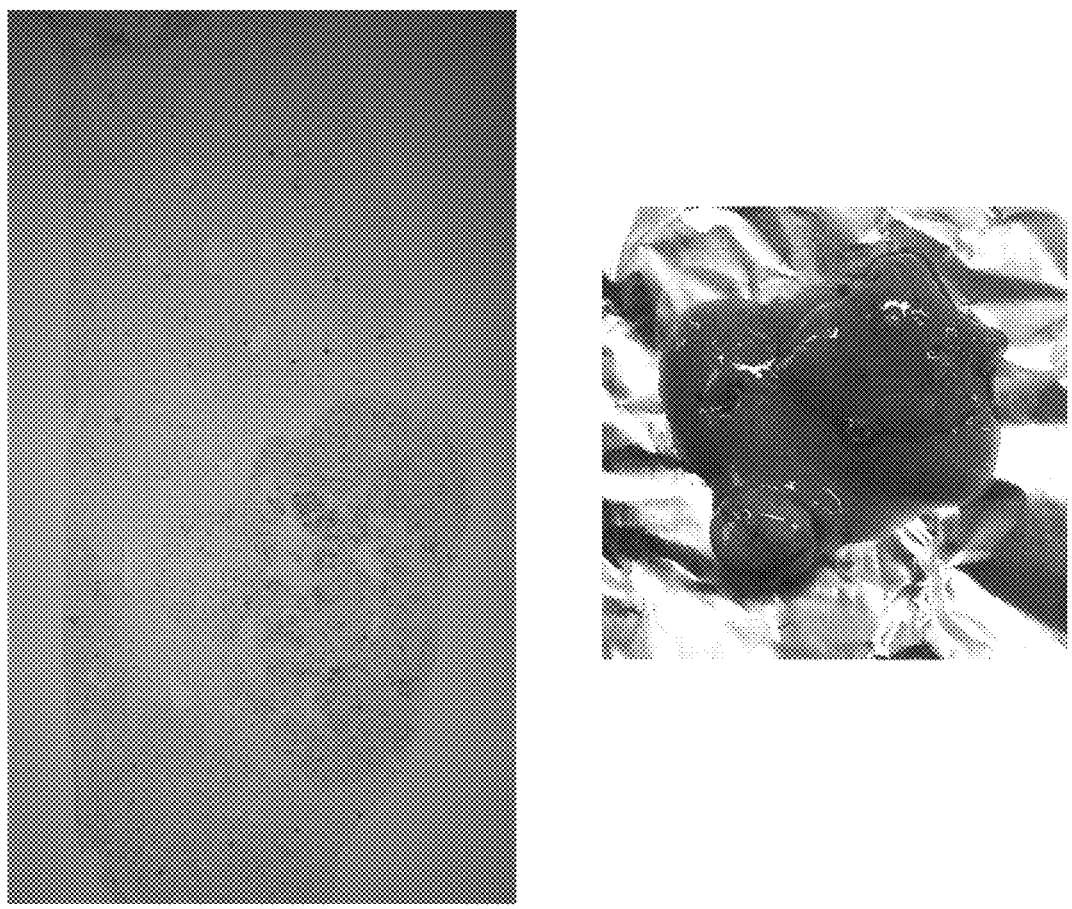
FIG. 34 illustrates aging phenotypes associated with a Het 83-2 ELOVL2 heterozygous mouse. The mouse showed aging phenotypes such as hair loss, obesity, and tumor formation.

Het 83-2 Elovl2 heterozygous mouse exhibited dramatic aging phenotypes including hair loss, obesity, tumor formation (FIG. 34).

Example 8. Effect of ELOVL2 on Memory and Senescence

FIG. 37 shows that senescence and Elovl2 deletion affect the spatial memory of mice in a Morris water maze. After six days of training, the old wild type (WT-O, n=20) and the young Elovl2$^{-/-}$ (−/−Y, n=20) mice show similar latency to reach the platforms while the young wild type (WT-Y, n=20) and the Elovl2$^{+/-}$ (+/−Y, n=20) mice were all able to reach the platforms in a significantly shorter time. See FIG. 37A. In the first quadrant, 10/20 WT-O and 17/20−/−Y mice failed to reach the platforms (WT-Y: 13.91±7.91 s; WT-O: 75.06±20.49 s; +/−Y: 35.78±21.79 s; −/−Y: 87.52±6.62 s). In the second quadrant, 10/20 WT-O and 11/20−/−Y mice failed to reach the platforms (WT-Y: 12.38±5.32 s; WT-O: 62.93±30.46 s; +/−Y: 18.18±13.7 s; −/−Y: 76.62±19.09 s). In the third quadrant, 6/20 WT-O and 13/20−/−Y mice failed to reach the platforms (WT-Y: 15.3±8.92 s; WT-O: 58.85±26.84 s; +/−Y: 16.53±10.41 s; −/−Y: 79.00±19.34 s). In the fourth quadrant, 6/20 WT-O and 8/20−/−Y mice failed to reach the platforms (WT-Y: 4.74±3.25 s; WT-O: 45.24±38.66 s; +/−Y: 9.83±9.55 s; −/−Y: 63.54±29.50 s). The results demonstrated a poor spatial memory of the WT-O and the −/−Y mice. In FIG. 37B, the escape-platforms were removed at Day 7. The frequency of appearance for mice in the original locations of platforms was measured in 90 s. The WT-Y (n=20) and the +/−Y (n=20) mice have a higher frequency of appearance compared to the WT-O (n=20) and the −/−Y (n=20) mice. In the first quadrant, WT-Y: 7.50±1.57 times; WT-O: 1.30±1.34 times; +/−Y: 6.75±1.62 times; −/−Y: 0.95±1.43 times. In the second quadrant, WT-Y: 7.90±1.89 times; WT-O: 1.60±1.50 times; +/−Y: 6.55±2.42 times; −/−Y: 0.50±0.89 times. In the third quadrant, WT-Y: 7.10±2.17 times; WT-O: 1.45±1.10 times; +/−Y: 6.65±1.63 times; −/−Y: 0.55±0.89 times. In the fourth quadrant, WT-Y: 7.00±1.97 times; WT-O: 1.65±1.18 times; +/−Y: 6.35±1.98 times; −/−Y: 0.60±0.75 times. These data indicated the WT-O and the –/–Y mice have decreased long-term spatial reference memory. In FIG. 37C, the escape-platforms have been removed for two days at Day 8. All groups have shown diminished frequency of appearance in the original locations of platforms. The WT-Y (n=20) and the +/–Y (n=20) mice still have a higher frequency of appearance compared to the WT-O (n=20) and the –/–Y (n=20) mice. In the first quadrant, WT-Y: 3.60±0.88 times; WT-O: 0.40±0.60 times; +/–Y: 3.40±0.88 times; –/–Y: 0.30±0.57 times. In the second quadrant, WT-Y: 3.40±0.94 times; WT-O: 0.45±0.76 times; +/–Y: 3.40±1.27 times; –/–Y: 0.35±0.67 times. In the third quadrant, WT-Y: 3.10±0.85 times; WT-O: 0.70±0.80 times; +/–Y: 2.80±0.77 times; –/–Y: 0.50±0.76 times. In the fourth quadrant, WT-Y: 3.10±1.02 times; WT-O: 0.45±0.69 times; +/–Y: 3.5±0.95 times; –/–Y: 0.45±0.60 times. It further confirmed the reduction on long-term spatial reference memory of the WT-O and the –/–Y mice. Four difference locations of the platforms were tested in all the experiments.

Figure 38A:
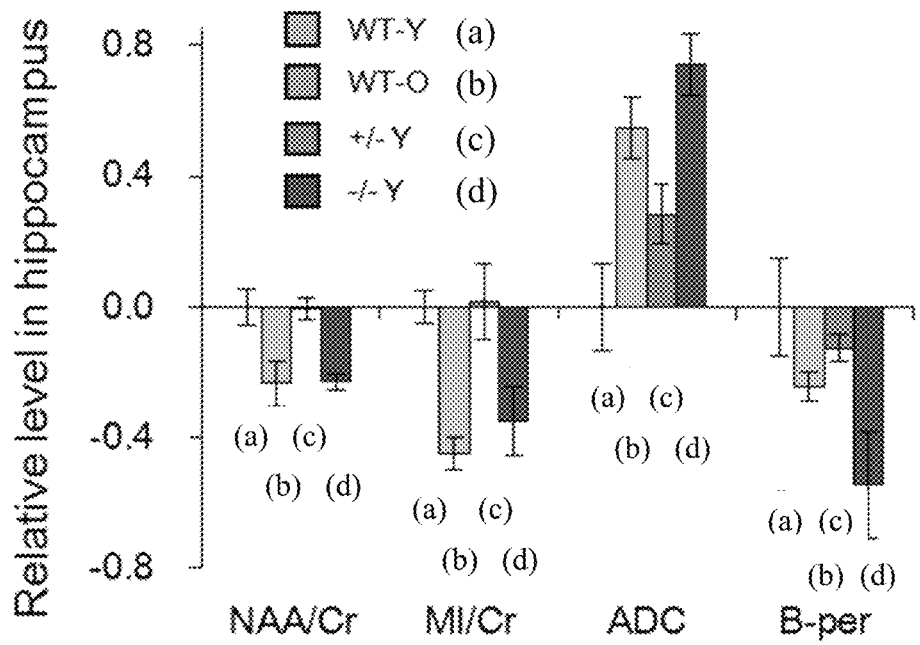
FIG. 38A-FIG. 38B show NAA/Cr and MI/Cr ratio, ADC, and Blood-perfusion (B-per) MRI analysis of wild type young (WT-Y) mice, wild type old (WT-0) mice, Elovl2 single (+/−Y) knock-out mice and Elovl2 double (−/−Y) knock-out mice.
Figure 38B:
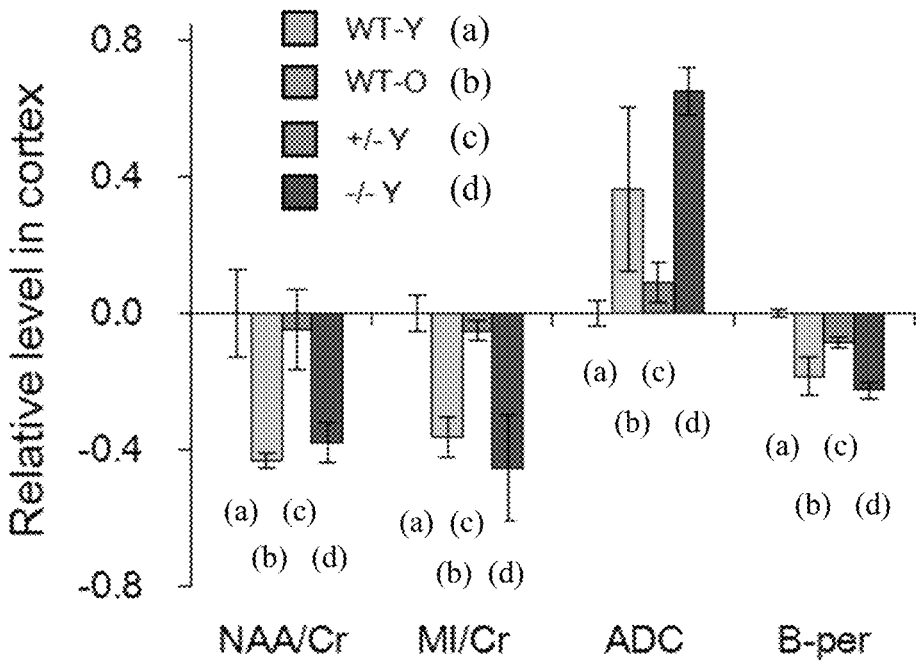

FIG. 38 shows NAA/Cr and MI/Cr ratio, ADC, and Blood-perfusion (B-per) MRI analysis of wild type young (WT-Y) mice, wild type old (WT-0) mice, Elovl2 single (+/–Y) knock-out mice and Elovl2 double (–/–Y) knock-out mice. In hippocampus (FIG. 38A) and cortex (FIG. 38B), the ratio of NAA/Cr (N-acetylaspartate/Creatine) and MI/Cr both decrease a lot in WT-old and Elovl2–/– mice show an increase of aged neuo-degenerative and loss of neuronal and Glial cells relative to WT-Y and Elovl2+/– mice, indicating an increase of accelerated aging neuodegenerative phenotype and Alzheimer's Disease. ADC (apparent diffusion coefficient) shows that the diffusion of water molecules within tissue in WT-O, +/–Y and –/–Y mice has increased. B-per value shows that the Elovl2–/– mice has the lowest blood flow relative to the other three groups of mice. NAA: neuronal cell marker, Cr: Energy metabolism, MI: Glial cell marker.

Example 9

Table 1A and Table 1B illustrate exemplary list of epigenetic markers for use with one or more methods described herein.

TABLE 1A

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg16867657 | 170.5444 | 0 | ELOVL2 | 6 | 11044877 | CGGCGGCTCAACGT CCACGGAGCCCCAG GAATACCCACCCGC TGCCCAGA | 1 | 6 | 11152863 |
| cg10501210 | -102.624 | 1.43E-294 | | 1 | 207997020 | CGGGACTGCGGCAC CTTACGGCGGGACC AAGATTTGGGTCTG CGCAGGCG | 2 | 1 | 206063643 |
| cg22454769 | 153.6159 | 2.92E-264 | FHL2 | 2 | 106015767 | CTTGGGAGCACAGT AGTTATCGGGAGCG TCGCCTCCGGCGTG GGCTCTCG | 3 | 2 | 105382199 |
| cg04875128 | 144.0318 | 1.87E-256 | OTUD7A | 15 | 31775895 | CGCCACGTACCCGC AGCAGAACCGCTCG CTGTCGTCGCAGAG CTACAGCC | 4 | 15 | 29563187 |
| cg24724428 | 170.6561 | 5.72E-248 | ELOVL2 | 6 | 11044888 | CGTCCACGGAGCCC CAGGAATACCCACC CGCTGCCCAGATCG GCAGCCGC | 5 | 6 | 11152874 |
| cg06639320 | 192.5145 | 1.36E-223 | FHL2 | 2 | 106015739 | AGGGCTCCTTTCTT CGTGCCCTCCGGGT CTTGGGAGCACAGT AGTTATCG | 6 | 2 | 105382171 |
| cg14556683 | 215.314 | 1.20E-222 | EPHX3 | 19 | 15342982 | GAGAACACCAGGCT CCACATGAAGGCGC GCAGCAGCTTCAGC GACAGGCG | 7 | 19 | 15203982 |
| cg23606718 | 271.9213 | 7.41E-221 | FAM123C | 2 | 131513927 | TCTCGGGGCCTTGG CGACTTACCGCTGG GGGCCCGCAGTGCA GCAGGGCG | 8 | 2 | 131230397 |
| cg07553761 | 222.4944 | 1.44E-217 | TRIM59 | 3 | 160167977 | CGCCGGTGGCCGAC GGCTTCTGAGGAAT TATCTTTTACTTGG CGCCACAC | 9 | 3 | 161650671 |
| cg14361627 | 259.4609 | 1.60E-214 | KLF14 | 7 | 130419116 | GCCCCCCGGCTAAG TCATGTTTAACAGC CTCAGAAATTATCT TGTCTCCG | 10 | 7 | 130069656 |

TABLE 1A-continued

| Marker | Coeff | PTest | UCSC_Ref Gene Name | CHR | MAP INFO | SourceSeq | SEQ ID NO: | Chromo- some_36 | Coordi- nate_36 |
|---|---|---|---|---|---|---|---|---|---|
| cg14692377 | 298.8267 | 1.36E-213 | SLC6A4 | 17 | 28562685 | GGCTGCGCGGGGAG GCTGGTCCCGGGCT GGGCAGGCGGGCTG GCCTCGCG | 11 | 17 | 25586811 |
| cg19283806 | -179.174 | 1.60E-213 | CCDC102B | 18 | 66389420 | GATTTCTCCTTGAA CAATCCCCGCAAAG ATAGCAGCCAAAAA AGGATGCG | 12 | 18 | 64540400 |
| cg00292135 | 281.1003 | 3.60E-213 | C7orf13; RNF32 | 7 | 156433068 | AGGCCCAGGTGGGC GGGCGGCTGAGGAG CGTGGCTGCGCCCA CAAAGCCG | 13 | 7 | 156125829 |
| cg08097417 | 335.8053 | 7.62E-203 | KLF14 | 7 | 130419133 | TGTTTAACAGCCTC AGAAATTATCTTGT CTCCGCGTTCTTTC TTCTGCCG | 14 | 7 | 130069673 |
| cg24079702 | 180.3007 | 4.70E-198 | FHL2 | 2 | 106015771 | CGCCCGAGAGCCCA CGCCGGAGGCGACG CTCCCGATAACTAC TGTGCTCC | 15 | 2 | 105382203 |
| cg02650266 | 274.1478 | 3.09E-191 | | 4 | 147558239 | GCTGTCCTCAGGAG CCGCCAGAGTGCTG GGGAAGGCGGCAGC AACGAGCG | 16 | 4 | 147777689 |
| cg06493994 | 327.7177 | 2.52E-189 | SCGN | 6 | 25652602 | AAGAAATACGGTGA AGGAGTCCTTCCCA AAGTTGTCTAGGTC CTTCCGCG | 17 | 6 | 25760581 |
| cg16419235 | 299.9665 | 2.12E-185 | PENK | 8 | 57360613 | CAAAGGGCTGATTT CTACAGTCGCTAGG ACCTGCAGCGGCGC TGCTCCCG | 18 | 8 | 57523167 |
| cg22736354 | 254.184 | 6.70E-185 | NHLRC1 | 6 | 18122719 | CTCGAGTGCAAGGT GTGCTTTGAGAAGT TTGGCCACCGGCAG CAGCGGCG | 19 | 6 | 18230698 |
| cg07547549 | 192.8751 | 2.24E-183 | SLC12A5 | 20 | 44658225 | GCTCAGCTCCATTG GAATGCTCCGGGCG CTGTCCAAGGTGCT GGAATGCG | 20 | 20 | 44091632 |
| cg21572722 | 229.9224 | 9.15E-183 | ELOVL2 | 6 | 11044894 | CGGAGCCCCAGGAA TACCCACCCGCTGC CCAGATCGGCAGCC GCTGCTGC | 21 | 6 | 11152880 |
| cg04400972 | 288.3508 | 1.18E-181 | TRIM45 | 1 | 117665053 | CGGTCTCCCGAACC GGTCCCCGTAACGC GAGCCTGAGATGCC CTCACCCC | 22 | 1 | 117466576 |
| cg26290632 | 273.449 | 2.57E-177 | CALB1 | 8 | 91094847 | CATCACAGCCTCAC AGTTTTTCGAGATC TGGCTCCATTTCGA CGCTGACG | 23 | 8 | 91164023 |
| cg21296230 | 270.4638 | 2.37E-176 | GREM1 | 15 | 33010536 | GCGGGGGTGAATTG TGAAGAACCATCGC GGGGTCCTTCCTGC TGAGGCCG | 24 | 15 | 30797828 |
| cg25778262 | 243.1574 | 1.21E-174 | CPM | 12 | 69327449 | TAGCCTCGCTGGGC AGCTTGGCACTGCT GGGAGCTTGGCTCG CCCTGCCG | 25 | 12 | 67613716 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg13649056 | 307.4308 | 3.80E-172 | | 9 | 136474626 | GGGGGATGCCGGGAGCGGCCTGGGGAGCTGTCCCTGGTGCTGACGGCTCG | 26 | 9 | 135464447 |
| cg00748589 | 267.9466 | 2.85E-171 | | 12 | 11653486 | GCTCTACCTCAAGGAGCTCAGGGCCATCGTGCTGAACCAACAGAGGCTCG | 27 | 12 | 11544753 |
| cg23500537 | 227.7268 | 4.82E-170 | | 5 | 140419819 | GCAGCCACACATCCAAGGCTGACAGGGCGGGCACTCTGCCAAGTCCTGCG | 28 | 5 | 140400003 |
| cg03607117 | 451.6398 | 1.76E-169 | SFMBT1 | 3 | 53080440 | CGCCCTGGCCCAGCCCCGATCCAGCCTGCGCCTCACCTCGGGTTGTAGAC | 29 | 3 | 53055480 |
| cg23091758 | 311.9045 | 7.86E-169 | NRIP3 | 11 | 9025767 | GGAGGCGGCGGCGCTGGTGGGGACTGACCCGGCAGTCCGAGAATCCACCG | 30 | 11 | 8982343 |
| cg07955995 | 425.3423 | 5.65E-168 | KLF14 | 7 | 130419159 | CGCTCTGTTACCATTACCTGGCTCGCCGGCAGAAGAAAGAACGCGGAGAC | 31 | 7 | 130069699 |
| cg04836038 | 405.8761 | 6.08E-166 | DOCK9 | 13 | 99739382 | AGAGGTCTCAGGAAAGTAGCCTTTATTTATGTGGCACCGATCGGAACCCG | 32 | 13 | 98537383 |
| cg20426994 | 414.7314 | 8.35E-165 | KLF14 | 7 | 130418324 | GTGGCGCTTGGCAGCAGGTGTGACAGACCTCCTCCGGGGCGCCTGATCCG | 33 | 7 | 130068864 |
| cg08128734 | -153.801 | 4.55E-164 | RASSF5 | 1 | 206685423 | CGGGGCTAAATCAAGGAAAACACACGCTACACACTCAGTGCTGCTGGGTG | 34 | 1 | 204752046 |
| cg24436906 | 272.7476 | 2.07E-162 | BOK | 2 | 242498081 | CGGGGAAGCTCGGAAAGCGTCTCCCCGACTCCGCCCCCAGGGTTGCCTTT | 35 | 2 | 242146754 |
| cg04908625 | 175.9083 | 1.42E-161 | ADCY5 | 3 | 123166882 | CGGCCGCGCGCCCCTTGCCCCGCCGCTCCTCCAGACCCACCTCCACCGAG | 36 | 3 | 124649572 |
| cg00481951 | 249.7016 | 2.89E-161 | SST | 3 | 187387650 | GTTTCAGCACCTGGGTCAGCGCTTCCCAGGGTCAGCACCAGGGATAGACG | 37 | 3 | 188870344 |
| cg15108590 | 324.0472 | 1.75E-156 | CBS | 21 | 44494906 | GTCTTGGGGAGCCCGCGGGTTCGGGTCTGGGTCGCCTGGCGAGCTTTCCG | 38 | 21 | 43367975 |
| cg22282410 | 284.9341 | 3.72E-154 | PTPRN2 | 7 | 158380884 | CCCGGTGCTGGGGGTCGCACTGTCCCTGGGGACGGCGGGGGCCTAAGCCG | 39 | 7 | 158073645 |
| cg21801378 | 403.3465 | 1.94E-153 | BRUNOL6 | 15 | 72612125 | CGGGCTAAACCCCGGTCCCGCCGTACCCATGAAGGACCACGACGCCATCA | 40 | 15 | 70399179 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg04940570 | 264.1321 | 3.97E-152 | TEAD1 | 11 | 12696758 | ACACACCCTCGGGC GCCTTGGACGGGGT GCGCTGGGGAGCCA GAAGTTCG | 41 | 11 | 12653334 |
| cg04084157 | 463.0799 | 5.79E-150 | VGF | 7 | 100809049 | AGCATTTCATTCAT TCATTCATTCATTC ATTTCCCGGAGCTC CGCTAGCG | 42 | 7 | 100595769 |
| cg25410668 | 202.9914 | 1.20E-148 | RPA2 | 1 | 28241577 | CACCGCGTGGAGTT GCTTGTTCTTTTAC ATAGGAGGTCACAT TCTCTTCG | 43 | 1 | 28114164 |
| cg04865692 | 240.2425 | 1.40E-144 | KCNC3 | 19 | 50831762 | GACGAGACCGACGT GGAGGCCTGCTGCT GGATGACCTACCGG CAGCATCG | 44 | 19 | 55523574 |
| cg04528819 | 344.067 | 2.76E-143 | KLF14 | 7 | 130418315 | CGCCCCGGAGGAGG TCTGTCACACCTGC TGCCAAGCGCCACC AATGCCCC | 45 | 7 | 130068855 |
| cg10804656 | 181.8587 | 3.81E-143 |  | 10 | 22623460 | CGGATCCCGCCAAA TTTGAACGCGAGAT TGTCAGGCCCTGAG GGGCTTGA | 46 | 10 | 22663466 |
| cg09499629 | 498.3802 | 5.10E-143 | KLF14 | 7 | 130419136 | CCCAGAAGTTCCGA CTGGGGAGTTTCGC TCTGTTACCATTAC CTGGCTCG | 47 | 7 | 130069676 |
| cg03032497 | 226.3201 | 8.93E-143 |  | 14 | 61108227 | ATCTAACTCAACCC CTTTAGATATTCTT CCAGGTGGAATTAT TGGATTCG | 48 | 14 | 60177980 |
| cg09401099 | 283.2574 | 3.24E-142 |  | 3 | 156534380 | CGCGAAGGCCACTC GCTGGCGACCCCTT CCCGGGTCTCCTAG CCCTGGCC | 49 | 3 | 158017074 |
| cg12373771 | 276.5215 | 1.04E-140 | CECR6 | 22 | 17601381 | AGCACCAGTACAGG TCGGTGACGGCGAT GAGGTACAGGTCCA GCAGGCCG | 50 | 22 | 15981381 |
| cg07927379 | 516.3105 | 2.87E-140 | C7orf13; RNF32 | 7 | 156433108 | CGGCCCTCACTACA CGAGGGCCTGGGCGC CTGCACGCCCCCGT GCTTCAGC | 51 | 7 | 156125869 |
| cg18473521 | 176.2876 | 7.69E-138 | HOXC4 | 12 | 54448265 | TTACCCATTCTCGC TCGTAAATCCAGTT CAATTGTGCTAACC CAGAGTCG | 52 | 12 | 52734532 |
| cg07806886 | 370.4424 | 3.83E-137 | STXBP5L | 3 | 120626899 | CGGCGCCAATCCTA GATTCGATAGGGTA AGTTCTGTGGTCTC CAGGGCAG | 53 | 3 | 122109589 |
| cg01528542 | -196.924 | 6.73E-137 |  | 12 | 81468232 | CGTTAACCTCTGCT AGTGATGACCAAAC CTGGTAAAGATTGT AAAGTGGG | 54 | 12 | 79992363 |
| cg03473532 | -226.757 | 9.80E-137 | MKLN1 | 7 | 131008743 | CGTATGTGTTTGAG ATAGCAGTTGTTTA CTATCACTTGAAAA TTCTGAAT | 55 | 7 | 130659283 |

TABLE 1A-continued

| Marker | Coeff | PTest | UCSC_Ref Gene Name | CHR | MAP INFO | SourceSeq | SEQ ID NO: | Chromo- some_36 | Coordi- nate_36 |
|---|---|---|---|---|---|---|---|---|---|
| cg25478614 | 251.6982 | 1.34E-134 | SST | 3 | 187387866 | GGACCCAGAAAAGCACCAAAACTCTTTAGAAGGACTGAGCATCCCTTACG | 56 | 3 | 188870560 |
| cg21186299 | 812.41 | 2.75E-134 | VGF | 7 | 100808810 | GCGACGGTCGAGGTCTGGCGTCCCGTGGGCTGGGCTCAGCTGGGTCGGCG | 57 | 7 | 100595530 |
| cg05093315 | -242.236 | 6.14E-134 | SAAL1 | 11 | 18127958 | CGAGACCAGCCTGGGCAACATAGATCAGAAGGCGAATAGAATAAGTCCGC | 58 | 11 | 18084534 |
| cg23441616 | 915.0279 | 3.75E-132 | MYCBP2 | 13 | 77901383 | GGGTTTGGGGCTGTTGGGTTGTGCGGAATCTGAAGTAGTCCACTTCTCCG | 59 | 13 | 76799384 |
| cg17321954 | 384.39 | 4.95E-132 | STXBP5L | 3 | 120626881 | CGATAGGGTAAGTTCTGTGGTCTCCAGGGCAGAAGAAATCTGTGGATAGG | 60 | 3 | 122109571 |
| cg03771840 | 183.5214 | 1.73E-131 | TRIM15 | 6 | 30140145 | CGCCCTTCGCGCGCCCCACTTCAGCCTTTCAGCGTAAGGCAGGAACCTTT | 61 | 6 | 30248124 |
| cg03545227 | 347.1845 | 1.01E-130 | PTPRN | 2 | 220173100 | AGGTCTAGTGGAGAGTCCTCGCTCTGTGACCCCTTCCTCTCTGGTAACCG | 62 | 2 | 219881344 |
| cg18826637 | -134.891 | 1.49E-130 |  | 2 | 145116633 | TCCATTGGAAACTCCCCTCTAAGCTGTGCATTTTTAGGCTGTGGTCATCG | 63 | 2 | 144833103 |
| cg23186333 | -163.283 | 2.02E-129 | CD44 | 11 | 35161900 | TTTCTTTGTCTATGTATGTACAGATAATTACATGGCCGATTTGCTTATCG | 64 | 11 | 35118476 |
| cg06570224 | 230.2161 | 3.56E-129 |  | 3 | 157812475 | AGCAGGGGAGATGGTGGCTCCCTCTCGGGGCCAGTCTGCCCCAAGCAGCG | 65 | 3 | 159295169 |
| cg13848598 | 196.8931 | 5.52E-129 | ADRB1 | 10 | 115804578 | GCAGGTACACGAAGGCCATGATGCACAGGGGCACGTAGAAGGAGACTACG | 66 | 10 | 115794568 |
| cg20482698 | 302.1472 | 3.25E-126 | ACTN2 | 1 | 236849994 | CCTCCTGGATCATGTACTCATCCTCGTCGTACACGTAGTTGTACTGCACG | 67 | 1 | 234916617 |
| cg24430580 | 506.5864 | 1.97E-125 | PITX2 | 4 | 111544235 | CACCAGGAAGCCCGCCTCTGGTTTTAAGATGTTAGGCCAACAGGGAAGCG | 68 | 4 | 111763684 |
| cg16181396 | 275.0637 | 2.22E-125 | ZIC1 | 3 | 147126206 | CTCTCTCTTGCGTTATTTTTCTGTTTTCTGCCTTTCCGTTGTCTCCTTCG | 69 | 3 | 148608896 |
| cg23744638 | -173.575 | 1.82E-124 |  | 11 | 10323902 | CACGAAGCTTTGGGGAGCACTCTAGCCCCTGCTACTCACCCATGCAAGCG | 70 | 11 | 10280478 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg11806672 | 567.9303 | 1.87E-124 | POU4F1 | 13 | 79176608 | TGTGGTACGTGGCGTCCGGCTTGAAAGGATGGCTCTTGCCCTGGGACACG | 71 | 13 | 78074609 |
| cg26005082 | 551.7073 | 2.46E-124 | MIR7-3; C19orf30 | 19 | 4769660 | ACCGAAGGAGGAGAATGCTATTTATTTCAGCACCAAATATCCGGACAGCG | 72 | 19 | 4720660 |
| cg09809672 | -183.887 | 5.19E-124 | EDARADD | 1 | 236557682 | TTCATCTAGAAGGTTTGACTCTGGCCAGACAACCAGCGAGCATCTTCTCG | 73 | 1 | 234624305 |
| cg22285878 | 513.3208 | 6.26E-124 | KLF14 | 7 | 130419173 | TCTTCTGCCGGCGAGCCAGGTAATGGTAACAGAGCGAAACTCCCCAGTCG | 74 | 7 | 130069713 |
| cg08706258 | 1112.51 | 1.92E-122 | WSB1 | 17 | 25621230 | CGGAGTCAACCACAGACAATAGACCCTGTACCCAGCCTCGCGCCTGCGGA | 75 | 17 | 22645357 |
| cg07920503 | 316.5951 | 2.90E-122 | FAM123A | 13 | 25745406 | GAGGAGCAGGACCCACGACGGACTTGCCGAGGTGCTGGTGCTGGAGAGCG | 76 | 13 | 24643406 |
| cg01429360 | 617.0854 | 3.26E-122 | IGF2BP3 | 7 | 23509546 | CGGGCCCACCTGAAAGCGCCTCGATGGCCTTGAGGGCCCAGCTCTCGTCC | 77 | 7 | 23476071 |
| cg12765028 | 242.6626 | 3.26E-121 | | 4 | 13526659 | GGGCTCTCCGAAACAGGCCGGGAAAGCTGAAAGCACAGTGACCTCCTTCG | 78 | 4 | 13135757 |
| cg08957484 | 224.7044 | 9.76E-121 | CCNI2 | 5 | 132083532 | GGTCCTGGGCCAGCTGCAAGTGGCAGAGCAGCCGGCGCTCGTCCAGGTCG | 79 | 5 | 132111431 |
| cg17621438 | -217.539 | 2.47E-120 | RNF180 | 5 | 63461216 | CTGGCAACGCTACCTGGGTTTAGTTTTCCCTTCGTATATCACTATCTTCG | 80 | 5 | 63496972 |
| cg18633600 | 232.9342 | 3.43E-119 | LRTM2; CACNA2D4 | 12 | 1940452 | GGGCAACTGGGCCAGGCCGTTGATGGACAGGTCCAGGTGGCGGAGCAGCG | 81 | 12 | 1810713 |
| cg18573383 | 394.9647 | 4.31E-118 | KCNC2 | 12 | 75603401 | GTGGAGACTGGCCGCAGGTCAGGAGAGCTCACCACTTGAAGGTGAAGTCG | 82 | 12 | 73889668 |
| cg10039299 | 305.1925 | 5.87E-117 | | 2 | 96192273 | GCAGTCCCTGAGCCTCTGCAGGCAGTTCTTGGAGCCCTCGGGCTTTTGCG | 83 | 2 | 95556000 |
| cg17101296 | 202.8553 | 1.51E-116 | | 8 | 145925708 | TGGGACAAGGACAGGTCAGCGGGTCACAGGCCGGAAGTGAGACTCGCCCG | 84 | 8 | 145896517 |
| cg08540945 | 261.6127 | 1.61E-116 | | 7 | 152591698 | CGCGCTCCGCCCTTTGCCTGCAGAGCGCTGGGGGTTTAAAGTCCTGAACC | 85 | 7 | 152222631 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg02561482 | 286.9963 | 1.88E-116 | TFAP2B | 6 | 50813551 | CGGCAGCCCCTCCAGCGGCTGATTCTATGTCCTCAACACGACTGGGCGCC | 86 | 6 | 50921510 |
| cg26842024 | 466.3294 | 2.91E-116 | KLF2 | 19 | 16436122 | CAACAGCGTGCTGGACTTCATCCTGTCCATGGGGCTGGATGGCCTGGGCG | 87 | 19 | 16297122 |
| cg16969368 | 216.3395 | 2.96E-116 | DHX40 | 17 | 57642752 | TGCAGAGACCACTGTGGCGTTGAAAAGAGGTGTCGTCGCGACCTTCGGCG | 88 | 17 | 54997534 |
| cg15626285 | -186.581 | 7.21E-116 | C1S | 12 | 7167781 | CGATTGCTTAATGCTATTTTTCAGCCAAAGGGTGTGTTTCTGAGTTTTCG | 89 | 12 | 7038042 |
| cg19470159 | 426.8016 | 1.15E-115 | C3orf50 | 3 | 167967842 | CGCTTGGAGAGAGCAGACAACAGTATGCCCCGCCCCACCTCGGACCTGGT | 90 | 3 | 169450536 |
| cg23361092 | 345.3453 | 1.95E-115 | | 13 | 79170923 | CGGAGAGTTCTGGAAATAAAATGAATTATAACAAGGAGCTAATTAAAAAC | 91 | 13 | 78068924 |
| cg03763391 | 1044.918 | 5.91E-115 | BUB1B | 15 | 40453091 | AGACAGCACCTGGGGGTATTTGTTTGCCTAAGCCTGCTGCACTTCCACG | 92 | 15 | 38240383 |
| cg03664992 | 406.7318 | 1.15E-114 | BMP8A | 1 | 39957393 | GAGGCCGGGGCTGTTCTGAGGGCTGGGACTGTCAGCCAATCCGTCTGTCG | 93 | 1 | 39729980 |
| cg08483876 | 338.5102 | 1.54E-114 | | 8 | 145910754 | AGGGCAGGGACACAACTCACTCTGGACAGGGTACAGTCACACCCACTTCG | 94 | 8 | 145881562 |
| cg18035229 | 381.9429 | 4.15E-114 | PRDM14 | 8 | 70984270 | TCTGTGAATGTGAATGGAACTAAGCGTTCCTTTCTCTCCCTCAATGGCCG | 95 | 8 | 71146824 |
| cg00664406 | 164.0497 | 7.58E-114 | GRM2 | 3 | 51740875 | CGGGGATTCAGCACCACGAGGCGGACAGCTCCAGGCCCTGAGGTCCCCAG | 96 | 3 | 51715915 |
| cg26720338 | 740.0267 | 6.22E-113 | JPH3 | 16 | 87635575 | ACCACAGGTGGTTTCTCCGGTGACAAACAATGCTTCCTTCTTCCTTCCG | 97 | 16 | 86193076 |
| cg11052516 | 804.1625 | 8.10E-113 | LOC645323 | 5 | 87957175 | CCTTGCAAGGCGGCTGCTAAGCCTGGCTAATTTTAGATCTCCAGAATGCG | 98 | 5 | 87992931 |
| cg07544187 | 245.416 | 1.67E-112 | CILP2 | 19 | 19651235 | CGCGTGGCCGCCGCTGCTCCAACTACCACGTGCGCTTCCGCTGCCCACTA | 99 | 19 | 19512235 |
| cg19674669 | 448.8857 | 1.15E-111 | GLB1L3 | 11 | 134146910 | CGGTGCCCAGCCGCTGGAGCCCCTGCCTGCGTGCCCACCCTGATTTTC | 100 | 11 | 133652120 |

TABLE 1A-continued

| Marker | Coeff | PTest | UCSC_Ref Gene Name | CHR | MAP INFO | SourceSeq | SEQ ID NO: | Chromo-some_36 | Coordi-nate_36 |
|---|---|---|---|---|---|---|---|---|---|
| cg07850154 | -199.617 | 1.95E-111 | RNF180 | 5 | 63461232 | CGAAGGGAAAACTAAACCCAGGTAGCGTTGCCAGCTTAAAAGTCCTAGGC | 101 | 5 | 63496988 |
| cg07583137 | -189.624 | 3.62E-111 | CHMP4C | 8 | 82644012 | CAGCCCCATTTAAGGTTTTTGATACACTGAGGATCATTCAGAAAACTTCG | 102 | 8 | 82806567 |
| cg25148589 | 265.0785 | 9.11E-111 | GRIA2 | 4 | 158141936 | CGGCAGCTCCGCTGAAAACTGCATTCAGCCAGTCCTCCGGACTTCTGGAG | 103 | 4 | 158361386 |
| cg07178825 | 214.9746 | 9.65E-111 | TP73 | 1 | 3649574 | CGACCTGCCCGACTGCAAGGCCCGCAAGCAGCCCATCAAGGAGGAGTTCA | 104 | 1 | 3639434 |
| cg10172783 | 341.995 | 1.02E-110 | NAGS | 17 | 42082036 | CGCCATGACGACAACCAACTCTTGCCCCCCAAGAGTGGCAGTCTGTCTGG | 105 | 17 | 39437562 |
| cg16247183 | 247.7465 | 2.90E-110 | | 1 | 225865110 | CGCTAGCGCCTCGGTTACAGCCTTTCCCGCAAGGCTTCATTCAGTCGCGC | 106 | 1 | 223931733 |
| cg03696327 | 555.4321 | 7.31E-110 | GPR88 | 1 | 101005121 | CACGATGCCCAGGTAGCAGTGCAGCAGCAGAGCTGTCTGCGCCAGCAGCG | 107 | 1 | 100777709 |
| cg05675373 | 346.861 | 1.37E-109 | KCNC4 | 1 | 110754257 | AGGCGGGTTCCCGGTAGGGTGCGCAGGGTGCTGCGGTAGGTCTCATGTCG | 108 | 1 | 110555780 |
| cg14044057 | 907.4472 | 2.19E-109 | SPDYA | 2 | 29033296 | CGTGTGAATACGGTGGCTTCTTGTGAGAAGGGGCCATTCTATTGTAACTG | 109 | 2 | 28886800 |
| cg01644850 | 996.0475 | 4.72E-109 | ZNF551 | 19 | 58193231 | CGGAGCTCTTCGGAGTGTGTCCACTGCTTTGACCTCTGCGAACTTGTATT | 110 | 19 | 62885043 |
| cg13636189 | 622.6708 | 1.09E-108 | NR4A3 | 9 | 102587074 | CGCAGCTCAGCAGGCCTCAGGGAAGGAACTGGGTGCCCAAACTCCGGCCT | 111 | 9 | 101626895 |
| cg21870884 | 252.246 | 2.30E-108 | GPR25 | 1 | 200842429 | GCTGGTGGATACCTTCGTGCTGCACCTGGCGGCAGCTGACCTGGGCTTCG | 112 | 1 | 199109052 |
| cg19392831 | 244.0071 | 1.26E-107 | PRLHR | 10 | 120355756 | CGGCCAAGCCAAAGGCAGGAGTCAGCACCACGGACAGCTTCCGCTGGATC | 113 | 10 | 120345746 |
| cg21255438 | 330.2059 | 1.96E-107 | PRDM14 | 8 | 70983760 | CGGGGAGAAAAAACCGAACACGTGTGCTACCCAGGGCCCCCAGATAAGC | 114 | 8 | 71146314 |
| cg26496307 | 497.0731 | 2.89E-107 | ZNF813 | 19 | 53970803 | CGGCCAGTAAGGTTGAGGCACTATTCAAAAGCCCTGGAATTGTCTGGAAC | 115 | 19 | 58662615 |

TABLE 1A-continued

| Marker | Coeff | PTest | UCSC_Ref Gene Name | CHR | MAP INFO | SourceSeq | SEQ ID NO: | Chromo- some_36 | Coordi- nate_36 |
|---|---|---|---|---|---|---|---|---|---|
| ch.1.3571292R | 602.477 | 3.81E-107 | DHX9 | 1 | 182831125 | CAGGTAGGTGCTGATGAATTGAGTGTGTTTAAATCTTAGACTTACTGTA | 116 | 1 | 181097747 |
| cg03399905 | 318.4912 | 4.54E-107 | ANKRD34C | 15 | 79576060 | CCATGCTCGGCCTTCTGGAAGATGCCCACAGACACTGGCAATAATGGACG | 117 | 15 | 77363115 |
| cg24834740 | 1060.466 | 4.85E-107 | PPP1R16B | 20 | 37434552 | CGCCCCGGCCCCCAGCTAGGTGATAGCAGGCTGGGACCACCTCCCCGCCC | 118 | 20 | 36867966 |
| cg02159381 | 438.4332 | 5.90E-107 | BSX | 11 | 122852523 | AACACAGAGACCCAACCTACCCAGGAGCTTGTCTTCTTGCCTCTCCAGCG | 119 | 11 | 122357733 |
| cg13782301 | 190.5049 | 7.31E-107 | PRRT1 | 6 | 32116875 | CGATGTATCCAAGTCTGACGGCCCCAGAAACGGGTGTGCAGGGCGCCCAT | 120 | 6 | 32224853 |
| cg16054275 | -244.386 | 1.97E-106 | F5 | 1 | 169556022 | CGTCCGTTACCACTGACCTGAGGCCTGCCTGGGTCCAAGCTCACACTTGG | 121 | 1 | 167822646 |
| cg18867659 | 694.0629 | 1.22E-105 | NETO2 | 16 | 47178357 | GGTCAAAACTTTGCCCAGCTCAGCCTTGCTCGACCCTGGGCAGGGAAGCG | 122 | 16 | 45735858 |
| cg22796704 | -184.335 | 1.84E-105 | ARHGAP22 | 10 | 49673534 | CGACCACACCAGGCACCCAGGAGCAAGTGCTTTGAAATGCGGCTTTCTCC | 123 | 10 | 49343540 |
| cg22158769 | 401.3016 | 2.00E-105 | LOC375196; LOC100271715 | 2 | 39187539 | ACGCGGGAACTCTTTGAGAGAGCGGCTCAGCGGCTTGGCCTTGCCGTGCG | 124 | 2 | 39041043 |
| cg08858751 | 776.6992 | 2.31E-105 | ZNF599 | 19 | 35264235 | TCCGTCCCTTGTAGCACTGCCTTCTGGGTAATGTAGTTTGACGGAATCCG | 125 | 19 | 39956075 |
| cg12052661 | 253.4845 | 2.47E-105 | CACNA1B | 9 | 140772545 | GTGAAGCAGTTCTGCTTGACCGGGATGGGGTTGTACAGCGCCATGGTCCG | 126 | 9 | 139892366 |
| cg11176990 | 422.1135 | 4.75E-105 | LOC375196; LOC100271715 | 2 | 39187533 | GAACTCTTTGAGAGAGCGGCTCAGCGGCTTGGCCTTGCCGTGCGCCTGCG | 127 | 2 | 39041037 |
| cg10328877 | 482.2751 | 7.70E-105 | MEIS2 | 15 | 37391187 | CGCCGCCTAGACTACTAGCCTGGGCTGCTTGTTTTGTCTCTGAAATTGAC | 128 | 15 | 35178479 |
| cg19855470 | 300.7657 | 1.03E-104 | CACNA1I | 22 | 40060836 | CAGCAGCTGGAACGTGCTGGATGGCTTTCTTGTCTTCGTGTCCATCATCG | 129 | 22 | 38390782 |
| cg12921750 | 479.2745 | 2.73E-104 | NETO1 | 18 | 70535336 | AGCCCCAAGCCATGACTAAGGAGCCCATTTGGTAACTCTGCCCTCTTCCG | 130 | 18 | 68686316 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg02286549 | 1008.269 | 3.07E-104 | TFEB | 6 | 41700710 | CGGTTTCTGCAGGCAACAGGGGTTTCCCCAACCACAGCTGTCATGAAAAC | 131 | 6 | 41808688 |
| cg09240095 | 825.5141 | 3.45E-104 | KCNMB4 | 12 | 70759304 | CGGTGACCCTTGTGGCAACTTAGGTCTCTGGCAGCCGAGTTGACCCCAAC | 132 | 12 | 69045571 |
| cg18760621 | 773.2701 | 3.64E-104 | | 1 | 158083299 | AAGGCAAATTGCCTGCCTCGTGCATAATAAGCCAGGCGTGGAGAGCAGCG | 133 | 1 | 156349923 |
| cg20199655 | 866.8009 | 3.94E-104 | KRAS | 12 | 25404314 | TGAGGGTGGCGGGGTGCTCTTCGCAGCTTCTCTGTGGAGACCGGTCAGCG | 134 | 12 | 25295581 |
| cg13464448 | 431.1235 | 2.04E-103 | ADAMTS8 | 11 | 130297513 | CCACGAGTAGGACCAAGCGGTTTGTGTCTGAGGCGCGCTTCGTGGAGACG | 135 | 11 | 129802723 |
| cg01974375 | -337.238 | 2.70E-103 | PI4KB | 1 | 151298954 | CGAGGGAGGTGTCAAAGTTGGAAATCCTGAATGGGAAGGGCACTGTCAAA | 136 | 1 | 149565578 |
| cg24809973 | 205.9183 | 2.93E-103 | | 8 | 72468820 | TGAGAGCTGGGAACCTGCGCCAGTGACTGCGCGACAGTGTTGACGGGCCG | 137 | 8 | 72631374 |
| cg10850791 | 237.5174 | 8.50E-103 | PABPC4L | 4 | 135122718 | CGGGCCAAGGGCGTCCTGAAGACCTAGGGGGCCCCTCCGACCTCCCGACC | 138 | 4 | 135342168 |
| cg24452260 | 266.3675 | 1.02E-102 | GRIA2 | 4 | 158143538 | TCGCGAGCTCCATGTTCTCCTCTTTGGGACAAGTTGTTGAAATGGTTCCG | 139 | 4 | 158362988 |
| cg02328239 | 308.6597 | 1.13E-102 | GDNF | 5 | 37837463 | ACCAAGCTCTGCTCCTCAAGTGACGGGGGCTCTGCTCTGCCAGGTGACCG | 140 | 5 | 37873220 |
| cg18445088 | 250.5134 | 2.66E-102 | CACNA1I | 22 | 40081812 | CGGGCAGCCTGCAGACCACGCTCGAGGACAGCCTGACCCTGAGCGACAGC | 141 | 22 | 38411758 |
| cg15121420 | -267.283 | 5.74E-102 | RAB17 | 2 | 238490819 | CGAGCCCTGAAGCTGGAAAGCCAACGTGCTGGCTGGAGCCAGAAGAGCAG | 142 | 2 | 238155558 |
| cg23355126 | 876.1891 | 7.97E-102 | TMEM50B | 21 | 34852107 | CGGTTGCCTGGCGCCGGAGACCCACAGACAGGACTCACCCAGCTTCCTCA | 143 | 21 | 33773977 |
| cg20209308 | 340.6068 | 8.36E-102 | GSC2 | 22 | 19137306 | CGCCACCGCACCATCTTCAGCGAAGAGCAGCTGCAGGCGCTCGAGGCGCT | 144 | 22 | 17517306 |
| cg20676716 | 270.1375 | 1.92E-101 | HOXD1 | 2 | 177053568 | GGCCCGAACCATGAGCTCCTACCTGGAGTACGTGTCATGCAGCAGCAGCG | 145 | 2 | 176761814 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg11873482 | 306.5791 | 2.16E-101 | TAC1 | 7 | 97361244 | CGTCGATGCCCATAACATCTGGACCCAATTGGGTTCTAAATGACGCAATT | 146 | 7 | 97199180 |
| cg09226692 | 566.8713 | 2.18E-101 | DLK2 | 6 | 43422490 | CGGACAGGCTGACCGGGAGCCCCAGAATGCACAACAGGCACACGAGATG | 147 | 6 | 43530468 |
| cg06475764 | 829.304 | 2.68E-101 | NETO2 | 16 | 47177480 | GGGAACATGGCCCTGGAGCGGCTCTGCTCGGTCCTCAAAGGTAAGGACCG | 148 | 16 | 45734981 |
| cg01820374 | -284.307 | 4.33E-101 | LAG3 | 12 | 6882083 | TCCTGGGCTTGCTGTTTCTGCAGCCGCTTTGGGTGGCTCCAGGTAAAACG | 149 | 12 | 6752344 |
| cg22016779 | -289.294 | 4.46E-101 | DNER | 2 | 230452311 | CGTGGCCTGGTTAACCAATCTGTTGCACTGGCTCCCTTTTAAGGGGCCTG | 150 | 2 | 230160555 |
| cg19505546 | 239.4817 | 3.94E-100 |  | 5 | 139017263 | GGGTGCAGAGGCCTAGGGCGGGCAGGCCGGCAGACTGGGGTCGGGCCACG | 151 | 5 | 138997447 |
| cg02830438 | 519.0376 | 7.14E-100 | C14orf109; MOAP1 | 14 | 93651416 | CGGCGGAGCCTGCTTGCAAAGCTGAGGTCCCGGATCTCACCTTCCTGTCC | 152 | 14 | 92721169 |
| cg27569300 | 317.7173 | 9.75E-100 | SYNM | 15 | 99645065 | CGCTGAGCCCGCCTGGCTAGCCCGCCACCCCGCCCGCTGTTACCCGACT | 153 | 15 | 97462588 |
| cg00852549 | 528.7081 | 1.13E-99 | NXPH1 | 7 | 8473457 | TGGGCCCACAGGGACAAGTGGCTCCCGCGGTGTCTTCGGTGGCCGCAGCG | 154 | 7 | 8439982 |
| cg03750778 | 988.2525 | 1.26E-99 | DST | 6 | 56708763 | ATCTGCGGCTTTGTTTCTCAGGCACCTGTTGTGGATCCCAAATAGAAACG | 155 | 6 | 56816722 |
| cg11847992 | -141.98 | 2.35E-99 |  | 5 | 95590917 | CGATGCTGCTTCATGATATGTGTCAAAATAAATGCAGGAAACAGCTTTTG | 156 | 5 | 95616673 |
| cg17729667 | 314.0009 | 4.10E-99 | NINL | 20 | 25566382 | GGCGGCTCTGGCCAGTTTGGAGCCTGGGGTGACCCTTGGAGCTGACCTCG | 157 | 20 | 25514382 |
| cg27067781 | 198.7199 | 4.35E-99 | PRRT1 | 6 | 32116853 | CGTCTCGCCTTGCGAGCAAGCTCGGAATCCAGTTCCTCAGGAACCCCTCC | 158 | 6 | 32224831 |
| cg08804013 | 965.0246 | 5.05E-99 | NFAT5; MIR1538; | 16 | 69600791 | CGACGGCGCAAAAACAAGCTGGAAAGGGAGGAAAATGGTGACCCTGCACT | 159 | 16 | 68158292 |
| cg26158959 | 461.8299 | 9.67E-99 | SYT14 | 1 | 210111162 | TTCAACCAAGGAGACCTGTCCATGGTCCTGACCACATCATTTGCCACTCG | 160 | 1 | 208177785 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg00171565 | 685.6216 | 9.82E-99 | PKM2; | 15 | 72523739 | CATTGGTCATCAGG TTTCTTAAAATGTG ACTCTGAATCTGTG TCCTTCCG | 161 | 15 | 70310793 |
| cg22059812 | 272.757 | 9.97E-99 | HTR6 | 1 | 19992564 | CCAGGCTGATGAGG CAGAGGTTGAGGAT GGAGGCGCTGCAGC ACATCACG | 162 | 1 | 19865151 |
| cg06998238 | 954.4673 | 1.10E-98 | ZNF121 | 19 | 9695323 | TTTCAGCCACATAG GACCCAGTCAAACA CAGAAATTGTAGTT TCTTCCCG | 163 | 19 | 9556323 |
| cg15500658 | 1024.487 | 1.17E-98 | SPEN; FLJ37453 | 1 | 16174610 | CATGGTCCGGGAAA CCAGGCATCTCTGG GTGGGCAACTTACC CGAGAACG | 164 | 1 | 16047197 |
| cg26946259 | 340.1318 | 1.31E-98 | | 2 | 119599545 | CGGAGACCAGGCGT GTCCCGCCAGACCC TTCAGACCCAGGCT AAACCCAA | 165 | 2 | 119316015 |
| cg21166964 | 329.2406 | 2.15E-98 | | 5 | 72529816 | CGGGCAGGCTCAAA AGAAAAAGAATAAT TAGGGATAATTGCT TGTGTCCA | 166 | 5 | 72565572 |
| cg11693709 | -160.409 | 2.40E-98 | PAK6 | 15 | 40542019 | GGCATTGGCAGGCC AGTATGGTCTGGGA GGGCAGCAAGGTGG GCACATCG | 167 | 15 | 38329311 |
| cg06369624 | 366.1836 | 4.10E-98 | KCNS1 | 20 | 43727355 | ACTCGCTCACAAAG GTTTCAGTGCTCCT CCCTGCGGACACCA GAAGGGCG | 168 | 20 | 43160769 |
| cg11436113 | -208.203 | 4.67E-98 | | 20 | 19191145 | AATAGAAACCCAAG AATCATTTCTGTGT GCCACAGGAGTGCT CTCCCCCG | 169 | 20 | 19139145 |
| cg17039022 | 239.849 | 5.60E-98 | ATP2B4 | 1 | 203595145 | CGGCTAATGACAGA GCCAACGATTCAAG ACCAAGTCAGACAG ACTCCAAA | 170 | 1 | 201861768 |
| cg12543649 | 1192.837 | 7.98E-98 | THBS3 | 1 | 155176868 | CGTTGTGGACACCA GGTGCCACTCCTGT GGGGGATCAGCACA GCATCTCC | 171 | 1 | 153443492 |
| cg09729848 | 723.7335 | 8.76E-98 | ADAMTS2 | 5 | 178770998 | CGAGGAGGAGCCTG GCAGTCACCTCTTC TACAATGTCACGGT CTTTGGCC | 172 | 5 | 178703604 |
| cg10833014 | 887.0278 | 1.09E-97 | WDR20; HSP90AA1 | 14 | 102605952 | CGGTCAACTAGACC CCACTAGCTGAAGC CGGCATCACCTGGG AAGCAGCC | 173 | 14 | 101675705 |
| cg01844642 | 214.6266 | 1.62E-97 | GPR62 | 3 | 51989764 | GGGGTTGATCCTGG CAGCTGTCGTGGAG GTGGGGGCACTGCT GGGCAACG | 174 | 3 | 51964804 |
| cg25321549 | 823.9165 | 1.77E-97 | ZSWIM6 | 5 | 60629121 | CATCCTGGAGGGCT GTTCGCCGGTTTCG GGGGTGGATGTGGA CAAAGGCG | 175 | 5 | 60664878 |

TABLE 1A-continued

| Marker | Coeff | PTest | UCSC_Ref Gene Name | CHR | MAP INFO | SourceSeq | SEQ ID NO: | Chromosome_36 | Coordinate_36 |
|---|---|---|---|---|---|---|---|---|---|
| cg08385097 | 915.1697 | 2.09E-97 | PAPOLG | 2 | 60984209 | CGGGAACTGTTTCTGACTTATCAAAGTGTGAACAAGAGGTACAGACCGGT | 176 | 2 | 60837713 |
| cg23032032 | 387.8131 | 2.33E-97 | FOXA1 | 14 | 38064513 | CGAGGAGGTGGGCACTCAAGCGACGTAAGATCCACATCAGCTCAACTGCA | 177 | 14 | 37134264 |
| cg17887993 | 738.1113 | 4.68E-97 | MATN4 | 20 | 43922449 | CGCGCCTGGAGGATCTGGAGAACCAGCTGGCCAACCAGAAGTGAGGGCCA | 178 | 20 | 43355863 |
| cg26456957 | 664.7293 | 4.78E-97 | PPP1R12C | 19 | 55629363 | GATGAATAGCAGACTGCCCCGGGGCAGTTAGGAATTCGACTGGACAGCCG | 179 | 19 | 60321175 |
| cg04588840 | 348.6705 | 5.42E-97 | CPXM1 | 20 | 2781685 | CTTGATGTCAGCAAAGTTTGCACAATGGGTCTTAACGTGCACTCATTCCG | 180 | 20 | 2729685 |
| cg17412974 | -326.896 | 5.69E-97 |  | 12 | 80496965 | TGCTGACCTTCGTAGTGTCCTCGTACAACCTGAACTTCATCGTCCTTTCG | 181 | 12 | 79021096 |
| cg07399288 | 1080.87 | 6.16E-97 | PMS2L4; STAG3L4 | 7 | 66767504 | CTGGGCTCCCATTGGCTGCTTTTGACGTTGTGCTCCACCCTTTCTGGGCG | 182 | 7 | 66404939 |
| cg26931990 | 241.6339 | 6.27E-97 | IFT140 | 16 | 1661230 | CGGCCGCCAGCTGCTTTCTTGGGGCGCTCCCTGCCTCGCTTGGCTCTGT | 183 | 16 | 1601231 |
| cg19049194 | 306.1541 | 2.12E-96 |  | 2 | 175193754 | TTTATCTAGAAAACTTTTCAAGCAAGACAAGGTCCTCTCGGCTTGTCCG | 184 | 2 | 174902000 |
| cg08677617 | 246.9861 | 2.32E-96 |  | 10 | 102484048 | TGTTGAGAGCGATTTTAATTCTCATTCTGTACCTGCAGATGCCGCGGCCG | 185 | 10 | 102474038 |
| cg05215004 | 663.8819 | 2.57E-96 | LOC285780 | 6 | 6546556 | CAAAGCAGATGACCTGGCAGGAACCAGCCGCAGTGAAGCCACCGCAACCG | 186 | 6 | 6491555 |
| cg14022202 | 722.7556 | 3.78E-96 | MTMR2 | 11 | 95656984 | CTTCAGAAACCAGAATCCGCGAATTGGGGCAACAATCCAGCAGGTCCCCG | 187 | 11 | 95296632 |
| cg21632975 | 263.091 | 8.60E-96 | NOVA2 | 19 | 46456210 | CGTCTACCTAGAGGCAAAGACAGGAGAGAGGGAGTCCGTAAAATCTGGAA | 188 | 19 | 51148050 |
| cg09434500 | 332.8079 | 1.01E-95 | GRIK5 | 19 | 42502897 | GGGCTCCAGAGCCAGGCCTCGGACTTCGCGGGGAACCAAAGGCAAAATCG | 189 | 19 | 47194737 |
| cg09175724 | 764.3869 | 1.65E-95 | CDC42EP2 | 11 | 65082792 | CGGCCGCAGCTAAAGATAGGAGAACAACTCACTATCGGCTAAAAATACGG | 190 | 11 | 64839368 |

TABLE 1A-continued

| Marker | Coeff | PTest | UCSC_Ref Gene Name | CHR | MAP INFO | SourceSeq | SEQ ID NO: | Chromo- some_36 | Coordi- nate_36 |
|---|---|---|---|---|---|---|---|---|---|
| cg21300373 | 207.977 | 1.80E-95 | | 4 | 165304540 | TCAGCGCTAAACCC AAGACAAAGGCTGC CCTGTGTCTTCCGT ACTCAGCG | 191 | 4 | 165523990 |
| cg01897823 | 787.5659 | 2.02E-95 | SOCS3 | 17 | 76356232 | GCTCAGCCTTTCTC TGCTGCGAGTAGTG ACTAAACATTACAA GAAGGCCG | 192 | 17 | 73867827 |
| cg16076997 | 420.1993 | 3.41E-95 | FOXD2 | 1 | 47905067 | CGGGGCAGGGCAGA GGCCTTCCTTCTCT ATAGACCACATCAT GGGCCACG | 193 | 1 | 47677654 |
| cg15822346 | 603.9391 | 3.59E-95 | SLC16A10 | 6 | 111408761 | GGTGCGGGGCTGTG ACCTAGAGGCTTCA GTGTCGATCCCCGA GGTGTTCG | 194 | 6 | 111515454 |
| cg06121469 | 978.0709 | 7.94E-95 | SPG11 | 15 | 44956098 | CGGCCTGCTACGCT AAGCTAGGCCTTCA AGCATGCCAGAGCA GTTAAGCA | 195 | 15 | 42743390 |
| cg14513680 | 909.9088 | 9.49E-95 | C9orf93 | 9 | 15552606 | CCTGCTTTTTGAAA CTGGTTCTTCTGCC CATCTTTAGAGCCA CAGCAACG | 196 | 9 | 15542606 |
| cg03301331 | 303.8438 | 1.21E-94 | RAB4A | 1 | 229406681 | CGGGACTCAGCCCC CAACGCCCCCACCT GCCGCTCTGCCCAC CTCAGCGC | 197 | 1 | 227473304 |
| cg02631838 | 279.3827 | 1.27E-94 | HPCA | 1 | 33358788 | CGCCGCTCCAGGCC CTCCACTGTCGGGC CCCGGTGTCCTCCA ACATCTCT | 198 | 1 | 33131375 |
| cg14408969 | 913.5962 | 1.28E-94 | C8orf40 | 8 | 42396118 | ATAGCATCCTGGCC ATATCCAGTTTTGA AAACACTACGGTGT CAGCCACG | 199 | 8 | 42515275 |

TABLE 1B

| Marker | UCSC_Ref- Gene_Name | UCSC_Ref- Gene Accession | UCSC_Ref- Gene Group | UCSC_CpG_Is- lands_Name | HMM_Island | Regulatory_Fea- ture_Name |
|---|---|---|---|---|---|---|
| cg16867657 | ELOVL2 | NM_017770 | TSS1500 | chr6:11043913- 11045206 | 6:11151611- 11153237 | 6:11044102- 11044892 |
| cg10501210 | | | | | 1:206063625-206063801 | |
| cg22454769 | FHL2 | NM_001039492; NM_001450; NM_201557; NM_201555 | TSS200; TSS200; 5'UTR; TSS200 | chr2:106014878- 106015884 | 2:105381311- 105382817 | 2:106014507- 106016259 |
| cg04875128 | OTUD7A | NM_130901 | Body | chr15:31775540- 31776988 | 15:29562601-29564280 | |
| cg24724428 | ELOVL2 | NM_017770 | TSS1500 | chr6:11043913- 11045206 | 6:11151611- 11153237 | 6:11044102- 11044892 |
| cg06639320 | FHL2 | NM_001039492; NM_001450; NM_201557; NM_201555 | TSS200; TSS200; 5'UTR; TSS200 | chr2:106014878- 106015884 | 2:105381311- 105382817 | 2:106014507- 106016259 |
| cg14556683 | EPHX3 | NM_024794; NM_001142886 | 1stExon; Body | chr19:15342626- 15343181 | 19:15203635- 15204238 | 19:15341951- 15343455 |

TABLE 1B-continued

| Marker | UCSC_Ref-Gene_Name | UCSC_Ref-Gene Accession | UCSC_Ref-Gene Group | UCSC_CpG_Islands_Name | HMM_Island | Regulatory_Feature_Name |
|---|---|---|---|---|---|---|
| cg23606718 | FAM123C | NM_152698; NM_001105194; NM_001105195; NM_001105194; NM_001105193; NM_001105195 | 5'UTR; 5'UTR; 1stExon; 1stExon; 5'UTR; 5'UTR | chr2:131513363-131514183 | 2:131229834-131230653 | 2:131513688-131513993 |
| cg07553761 | TRIM59 | NM_173084 | TSS1500 | chr3:160167184-160168200 | 3:161649892-161650878 | 3:160166409-160168278 |
| cg14361627 | KLF14 | NM_138693 | TSS1500 | chr7:130417912-130419378 | 7:130068467-130069793 | 7:130418325-130419878 |
| cg14692377 | SLC6A4 | NM_001045; NM_001045 | 1stExon; 5'UTR | chr17:28562387-28563186 | 17:25586344-25587312 | 17:28562266-28563419 |
| cg19283806 | CCDC102B | NM_001093729 | 5'UTR | | | 18:66388995-66389733 |
| cg00292135 | C7orf13; RNF32 | NR_026865; NM_030936 | Body; TSS1500 | chr7:156432433-156433670 | 7:156125195-156126707 | 7:156432754-156434135 |
| cg08097417 | KLF14 | NM_138693 | TSS1500 | chr7:130417912-130419378 | 7:130068467-130069793 | 7:130418325-130419878 |
| cg24079702 | FHL2 | NM_001039492; NM_001450; NM_201557; NM_201555 | TSS200; TSS200; 5'UTR; TSS200 | chr2:106014878-106015884 | 2:105381311-105382817 | 2:106014507-106016259 |
| cg02650266 | | | | chr4:147558231-147558583 | 4:147777501-147778016 | 4:147557996-147558356 |
| cg06493994 | SCGN | NM_006998; NM_006998 | 1stExon; 5'UTR | chr6:25652380-25652709 | 6:25760360-25760750 | 6:25652510-25652746 |
| cg16419235 | PENK | NM_001135690 | TSS1500 | chr8:57360585-57360815 | 8:57522950-57523369 | 8:57360377-57362115 |
| cg22736354 | NHLRC1 | NM_198586 | 1stExon | chr6:18122250-18122994 | 6:18230230-18231229 | 6:18122473-18123542 |
| cg07547549 | SLC12A5 | NM_020708; NM_001134771 | Body;Body | chr20:44657463-44659243 | 20:44090882-44092713 | 20:44657985-44658436 |
| cg21572722 | ELOVL2 | NM_017770 | TSS1500 | chr6:11043913-11045206 | 6:11151611-11153237 | |
| cg04400972 | TRIM45 | NM_025188; NM_001145635 | TSS1500; TSS1500 | chr1:117664180-117665148 | 1:117465578-117466781 | 1:117663907-117665512 |
| cg26290632 | CALB1 | NM_004929 | 1stExon | | 8:91163987-91164262 | |
| cg21296230 | GREM1 | NM_013372 | 5'UTR | chr15:33009530-33011696 | 15:30796823-30799072 | |
| cg25778262 | CPM | NM_198320; NM_001005502; NM_001874 | TSS1500; TSS1500; 5'UTR | chr12:69327021-69327532 | 12:67612814-67613799 | 12:69326064-69327911 |
| cg13649056 | | | | chr9:136474170-136474748 | 9:135463992-135464726 | 9:136474269-136474939 |
| cg00748589 | | | | chr12:11653232-11653775 | 12:11544500-11545229 | 12:11653353-11654101 |
| cg23500537 | | | | | | 5:140400003-140400154 |
| cg03607117 | SFMBT1 | NM_001005159; NM_016329; NM_001005158 | TSS1500; TSS1500; TSS1500 | chr3:53078956-53081101 | 3:53053856-53056190 | |
| cg23091758 | NRIP3 | NM_020645 | TSS200 | chr11:9025095-9026315 | 11:8981699-8983012 | |
| cg07955995 | KLF14 | NM_138693 | TSS1500 | chr7:130417912-130419378 | 7:130068467-130069793 | 7:130418325-130419878 |
| cg04836038 | DOCK9 | NM_015296; NM_001130049 | TSS1500; TSS1500 | chr13:99738331-99740022 | 13:98535557-98538321 | 13:99739202-99739439 |
| cg20426994 | KLF14 | NM_138693 | 1stExon | chr7:130417912-130419378 | 7:130068467-130069793 | |
| cg08128734 | RASSF5 | NM_182663; NM_182664 | Body;Body | chr1:206680236-206681444 | | |
| cg24436906 | BOK | NM_032515 | TSS200 | chr2:242498013-242499274 | 2:242146569-242147947 | |
| cg04908625 | ADCY5 | NM_183357 | 1stExon | chr3:123166218-123168567 | 3:124648975-124651818 | 3:123166803-123167158 |
| cg00481951 | SST | NM_001048 | Body | chr3:187387914-187388176 | 3:188870246-188870359 | |
| cg15108590 | CBS | NM_000071 | 5'UTR | chr21:44494624-44496989 | 21:43367599-43370089 | |
| cg22282410 | PTPRN2 | NM_130843; NM_130842; NM_002847 | TSS1500; TSS1500; TSS1500 | chr7:158379328-158381221 | 7:158072055-158074219 | 7:158379935-158381567 |

TABLE 1B-continued

| Marker | UCSC_Ref-Gene_Name | UCSC_Ref-Gene Accession | UCSC_Ref-Gene Group | UCSC_CpG_Islands_Name | HMM_Island | Regulatory_Feature_Name |
|---|---|---|---|---|---|---|
| cg21801378 | BRUNOL6 | NM_052840 | 1stExon | chr15:72611946-72612802 | 15:70399042-70400040 | 15:72611781-72613209 |
| cg04940570 | TEAD1 | NM_021961 | 5'UTR | chr11:12695414-12696981 | 11:12651991-12653557 | 11:12695339-12696865 |
| cg04084157 | VGF | NM_003378 | TSS200 | chr7:100806279-100809064 | 7:100594926-100596772 | 7:100808711-100809141 |
| cg25410668 | RPA2 | NM_002946 | TSS1500 | chr1:28240584-28241535 | 1:28113187-28114165 | 1:28240552-28241702 |
| cg04865692 | KCNC3 | NM_004977 | 1stExon | chr19:50831454-50832070 | 19:55523267-55524969 | 19:50831452-50833214 |
| cg04528819 | KLF14 | NM_138693 | 1stExon | chr7:130417912-130419378 | 7:130068467-130069793 | |
| cg10804656 | | | | chr10:22623350-22625875 | 10:22663357-22663769 | |
| cg09499629 | KLF14 | NM_138693 | TSS1500 | chr7:130417912-130419378 | 7:130068467-130069793 | 7:130418325-130419878 |
| cg03032497 | | | | chr14:61108954-61109786 | 14:60177929-60179820 | |
| cg09401099 | | | | chr3:156533839-156535131 | 3:158016534-158017978 | |
| cg12373771 | CECR6 | NM_031890; NM_001163079 | 1stExon; 5'UTR | chr22:17600563-17602611 | 22:15980564-15982862 | |
| cg07927379 | C7orf13; RNF32 | NR_026865; NM_030936 | Body; TSS1500 | chr7:156432433-156433670 | 7:156125195-156126707 | 7:156432754-156434135 |
| cg18473521 | HOXC4 | NM_153633; NM_014620 | Body;Body | chr12:54447744-54448091 | 12:52734084-52734533 | 12:54447856-54448358 |
| cg07806886 | STXBP5L | NM_014980 | TSS200 | chr3:120626880-120627579 | 3:122109343-122110635 | |
| cg01528542 | | | | chr12:81471569-81472119 | | |
| cg03473532 | MKLN1 | NM_001145354 | Body | chr7:131012460-131013190 | | 7:131008672-131009115 |
| cg25478614 | SST | NM_001048 | Body | chr3:187387914-187388176 | 3:188870501-188870889 | |
| cg21186299 | VGF | NM_003378; NM_003378 | 1stExon; 5'UTR | chr7:100806279-100809064 | 7:100594926-100596772 | 7:100808711-100809141 |
| cg05093315 | SAAL1 | NM_138421 | TSS1500 | chr11:18127296-18128711 | | 11:18127220-18128173 |
| cg23441616 | MYCBP2 | NM_015057 | TSS1500 | chr13:77900504-77901140 | 13:76798159-76799513 | 13:77901146-77901558 |
| cg17321954 | STXBP5L | NM_014980 | TSS200 | chr3:120626880-120627579 | 3:122109343-122110635 | |
| cg03771840 | TRIM15 | NM_033229 | 3'UTR | chr6:30139718-30140263 | 6:30247613-30248242 | 6:30137754-30140152 |
| cg03545227 | PTPRN | NM_002846 | Body | chr2:220173021-220173271 | 2:219881281-219882527 | 2:220172822-220173572 |
| cg18826637 | | | | | | 2:145116478-145116676 |
| cg23186333 | CD44 | NM_001001389; NM_001001392; NM_000610; NM_001001390; NM_001001391 | Body; Body;Body; Body;Body | chr11:35160375-35161000 | | 11:35160307-35162010 |
| cg06570224 | | | | chr3:157812053-157812764 | 3:159294712-159295751 | |
| cg13848598 | ADRB1 | NM_000684 | 1stExon | chr10:115803358-115805468 | 10:115792700-115795458 | |
| cg20482698 | ACTN2 | NM_001103 | 1stExon | chr1:234916096-236850323 | 1:236849472-236849946 | 1:236849424-236850009 |
| cg24430580 | PITX2 | NM_000325; NM_000325; NM_153426; NM_153427 | 1stExon; 5'UTR; Body;Body | chr4:111542062-111544464 | 4:111762274-111764019 | 4:111544213-111544369 |
| cg16181396 | ZIC1 | NM_003412 | TSS1500 | chr3:147126988-147128999 | 3:148608809-148608897 | |
| cg23744638 | | | | chr11:10324353-10324828 | | |
| cg11806672 | POU4F1 | NM_006237 | Body | chr13:79175610-79177985 | 13:78073612-78074696 | |
| cg26005082 | MIR7-3; C19orf30 | NR_029607; NR_027148 | TSS1500;Body | | 19:4720522-4720736 | 19:4769500-4769890 |
| cg09809672 | EDARADD | NM_080738; NM_145861; NM_145861 | TSS1500; 5'UTR; 1stExon | chr1:236558459-236559336 | | |
| cg22285878 | KLF14 | NM_138693 | TSS1500 | chr7:130417912-130419378 | 7:130068467-130069793 | 7:130418325-130419878 |

TABLE 1B-continued

| Marker | UCSC_Ref-Gene_Name | UCSC_Ref-Gene Accession | UCSC_Ref-Gene Group | UCSC_CpG_Islands_Name | HMM_Island | Regulatory_Feature_Name |
|---|---|---|---|---|---|---|
| cg08706258 | WSB1 | NM_015626; NM_134265; NM_015626; NM_134265 | 5'UTR; 5'UTR; 1stExon; 1stExon | chr17:25620999-25621730 | 17:22645071-22645997 | 17:25620827-25621911 |
| cg07920503 | FAM123A | NM_199138; NM_152704 | 1stExon; 1stExon | chr13:25743998-25746127 | 13:24641999-24644089 | 13:25745311-25745491 |
| cg01429360 | IGF2BP3 | NM_006547 | Body | chr7:23508184-23509712 | 7:23474024-23476225 | |
| cg12765028 | | | | chr4:13526553-13526770 | 4:13133203-13135868 | |
| cg08957484 | CCNI2 | NM_001039780 | 1stExon | chr5:132082873-132083911 | 5:132110589-132111953 | 5:132082544-132084072 |
| cg17621438 | RNF180 | NM_001113561; NM_178532 | TSS1500; TSS1500 | chr5:63461448-63462106 | | |
| cg18633600 | LRTM2; CACNA2D4 | NM_001163925; NM_001039029; NM_172364; NM_001163926 | 12:1810610-1810818 | 12:1939931-1940497 | | |
| cg18573383 | KCNC2 | NM_153748; NM_139137; NM_153748; NM_139137; NM_139136; NM_139136 | 1stExon; 1stExon; 5'UTR; 5'UTR; 1stExon; 5'UTR | chr12:75601081-75601752 | | |
| cg10039299 | | | | chr2:96192055-96193072 | 2:95555724-95556799 | 2:96191893-96192915 |
| cg17101296 | | | | chr8:145925410-145926101 | 8:145895807-145896910 | |
| cg08540945 | | | | chr7:152591458-152591706 | 7:152222028-152222744 | 7:152590901-152592150 |
| cg02561482 | TFAP2B | NM_003221 | 3'UTR | chr6:50813314-50813699 | 6:50921228-50921944 | |
| cg26842024 | KLF2 | NM_016270 | Body | chr19:16435202-16438064 | 19:16296270-16299051 | |
| cg16969368 | DHX40 | NM_001166301; NM_024612 | TSS200; TSS200 | chr17:57642720-57643294 | 17:54997503-54998169 | 17:57642284-57643729 |
| cg15626285 | C1S | NM_001734; NM_201442 | TSS200; TSS200 | | | |
| cg19470159 | C3orf50 | NR_021485 | Body | chr3:167967246-167968130 | 3:169449281-169450798 | 3:167967472-167967926 |
| cg23361092 | | | | chr13:79170114-79171231 | | |
| cg03763391 | BUB1B | NM_001211 | TSS200 | chr15:40453005-40453685 | 15:38240321-38240977 | 15:40452682-40453925 |
| cg03664992 | BMP8A | NM_181809; NM_181809 | 1stExon; 5'UTR | chr1:39956424-39958137 | 1:39728549-39730700 | 1:39956370-39957859 |
| cg08483876 | | | | chr8:145909676-145912846 | 8:145880426-145883921 | |
| cg18035229 | PRDM14 | NM_024504 | TSS1500 | chr8:70981873-70984888 | 8:71144880-71147746 | |
| cg00664406 | GRM2 | NM_000839; NM_001130063 | TSS1500; TSS1500 | chr3:51740740-51741413 | 3:51715881-51716416 | 3:51740394-51741198 |
| cg26720338 | JPH3 | NM_020655 | TSS1500 | chr16:87636506-87637284 | 16:86192682-86195809 | |
| cg11052516 | LOC645323 | NR_015436 | Body | chr5:87956489-87957187 | | |
| cg07544187 | CILP2 | NM_153221 | Body | chr19:19650683-19651274 | 19:19511515-19513041 | |
| cg19674669 | GLB1L3 | NM_001080407 | Body | chr11:134145559-134147180 | 11:133650782-133652625 | |
| cg07850154 | RNF180 | NM_001113561; NM_178532 | TSS1500; TSS1500 | chr5:63461448-63462106 | | |
| cg07583137 | CHMP4C | NM_152284 | TSS1500 | chr8:82644603-82644849 | | |
| cg25148589 | GRIA2 | NM_001083619; NM_000826; NM_001083620; NM_000826; NM_001083619 | 1stExon; 5'UTR; 5'UTR; 1stExon; 5'UTR | chr4:158143296-158144053 | | |
| cg07178825 | TP73 | NM_001126240; NM_005427; NM_001126242; NM_001126241 | Body;Body; 3'UTR; 3'UTR | chr1:3649294-3649674 | 1:3639248-3639685 | 1:3649524-3649611 |

TABLE 1B-continued

| Marker | UCSC_Ref-Gene_Name | UCSC_Ref-Gene Accession | UCSC_Ref-Gene Group | UCSC_CpG_Islands_Name | HMM_Island | Regulatory_Feature_Name |
|---|---|---|---|---|---|---|
| cg10172783 | NAGS; PYY | NM_153006; NM_004160 | 1stExon; TSS200 | chr17:42082027-42084972 | 17:39437458-39440004 | |
| cg16247183 | | | | chr1:225865068-225865328 | | 1:223931692-223932027 |
| cg03696327 | GPR88 | NM_022049 | Body | chr1:101004471-101005885 | 1:100777157-100778458 | 1:101004217-101005756 |
| cg05675373 | KCNC4 | NM_001039574; NM_004978; NM_153763 | 1stExon; 1stExon; 1stExon | chr1:110752256-110754794 | | 1:110553818-110556317 |
| cg14044057 | SPDYA | NM_182756; NM_001142634 | TSS1500; TSS1500 | chr2:29033351-29034011 | | 2:29033093-29034127 |
| cg01644850 | ZNF551 | NM_138347 | TSS200 | chr19:58193268-58193638 | 19:62884977-62885628 | 19:58192869-58194184 |
| cg13636189 | NR4A3 | NM_173199; NM_173198; NM_006981 | 5'UTR; 5'UTR; 5'UTR | chr9:102581791-102587561 | 9:101625826-101627570 | 9:102586760-102587409 |
| cg21870884 | GPR25 | NM_005298 | 1stExon | chr1:200842196-200843388 | | 1:199108820-199110011 |
| cg19392831 | PRLHR | NM_004248 | TSS1500 | chr10:120353692-120355821 | 10:120344980-120346127 | 10:120355066-120355940 |
| cg21255438 | PRDM14 | NM_024504 | TSS200 | chr8:70981873-70984888 | 8:71144880-71147746 | |
| cg26496307 | ZNF813 | NM_001004301 | TSS200 | chr19:53970802-53971473 | 19:58662500-58663285 | 19:53970386-53971554 |
| ch.1.3571292R | DHX9 | NM_001357 | Body | | | |
| cg03399905 | ANKRD34C | NM_001146341 | 5'UTR | chr15:79576059-79576270 | 15:77363046-77363443 | |
| cg24834740 | PPP1R16B | NM_015568 | 5'UTR | chr20:37434206-37435592 | 20:36867542-36869198 | 20:37434191-37434662 |
| cg02159381 | BSX | NM_001098169 | TSS200 | chr11:122852411-122852699 | 11:122357622-122357909 | 11:122852441-122852883 |
| cg13782301 | PRRT1 | NM_030651 | 3'UTR | chr6:32116590-32117229 | 6:32224481-32225389 | 6:32116667-32116975 |
| cg16054275 | F5 | NM_000130 | TSS1500 | | | 1:169555452-169556050 |
| cg18867659 | NETO2 | NM_018092 | TSS1500 | chr16:47176787-47178446 | 16:45734289-45736098 | 16:47177731-47178968 |
| cg22796704 | ARHGAP22 | NM_021226 | Body | chr10:49674243-49674776 | | |
| cg22158769 | LOC375196; LOC100271715 | NR_028386; NM_001145451 | TSS200; Body | chr2:39186777-39187968 | 2:39040222-39041697 | 2:39187021-39187940 |
| cg08858751 | ZNF599 | NM_001007248 | TSS200 | chr19:35263648-35264275 | 19:39955442-39956076 | 19:35263430-35264597 |
| cg12052661 | CACNA1B | NM_000718 | 1stExon | chr9:140771300-140773513 | 9:139891122-139893552 | 9:140772183-140772743 |
| cg11176990 | LOC375196; LOC100271715 | NR_028386; NM_001145451 | TSS200; Body | chr2:39186777-39187968 | 2:39040222-39041697 | 2:39187021-39187940 |
| cg10328877 | MEIS2 | NM_172316; NM_170674; NM_002399; NM_170675; NM_172316; NM_170677; NM_172315; NM_170676 | 1stExon; Body; 5'UTR; Body; 5'UTR; Body; TSS1500; Body | chr15:37392601-37392829 | 15:35178347-35178799 | 15:37390925-37391332 |
| cg19855470 | CACNA1I; CACNA1I | NM_001003406; NM_021096 | Body;Body | chr22:40060601-40061031 | 22:38389756-38390938 | |
| cg12921750 | NETO1 | NM_138966 | TSS1500 | chr18:70533965-70536871 | 18:68684946-68688303 | 18:70535222-70535468 |
| cg02286549 | TFEB | NM_001167827; NM_007162 | 5'UTR; 5'UTR | chr6:41701881-41703481 | | 6:41700492-41700940 |
| cg09240095 | KCNMB4 | NM_014505 | TSS1500 | chr12:70759437-70761052 | 12:69045232-69046021 | 12:70759300-70759423 |
| cg18760621 | | | | chr1:158083270-158083540 | 1:156349654-156350159 | 1:158082972-158083710 |
| cg20199655 | KRAS | NM_004985; NM_033360 | TSS1500; TSS1500 | | 12:25294434-25295836 | |
| cg13464448 | ADAMTS8 | NM_007037 | 1stExon | chr11:130297401-130298517 | 11:129802612-129803797 | 11:130297323-130298140 |
| cg01974375 | PI4KB | NM_002651 | TSS1500 | chr1:151300522-151300724 | | 1:151298798-151298969 |
| cg24809973 | | | | chr8:72468560-72469561 | 8:72631115-72632846 | |

TABLE 1B-continued

| Marker | UCSC_Ref-Gene_Name | UCSC_Ref-Gene Accession | UCSC_Ref-Gene Group | UCSC_CpG_Islands_Name | HMM_Island | Regulatory_Feature_Name |
|---|---|---|---|---|---|---|
| cg10850791 | PABPC4L | NM_001114734 | 5'UTR | | | 4:135341838-135342385 |
| cg24452260 | GRIA2 | NM_001083619; NM_000826; NM_001083620 | Body; Body;Body | chr4:158143296-158144053 | | 4:158362127-158363368 |
| cg02328239 | GDNF | NM_000514 | 5'UTR | chr5:37836747-37840726 | | 5:37872149-37873835 |
| cg18445088 | CACNA1I | NM_001003406; NM_021096 | Body;Body | chr22:40081519-40082390 | 22:38411527-38412481 | 22:40081445-40082681 |
| cg15121420 | RAB17 | NM_022449 | Body | | | 2:238490196-238490845 |
| cg23355126 | TMEM50B | NM_006134 | 5'UTR | chr21:34851229-34852702 | 21:33773438-33774743 | 21:34852040-34852861 |
| cg20209308 | GSC2 | NM_005315 | Body | chr22:19136293-19138512 | 22:17516155-17518857 | 22:19136359-19137652 |
| cg20676716 | HOXD1 | NM_024501 | 1stExon | chr2:177052957-177054350 | 2:176761016-176762831 | 2:177053532-177054285 |
| cg11873482 | TAC1 | NM_013998; NM_013997; NM_013996; NM_003182 | TSS200; TSS200; TSS200; TSS200 | chr7:97361132-97363018 | 7:97199050-97199704 | |
| cg09226692 | DLK2 | NM_206539; NM_023932 | Body;Body | chr6:43422368-43423705 | 6:43530362-43531683 | 6:43421555-43422964 |
| cg06475764 | NETO2 | NM_018092 | Body | chr16:47176787-47178446 | 16:45734289-45736098 | 16:47177261-47177605 |
| cg01820374 | LAG3 | NM_002286 | Body | chr12:6882855-6883184 | | 12:6881253-6882742 |
| cg22016779 | DNER | NM_139072 | Body | | | 2:230451331-230452578 |
| cg19505546 | | | | chr5:139017133-139017668 | 5:138997178-138998057 | 5:139017085-139017489 |
| cg02830438 | C14orf109; MOAP1 | NM_015676; NM_001098621; NM_001098621; NM_022151 | 5'UTR; 5'UTR; 1stExon; TSS200 | chr14:93650745-93651652 | 14:92720388-92721575 | 14:93650342-93652057 |
| cg27569300 | SYNM | NM_145728; NM_015286 | TSS1500; TSS1500 | chr15:99645030-99646444 | 15:97462554-97464153 | |
| cg00852549 | NXPH1 | NM_152745 | TSS200 | chr7:8473139-8475199 | 7:8439680-8442368 | |
| cg03750778 | DST | NM_001144770; NM_001144771; NM_183380; NM_001144769 | Body; Body; TSS1500; Body | chr6:56708059-56709166 | 6:56815609-56817067 | 6:56707727-56709327 |
| cg11847992 | | | | | | |
| cg17729667 | NINL | NM_025176 | TSS1500 | chr20:25565437-25566547 | 20:25513460-25514516 | 20:25565222-25566520 |
| cg27067781 | PRRT1 | NM_030651 | 3'UTR | chr6:32116590-32117229 | 6:32224481-32225389 | 6:32116667-32116975 |
| cg08804013 | NFAT5 | NM_138714; NM_001113178; NM_138713; NM_173214; NR_031719; NM_006599 | 5'UTR; Body;Body; 5'UTR; TSS1500; Body | chr16:69599437-69600736 | 16:68156939-68158313 | 16:69600528-69600817 |
| cg26158959 | SY114 | NM_001146261; NR_027458; NR_027459; NM_001146264; NM_153262; NM_001146262 | TSS1500; TSS1500; TSS1500; TSS1500; TSS1500; TSS1500 | chr1:210111179-210112054 | | 1:210110983-210111308 |
| cg00171565 | PKM2 | NM_002654; NM_182470; NM_182471 | TSS200; TSS200; TSS200 | chr15:72522131-72524238 | 15:70309363-70311340 | 15:72523315-72523809 |
| cg22059812 | HTR6 | NM_000871 | 1stExon | chr1:19991146-19992788 | 1:19863734-19865375 | |
| cg06998238 | ZNF121 | NM_001008727 | TSS200 | chr19:9694921-9695433 | 19:9555900-9556398 | 19:9694602-9695488 |
| cg15500658 | SPEN; FLJ37453 | NM_015001; NR_024279 | 1stExon; Body | chr1:16173889-16175396 | 1:16046263-16047983 | 1:16173682-16176432 |
| cg26946259 | | | | chr2:119599458-119600966 | 2:119315907-119316219 | |
| cg21166964 | | | | chr5:72529099-72529976 | 5:72564856-72565732 | |
| cg11693709 | PAK6 | NM_020168; NM_001128628; NM_001128629 | 5'UTR; 5'UTR; 5'UTR | chr15:40544352-40545512 | | |

TABLE 1B-continued

| Marker | UCSC_Ref-Gene_Name | UCSC_Ref-Gene Accession | UCSC_Ref-Gene Group | UCSC_CpG_Islands_Name | HMM_Island | Regulatory_Feature_Name |
|---|---|---|---|---|---|---|
| cg06369624 | KCNS1 | NM002251 | Body | chr20:43726297-43727372 | | 20:43726268-43727871 |
| cg11436113 | | | | chr20:19192459-19193902 | | |
| cg17039022 | ATP2B4 | NM_001001396; NM_001684 | TSS1500; TSS1500 | chr1:203598471-203598853 | | 1:203594755-203596253 |
| cg12543649 | THBS3 | NM_007112 | Body | chr1:155178547-155178980 | | 1:155175976-155177609 |
| cg09729848 | ADAMTS2 | NM_021599; NM_014244 | Body;Body | chr5:178770724-178772794 | 5:178703118-178705392 | 5:178769342-178771312 |
| cg10833014 | WDR20; HSP90AA1 | NM_181291; NM_181308; NM_001017963; NM_001017963; NM_144574; NM_181302 | TSS1500; TSS1500; 1stExon; 5'UTR; TSS1500; TSS1500 | chr14:102605597-102606977 | 14:101675134-101676861 | 14:102605541-102606369 |
| cg01844642 | GPR62 | NM_080865 | 1stExon | chr3:51989763-51990639 | 3:51964804-51965628 | |
| cg25321549 | ZSWIM6 | NM_020928 | Body | chr5:60626505-60629809 | 5:60661968-60665553 | |
| cg08385097 | PAPOLG | NM_022894 | Body | chr2:60983193-60983870 | | 2:60982720-60984542 |
| cg23032032 | FOXA1 | NM_004496 | TSS200 | chr14:38063663-38065665 | 14:37133439-37134763 | |
| cg17887993 | MATN4 | NM_030592; NM_030590; NM_003833 | Body; Body;Body | chr20:43921949-43922642 | 20:43355572-43356029 | 20:43921750-43923312 |
| cg26456957 | PPP1R12C | NM_017607 | TSS1500 | chr19:55628488-55629105 | 19:60320109-60321178 | 19:55628884-55629492 |
| cg04588840 | CPXM1 | NM_019609 | TSS1500 | chr20:2780978-2781497 | | 20:2780246-2781714 |
| cg17412974 | | | | | 12:79021088-79021218 | |
| cg07399288 | PMS2L4; STAG3L4 | NR_022007; NM_022906 | TSS200; TSS200 | chr7:66767145-66768031 | 7:66404594-66405450 | 7:66766960-66768186 |
| cg26931990 | IFT140 | NM_014714 | 5'UTR | chr16:1660054-1665095 | | 16:1659488-1661475 |
| cg19049194 | | | | chr2:175193398-175193764 | 2:174901271-174902076 | |
| cg08677617 | | | | chr10:102484200-102484476 | 10:102474032-102474107 | |
| cg05215004 | LOC285780 | NR_026970 | Body | chr6:6546370-6547230 | 6:6491370-6492312 | 6:6546161-6548100 |
| cg14022202 | MTMR2 | NM_201281; NM_016156; NR_023356; NM_201278 | 5'UTR; Body;Body; 5'UTR | chr11:95656912-95657365 | 11:95296479-95297009 | 11:95656229-95657555 |
| cg21632975 | NOVA2 | NM_002516 | Body | chr19:46456209-46456503 | 19:51147814-51148279 | |
| cg09434500 | GRIK5 | NM_002088 | 3'UTR | chr19:42502730-42503484 | 19:47194629-47195338 | 19:42500888-42503553 |
| cg09175724 | CDC42EP2 | NM_006779 | 5'UTR | chr11:65081937-65083333 | 11:64838535-64839930 | 11:65081771-65083639 |
| cg21300373 | | NM_001166373 | TSS200 | chr4:165304328-165305177 | 4:165523779-165524912 | |
| cg01897823 | SOCS3 | NM_003955 | TSS200 | chr17:76354818-76357038 | 17:73866128-73868633 | 17:76356011-76356507 |
| cg16076997 | FOXD2 | NM_004474 | 1stExon | chr1:47902793-47905518 | 1:47675329-47678200 | |
| cg15822346 | SLC16A10 | NM_018593 | TSS200 | chr6:111408426-111409484 | 6:111515073-111516544 | 6:111408087-111409949 |
| cg06121469 | SPG11 | NM_025137; NM_001160227 | TSS1500; TSS1500 | chr15:44955291-44955983 | | 15:44954821-44956641 |
| cg14513680 | C9orf93 | NM_173550 | TSS1500 | chr9:15552733-15553334 | | 9:15552576-15553107 |
| cg03301331 | RAB4A | NM_004578 | TSS200 | chr1:229406646-229407129 | 1:227473083-227474029 | 1:229406323-229407948 |
| cg02631838 | HPCA | NM_002143 | Body | chr1:33358469-33359449 | 1:33131039-33132010 | 1:33357886-33359585 |
| cg14408969 | C8orf40 | NM_001135675; NM_001135674; NM_138436; NM_006749; NM_001135676 | TSS1500; TSS1500; TSS1500; 5'UTR; TSS200 | chr8:42396235-42397195 | | |

Example 10. The Effect of Meditation on Genomic DNA Methylation, BDNF Level, and Cortisol Level Table 2 illustrates the demographics of participants.

| DEMOGRAPHICS | | |
|---|---|---|
| | Mean (SD) | Range |
| Gender | 19 M:19 F | |
| Age (years) | 34.28 (8.84) | 21-59 |
| Height (inches) | 67.18 (4.20) | 60-75 |
| Weight (pounds) | 142.26 (30.03) | 96.2-216.0 |
| Body Mass Index (BMI) (kg/m$^2$) | 22.05 (3.70) | 17.04-34.38 |
| Years of Yoga/Meditation Experience | 4.54 (3.26) | 0.2-15 |
| Length of daily practice (minutes) | 127.50 (41.22) | 45-180 |

Table 3 illustrates the psychometrics including Brief Symptom Inventory (BSI) criteria, Freiburg Mindfulness, and Tellegen Absorption scale.

| PSYCHOMETRICS | | | | | |
|---|---|---|---|---|---|
| N = 34 | Pre Mean (SD) | Post Mean (SD) | t | df | p |
| BSI-18 Total | 79.5 (11.0) | 86.9 (6.02) | −4.66 | 33 | <0.0001 |
| BSI-Depression | 26.9 (4.39) | 28.7 (1.96) | −2.84 | 33 | <0.01 |
| BSI-Anxiety | 26.2 (4.20) | 28.8 (2.07) | −4.22 | 33 | <0.0001 |
| BSI-Somatic | 26.3 (3.62) | 28.4 (2.83) | −4.66 | 33 | <0.0001 |
| Freiburg Mindfulness | 39.6 (7.65) | 44.5 (7.07) | −4.42 | 33 | <0.0001 |
| Tellegen Absorption | 88.6 (29.6) | 91.3 (28.9) | −0.86 | 33 | 0.4 |

Tables 4A and 4B illustrate the BDNF level from pre- and post-meditation sample.

TABLE 4A

| BIOMARKERS (n = 38) | | | | | | |
|---|---|---|---|---|---|---|
| | Pre Mean (SD) | | Post Mean (SD) | | | |
| | Raw | Ln | Raw | Ln | t | Valid N | p |
| B.M.I. (kg/m$^2$) | 22.1 (3.7) | — | 21.2 (3.1) | — | 4.37 | 36 | <0.0001 |
| BDNF (pg/ml) | 2513 (1484) | 7.65 (0.64) | 7039 (5274) | 8.44 (1.12) | 5.07 | 32 | <0.0001 |

TABLE 4B

| BIOMARKERS (n = 28) | | | | | | |
|---|---|---|---|---|---|---|
| | Pre Mean (SD) | | Post Mean (SD) | | | |
| | Raw | Ln | Raw | Ln | t | Valid N | p |
| B.M.I. (kg/m$^2$) | 24.1 (6.0) | — | 22.8 (4.9) | — | 2.74 | 8 | <0.05 |
| BDNF (pg/ml) | 2005 (747) | 7.51 (0.48) | 7629 (4649) | 8.70 (0.82) | 7.38 | 8 | <0.0001 |

Figure 35:
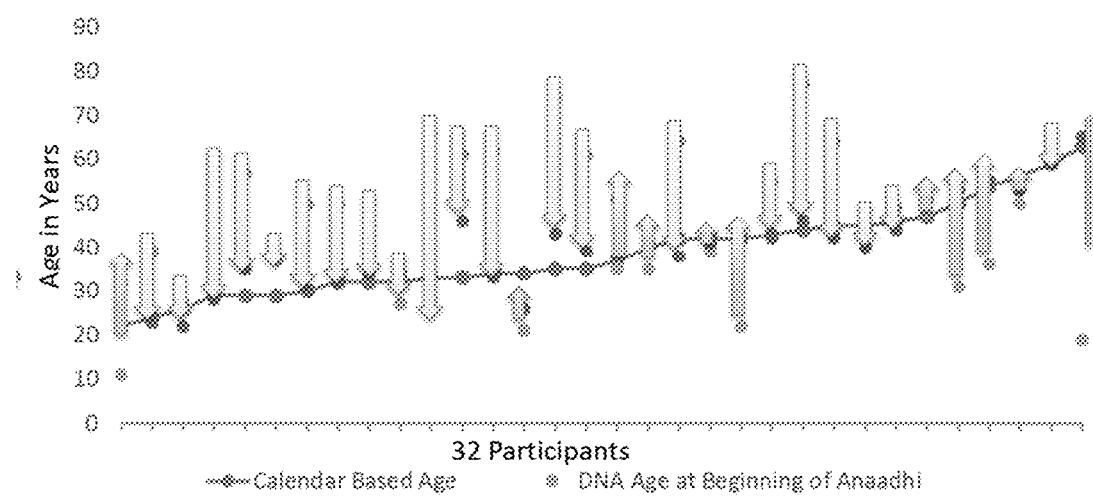
FIG. 35 shows the methylation age of 32 participants. Arrows going down (green): meditators with younger DNA at end of yoga intervention. Arrows going up (orange): meditators with older DNA at the end of yoga intervention. Blue line (dot) indicates meditator's calendar age.

FIG. 35 shows the methylation age of 32 participants. Arrows going down (green): meditators with younger DNA at end of yoga intervention. Arrows going up (orange): meditators with older DNA at the end of yoga intervention. Blue line (dot) indicates meditators calendar age.

Figure 36:
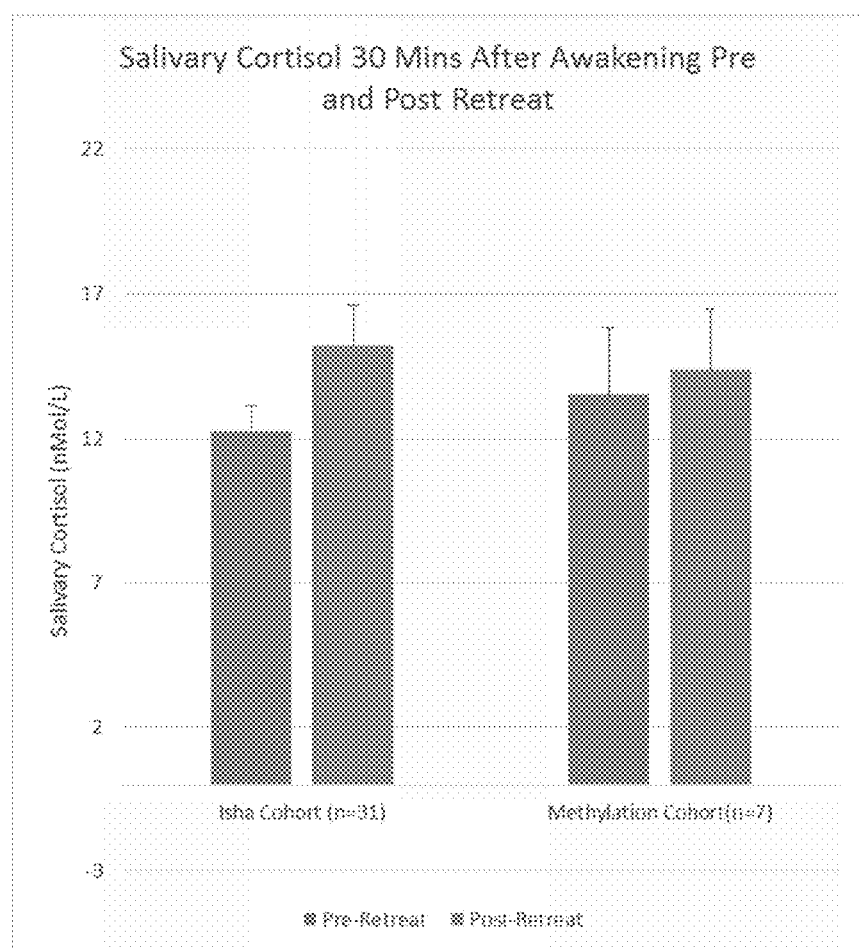
FIG. 36 shows the salivary cortisol level at 30 minutes after meditation either taken prior to attendance of a yoga retreat (Anaadhi yoga retreat) or post attendance of the yoga retreat.

FIG. 36 shows the salivary cortisol level at 30 minutes after meditation either taken prior to attendance of a yoga retreat (Anaadhi yoga retreat) or post attendance of the yoga retreat.

Embodiment 1 comprises a method of increasing the expression rate of ELOVL2, KLF14, PENK, or a combination thereof in a first subject, comprising: (a) administering to the first subject a therapeutically effective dose of vitamin C or its derivatives, metabolites, or pharmaceutically acceptable salts thereof for a first time period; (b) obtaining a sample from the first subject; and (c) determining whether the expression level of ELOVL2, KLF14, PENK, or a combination thereof has increased in the first subject relative to a control by contacting the sample with a probe that recognizes ELOVL2, KLF14, or PENK and detecting binding between ELOVL2, KLF14, or PENK and the probe.

Embodiment 2 comprises the method of embodiment 1, wherein vitamin C or its derivatives, metabolites, or pharmaceutically acceptable salts thereof is L-ascorbic acid 2-phosphate.

Embodiment 3 comprises the method of embodiment 1, wherein the expression level of ELOVL2 is determined by contacting the sample with a probe that recognizes ELOVL2 and detecting binding between the probe and ELOVL2.

Embodiment 4 comprises the method of embodiment 1, wherein the expression level of KLF14 is determined by contacting the sample with a probe that recognizes KLF14 and detecting binding between the probe and KLF14.

Embodiment 5 comprises the method of embodiment 1, wherein the expression levels of ELOVL2 and KLF14 are determined by contacting the sample with a probe that recognizes ELOVL2 and a probe that recognizes KLF14 and detecting each respective binding between the probes and ELOVL2 and KLF14.

Embodiment 6 comprises the method of embodiment 1, wherein the expression levels of ELOVL2, KLF14, and PENK are determined.

Embodiment 7 comprises the method of any one of the embodiments 1-6, wherein an increase in the expression rate of ELOVL2, KLF14, PENK, or a combination thereof further correlates to a decrease in cell senescence, an increase in cell proliferation, an increase in cell survival, or a decrease in DNA methylation.

Embodiment 8 comprises the method of any one of the embodiments 1-7, wherein an increase in the expression rate of ELOVL2, KLF14, PENK, or a combination thereof leads to a methylation pattern that mimics the methylation pattern of a sample obtained from a second subject.

Embodiment 9 comprises the method of embodiment 8, wherein the second subject is younger in chronological age relative to the first subject.

Embodiment 10 comprises the method of embodiment 8 or 9, wherein the second subject is younger in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

Embodiment 11 comprises the method of embodiment 1, wherein the control comprises the expression level of ELOVL2, KLF14, PENK, or a combination thereof obtained from a sample from the subject prior to administration of vitamin C or its derivatives, metabolites, or pharmaceutically acceptable salts thereof.

Embodiment 12 comprises the method of embodiment 1, wherein the control comprises a normalized expression level of ELOVL2, KLF14, PENK, or a combination thereof obtained from a set of samples without exposure to vitamin C or its derivatives, metabolites, or pharmaceutically acceptable salts thereof.

Embodiment 13 comprises the method of embodiment 12, wherein the set of samples are a set of cell samples.

Embodiment 14 comprises the method of embodiment 1, further comprising increasing the dose of vitamin C or its derivatives, metabolites, or pharmaceutically acceptable salts thereof if the expression level of ELOVL2, KLF14, PENK, or a combination thereof has not increased relative to the control.

Embodiment 15 comprises the method of embodiment 1, further comprising increasing the dose of vitamin C or its derivatives, metabolites, or pharmaceutically acceptable salts thereof if the expression level of ELOVL2, KLF14, PENK, or a combination thereof has increased relative to the control and at a rate that is below a target range.

Embodiment 16 comprises the method of embodiment 1, further comprising decreasing or maintaining the dose of vitamin C or its derivatives, metabolites, or pharmaceutically acceptable salts thereof if the expression level of ELOVL2, KLF14, PENK, or a combination thereof has increased relative to the control.

Embodiment 17 comprises the method of embodiment 1, further comprising maintaining the dose of vitamin C or its derivatives, metabolites, or pharmaceutically acceptable salts thereof if the expression level of ELOVL2, KLF14, PENK, or a combination thereof has increased relative to the control and at a rate that is within a target range.

Embodiment 18 comprises the method of embodiment 1, further comprising decreasing the dose of vitamin C or its derivatives, metabolites, or pharmaceutically acceptable salts thereof if the expression level of ELOVL2, KLF14, PENK, or a combination thereof has increased relative to the control and at a rate that is above a target range.

Embodiment 19 comprises the method of embodiment 14 or 16, wherein the dose of vitamin C or its derivatives, metabolites, or pharmaceutically acceptable salts thereof is increased, decreased, or maintained for a second period of time prior to redetermining the expression level of ELOVL2, KLF14, PENK, or a combination thereof.

Embodiment 20 comprises the method of embodiment 1, wherein the first period of time comprises at least one day, two days, three days, four days, five days, one week, two weeks, three weeks, four weeks, one month, two months, three months, four months, five months, six months, 1 year, two years, three years, or more.

Embodiment 21 comprises the method of embodiment 19, wherein the second period of time comprises at least one day, two days, three days, four days, five days, one week, two weeks, three weeks, four weeks, one month, two months, three months, four months, five months, six months, 1 year, two years, three years, or more.

Embodiment 22 comprises the method of any one of the embodiments 1-21, further comprising determining the expression level of FHL2, SMC4, SLC12A5, TEZM151A, TTF2, TRIM45, TRIM59, ACSS3, ARID5A, BLMH, BRD4, CD28, EPHX3, SLX1, BDNF, NDF, GDNF, cortisol, or a combination thereof.

Embodiment 23 comprises the method of any one of the embodiments 1-22, further comprising determining the expression level of an epigenetic marker selected from Table 1.

Embodiment 24 comprises a method of modulating the methylation pattern of ELOVL2, KLF14, PENK or a combination thereof in a first subject, comprising: (a) administering to the first subject a therapeutically effective dose of vitamin C or its derivatives, metabolites, or pharmaceutically acceptable salts thereof for a first time period; (b) obtaining a sample from the first subject; and (c) determining whether the methylation pattern of ELOVL2, KLF14, PENK or a combination thereof has changed in the first subject relative to a control by contacting the sample with a set of probes and detecting a set of hybridization products to determine the methylation pattern of ELOVL2, KLF14, PENK or a combination thereof.

Embodiment 25 comprises the method of embodiment 24, wherein vitamin C or its derivatives, metabolites, or pharmaceutically acceptable salts thereof is L-ascorbic acid 2-phoshate.

Embodiment 26 comprises the method of embodiment 24, wherein the sample is further treated with a deaminating agent prior to determining the methylation pattern.

Embodiment 27 comprises the method of embodiment 24, wherein the methylation pattern of ELOVL2 is determined.

Embodiment 28 comprises the method of embodiment 24, wherein the methylation pattern of KLF14 is determined.

Embodiment 29 comprises the method of embodiment 24, wherein the methylation pattern of PENK is determined.

Embodiment 30 comprises the method of embodiment 24, wherein the methylation patterns of ELOVL2 and KLF14 are determined.

Embodiment 31 comprises the method of embodiment 24, wherein the methylation patterns of ELOVL2, KLF14, and PENK are determined.

Embodiment 32 comprises the method of any one of the embodiments 24-31, wherein a change in the methylation pattern of ELOVL2, KLF14, PENK, or a combination thereof is a decrease in methylation status of ELOVL2, KLF14, PENK, or a combination thereof.

Embodiment 33 comprises the method of embodiment 32, wherein a decrease in the methylation status of ELOVL2, KLF14, PENK, or a combination thereof further correlates to a decrease in cell senescence, an increase in cell proliferation, or an increase in cell survival.

Embodiment 34 comprises the method of embodiment 32, wherein a decrease in the methylation status of ELOVL2, KLF14, PENK, or a combination thereof leads to a methylation pattern that mimics the methylation pattern of a sample obtained from a second subject.

Embodiment 35 comprises the method of embodiment 34, wherein the second subject is younger in chronological age relative to the first subject.

Embodiment 36 comprises the method of embodiment 34 or 35, wherein the second subject is younger in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

Embodiment 37 comprises the method of embodiment 24, wherein the control comprises the methylation pattern of ELOVL2, KLF14, PENK, or a combination thereof obtained from a sample from the subject prior to administration of vitamin C or its derivatives, metabolites, or pharmaceutically acceptable salts thereof.

Embodiment 38 comprises the method of embodiment 24, wherein the control comprises a normalized methylation pattern of ELOVL2, KLF14, PENK, or a combination thereof obtained from a set of samples without exposure to vitamin C or its derivatives, metabolites, or pharmaceutically acceptable salts thereof.

Embodiment 39 comprises the method of embodiment 38, wherein the set of samples are a set of cell samples.

Embodiment 40 comprises the method of embodiment 24, further comprising increasing the dose of vitamin C or its derivatives, metabolites, or pharmaceutically acceptable salts thereof if the methylation pattern of ELOVL2, KLF14, PENK, or a combination thereof has not changed relative to the control.

Embodiment 41 comprises the method of embodiment 24, further comprising increasing the dose of vitamin C or its derivatives, metabolites, or pharmaceutically acceptable salts thereof if the methylation pattern of ELOVL2, KLF14, PENK, or a combination thereof has changed relative to the control and to a degree lower than a target range.

Embodiment 42 comprises the method of embodiment 24, further comprising decreasing or maintaining the dose of vitamin C or its derivatives, metabolites, or pharmaceutically acceptable salts thereof if the methylation pattern of ELOVL2, KLF14, PENK, or a combination thereof has changed relative to the control.

Embodiment 43 comprises the method of embodiment 24, further comprising maintaining the dose of vitamin C or its derivatives, metabolites, or pharmaceutically acceptable salts thereof if the methylation pattern of ELOVL2, KLF14, PENK, or a combination thereof has changed relative to the control and to a degree within a target range.

Embodiment 44 comprises the method of embodiment 24, further comprising decreasing the dose of vitamin C or its derivatives, metabolites, or pharmaceutically acceptable salts thereof if the methylation pattern of ELOVL2, KLF14, PENK, or a combination thereof has changed relative to the control and to a degree above a target range.

Embodiment 45 comprises the method of embodiment 40 or 41, wherein the dose of vitamin C or its derivatives, metabolites, or pharmaceutically acceptable salts thereof is increased, decreased, or maintained for a second period of time prior to redetermining the methylation pattern of ELOVL2, KLF14, PENK, or a combination thereof.

Embodiment 46 comprises the method of embodiment 24, wherein the first period of time comprises at least one day, two days, three days, four days, five days, one week, two weeks, three weeks, four weeks, one month, two months, three months, four months, five months, six months, 1 year, two years, three years, or more.

Embodiment 47 comprises the method of embodiment 43, wherein the second period of time comprises at least one day, two days, three days, four days, five days, one week, two weeks, three weeks, four weeks, one month, two months, three months, four months, five months, six months, 1 year, two years, three years, or more.

Embodiment 48 comprises the method of any one of the embodiments 24-47, further comprising determining the methylation pattern of FHL2, SMC4, SLC12A5, TEDZM151A, TTF2, TRIM45, TRIM59, ACSS3, ARID5A, BLMH, BRD4, CD28, EPHX3, SLX1, BDNF, NDF, GDNF, cortisol, or a combination thereof.

Embodiment 49 comprises the method of any one of the embodiments 24-48, further comprising determining the methylation pattern of an epigenetic marker selected from Table 1.

Embodiment 50 comprises the method of any one of the embodiments 1-49, wherein the therapeutically effective dose of vitamin C or its derivatives, metabolites, or pharmaceutically acceptable salts thereof comprises from about 0.1 µg/mL to about 200 µg/mL, from about 1 µg/mL to about 150 µg/mL, from about 5 µg/mL to about 100 µg/mL, from about 10 µg/mL to about 100 µg/mL, from about 20 µg/mL to about 100 µg/mL, from about 30 µg/mL to about 100 µg/mL, from about 50 µg/mL to about 100 µg/mL, from about 1 µg/mL to about 50 µg/mL, from about 5 µg/mL to about 50 µg/mL, from about 10 µg/mL to about 50 µg/mL, or from about 50 µg/mL to about 200 µg/mL.

Embodiment 51 comprises the method of any one of the embodiments 1-49, wherein a dose of vitamin C or its derivatives, metabolites, or pharmaceutically acceptable salts thereof greater than 200 µg/mL increases reactive oxidative species.

Embodiment 52 comprises the method of any one of the embodiments 1-49, wherein a dose of vitamin C or its derivatives, metabolites, or pharmaceutically acceptable salts thereof greater than 200 µg/mL leads to a methylation pattern that mimics the methylation pattern of a sample obtained from a third subject who is older in chronological age relative to the first subject.

Embodiment 53 comprises the method of embodiment 52, wherein the third subject is older in chronological age relative to the first subject by at least 1 year, 2 years, 3 years, 4 years, 5 years, 6 years, 7 years, 8 years, 9 years, 10 years, 15 years, 20 years, 25 years, 30 years, 35 years, 40 years, 50 years, or more.

Embodiment 54 comprises the method of any one of the embodiments 1-53, wherein the probe hybridizes to a sequence selected from the group consisting of SEQ ID NOs: 1-199.

Embodiment 55 comprises the method of any one of the embodiments 1-56, further comprising administering to the first subject an additional therapeutic agent.

Embodiment 56 comprises the method of any one of the embodiments 1-55, wherein the sample is obtained from a subject having a metabolic disease or condition.

Embodiment 57 comprises the method of embodiment 56, wherein the metabolic disease or condition comprises diabetes or pre-diabetes.

Embodiment 58 comprises the method of embodiment 57, wherein diabetes is type I diabetes, type II diabetes, or type IV diabetes.

Embodiment 59 comprises the method of any one of the embodiments 1-55, wherein the sample is obtained from a subject having a ELOVL2-associated disease or indication, a KLF14-associated disease or indication, or a PENK-associated disease or indication.

Embodiment 60 comprises the method of any one of the embodiments 1-55, wherein the sample is obtained from a subject having Werner syndrome, progeria, or post-traumatic stress disorder.

Embodiment 61 comprises the method of any one of the embodiments 1-55, wherein the sample is obtained from a subject having an elevated body mass index (BMI).

Embodiment 62 comprises the method of embodiment 61, wherein the elevated BMI is a BMI of 25 kg/m$^2$, 26 kg/m$^2$, 27 kg/m$^2$, 28 kg/m$^2$, 29 kg/m$^2$, 30 kg/m$^2$, 35 kg/m$^2$, 40 kg/m$^2$ or more.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of detecting an expression level of ELOVL2, KLF14, and PENK in a first subject, comprising:
   a) administering to the first subject a therapeutically effective dose of vitamin C or its derivatives, metabolites, or pharmaceutically acceptable salts thereof for a first time period;
   b) obtaining a sample from the first subject after the first time period; and
   c) detecting the expression level of ELOVL2, KLF14, and PENK in the first subject by contacting the sample with one set and no more than one set of nucleic acid probes, wherein the one set of nucleic acid probes hybridizes to three markers and no more than three markers, wherein the three markers are ELOVL2, KLF14, and PENK and detecting binding between ELOVL2, KLF14, or PENK and the nucleic acid probes.

2. The method of claim 1, wherein vitamin C or its derivatives, metabolites, or pharmaceutically acceptable salts thereof is L-ascorbic acid 2-phosphate.

3. The method of claim 1, wherein at least one of the nucleic acid probes hybridizes to a sequence selected from the group consisting of SEQ ID NOs: 1, 5, 10, 14, 18, 21, 31, 33, 45, 47, and 74.

4. The method of claim 1, wherein the sample is a cell sample.

5. The method of claim 1, wherein the first time period comprises at least one day, two days, three days, four days, five days, one week, two weeks, three weeks, four weeks, one month, two months, three months, four months, five months, six months, 1 year, two years, three years, or more.

6. The method of claim 1, wherein the therapeutically effective dose of vitamin C or its derivatives, metabolites, or pharmaceutically acceptable salts thereof comprises from about 0.1 µg/mL to about 200 µg/mL, from about 1 µg/mL to about 150 µg/mL, from about 5 µg/mL to about 100 µg/mL, from about 10 µg/mL to about 100 µg/mL, from about 20 µg/mL to about 100 µg/mL, from about 30 µg/mL to about 100 µg/mL, from about 50 µg/mL to about 100 µg/mL, from about 1 µg/mL to about 50 µg/mL, from about 5 µg/mL to about 50 µg/mL, from about 10 µg/mL to about 50 µg/mL, or from about 50 µg/mL to about 200 µg/mL.

7. The method of claim 1, wherein a dose of vitamin C or its derivatives, metabolites, or pharmaceutically acceptable salts thereof greater than 200 µg/mL increases reactive oxidative species.

8. The method of claim 1, wherein the sample is obtained from a subject having a metabolic disease or condition.

9. The method of claim 1, wherein the sample is obtained from a subject having diabetes.

10. The method of claim 1, wherein the sample is obtained from a subject having Werner syndrome, progeria, or post-traumatic stress disorder.

11. A method of detecting the expression level of a plurality of markers in a first subject, comprising:
   a) administering to the first subject a therapeutically effective dose of vitamin C or its derivatives, metabolites, or pharmaceutically acceptable salts thereof for a first time period;
   b) obtaining a sample from the first subject after the first time period; and
   c) detecting the expression level of ELOVL2, KLF14, PENK, and one or more markers selected from the group consisting of FHL2, SMC4, SLC12A5, TEZM151A, TTF2, TRIM45, TRIM59, ACSS3, ARID5A, BLMH, BRD4, CD28, EPHX3, SLX1, BDNF, NDF, and GDNF in the first subject by:
      i) contacting the sample with two sets and no more than two sets of nucleic acid probes, wherein the first set of nucleic acid probes hybridizes to three markers and no more than three markers, wherein the three markers are ELOVL2, KLF14, and PENK and wherein the second set of nucleic acid probes hybridizes to at least one but no more than 19 markers selected from the group consisting of FHL2, SMC4, SLC12A5, TEZM151A, TTF2, TRIM45, TRIM59, ACSS3, ARID5A, BLMH, BRD4, CD28, EPHX3, RIN1, SLX1, BDNF, NDF, GDNF, and combinations thereof; and
      ii) detecting binding between ELOVL2, KLF14, or PENK and nucleic acid probes in the first set of nucleic acid probes and between one or more markers selected from the group consisting of FHL2, SMC4, SLC12A5, TEZM151A, TTF2, TRIM45, TRIM59, ACSS3, ARID5A, BLMH, BRD4, CD28, EPHX3, RIN1, SLX1, BDNF, NDF, and GDNF and nucleic acid probes in the second set of nucleic acid probes.

12. The method of claim 11, wherein vitamin C or its derivatives, metabolites, or pharmaceutically acceptable salts thereof is L-ascorbic acid 2-phosphate.

13. The method of claim 11, wherein at least one of the nucleic acid probes from the first set and second set of nucleic acid probes hybridizes to a sequence selected from the group consisting of SEQ ID NOs: 1, 3, 5, 6, 7, 9, 10, 14, 15, 18, 20, 21, 22, 31, 33, 45, 47, 74, and 140.

14. The method of claim 11, wherein the first time period comprises at least one day, two days, three days, four days, five days, one week, two weeks, three weeks, four weeks, one month, two months, three months, four months, five months, six months, 1 year, two years, three years, or more.

15. The method of claim 11, wherein the therapeutically effective dose of vitamin C or its derivatives, metabolites, or pharmaceutically acceptable salts thereof comprises from about 0.1 µg/mL to about 200 µg/mL, from about 1 µg/mL to about 150 µg/mL, from about 5 µg/mL to about 100 µg/mL, from about 10 µg/mL to about 100 µg/mL, from about 20 µg/mL to about 100 µg/mL, from about 30 µg/mL to about 100 µg/mL, from about 50 µg/mL to about 100 µg/mL, from about 1 µg/mL to about 50 µg/mL, from about 5 µg/mL to about 50 µg/mL, from about 10 µg/mL to about 50 µg/mL, or from about 50 µg/mL to about 200 µg/mL.

16. The method of claim 11, wherein a dose of vitamin C or its derivatives, metabolites, or pharmaceutically acceptable salts thereof greater than 200 µg/mL increases reactive oxidative species.

17. The method of claim 11, wherein the method further comprises detecting a level of cortisol in the first subject after administration of the therapeutically effective dose of vitamin C or its derivatives, metabolites, or pharmaceutically acceptable salts thereof.

18. The method of claim 11, wherein the sample is obtained from a subject having a metabolic disease or condition.

19. The method of claim 11, wherein the sample is obtained from a subject having diabetes.

20. The method of claim 11, wherein the sample is obtained from a subject having Werner syndrome, progeria, or post-traumatic stress disorder.

21. The method of claim 11, wherein the sample is a cell sample.

* * * * *

SEQUENCE LISTING

<160> NUMBER OF SEQ ID NOS: 199

<210> SEQ ID NO 1
<211> LENGTH: 50
<212> TYPE: DNA
<213> ORGANISM: Homo sapiens

<400> SEQUENCE: 1
cggcggctca acgtccacgg agccccagga atacccaccc gctgcccaga            50

<210> SEQ ID NO 2
<211> LENGTH: 50
<212> TYPE: DNA
<213> ORGANISM: Homo sapiens

<400> SEQUENCE: 2
cgggactgcg gcaccttacg gcgggaccaa gatttgggtc tgcgcaggcg            50

<210> SEQ ID NO 3
<211> LENGTH: 50
<212> TYPE: DNA
<213> ORGANISM: Homo sapiens

<400> SEQUENCE: 3
cttgggagca cagtagttat cgggagcgtc gcctccggcg tgggctctcg            50

<210> SEQ ID NO 4
<211> LENGTH: 50
<212> TYPE: DNA
<213> ORGANISM: Homo sapiens

<400> SEQUENCE: 4
cgccacgtac ccgcagcaga accgctcgct gtcgtcgcag agctacagcc            50

<210> SEQ ID NO 5
<211> LENGTH: 50
<212> TYPE: DNA
<213> ORGANISM: Homo sapiens

<400> SEQUENCE: 5
cgtccacgga gccccaggaa tacccacccg ctgcccagat cggcagccgc            50

<210> SEQ ID NO 6
<211> LENGTH: 50
<212> TYPE: DNA
<213> ORGANISM: Homo sapiens

<400> SEQUENCE: 6
agggctcctt tcttcgtgcc ctccgggtct tgggagcaca gtagttatcg            50

<210> SEQ ID NO 7
<211> LENGTH: 50
<212> TYPE: DNA
<213> ORGANISM: Homo sapiens

<400> SEQUENCE: 7
gagaacacca ggctccacat gaaggcgcgc agcagcttca gcgacaggcg            50

<210> SEQ ID NO 8
<211> LENGTH: 50
<212> TYPE: DNA
<213> ORGANISM: Homo sapiens

<400> SEQUENCE: 8
tctcggggcc ttggcgactt accgctgggg gcccgcagtg cagcagggcg        50

<210> SEQ ID NO 9
<211> LENGTH: 50
<212> TYPE: DNA
<213> ORGANISM: Homo sapiens

<400> SEQUENCE: 9
cgccggtggc cgacggcttc tgaggaatta tcttttactt ggcgccacac        50

<210> SEQ ID NO 10
<211> LENGTH: 50
<212> TYPE: DNA
<213> ORGANISM: Homo sapiens

<400> SEQUENCE: 10 gcccccggc taagtcatgt ttaacagcct cagaaattat cttgtctccg         50

<210> SEQ ID NO 11
<211> LENGTH: 50
<212> TYPE: DNA
<213> ORGANISM: Homo sapiens

<400> SEQUENCE: 11
ggctgcgcgg ggaggctggt cccgggctgg gcaggcgggc tggcctcgcg        50

<210> SEQ ID NO 12
<211> LENGTH: 50
<212> TYPE: DNA
<213> ORGANISM: Homo sapiens

<400> SEQUENCE: 12
gatttctcct tgaacaatcc ccgcaaagat agcagccaaa aaaggatgcg        50

<210> SEQ ID NO 13
<211> LENGTH: 50
<212> TYPE: DNA
<213> ORGANISM: Homo sapiens

<400> SEQUENCE: 13
aggcccaggt gggcgggcgg ctgaggagcg tggctgcgcc cacaaagccg        50

<210> SEQ ID NO 14
<211> LENGTH: 50
<212> TYPE: DNA
<213> ORGANISM: Homo sapiens

<400> SEQUENCE: 14
tgtttaacag cctcagaaat tatcttgtct ccgcgttctt tcttctgccg        50

<210> SEQ ID NO 15
<211> LENGTH: 50
<212> TYPE: DNA
<213> ORGANISM: Homo sapiens

<400> SEQUENCE: 15
cgcccgagag cccacgccgg aggcgacgct cccgataact actgtgctcc        50

<210> SEQ ID NO 16
<211> LENGTH: 50
<212> TYPE: DNA
<213> ORGANISM: Homo sapiens

```
<400> SEQUENCE: 16
gctgtcctca ggagccgcca gagtgctggg gaaggcggca gcaacgagcg                50

<210> SEQ ID NO 17
<211> LENGTH: 50
<212> TYPE: DNA
<213> ORGANISM: Homo sapiens

<400> SEQUENCE: 17
aagaaatacg gtgaaggagt ccttcccaaa gttgtctagg ccttccgcg                 50

<210> SEQ ID NO 18
<211> LENGTH: 50
<212> TYPE: DNA
<213> ORGANISM: Homo sapiens

<400> SEQUENCE: 18
caaagggctg atttctacag tcgctaggac ctgcagcggc gctgctcccg                50

<210> SEQ ID NO 19
<211> LENGTH: 50
<212> TYPE: DNA
<213> ORGANISM: Homo sapiens

<400> SEQUENCE: 19
ctcgagtgca aggtgtgctt tgagaagttt ggccaccggc agcagcggcg                50

<210> SEQ ID NO 20
<211> LENGTH: 50
<212> TYPE: DNA
<213> ORGANISM: Homo sapiens

<400> SEQUENCE: 20
gctcagctcc attggaatgc tccgggcgct gtccaaggtg ctggaatgcg                50

<210> SEQ ID NO 21
<211> LENGTH: 50
<212> TYPE: DNA
<213> ORGANISM: Homo sapiens

<400> SEQUENCE: 21
cggagcccca ggaataccca cccgctgccc agatcggcag ccgctgctgc                50

<210> SEQ ID NO 22
<211> LENGTH: 50
<212> TYPE: DNA
<213> ORGANISM: Homo sapiens

<400> SEQUENCE: 22
cggtctcccg aaccggtccc cgtaacgcga gcctgagatg ccctcacccc                50

<210> SEQ ID NO 23
<211> LENGTH: 50
<212> TYPE: DNA
<213> ORGANISM: Homo sapiens

<400> SEQUENCE: 23
catcacagcc tcacagtttt tcgagatctg gctccatttc gacgctgacg                50

<210> SEQ ID NO 24
<211> LENGTH: 50
<212> TYPE: DNA
<213> ORGANISM: Homo sapiens
```

<400> SEQUENCE: 24 gcggggtga attgtgaaga accatcgcgg ggtccttcct gctgaggccg         50

<210> SEQ ID NO 25
<211> LENGTH: 50
<212> TYPE: DNA
<213> ORGANISM: Homo sapiens

<400> SEQUENCE: 25
tagcctcgct gggcagcttg gcactgctgg gagcttggct cgccctgccg         50

<210> SEQ ID NO 26
<211> LENGTH: 50
<212> TYPE: DNA
<213> ORGANISM: Homo sapiens

<400> SEQUENCE: 26
gggggatgcc gggagcggcc tggggagctg tccctggtgc tgacggctcg         50

<210> SEQ ID NO 27
<211> LENGTH: 50
<212> TYPE: DNA
<213> ORGANISM: Homo sapiens

<400> SEQUENCE: 27
gctctacctc aaggagctca gggccatcgt gctgaaccaa cagaggctcg         50

<210> SEQ ID NO 28
<211> LENGTH: 50
<212> TYPE: DNA
<213> ORGANISM: Homo sapiens

<400> SEQUENCE: 28
gcagccacac atccaaggct gacagggcgg gcactctgcc aagtcctgcg         50

<210> SEQ ID NO 29
<211> LENGTH: 50
<212> TYPE: DNA
<213> ORGANISM: Homo sapiens

<400> SEQUENCE: 29
cgccctggcc cagccccgat ccagcctgcg cctcacctcg ggttgtagac         50

<210> SEQ ID NO 30
<211> LENGTH: 50
<212> TYPE: DNA
<213> ORGANISM: Homo sapiens

<400> SEQUENCE: 30
ggaggcggcg gcgctggtgg ggactgaccc ggcagtccga gaatccaccg         50

<210> SEQ ID NO 31
<211> LENGTH: 50
<212> TYPE: DNA
<213> ORGANISM: Homo sapiens

<400> SEQUENCE: 31
cgctctgtta ccattacctg gctcgccggc agaagaaaga acgcggagac         50

<210> SEQ ID NO 32
<211> LENGTH: 50
<212> TYPE: DNA

<213> ORGANISM: Homo sapiens

<400> SEQUENCE: 32
agaggtctca ggaaagtagc ctttatttat gtggcaccga tcggaacccg        50

<210> SEQ ID NO 33
<211> LENGTH: 50
<212> TYPE: DNA
<213> ORGANISM: Homo sapiens

<400> SEQUENCE: 33
gtggcgcttg gcagcaggtg tgacagacct cctccggggc gcctgatccg        50

<210> SEQ ID NO 34
<211> LENGTH: 50
<212> TYPE: DNA
<213> ORGANISM: Homo sapiens

<400> SEQUENCE: 34
cggggctaaa tcaaggaaaa cacacgctac acactcagtg ctgctgggtg        50

<210> SEQ ID NO 35
<211> LENGTH: 50
<212> TYPE: DNA
<213> ORGANISM: Homo sapiens

<400> SEQUENCE: 35
cggggaagct cggaaagcgt ctccccgact ccgccccag ggttgccttt         50

<210> SEQ ID NO 36
<211> LENGTH: 50
<212> TYPE: DNA
<213> ORGANISM: Homo sapiens

<400> SEQUENCE: 36
cggccgcgcg ccccttgccc cgccgctcct ccagacccac ctccaccgag        50

<210> SEQ ID NO 37
<211> LENGTH: 50
<212> TYPE: DNA
<213> ORGANISM: Homo sapiens

<400> SEQUENCE: 37
gtttcagcac ctgggtcagc gcttcccagg gtcagcacca gggatagacg        50

<210> SEQ ID NO 38
<211> LENGTH: 50
<212> TYPE: DNA
<213> ORGANISM: Homo sapiens

<400> SEQUENCE: 38
gtcttgggga gcccgcgggt tcgggtctgg gtcgcctggc gagctttccg        50

<210> SEQ ID NO 39
<211> LENGTH: 50
<212> TYPE: DNA
<213> ORGANISM: Homo sapiens

<400> SEQUENCE: 39
cccggtgctg ggggtcgcac tgtccctggg gacggcgggg gcctaagccg        50

<210> SEQ ID NO 40
<211> LENGTH: 50

```
<212> TYPE: DNA
<213> ORGANISM: Homo sapiens

<400> SEQUENCE: 40
cgggctaaac cccggtcccg ccgtacccat gaaggaccac gacgccatca         50

<210> SEQ ID NO 41
<211> LENGTH: 50
<212> TYPE: DNA
<213> ORGANISM: Homo sapiens

<400> SEQUENCE: 41
acacaccctc gggcgccttg gacggggtgc gctggggagc cagaagttcg         50

<210> SEQ ID NO 42
<211> LENGTH: 50
<212> TYPE: DNA
<213> ORGANISM: Homo sapiens

<400> SEQUENCE: 42
agcatttcat tcattcattc attcattcat ttcccggagc tccgctagcg         50

<210> SEQ ID NO 43
<211> LENGTH: 50
<212> TYPE: DNA
<213> ORGANISM: Homo sapiens

<400> SEQUENCE: 43
caccgcgtgg agttgcttgt tcttttacat aggaggtcac attctcttcg         50

<210> SEQ ID NO 44
<211> LENGTH: 50
<212> TYPE: DNA
<213> ORGANISM: Homo sapiens

<400> SEQUENCE: 44
gacgagaccg acgtggaggc ctgctgctgg atgacctacc ggcagcatcg         50

<210> SEQ ID NO 45
<211> LENGTH: 50
<212> TYPE: DNA
<213> ORGANISM: Homo sapiens

<400> SEQUENCE: 45
cgccccggag gaggtctgtc acacctgctg ccaagcgcca ccaatgcccc         50

<210> SEQ ID NO 46
<211> LENGTH: 50
<212> TYPE: DNA
<213> ORGANISM: Homo sapiens

<400> SEQUENCE: 46
cggatcccgc caaatttgaa cgcgagattg tcaggccctg aggggcttga         50

<210> SEQ ID NO 47
<211> LENGTH: 50
<212> TYPE: DNA
<213> ORGANISM: Homo sapiens

<400> SEQUENCE: 47
cccagaagtt ccgactgggg agtttcgctc tgttaccatt acctggctcg         50

<210> SEQ ID NO 48
```

```
<211> LENGTH: 50
<212> TYPE: DNA
<213> ORGANISM: Homo sapiens

<400> SEQUENCE: 48
atctaactca accoctttag atattcttcc aggtggaatt attggattcg              50

<210> SEQ ID NO 49
<211> LENGTH: 50
<212> TYPE: DNA
<213> ORGANISM: Homo sapiens

<400> SEQUENCE: 49
cgcgaaggcc actcgctggc gaccccttcc cgggtctcct agccctggcc              50

<210> SEQ ID NO 50
<211> LENGTH: 50
<212> TYPE: DNA
<213> ORGANISM: Homo sapiens

<400> SEQUENCE: 50
agcaccagta caggtcggtg acggcgatga ggtacaggtc cagcaggccg              50

<210> SEQ ID NO 51
<211> LENGTH: 50
<212> TYPE: DNA
<213> ORGANISM: Homo sapiens

<400> SEQUENCE: 51
cggccctcac tacacgaggc ctgggcgcct gcacgccccc gtgcttcagc              50

<210> SEQ ID NO 52
<211> LENGTH: 50
<212> TYPE: DNA
<213> ORGANISM: Homo sapiens

<400> SEQUENCE: 52
ttacccattc tcgctcgtaa atccagttca attgtgctaa cccagagtcg              50

<210> SEQ ID NO 53
<211> LENGTH: 50
<212> TYPE: DNA
<213> ORGANISM: Homo sapiens

<400> SEQUENCE: 53
cggcgccaat cctagattcg atagggtaag ttctgtggtc tccagggcag              50

<210> SEQ ID NO 54
<211> LENGTH: 50
<212> TYPE: DNA
<213> ORGANISM: Homo sapiens

<400> SEQUENCE: 54
cgttaacctc tgctagtgat gaccaaacct ggtaaagatt gtaaagtggg              50

<210> SEQ ID NO 55
<211> LENGTH: 50
<212> TYPE: DNA
<213> ORGANISM: Homo sapiens

<400> SEQUENCE: 55
cgtatgtgtt tgagatagca gttgtttact atcacttgaa aattctgaat              50
```

```
<210> SEQ ID NO 56
<211> LENGTH: 50
<212> TYPE: DNA
<213> ORGANISM: Homo sapiens

<400> SEQUENCE: 56
ggacccagaa aagcaccaaa actctttaga aggactgagc atcccttacg            50

<210> SEQ ID NO 57
<211> LENGTH: 50
<212> TYPE: DNA
<213> ORGANISM: Homo sapiens

<400> SEQUENCE: 57
gcgacggtcg aggtctggcg tcccgtgggc tgggctcagc tgggtcggcg            50

<210> SEQ ID NO 58
<211> LENGTH: 50
<212> TYPE: DNA
<213> ORGANISM: Homo sapiens

<400> SEQUENCE: 58
cgagaccagc ctgggcaaca tagatcagaa ggcgaataga ataagtccgc            50

<210> SEQ ID NO 59
<211> LENGTH: 50
<212> TYPE: DNA
<213> ORGANISM: Homo sapiens

<400> SEQUENCE: 59
gggtttgggg ctgttgggtt gtgcggaatc tgaagtagtc cacttctccg            50

<210> SEQ ID NO 60
<211> LENGTH: 50
<212> TYPE: DNA
<213> ORGANISM: Homo sapiens

<400> SEQUENCE: 60
cgatagggta agttctgtgg tctccagggc agaagaaatc tgtggatagg            50

<210> SEQ ID NO 61
<211> LENGTH: 50
<212> TYPE: DNA
<213> ORGANISM: Homo sapiens

<400> SEQUENCE: 61
cgcccttcgc gcgcccccact tcagcctttc agcgtaaggc aggaaccttt           50

<210> SEQ ID NO 62
<211> LENGTH: 50
<212> TYPE: DNA
<213> ORGANISM: Homo sapiens

<400> SEQUENCE: 62
aggtctagtg gagagtcctc gctctgtgac cccttcctct ctggtaaccg            50

<210> SEQ ID NO 63
<211> LENGTH: 50
<212> TYPE: DNA
<213> ORGANISM: Homo sapiens

<400> SEQUENCE: 63
tccattggaa actcccctct aagctgtgca tttttaggct gtggtcatcg            50
```

<210> SEQ ID NO 64
<211> LENGTH: 50
<212> TYPE: DNA
<213> ORGANISM: Homo sapiens

<400> SEQUENCE: 64
tttctttgtc tatgtatgta cagataatta catggccgat ttgcttatcg        50

<210> SEQ ID NO 65
<211> LENGTH: 50
<212> TYPE: DNA
<213> ORGANISM: Homo sapiens

<400> SEQUENCE: 65
agcaggggag atggtggctc cctctcgggg ccagtctgcc ccaagcagcg        50

<210> SEQ ID NO 66
<211> LENGTH: 50
<212> TYPE: DNA
<213> ORGANISM: Homo sapiens

<400> SEQUENCE: 66
gcaggtacac gaaggccatg atgcacaggg gcacgtagaa ggagactacg        50

<210> SEQ ID NO 67
<211> LENGTH: 50
<212> TYPE: DNA
<213> ORGANISM: Homo sapiens

<400> SEQUENCE: 67
cctcctggat catgtactca tcctcgtcgt acacgtagtt gtactgcacg        50

<210> SEQ ID NO 68
<211> LENGTH: 50
<212> TYPE: DNA
<213> ORGANISM: Homo sapiens

<400> SEQUENCE: 68
caccaggaag cccgcctctg gttttaagat gttaggccaa cagggaagcg        50

<210> SEQ ID NO 69
<211> LENGTH: 50
<212> TYPE: DNA
<213> ORGANISM: Homo sapiens

<400> SEQUENCE: 69
ctctctcttg cgttattttt ctgttttctg cctttccgtt gtctccttcg        50

<210> SEQ ID NO 70
<211> LENGTH: 50
<212> TYPE: DNA
<213> ORGANISM: Homo sapiens

<400> SEQUENCE: 70
cacgaagctt tggggagcac tctagcccct gctactcacc catgcaagcg        50

<210> SEQ ID NO 71
<211> LENGTH: 50
<212> TYPE: DNA
<213> ORGANISM: Homo sapiens

<400> SEQUENCE: 71
tgtggtacgt ggcgtccggc ttgaaaggat ggctcttgcc ctgggacacg        50

<210> SEQ ID NO 72
<211> LENGTH: 50
<212> TYPE: DNA
<213> ORGANISM: Homo sapiens

<400> SEQUENCE: 72
accgaaggag gagaatgcta tttatttcag caccaaatat ccggacagcg          50

<210> SEQ ID NO 73
<211> LENGTH: 50
<212> TYPE: DNA
<213> ORGANISM: Homo sapiens

<400> SEQUENCE: 73
ttcatctaga aggtttgact ctggccagac aaccagcgag catcttctcg          50

<210> SEQ ID NO 74
<211> LENGTH: 50
<212> TYPE: DNA
<213> ORGANISM: Homo sapiens

<400> SEQUENCE: 74
tcttctgccg gcgagccagg taatggtaac agagcgaaac tccccagtcg          50

<210> SEQ ID NO 75
<211> LENGTH: 50
<212> TYPE: DNA
<213> ORGANISM: Homo sapiens

<400> SEQUENCE: 75
cggagtcaac cacagacaat agaccctgta cccagcctcg cgcctgcgga          50

<210> SEQ ID NO 76
<211> LENGTH: 50
<212> TYPE: DNA
<213> ORGANISM: Homo sapiens

<400> SEQUENCE: 76
gaggagcagg acccacgacg gacttgccga ggtgctggtg ctggagagcg          50

<210> SEQ ID NO 77
<211> LENGTH: 50
<212> TYPE: DNA
<213> ORGANISM: Homo sapiens

<400> SEQUENCE: 77
cgggcccacc tgaaagcgcc tcgatggcct tgagggccca gctctcgtcc          50

<210> SEQ ID NO 78
<211> LENGTH: 50
<212> TYPE: DNA
<213> ORGANISM: Homo sapiens

<400> SEQUENCE: 78
gggctctccg aaacaggccg ggaaagctga agcacagtg acctccttcg           50

<210> SEQ ID NO 79
<211> LENGTH: 50
<212> TYPE: DNA
<213> ORGANISM: Homo sapiens

<400> SEQUENCE: 79

```
ggtcctgggc cagctgcaag tggcagagca gccggcgctc gtccaggtcg         50

<210> SEQ ID NO 80
<211> LENGTH: 50
<212> TYPE: DNA
<213> ORGANISM: Homo sapiens

<400> SEQUENCE: 80
ctggcaacgc tacctgggtt tagttttccc ttcgtatatc actatcttcg         50

<210> SEQ ID NO 81
<211> LENGTH: 50
<212> TYPE: DNA
<213> ORGANISM: Homo sapiens

<400> SEQUENCE: 81
gggcaactgg gccaggccgt tgatggacag gtccaggtgg cggagcagcg         50

<210> SEQ ID NO 82
<211> LENGTH: 50
<212> TYPE: DNA
<213> ORGANISM: Homo sapiens

<400> SEQUENCE: 82
gtggagactg gccgcaggtc aggagagctc accacttgaa ggtgaagtcg         50

<210> SEQ ID NO 83
<211> LENGTH: 50
<212> TYPE: DNA
<213> ORGANISM: Homo sapiens

<400> SEQUENCE: 83
gcagtccctg agcctctgca ggcagttctt ggagccctcg ggcttttgcg         50

<210> SEQ ID NO 84
<211> LENGTH: 50
<212> TYPE: DNA
<213> ORGANISM: Homo sapiens

<400> SEQUENCE: 84
tgggacaagg acaggtcagc gggtcacagg ccggaagtga gactcgcccg         50

<210> SEQ ID NO 85
<211> LENGTH: 50
<212> TYPE: DNA
<213> ORGANISM: Homo sapiens

<400> SEQUENCE: 85
cgcgctccgc cctttgcctg cagagcgctg ggggtttaaa gtcctgaacc         50

<210> SEQ ID NO 86
<211> LENGTH: 50
<212> TYPE: DNA
<213> ORGANISM: Homo sapiens

<400> SEQUENCE: 86
cggcagcccc tccagcggct gattctatgt cctcaacacg actgggcgcc         50

<210> SEQ ID NO 87
<211> LENGTH: 50
<212> TYPE: DNA
<213> ORGANISM: Homo sapiens

<400> SEQUENCE: 87
```

```
caacagcgtg ctggacttca tcctgtccat ggggctggat ggcctgggcg            50
```

<210> SEQ ID NO 88
<211> LENGTH: 50
<212> TYPE: DNA
<213> ORGANISM: Homo sapiens

<400> SEQUENCE: 88

```
tgcagagacc actgtggcgt tgaaaagagg tgtcgtcgcg accttcggcg            50
```

<210> SEQ ID NO 89
<211> LENGTH: 50
<212> TYPE: DNA
<213> ORGANISM: Homo sapiens

<400> SEQUENCE: 89

```
cgattgctta atgctatttt tcagccaaag ggtgtgtttc tgagttttcg            50
```

<210> SEQ ID NO 90
<211> LENGTH: 50
<212> TYPE: DNA
<213> ORGANISM: Homo sapiens

<400> SEQUENCE: 90

```
cgcttggaga gagcagacaa cagtatgccc cgccccacct cggacctggt            50
```

<210> SEQ ID NO 91
<211> LENGTH: 50
<212> TYPE: DNA
<213> ORGANISM: Homo sapiens

<400> SEQUENCE: 91

```
cggagagttc tggaaataaa atgaattata acaaggagct aattaaaaac            50
```

<210> SEQ ID NO 92
<211> LENGTH: 50
<212> TYPE: DNA
<213> ORGANISM: Homo sapiens

<400> SEQUENCE: 92

```
agacagcacc tggggtatt tgttttgcct aagcctgctg cacttccacg             50
```

<210> SEQ ID NO 93
<211> LENGTH: 50
<212> TYPE: DNA
<213> ORGANISM: Homo sapiens

<400> SEQUENCE: 93

```
gaggccgggg ctgttctgag ggctgggact gtcagccaat ccgtctgtcg            50
```

<210> SEQ ID NO 94
<211> LENGTH: 50
<212> TYPE: DNA
<213> ORGANISM: Homo sapiens

<400> SEQUENCE: 94

```
agggcaggga cacaactcac tctggacagg gtacagtcac acccacttcg            50
```

<210> SEQ ID NO 95
<211> LENGTH: 50
<212> TYPE: DNA
<213> ORGANISM: Homo sapiens

<400> SEQUENCE: 95
tctgtgaatg tgaatggaac taagcgttcc tttctctccc tcaatggccg                    50

<210> SEQ ID NO 96
<211> LENGTH: 50
<212> TYPE: DNA
<213> ORGANISM: Homo sapiens

<400> SEQUENCE: 96
cggggattca gcaccacgag gcggacagct ccaggccctg aggtccccag                    50

<210> SEQ ID NO 97
<211> LENGTH: 50
<212> TYPE: DNA
<213> ORGANISM: Homo sapiens

<400> SEQUENCE: 97
accacaggtg gttttctccg gtgacaaaca atgcttcctt cttccttccg                    50

<210> SEQ ID NO 98
<211> LENGTH: 50
<212> TYPE: DNA
<213> ORGANISM: Homo sapiens

<400> SEQUENCE: 98
ccttgcaagg cggctgctaa gcctggctaa ttttagatct ccagaatgcg                    50

<210> SEQ ID NO 99
<211> LENGTH: 50
<212> TYPE: DNA
<213> ORGANISM: Homo sapiens

<400> SEQUENCE: 99
cgcgtggccg ccgctgctcc aactaccacg tgcgcttccg ctgcccacta                    50

<210> SEQ ID NO 100
<211> LENGTH: 50
<212> TYPE: DNA
<213> ORGANISM: Homo sapiens

<400> SEQUENCE: 100
cggtgcccag ccgctggagc ccctggcctg cgtgccccac cctgattttc                    50

<210> SEQ ID NO 101
<211> LENGTH: 50
<212> TYPE: DNA
<213> ORGANISM: Homo sapiens

<400> SEQUENCE: 101
cgaagggaaa actaaaccca ggtagcgttg ccagcttaaa agtcctaggc                    50

<210> SEQ ID NO 102
<211> LENGTH: 50
<212> TYPE: DNA
<213> ORGANISM: Homo sapiens

<400> SEQUENCE: 102 cagcccccatt taaggttttt gatacactga ggatcattca gaaaacttcg                   50

<210> SEQ ID NO 103
<211> LENGTH: 50
<212> TYPE: DNA
<213> ORGANISM: Homo sapiens

<400> SEQUENCE: 103
cggcagctcc gctgaaaact gcattcagcc agtcctccgg acttctggag         50

<210> SEQ ID NO 104
<211> LENGTH: 50
<212> TYPE: DNA
<213> ORGANISM: Homo sapiens

<400> SEQUENCE: 104
cgacctgccc gactgcaagg cccgcaagca gcccatcaag gaggagttca         50

<210> SEQ ID NO 105
<211> LENGTH: 50
<212> TYPE: DNA
<213> ORGANISM: Homo sapiens

<400> SEQUENCE: 105
cgccatgacg acaaccaact cttgccccccc aagagtggca gtctgtctgg         50

<210> SEQ ID NO 106
<211> LENGTH: 50
<212> TYPE: DNA
<213> ORGANISM: Homo sapiens

<400> SEQUENCE: 106
cgctagcgcc tcggttacag cctttcccgc aaggcttcat tcagtcgcgc         50

<210> SEQ ID NO 107
<211> LENGTH: 50
<212> TYPE: DNA
<213> ORGANISM: Homo sapiens

<400> SEQUENCE: 107
cacgatgccc aggtagcagt gcagcagcag agctgtctgc gccagcagcg         50

<210> SEQ ID NO 108
<211> LENGTH: 50
<212> TYPE: DNA
<213> ORGANISM: Homo sapiens

<400> SEQUENCE: 108
aggcgggttc ccggtagggt gcgcagggtg ctgcggtagg tctcatgtcg         50

<210> SEQ ID NO 109
<211> LENGTH: 50
<212> TYPE: DNA
<213> ORGANISM: Homo sapiens

<400> SEQUENCE: 109
cgtgtgaata cggtggcttc ttgtgagaag gggccattct attgtaactg         50

<210> SEQ ID NO 110
<211> LENGTH: 50
<212> TYPE: DNA
<213> ORGANISM: Homo sapiens

<400> SEQUENCE: 110
cggagctctt cggagtgtgt ccactgcttt gacctctgcg aacttgtatt         50

<210> SEQ ID NO 111
<211> LENGTH: 50
<212> TYPE: DNA

<213> ORGANISM: Homo sapiens

<400> SEQUENCE: 111
cgcagctcag caggcctcag ggaaggaact gggtgcccaa actccggcct                 50

<210> SEQ ID NO 112
<211> LENGTH: 50
<212> TYPE: DNA
<213> ORGANISM: Homo sapiens

<400> SEQUENCE: 112
gctggtggat accttcgtgc tgcacctggc ggcagctgac ctgggcttcg                 50

<210> SEQ ID NO 113
<211> LENGTH: 50
<212> TYPE: DNA
<213> ORGANISM: Homo sapiens

<400> SEQUENCE: 113
cggccaagcc aaaggcagga gtcagcacca cggacagctt ccgctggatc                 50

<210> SEQ ID NO 114
<211> LENGTH: 50
<212> TYPE: DNA
<213> ORGANISM: Homo sapiens

<400> SEQUENCE: 114
cggggagaaa aaaccgaac acgtgtgcta cccagggccc ccagataagc                  50

<210> SEQ ID NO 115
<211> LENGTH: 50
<212> TYPE: DNA
<213> ORGANISM: Homo sapiens

<400> SEQUENCE: 115
cggccagtaa ggttgaggca ctattcaaaa gccctggaat tgtctggaac                 50

<210> SEQ ID NO 116
<211> LENGTH: 50
<212> TYPE: DNA
<213> ORGANISM: Homo sapiens

<400> SEQUENCE: 116
caggtaggtg ctgatgaatt tgagtgtgtt taaatcttag acttactgta                 50

<210> SEQ ID NO 117
<211> LENGTH: 50
<212> TYPE: DNA
<213> ORGANISM: Homo sapiens

<400> SEQUENCE: 117
ccatgctcgg ccttctggaa gatgcccaca gacactggca ataatggacg                 50

<210> SEQ ID NO 118
<211> LENGTH: 50
<212> TYPE: DNA
<213> ORGANISM: Homo sapiens

<400> SEQUENCE: 118
cgccccggcc cccagctagg tgatagcagg ctgggaccac ctccccgccc                 50

<210> SEQ ID NO 119
<211> LENGTH: 50

```
<212> TYPE: DNA
<213> ORGANISM: Homo sapiens

<400> SEQUENCE: 119
aacacagaga cccaacctac ccaggagctt gtcttcttgc ctctccagcg         50

<210> SEQ ID NO 120
<211> LENGTH: 50
<212> TYPE: DNA
<213> ORGANISM: Homo sapiens

<400> SEQUENCE: 120
cgatgtatcc aagtctgacg gccccagaaa cgggtgtgca gggcgcccat         50

<210> SEQ ID NO 121
<211> LENGTH: 50
<212> TYPE: DNA
<213> ORGANISM: Homo sapiens

<400> SEQUENCE: 121
cgtccgttac cactgacctg aggcctgcct gggtccaagc tcacacttgg         50

<210> SEQ ID NO 122
<211> LENGTH: 50
<212> TYPE: DNA
<213> ORGANISM: Homo sapiens

<400> SEQUENCE: 122
ggtcaaaact ttgcccagct cagccttgct cgaccctggg cagggaagcg         50

<210> SEQ ID NO 123
<211> LENGTH: 50
<212> TYPE: DNA
<213> ORGANISM: Homo sapiens

<400> SEQUENCE: 123
cgaccacacc aggcacccag gagcaagtgc tttgaaatgc ggctttctcc         50

<210> SEQ ID NO 124
<211> LENGTH: 50
<212> TYPE: DNA
<213> ORGANISM: Homo sapiens

<400> SEQUENCE: 124
acgcgggaac tctttgagag agcggctcag cggcttggcc ttgccgtgcg         50

<210> SEQ ID NO 125
<211> LENGTH: 50
<212> TYPE: DNA
<213> ORGANISM: Homo sapiens

<400> SEQUENCE: 125 tccgtcccstt gtagcactgc cttctgggta atgtagtttg acggaatccg         50

<210> SEQ ID NO 126
<211> LENGTH: 50
<212> TYPE: DNA
<213> ORGANISM: Homo sapiens

<400> SEQUENCE: 126
gtgaagcagt tctgcttgac cgggatgggg ttgtacagcg ccatggtccg         50

<210> SEQ ID NO 127
```

```
<211> LENGTH: 50
<212> TYPE: DNA
<213> ORGANISM: Homo sapiens

<400> SEQUENCE: 127
gaactctttg agagagcggc tcagcggctt ggccttgccg tgcgcctgcg          50

<210> SEQ ID NO 128
<211> LENGTH: 50
<212> TYPE: DNA
<213> ORGANISM: Homo sapiens

<400> SEQUENCE: 128
cgccgcctag actactagcc tgggctgctt gttttgtctc tgaaattgac          50

<210> SEQ ID NO 129
<211> LENGTH: 50
<212> TYPE: DNA
<213> ORGANISM: Homo sapiens

<400> SEQUENCE: 129
cagcagctgg aacgtgctgg atggctttct tgtcttcgtg tccatcatcg          50

<210> SEQ ID NO 130
<211> LENGTH: 50
<212> TYPE: DNA
<213> ORGANISM: Homo sapiens

<400> SEQUENCE: 130
agccccaagc catgactaag gagcccattt ggtaactctg ccctcttccg          50

<210> SEQ ID NO 131
<211> LENGTH: 50
<212> TYPE: DNA
<213> ORGANISM: Homo sapiens

<400> SEQUENCE: 131
cggtttctgc aggcaacagg ggtttcccca accacagctg tcatgaaaac          50

<210> SEQ ID NO 132
<211> LENGTH: 50
<212> TYPE: DNA
<213> ORGANISM: Homo sapiens

<400> SEQUENCE: 132
cggtgaccct tgtggcaact taggtctctg gcagccgagt tgaccccaac          50

<210> SEQ ID NO 133
<211> LENGTH: 50
<212> TYPE: DNA
<213> ORGANISM: Homo sapiens

<400> SEQUENCE: 133
aaggcaaatt gcctgcctcg tgcataataa gccaggcgtg gagagcagcg          50

<210> SEQ ID NO 134
<211> LENGTH: 50
<212> TYPE: DNA
<213> ORGANISM: Homo sapiens

<400> SEQUENCE: 134
tgagggtggc ggggtgctct tcgcagcttc tctgtggaga ccggtcagcg          50
```

```
<210> SEQ ID NO 135
<211> LENGTH: 50
<212> TYPE: DNA
<213> ORGANISM: Homo sapiens

<400> SEQUENCE: 135
ccacgagtag gaccaagcgg tttgtgtctg aggcgcgctt cgtggagacg          50

<210> SEQ ID NO 136
<211> LENGTH: 50
<212> TYPE: DNA
<213> ORGANISM: Homo sapiens

<400> SEQUENCE: 136
cgagggaggt gtcaaagttg gaaatcctga atgggaaggg cactgtcaaa          50

<210> SEQ ID NO 137
<211> LENGTH: 50
<212> TYPE: DNA
<213> ORGANISM: Homo sapiens

<400> SEQUENCE: 137
tgagagctgg gaacctgcgc cagtgactgc gcgacagtgt tgacgggccg          50

<210> SEQ ID NO 138
<211> LENGTH: 50
<212> TYPE: DNA
<213> ORGANISM: Homo sapiens

<400> SEQUENCE: 138
cgggccaagg gcgtcctgaa gacctagggg gccccctccga cctcccgacc         50

<210> SEQ ID NO 139
<211> LENGTH: 50
<212> TYPE: DNA
<213> ORGANISM: Homo sapiens

<400> SEQUENCE: 139
tcgcgagctc catgttctcc tctttgggac aagttgttga aatggttccg          50

<210> SEQ ID NO 140
<211> LENGTH: 50
<212> TYPE: DNA
<213> ORGANISM: Homo sapiens

<400> SEQUENCE: 140
accaagctct gctcctcaag tgacgggggc tctgctctgc caggtgaccg          50

<210> SEQ ID NO 141
<211> LENGTH: 50
<212> TYPE: DNA
<213> ORGANISM: Homo sapiens

<400> SEQUENCE: 141
cgggcagcct gcagaccacg ctcgaggaca gcctgaccct gagcgacagc          50

<210> SEQ ID NO 142
<211> LENGTH: 50
<212> TYPE: DNA
<213> ORGANISM: Homo sapiens

<400> SEQUENCE: 142
cgagccctga agctggaaag ccaacgtgct ggctggagcc agaagagcag          50
```

```
<210> SEQ ID NO 143
<211> LENGTH: 50
<212> TYPE: DNA
<213> ORGANISM: Homo sapiens

<400> SEQUENCE: 143
cggttgcctg gcgccggaga cccacagaca ggactcaccc agcttcctca        50

<210> SEQ ID NO 144
<211> LENGTH: 50
<212> TYPE: DNA
<213> ORGANISM: Homo sapiens

<400> SEQUENCE: 144
cgccaccgca ccatcttcag cgaagagcag ctgcaggcgc tcgaggcgct        50

<210> SEQ ID NO 145
<211> LENGTH: 50
<212> TYPE: DNA
<213> ORGANISM: Homo sapiens

<400> SEQUENCE: 145
ggcccgaacc atgagctcct acctggagta cgtgtcatgc agcagcagcg        50

<210> SEQ ID NO 146
<211> LENGTH: 50
<212> TYPE: DNA
<213> ORGANISM: Homo sapiens

<400> SEQUENCE: 146
cgtcgatgcc cataacatct ggacccaatt gggttctaaa tgacgcaatt        50

<210> SEQ ID NO 147
<211> LENGTH: 50
<212> TYPE: DNA
<213> ORGANISM: Homo sapiens

<400> SEQUENCE: 147
cggacaggct gaccgggagc ccccagaatg cacaacaggc acacgagatg        50

<210> SEQ ID NO 148
<211> LENGTH: 50
<212> TYPE: DNA
<213> ORGANISM: Homo sapiens

<400> SEQUENCE: 148
gggaacatgg ccctggagcg gctctgctcg gtcctcaaag gtaaggaccg        50

<210> SEQ ID NO 149
<211> LENGTH: 50
<212> TYPE: DNA
<213> ORGANISM: Homo sapiens

<400> SEQUENCE: 149
tcctgggctt gctgtttctg cagccgcttt gggtggctcc aggtaaaacg        50

<210> SEQ ID NO 150
<211> LENGTH: 50
<212> TYPE: DNA
<213> ORGANISM: Homo sapiens

<400> SEQUENCE: 150
cgtggcctgg ttaaccaatc tgttgcactg gctcccttttt aagggggcctg       50
```

<210> SEQ ID NO 151
<211> LENGTH: 50
<212> TYPE: DNA
<213> ORGANISM: Homo sapiens

<400> SEQUENCE: 151
gggtgcagag gcctagggcg ggcaggccgg cagactgggg tcgggccacg          50

<210> SEQ ID NO 152
<211> LENGTH: 50
<212> TYPE: DNA
<213> ORGANISM: Homo sapiens

<400> SEQUENCE: 152
cggcggagcc tgcttgcaaa gctgaggtcc cggatctcac cttcctgtcc          50

<210> SEQ ID NO 153
<211> LENGTH: 50
<212> TYPE: DNA
<213> ORGANISM: Homo sapiens

<400> SEQUENCE: 153
cgctgagccc ggcctggcta gcccgccacc ccgcccgctg ttacccgact          50

<210> SEQ ID NO 154
<211> LENGTH: 50
<212> TYPE: DNA
<213> ORGANISM: Homo sapiens

<400> SEQUENCE: 154
tgggcccaca gggacaagtg gctcccgcgg tgtcttcggt ggccgcagcg          50

<210> SEQ ID NO 155
<211> LENGTH: 50
<212> TYPE: DNA
<213> ORGANISM: Homo sapiens

<400> SEQUENCE: 155
atctgcggct ttgtttctca ggcacctgtt gtggatccca aatagaaacg          50

<210> SEQ ID NO 156
<211> LENGTH: 50
<212> TYPE: DNA
<213> ORGANISM: Homo sapiens

<400> SEQUENCE: 156
cgatgctgct tcatgatatg tgtcaaaata aatgcaggaa acagcttttg          50

<210> SEQ ID NO 157
<211> LENGTH: 50
<212> TYPE: DNA
<213> ORGANISM: Homo sapiens

<400> SEQUENCE: 157
ggcggctctg gccagtttgg agcctggggt gaccctggga gctgacctcg          50

<210> SEQ ID NO 158
<211> LENGTH: 50
<212> TYPE: DNA
<213> ORGANISM: Homo sapiens

<400> SEQUENCE: 158
cgtctcgcct tgcgagcaag ctcggaatcc agttcctcag gaacccctcc          50

<210> SEQ ID NO 159
<211> LENGTH: 50
<212> TYPE: DNA
<213> ORGANISM: Homo sapiens

<400> SEQUENCE: 159
cgacggcgca aaacaagct ggaaagggag gaaaatggtg accctgcact          50

<210> SEQ ID NO 160
<211> LENGTH: 50
<212> TYPE: DNA
<213> ORGANISM: Homo sapiens

<400> SEQUENCE: 160
ttcaaccaag gagacctgtc catggtcctg accacatcat ttgccactcg          50

<210> SEQ ID NO 161
<211> LENGTH: 50
<212> TYPE: DNA
<213> ORGANISM: Homo sapiens

<400> SEQUENCE: 161
cattggtcat caggtttctt aaaatgtgac tctgaatctg tgtccttccg          50

<210> SEQ ID NO 162
<211> LENGTH: 50
<212> TYPE: DNA
<213> ORGANISM: Homo sapiens

<400> SEQUENCE: 162
ccaggctgat gaggcagagg ttgaggatgg aggcgctgca gcacatcacg          50

<210> SEQ ID NO 163
<211> LENGTH: 50
<212> TYPE: DNA
<213> ORGANISM: Homo sapiens

<400> SEQUENCE: 163
tttcagccac ataggaccca gtcaaacaca gaaattgtag tttcttcccg          50

<210> SEQ ID NO 164
<211> LENGTH: 50
<212> TYPE: DNA
<213> ORGANISM: Homo sapiens

<400> SEQUENCE: 164
catggtccgg gaaaccaggc atctctgggt gggcaactta cccgagaacg          50

<210> SEQ ID NO 165
<211> LENGTH: 50
<212> TYPE: DNA
<213> ORGANISM: Homo sapiens

<400> SEQUENCE: 165
cggagaccag gcgtgtcccg ccagacccct cagacccagg ctaaacccaa          50

<210> SEQ ID NO 166
<211> LENGTH: 50
<212> TYPE: DNA
<213> ORGANISM: Homo sapiens

<400> SEQUENCE: 166
cgggcaggct caaaagaaaa agaataatta gggataattg cttgtgtcca         50

<210> SEQ ID NO 167
<211> LENGTH: 50
<212> TYPE: DNA
<213> ORGANISM: Homo sapiens

<400> SEQUENCE: 167
ggcattggca ggccagtatg gtctgggagg gcagcaaggt gggcacatcg         50

<210> SEQ ID NO 168
<211> LENGTH: 50
<212> TYPE: DNA
<213> ORGANISM: Homo sapiens

<400> SEQUENCE: 168
actcgctcac aaaggtttca gtgctcctcc ctgcggacac cagaagggcg         50

<210> SEQ ID NO 169
<211> LENGTH: 50
<212> TYPE: DNA
<213> ORGANISM: Homo sapiens

<400> SEQUENCE: 169
aatagaaacc caagaatcat ttctgtgtgc cacaggagtg ctctccccg          50

<210> SEQ ID NO 170
<211> LENGTH: 50
<212> TYPE: DNA
<213> ORGANISM: Homo sapiens

<400> SEQUENCE: 170
cggctaatga cagagccaac gattcaagac caagtcagac agactccaaa         50

<210> SEQ ID NO 171
<211> LENGTH: 50
<212> TYPE: DNA
<213> ORGANISM: Homo sapiens

<400> SEQUENCE: 171
cgttgtggac accaggtgcc actcctgtgg gggatcagca cagcatctcc         50

<210> SEQ ID NO 172
<211> LENGTH: 50
<212> TYPE: DNA
<213> ORGANISM: Homo sapiens

<400> SEQUENCE: 172
cgaggaggag cctggcagtc acctcttcta caatgtcacg gtctttggcc         50

<210> SEQ ID NO 173
<211> LENGTH: 50
<212> TYPE: DNA
<213> ORGANISM: Homo sapiens

<400> SEQUENCE: 173
cggtcaacta gaccccacta gctgaagccg gcatcacctg ggaagcagcc         50

<210> SEQ ID NO 174
<211> LENGTH: 50
<212> TYPE: DNA
<213> ORGANISM: Homo sapiens

<400> SEQUENCE: 174
ggggttgatc ctggcagctg tcgtggaggt gggggcactg ctgggcaacg   50

<210> SEQ ID NO 175
<211> LENGTH: 50
<212> TYPE: DNA
<213> ORGANISM: Homo sapiens

<400> SEQUENCE: 175
catcctggag ggctgttcgc cggtttcggg ggtggatgtg gacaaaggcg   50

<210> SEQ ID NO 176
<211> LENGTH: 50
<212> TYPE: DNA
<213> ORGANISM: Homo sapiens

<400> SEQUENCE: 176
cgggaactgt ttctgactta tcaaagtgtg aacaagaggt acagaccggt   50

<210> SEQ ID NO 177
<211> LENGTH: 50
<212> TYPE: DNA
<213> ORGANISM: Homo sapiens

<400> SEQUENCE: 177
cgaggaggtg ggcactcaag cgacgtaaga tccacatcag ctcaactgca   50

<210> SEQ ID NO 178
<211> LENGTH: 50
<212> TYPE: DNA
<213> ORGANISM: Homo sapiens

<400> SEQUENCE: 178
cgcgcctgga ggatctggag aaccagctgg ccaaccagaa gtgagggcca   50

<210> SEQ ID NO 179
<211> LENGTH: 50
<212> TYPE: DNA
<213> ORGANISM: Homo sapiens

<400> SEQUENCE: 179
gatgaatagc agactgcccc ggggcagtta ggaattcgac tggacagccg   50

<210> SEQ ID NO 180
<211> LENGTH: 50
<212> TYPE: DNA
<213> ORGANISM: Homo sapiens

<400> SEQUENCE: 180
cttgatgtca gcaaagtttg cacaatgggt cttaacgtgc actcattccg   50

<210> SEQ ID NO 181
<211> LENGTH: 50
<212> TYPE: DNA
<213> ORGANISM: Homo sapiens

<400> SEQUENCE: 181
tgctgacctt cgtagtgtcc tcgtacaacc tgaacttcat cgtcctttcg   50

<210> SEQ ID NO 182
<211> LENGTH: 50
<212> TYPE: DNA
<213> ORGANISM: Homo sapiens

```
<400> SEQUENCE: 182
ctgggctccc attggctgct tttgacgttg tgctccaccc tttctgggcg            50

<210> SEQ ID NO 183
<211> LENGTH: 50
<212> TYPE: DNA
<213> ORGANISM: Homo sapiens

<400> SEQUENCE: 183
cggccgccag ctgctttctt gggggcgctc cctgcctcgc ttggctctgt            50

<210> SEQ ID NO 184
<211> LENGTH: 50
<212> TYPE: DNA
<213> ORGANISM: Homo sapiens

<400> SEQUENCE: 184
tttatctaga aaactttcca agcaaagaca aggtcctctc ggcttgtccg            50

<210> SEQ ID NO 185
<211> LENGTH: 50
<212> TYPE: DNA
<213> ORGANISM: Homo sapiens

<400> SEQUENCE: 185
tgttgagagc gattttaatt ctcattctgt acctgcagat gccgcggccg            50

<210> SEQ ID NO 186
<211> LENGTH: 50
<212> TYPE: DNA
<213> ORGANISM: Homo sapiens

<400> SEQUENCE: 186
caaagcagat gacctggcag gaaccagccg cagtgaagcc accgcaaccg            50

<210> SEQ ID NO 187
<211> LENGTH: 50
<212> TYPE: DNA
<213> ORGANISM: Homo sapiens

<400> SEQUENCE: 187
cttcagaaac cagaatccgc gaattggggc aacaatccag caggtccccg            50

<210> SEQ ID NO 188
<211> LENGTH: 50
<212> TYPE: DNA
<213> ORGANISM: Homo sapiens

<400> SEQUENCE: 188
cgtctaccta gaggcaaaga caggagagag ggagtccgta aaatctggaa            50

<210> SEQ ID NO 189
<211> LENGTH: 50
<212> TYPE: DNA
<213> ORGANISM: Homo sapiens

<400> SEQUENCE: 189
gggctccaga gccaggcctc ggacttcgcg gggaaccaaa ggcaaaatcg            50

<210> SEQ ID NO 190
<211> LENGTH: 50
<212> TYPE: DNA
```

<213> ORGANISM: Homo sapiens

<400> SEQUENCE: 190
cggccgcagc taaagatagg agaacaactc actatcggct aaaaatacgg     50

<210> SEQ ID NO 191
<211> LENGTH: 50
<212> TYPE: DNA
<213> ORGANISM: Homo sapiens

<400> SEQUENCE: 191
tcagcgctaa acccaagaca aaggctgccc tgtgtcttcc gtactcagcg     50

<210> SEQ ID NO 192
<211> LENGTH: 50
<212> TYPE: DNA
<213> ORGANISM: Homo sapiens

<400> SEQUENCE: 192
gctcagcctt tctctgctgc gagtagtgac taaacattac aagaaggccg     50

<210> SEQ ID NO 193
<211> LENGTH: 50
<212> TYPE: DNA
<213> ORGANISM: Homo sapiens

<400> SEQUENCE: 193
cggggcaggg cagaggcctt ccttctctat agaccacatc atgggccacg     50

<210> SEQ ID NO 194
<211> LENGTH: 50
<212> TYPE: DNA
<213> ORGANISM: Homo sapiens

<400> SEQUENCE: 194
ggtgcggggc tgtgacctag aggcttcagt gtcgatcccc gaggtgttcg     50

<210> SEQ ID NO 195
<211> LENGTH: 50
<212> TYPE: DNA
<213> ORGANISM: Homo sapiens

<400> SEQUENCE: 195
cggcctgcta cgctaagcta ggccttcaag catgccagag cagttaagca     50

<210> SEQ ID NO 196
<211> LENGTH: 50
<212> TYPE: DNA
<213> ORGANISM: Homo sapiens

<400> SEQUENCE: 196
cctgcttttt gaaactggtt cttctgccca tctttagagc cacagcaacg     50

<210> SEQ ID NO 197
<211> LENGTH: 50
<212> TYPE: DNA
<213> ORGANISM: Homo sapiens

<400> SEQUENCE: 197
cgggactcag cccccaacgc ccccacctgc cgctctgccc acctcagcgc     50

<210> SEQ ID NO 198
<211> LENGTH: 50

-continued

```
<212> TYPE: DNA
<213> ORGANISM: Homo sapiens

<400> SEQUENCE: 198
cgccgctcca ggccctccac tgtcgggccc cggtgtcctc caacatctct          50

<210> SEQ ID NO 199
<211> LENGTH: 50
<212> TYPE: DNA
<213> ORGANISM: Homo sapiens

<400> SEQUENCE: 199
atagcatcct ggccatatcc agttttgaaa acactacggt gtcagccacg          50
```